US008632968B2

(12) United States Patent
Perera et al.

(10) Patent No.: US 8,632,968 B2
(45) Date of Patent: Jan. 21, 2014

(54) METHOD FOR THE DETECTION AND/OR IDENTIFICATION OF A MICROORGANISM

(75) Inventors: Viraj N. Perera, Coventry (GB); Benjamin N. Fry, Lovely Banks (AU)

(73) Assignee: Diagnostic Array Systems Pty Ltd, Bundoora (AU)

( * ) Notice: Subject to any disclaimer, the term of this patent is extended or adjusted under 35 U.S.C. 154(b) by 1195 days.

(21) Appl. No.: 11/989,509

(22) PCT Filed: Jul. 27, 2006

(86) PCT No.: PCT/AU2006/001056
§ 371 (c)(1), (2), (4) Date: Feb. 27, 2009

(87) PCT Pub. No.: WO2007/012131
PCT Pub. Date: Feb. 1, 2007

(65) Prior Publication Data

US 2009/0318300 A1 Dec. 24, 2009

(30) Foreign Application Priority Data

Jul. 27, 2005 (AU) ................................ 2005904015

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC .......... 435/6.1; 435/91.2; 536/23.1; 536/24.3

(58) Field of Classification Search
None
See application file for complete search history.

(56) References Cited

U.S. PATENT DOCUMENTS 6,489,110 B1 12/2002 Oudshoorn et al.

FOREIGN PATENT DOCUMENTS

WO WO-01/23604 4/2001

OTHER PUBLICATIONS

Buck, G.A. et al., Biotechniques, vol. 27, pp. 528-536 (1999).*
Ko, K.S. et al., J. Clin. Microbiol., vol. 45, pp. 2516-2519 (2005).*
Everett, K.D. et al., Int. J. Systematic Bacteriol., vol. 49, pp. 415-440 (1999).*
*Heamophilus*, Wikipedia, Aug. 24, 2012.*
Yu, V.L. et al., J. Infect. Dis., vol. 186, pp. 127-128 (2002).*
*Mycoplasma*, Wikipedia, Sep. 10, 2012.*
*Mycobacteria*, Wikipedia, Aug. 3, 2012.*
*Staphylococcus*, Wikipedia, Sep. 14, 2012.*
Innings, A. et al., J. Clin. Microbiol., vol. 43, pp. 5983-5991 (2005).*
*Pseudomonas*, Wikipedia, Aug. 6, 2010.*
*Moraxella*, Wikipedia, Aug. 22, 2012.*
*Fusobacterium*, Wikipedia, May 9, 2012.*
*Stenotrophomonas*, Wikipedia, Jun. 13, 2012.*
*Burkholderia*, Wikipedia, Mar. 17, 2012.*
*Enterococcus*, Wikipedia, Sep. 12, 2012.*
*Corynebacterium*, Wikipedia, Aug. 1, 2012.*
*Neisseria*, Wikipedia, Aug. 28, 2012.*
International Search Report Re: PCT/AU2006/001056 dated Oct. 9, 2006.
Martineau F. et al., 2001, Development of a PCR assay for identification of *staphylococci* at genus and species levels, Journal of Clinical Microbiology, 39(7):2541-2547.
Ke, D. et al., 1999, Development of a PCR assay for rapid detection of *enterococci*, Journal of Clinical Microbiology, 37(11): 3497-3503.
Ventura, M. et al, 2003, Analysis, characterization, and loci of the tuf genes in *Lactobacillus* and *Bifidobacterium* species and their direct application for species identification, Applied and Environmental Microbiology, 69(11): 6908-6922.
Luneberg, E. et al, 1993, Detection of *Mycoplasma pneumoniae* by polymerase chain reaction and nonradioactive hybridization in microtiter plates, Journal of Clinical Microbiology, 31(5): 1088-1094.

* cited by examiner

*Primary Examiner* — Teresa E Strzelecka
(74) *Attorney, Agent, or Firm* — Edwards Wildman Palmer LLP; Jeffrey D. Hsi

(57) ABSTRACT

The present invention relates generally to a method of identifying micro-organisms in a sample and in particular to the identification of prokaryotic micro-organisms. In some embodiments, the present invention relates to a method for the detection and/or identification of at least one microorganism or for the simultaneous detection and/or identification of several microorganisms in a test sample wherein the test sample is contacted with one or more probes derived from a tuf gene variable region.

2 Claims, 6 Drawing Sheets

METHOD FOR THE DETECTION AND/OR IDENTIFICATION OF A MICROORGANISM

FIELD

The present invention relates generally to a method of identifying micro-organisms in a sample and in particular to the identification of prokaryotic micro-organisms. The method of the present invention is useful, inter alia, for the prognosis, diagnosis, prevention, and treatment of diseases associated with pathogens (including human pathogens) and in particular to diseases such as respiratory infections, gastrointestinal tract infections, dermal infection, genital tract infections and nosocomial infections. The present invention also relates to kits used for identifying micro-organisms, particularly prokaryotic micro-organisms.

BACKGROUND

Currently, the standard method used for the diagnosis of bacterial infections is the culture of clinical samples obtained from patients. Culture techniques have been used for many years for clinical diagnosis. Apart from being slow, time-consuming and labour intensive, the reliability of results obtained by culture techniques is very low. Consequently, this has hindered the prescription of effective drugs for treating bacterial infections, resulting in more patient suffering and/or death.

Other shortcomings of present methods of microbial identification include the need for special growth media, the inability to distinguish between closely related species and strains, and the need for large amounts of sample. Importantly, previous methods of microbial detection have found it difficult to simultaneously detect more than one micro-organism in a sample. Consequently, there is a need to develop methods of identifying micro-organisms in samples which are rapid, sensitive and accurate.

SUMMARY

Accordingly, in a first aspect the invention provides a method for the detection and/or identification of at least one microorganism or for the simultaneous detection and/or identification of several microorganisms in a test sample comprising:

(a) providing a test sample suspected of containing one or more target microorganisms;

(b) optionally, releasing, isolating and/or concentrating polynucleic acids from said at least one microorganism(s) from said test sample, if present in the test sample, the or each said polynucleic acid comprising at least a portion of a tuf gene variable region;

(c) contacting said test sample or said polynucleic acid from said test sample with one or more probes derived from said tuf gene variable region for a time and under conditions sufficient for hybridization to take place; and (d) detecting any hybridization which has taken place in step (c);

wherein the presence or absence of hybridization is indicative of the presence or absence of said one or more said microorganisms in said test sample.

It is preferable that the polynucleic acid in said test sample is amplified, for example, using an amplification technique such as polymerase chain reaction (PCR).

Accordingly, in a second aspect the present invention provides a method for the detection and/or identification of at least one microorganism or for the simultaneous detection and/or identification of several microorganisms in a test sample comprising:

(a) optionally, releasing, isolating and/or concentrating polynucleic acids from said at least one microorganism(s) to be detected;

(b) optionally, amplifying at least a portion of a tuf gene variable region from said microorganism(s) with at least one primer pair;

(c) contacting said test sample or said polynucleic acid from said test sample with one or more probes derived from said tuf gene variable region for a time and under conditions sufficient for hybridization to take place; and (d) detecting any hybridization which has taken place in step (c);

wherein the presence or absence of hybridization is indicative of the presence or absence of said one or more said microorganisms in said test sample.

In some embodiments the polynucleic acid is derived from a tuf gene variable region as shown in SEQ ID NOs.:1 to 11. Preferably, the polynucleic acid consists essentially of nucleotides 108-220, 393-591, 708-774, 792-816, and/or 885-945 of SEQ ID NOs.:1 to 11.

In other embodiments the polynucleic acid has a sequence which is antisense to a tuf gene variable region as shown in SEQ ID NOs.:1 to 11. Preferably, the polynucleic acid is consists essentially of nucleotides antisense to the nucleotides 108-220, 393-591, 708-774, 792-816, and/or 885-945 of SEQ ID NOs.:1 to 11.

In some embodiments, the step of contacting the test sample comprises hybridization with at least a portion of a tuf gene variable region with a set of probes comprising at least one probe selected from the group consisting of SEQ ID NOs:12 to 84, 208 to 251, 254-315 and 330 to 393.

Accordingly, in a third aspect the present invention provides a method for the detection and/or identification of at least one microorganism or for the simultaneous detection and/or identification of several microorganisms in a test sample comprising:

(a) optionally, releasing, isolating and/or concentrating polynucleic acids from said at least one microorganism(s) to be detected;

(b) optionally, amplifying at least a portion of a tuf gene variable region from said microorganism(s) with at least one primer pair;

(c) hybridizing at least a portion of a tuf gene variable region from said microorganism(s) with a set of probes comprising at least one probe selected from the group consisting of SEQ ID NOs: 12 to 84, 208 to 251, 254-315 and 330 to 393;

(d) detecting hybrids formed in step (c); and (e) identifying said at least one microorganism from said detecting of step (d).

In other embodiments, the at least one probe is selected from the group consisting of SEQ ID NOs: 12 to 84, 208 to 315 and 330 to 393. In other embodiments, the at least one probe is selected from the group consisting of SEQ ID NOs: 12 to 392 and 393.

In a fourth aspect, the present invention provides a method for the diagnosis and/prognosis of a disease associated with a target microorganism comprising:

(a) optionally, releasing, isolating and/or concentrating polynucleic acids from said at least one microorganism(s) to be detected;

(b) optionally, amplifying at least a portion of a tuf gene variable region from said microorganism(s) with at least one primer pair;

(c) contacting said test sample or said polynucleic acid from said test sample with one or more probes derived from said tuf gene variable region for a time and under conditions sufficient for hybridization to take place; and (d) detecting any hybridization which has taken place in step (c);

wherein the presence or absence of hybridization is indicative of the presence or absence of the target microorganism in said test sample;

(e) associating the presence of said one or more said target microorganisms with a disease; and (f) determine diagnosis and/or prognosis for said disease.

In a fifth aspect, the present invention provides a method for the prevention or treatment of a disease associated with a target microorganism comprising:

(a) optionally, releasing, isolating and/or concentrating polynucleic acids from said at least one microorganism(s) to be detected;

(b) optionally, amplifying at least a portion of a tuf gene variable region from said microorganism(s) with at least one primer pair;

(c) contacting said test sample or said polynucleic acid from said test sample with one or more probes derived from said tuf gene variable region for a time and under conditions sufficient for hybridization to take place; and (d) detecting any hybridization which has taken place in step (c);

wherein the presence or absence of hybridization is indicative of the presence or absence of the target microorganism in said test sample;

(e) associating the presence of said one or more said target microorganisms with a disease; and (f) prescribing prevention or treatment of said disease.

In some embodiments, the step of associating the presence of one or more target microorganisms with a disease or the step of prescribing a treatment comprise the step of using a computer program.

In some embodiments, the disease may be a bacterial infection, respiratory infection, gastrointestinal tract infection, dermal infection, bloodstream infection, meningitis or central nervous system infection, urinary tract infection, genital tract infection, wound infection, or nosocomial infection.

In some embodiments, the microorganism detected and/or identified is selected from the group consisting of *Bordetella* species, *Chlamydophila* species, *Haemophilus* species, *Legionella* species, *Mycoplasma* species, *Mycobacterium* species, *Staphylococcus* species, *Streptococcus* species, *Pseudomonas* species, *Moraxella* species and *Fusobacterium* species, *Stenotrophomonas* species, *Burkholderi* species, *Enterococcus* species, *Corynebacterium* species and *Neisseria* species.

In some embodiments, the step of amplifying at least a portion of a tuf gene variable region from the microorganism(s) utilizes at least one primer pair, wherein at least one of the primers is selected from the group consisting of SEQ ID NOs:394-396, or equivalents thereof, provided said equivalents specifically amplify the tuf variable region or a part thereof of different species of microorganism at the same time.

In a sixth aspect, the present invention provides a composition comprising at least one probe selected from the group consisting of SEQ ID NOs:12-393 or equivalents thereof, provided that said equivalents specifically bind to a tuf gene variable region of a microorganism to be detected.

In a seventh aspect, the present invention provides a composition comprising at least one primer selected from the group consisting of SEQ ID NOs:394-396, or equivalents thereof, provided said equivalents specifically amplify the tuf gene variable region or a part thereof of a microorganism to be detected.

In an eighth aspect, the present invention provides an oligonucleotide probe for the detection and/or identification of at least one microorganism found in test sample selected from the group consisting of *Bordetella* species, *Chlamydophila* species, *Haemophilus* species, *Legionella* species, *Mycoplasma* species, *Mycobacterium* species, *Staphylococcus* species, *Streptococcus* species, *Pseudomonas* species, *Moraxella* species and *Fusobacterium* species, *Stenotrophomonas* species, *Burkholderi* species, *Enterococcus* species, *Corynebacterium* species and *Neisseria* species, wherein said probe is selected from the group consisting of:

for *Haemophilus influenzae*:

| | |
|---|---|
| TATTATCCGTACAGGTGATGAAGTAGAAA; | (SEQ ID NO.: 12) |
| AAAGATACAGCGAAAACTACTGTAACG; | (SEQ ID NO.: 13) |
| CATCGGTGCATTATTACGTGGTAC; | (SEQ ID NO.: 14) |
| CATACTCCATTCTTCAAAGGTTACCG; | (SEQ ID NO.: 15) |
| TGACTGGTACAATCGAATTACCAGAA; | (SEQ ID NO.: 16) |
| CCGTAAATTACTTGACGAAGGTCG; | (SEQ ID NO.: 17) |
| ACTTCGAATC AGAAGTGTAC; | (SEQ ID NO.: 64) |
| CAAACGTGAA GAAATCGAAC; | (SEQ ID NO.: 65) |
| CGATAACATC AAGATGACAG T; | (SEQ ID NO.: 66) |

for *Moraxella catarrhalis*:

| | |
|---|---|
| TGAGCGTGACATCGATAAGTCA; | (SEQ ID NO.: 18) |
| CAGGCATTATTAAAGTTGGTGATGAAATT; | (SEQ ID NO.: 19) |
| AAACCAACTACTAAAACCACTTGTACTG; | (SEQ ID NO.: 20) |
| CGTAAGCTGCTAGACGAAGGT; | (SEQ ID NO.: 21) |
| TACCCCATTCCTAAATGGCTATCG; | (SEQ ID NO.: 22) |
| TAACTGGTGCCATCACCCTAC; | (SEQ ID NO.: 23) |
| AGTTTGATGCAGAAGTATACG | (SEQ ID NO.: 208) |
| TATCCTACTACGTGGTACTAA | (SEQ ID NO.: 209) |
| ATAACGTTGAGATGAGCG | (SEQ ID NO.: 210) |

for *Enterococcus faecalis*:

| | |
|---|---|
| AAGGCGACGAGTCTTATGAAGA; | (SEQ ID NO.: 24) |
| AATTAATGGCTGCAGTTGACGAAT; | (SEQ ID NO.: 25) |
| GAAGTTCGCGTTGGTGACG; | (SEQ ID NO.: 26) |
| GACGAAACATCTAAAACAACTGTTACAG; | (SEQ ID NO.: 27) |
| TGGTGTTGTAGAATTGCCAGAAG; | (SEQ ID NO.: 28) |
| TAAACCAGCTACAATCACTCCACA; | (SEQ ID NO.: 29) |

for *Staphylococcus aureus*:

GTTGACATGGTTGACGATGAAGAATTA; (SEQ ID NO.: 30)

CTTAGAATTAATGGAAGCTGTAGATACTTACA; (SEQ ID NO.: 31)

ATCATCGGTTTACATGACACATCTAAAA; (SEQ ID NO.: 32)

CACCACATACTGAATTTAAAGCAGAAGTA; (SEQ ID NO.: 33)

CATTCTTCTCAAACTATCGTCCACAA; (SEQ ID NO.: 34)

CTGGTGTTGTTCACTTACCAGAAG; (SEQ ID NO.: 35)

TACTGAAATGGTAATGCCTGGTGATA; (SEQ ID NO.: 36)

CCAATCGCGATTGAAGACGG; (SEQ ID NO.: 37)

CTGGTTCAGCATTAAAAGCTTTAGAAG; (SEQ ID NO.: 38)

TGACAACATTGGTGCATTATTACGT; (SEQ ID NO.: 39)

TGTTACAGGTGTTGAAATGTTCCG; (SEQ ID NO.: 40)

GTATTATCAAAAGACGAAGGTGGACG; (SEQ ID NO.: 41)

GCGATGCTCAATACGAAGAAAAAATC; (SEQ ID NO.: 42)

TGAATTCAAA GCAGAAGTAT AC; (SEQ ID NO.: 76)

ATTATTACGT GGTGTTGCTC; (SEQ ID NO.: 77)

GTGATAACGT TGAAATGACA G; (SEQ ID NO.: 78)

for *Staphylococcus epidermidis*:

TAGACTTAATGCAAGCAGTTGATGATTAC; (SEQ ID NO.: 43)

CCACACACAAAATTCAAAGCTGAAG; (SEQ ID NO.: 44)

CTGGTGTTGTAAACTTACCAGAAGG; (SEQ ID NO.: 45)

GAAATGGTTATGCCTGGCGAC; (SEQ ID NO.: 46)

CTGGTTCTGCATTAAAAGCATTAGAAG; (SEQ ID NO.: 47)

TGACAACATCGGTGCTTTATTACG; (SEQ ID NO.: 48)

CTGTTACTGGTGTAGAAATGTTCCG; (SEQ ID NO.: 49)

CGTATTATCTAAAGATGAAGGTGGACG; (SEQ ID NO.: 50)

for *Pseudomonas aeruginosa*:

AAGTTCGAGTGCGAAGT; (SEQ ID NO.: 51)

AAGGCGTAGAGATGGTAAT; (SEQ ID NO.: 52)

TTCTTCAAGGGCTACCG; (SEQ ID NO.: 53)

ATCATCAAGGTCCAGGAAGAAGT; (SEQ ID NO.: 54)

ACCAAGACTACCTGCACCG; (SEQ ID NO.: 55)

TGTACGTGCTGTCCAAGGAA; (SEQ ID NO.: 56)

CCGGTAACTGCGAACTGC; (SEQ ID NO.: 57)

CACGTTGACTGCCCCGGTCACGC; (SEQ ID NO.: 85)

ACGCCTTCCGGCAGTTCGCAGTTAC; (SEQ ID NO.: 86)

ATCGGTCACGTTGACCATGGCA; (SEQ ID NO.: 87)

GCCGCCTTCGCGGATCGCGAA; (SEQ ID NO.: 88)

for *Bordetella pertussis*:

GTACATTCTG TCCAAGGAAG; (SEQ ID NO.: 58)

GACAACGTGG GTATCTTG; (SEQ ID NO.: 59)

GACAAGGAAA TGGTGCT; (SEQ ID NO.: 60)

for *Chlamydophila pneumoniae*:

AATTTAAGTC AGCTGTTTAC G; (SEQ ID NO.: 61)

GAGGTATTGG AAAGAACGAT; (SEQ ID NO.: 62)

ATAACGTTGA GCTTGATGTT; (SEQ ID NO.: 63)

for *Legionella pneumophila*:

AGTTTGAAGC AGAAGTGTAT; (SEQ ID NO.: 67)

TGTTATTACG AGGTACGAAG; (SEQ ID NO.: 68)

AGATAATGTG CAATTAGTTG TTA; (SEQ ID NO.: 69)

for *Mycoplasma pneumoniae*:

GAAATTTAAA GCGGAAATCT ATG; (SEQ ID NO.: 70)

GAACGTGGTC AAGTGTTAG; (SEQ ID NO.: 71)

GACAATACCT CGATTACAGT; (SEQ ID NO.: 72)

for *Mycobacterium tuberculosis*

AACATCTCGG TGAAGTTGAT; (SEQ ID NO.: 73)

TGACAACACC AACATCTC; (SEQ ID NO.: 74)

ACGAAGGTCT GCGTTT; (SEQ ID NO.: 75)

for *Streptococcus pneumoniae*

AATTCAAAGG TGAAGTCTAC A; (SEQ ID NO.: 79)

CAACGTGATG AAATCGAAC; (SEQ ID NO.: 80)

GACAATCGAC GTTGAGTT; (SEQ ID NO.: 81)

for *Streptococcus pyogenes*

CAAAGGTGAA GTATATATCC TTTC; (SEQ ID NO.: 82)

CAACGTGACG AAATCGAA; (SEQ ID NO.: 83)

CGTGACAATC AACGTTGA; (SEQ ID NO.: 84)

and combinations thereof.

In a ninth aspect, the present invention provides a method of hybridization comprising contacting a test sample suspected of containing a polynucleic acid with a solid support, which has immobilized thereon one or more probes selected from the group consisting of SEQ ID NOs: 12-392 and 393.

In some embodiments, certain aspects of the invention are provided as kits.

Accordingly, in a tenth aspect, the present invention provides a kit for the detection and/or identification of at least one microorganism or the detection and/or identification of sev=- eral microorganisms simultaneously in a test sample, comprising (a) optionally, at least one primer pair allowing amplification of at least a portion of a tuf gene variable region;
(b) the composition according to the sixth aspect;
(c) a buffer, or components necessary to produce the buffer enabling a hybridization reaction between the probe(s) contained in said composition and a polynucleic acid present in the sample, or the amplified products thereof;
(d) a solution, or components necessary for producing the solution, enabling washing of the hybrids formed under the appropriate wash conditions;
(e) optionally, a means for detecting the hybrids resulting from the preceding hybridization.

In an eleventh aspect, the present invention provides a method for the detection and/or identification of at least one microorganism or for the simultaneous detection and/or identification of several microorganisms in a sputum sample comprising the steps of (a) optionally, releasing, isolating and/or concentrating polynucleic acids from said at least one microorganism(s) to be detected;
(b) optionally, amplifying at least a portion of a tuf gene variable region from said microorganism(s) with at least one primer pair;
(c) hybridizing at least a portion of a tuf gene variable region from said microorganism(s) with a set of probes comprising at least one probe selected from the group consisting of SEQ ID NOs: 12 to 84, 208 to 251, 254-315 and 330 to 393;
(d) detecting hybrids formed in step (c);
(e) identifying said at least one microorganism from said detecting of step (d).

In a twelfth aspect, the present invention provides a microarray comprising at least one probe selected from the group consisting of SEQ ID NOs: 12-393 or equivalents thereof, provided that said equivalents specifically bind to the tuf gene variable region of a microorganism.

DETAILED DESCRIPTION

Figure 1:
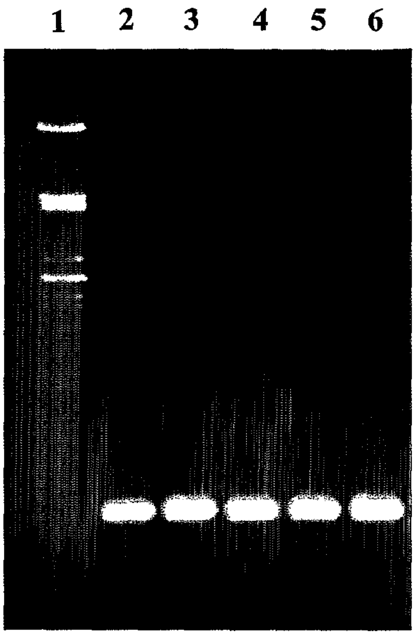
FIG. 1 is a PCR amplification of the tuf gene fragment. Lane 1, DNA standard marker; lane 2, *Streptococcus pneumoniae*; Lane 3, *Moraxella catarrhalis*; Lane 4, *Legionella pneumophila*; Lane 5, *Staphylococcus aureus*; Lane 6, *Haemophilus influenzae.*
Figure 2:
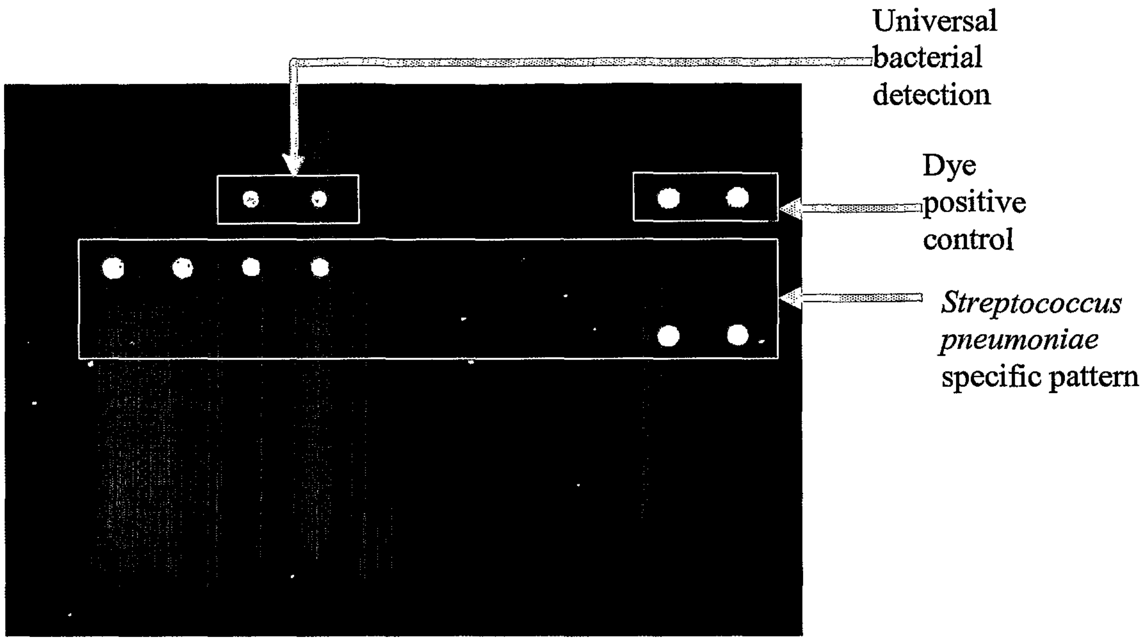
FIG. 2 shows the detection of *Streptococcus pneumoniae*. Tests 1, 2 and 3-positive test results in duplicate indicating the presence of *Streptococcus pneumoniae*, one of the causative agents of bacterial pneumonia.
Test 1—SEQ ID NO.:79
Test 2—SEQ ID NO.:80
Test 3—SEQ ID NO.:81
Figure 3:
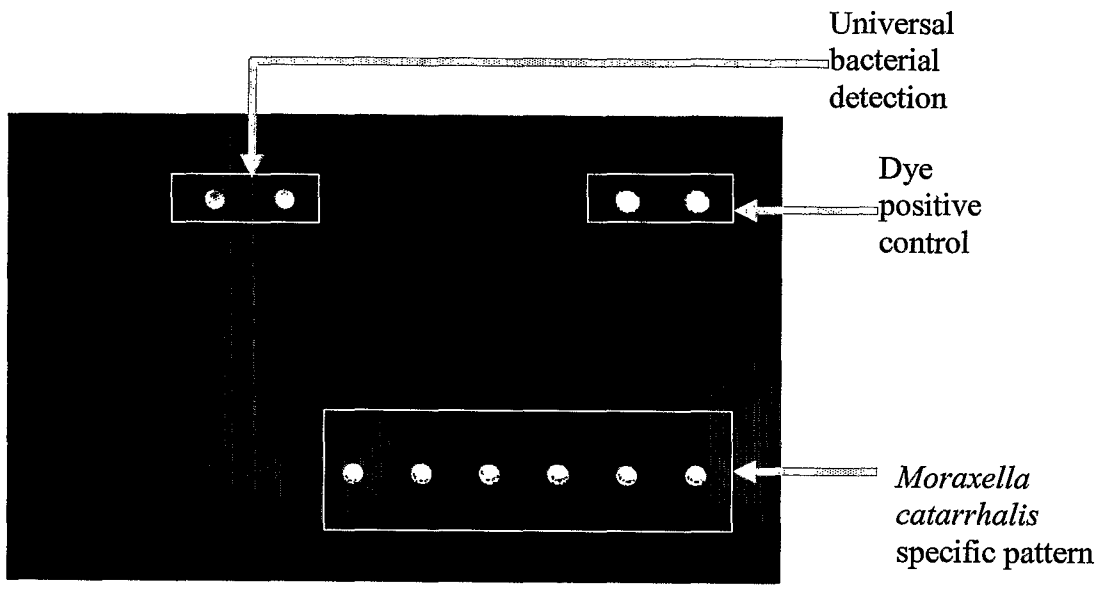
FIG. 3 shows the detection of *Moraxella catarrhalis*. Tests 1, 2 and 3-positive test results in duplicate indicating the presence of *Moraxella catarrhalis*, one of the causative agents of chronic obstructive pulmonary disease.
Test 1—SEQ ID NO.:208
Test 2—SEQ ID NO.:209
Test 3—SEQ ID NO.:210
Figure 4:
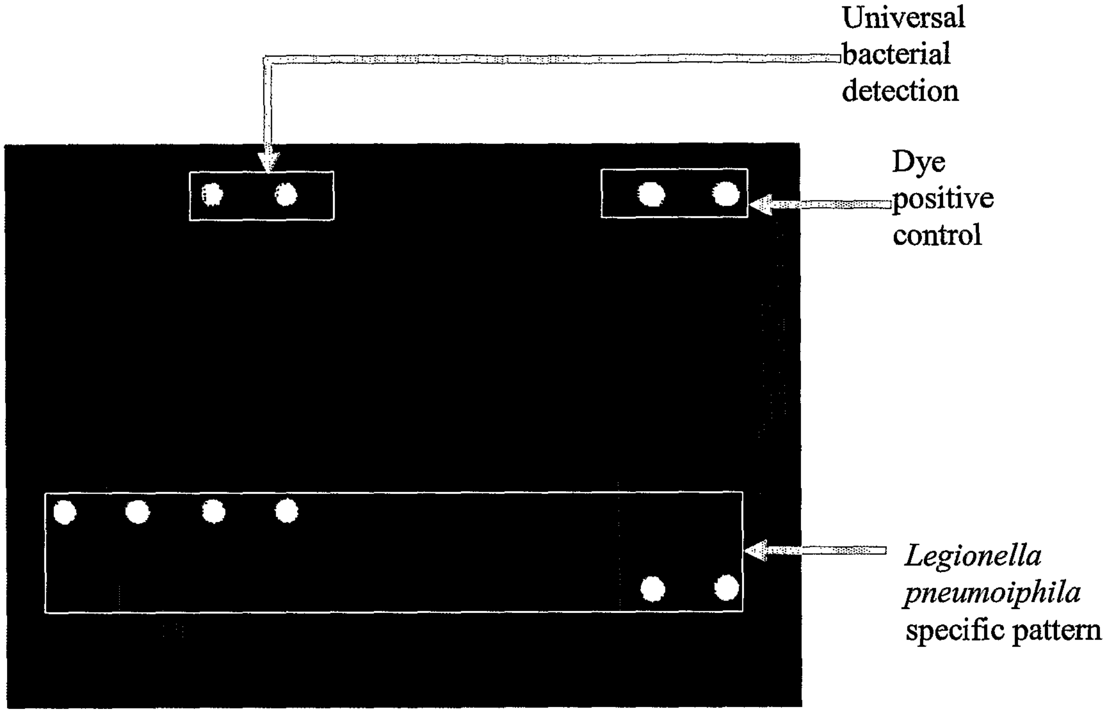
FIG. 4 shows the detection of *Legionella pneumophila*. Tests 1, 2 and 3-positive test results in duplicate indicating the presence of *Legionella pneumophila*, the main causative agent of Legionnaire's disease.
Test 1—SEQ ID NO.:67
Test 2—SEQ ID NO.:68
Test 3—SEQ ID NO.:69
Figure 5:
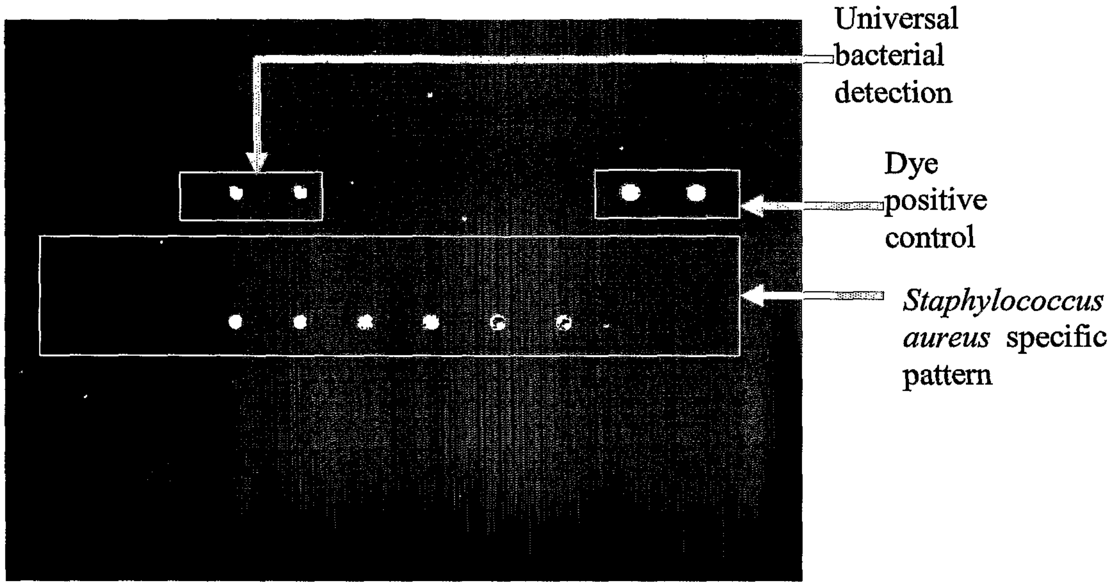
FIG. 5 shows the detection of *Staphylococcus aureus*. Tests 1, 2 and 3-positive test results in duplicate indicating the presence of *Staphylococcus aureus*, one of the causative agents of soft tissue infections and pneumonia in the elderly.
Test 1—SEQ ID NO.:76
Test 2—SEQ ID NO.:77
Test 3—SEQ ID NO.:78
Figure 6:
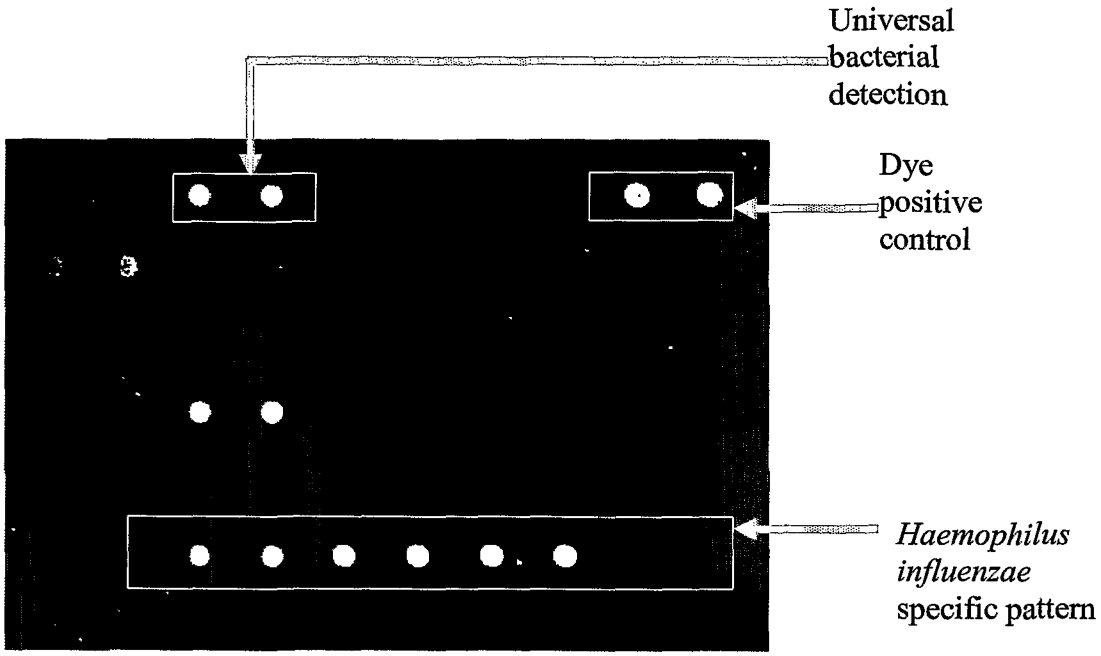
FIG. 6 shows the detection of *Haemophilus influenzae*. Tests 1, 2 and 3, positive test results in duplicate indicating the presence of *Haemophilus influenzae*, one of the causative agents of bacterial pneumonia.
Test 1—SEQ ID NO.:64
Test 2—SEQ ID NO.:65
Test 3—SEQ ID NO.:66

Before describing preferred embodiments in detail, it is to be understood that the terminology used herein is for the purpose of describing particular embodiments of the invention only and is not intended to be limiting.

All publications, patents and patent applications cited herein, whether supra or infra, are hereby incorporated by reference in their entirety. However, publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

The practice of the present invention will employ, unless otherwise indicated, conventional techniques of microbiology and molecular biology which are within the skill of the art. Such techniques are described in the literature. See, for example, Immunochemical Methods in Cell and Molecular Biology (Mayer and Walker, eds., Academic Press, London, 1987); "Molecular Cloning: A Laboratory Manual", $2^{nd}$ Ed., (ed. by Sambrook, Fritsch and Maniatis) (Cold Spring Harbor Laboratory Press: 1989); "Nucleic Acid Hybridization", (Hames & Higgins eds. 1984); "Oligonucleotide Synthesis" (Gait ed., 1984); Remington's Pharmaceutical Sciences, $17^{th}$ Edition, Mack Publishing Company, Easton, Pa., USA.; "The Merck Index", $12^{th}$ Edition (1996), Therapeutic Category and Biological Activity Index; and "Transcription & Translation", (Hames & Higgins eds. 1984).

It must be noted that as used herein and in the appended claims, the singular forms "a," "an," and "the" include plural reference unless the context clearly dictates otherwise. Thus, for example, a reference to "a microorganism" includes a plurality of microorganisms and "a nucleic acid molecule" refers to a plurality of nucleic acid molecules, and so forth.

Unless defined otherwise, all technical and scientific terms used herein have the same meanings as commonly understood by one of ordinary skill in the art to which this invention belongs.

In the description that follows, if there is no instruction, it will be appreciated that cell culture techniques are well-known in this field and any such technique may be adopted.

Although any materials and methods similar or equivalent to those described herein can be used to practice or test the present invention, the preferred materials and methods are now described.

By "comprising" is meant including, but not limited to, whatever follows the word comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

In work leading up to the present invention, the inventors discovered that the tuf gene contained variable region which differed between different microorganisms and therefore could be used to identify different microorganisms. Different microorganisms in a test sample can be identified by detecting hybridization between the variable region and a probe specific for the variable region.

Therefore, the present invention relates to polynucleic acid derived from a tuf gene variable region. As used herein, a "gene" is a polynucleic acid molecule that contains the information for a specific function, such as the sequence encoding a specific protein. Genes may also comprise non-coding information, such as one or more of a signal sequence, an origin of replication, an enhancer element, a promoter, and/or a transcription termination sequence. The term "polynucleic acid" as used herein designates mRNA, RNA, cRNA, cDNA or DNA.

The tuf genes are universally present in all bacteria and generally comprise uniform sequences i.e., sequence in common between all species. Examples of other universal bacterial genes include the 16s ribosomal RNA, 23s ribosomal RNA, and rpoB. Examples of tuf sequences of different microorganisms are set out in SEQ ID Nos.: 1 to 11.

It will be appreciated by those skilled in the art that the sequences disclosed herein may vary from the sequences provided in any of SEQ ID NOs.:1 to 11, without departing from the invention. In particular, the tuf gene sequence might vary by up to 30%, provided that a biological activity of the variant is retained. Specifically, the variant must have a variable region which can be used to identify a target microorganism.

A "tuf gene variable region" is those nucleotide sequences which vary in the tuf gene between species, subspecies, and substrains of a microorganism. In some embodiments, the tuf gene variable region consists essentially of nucleotides 108-220, 393-591, 708-774, 792-816, and/or 885-945 of SEQ ID NOs.:1 to 11.

In some embodiments, the tuf gene variable region is from *Berkholderia cepacia*, which can be used to specifically identify this species in sputum samples of patients with cystic fibrosis. In some embodiments, one or more of SEQ ID Nos.: 269 to 275, which correspond to tuf gene variable region of *Berkholderia cepacia*, can be used.

In other embodiments, the tuf gene variable region is from the tuf gene of *Stenotrophomonas maltophilia*, which can be used to specifically identify this species in sputum samples of patients with pneumonia subsequent to a *Pseudomonas aeruginosa* infection. In some embodiments, one or more of SEQ ID NO.:264 to 268, which correspond to tuf gene variable regions of *Stenotrophomonas maltophilia*, can be used.

As used herein, a polynucleic acid comprises at least some part of a tuf gene including a tuf gene variable region or is derived from a tuf gene. The polynucleic acid sequence may have the nucleotide sequence of an entire tuf gene per se or a part thereof as long as it contains at least one tuf gene variable region or part thereof. The polynucleic acid may also be antisense to the tuf gene. In the present invention, the term "antisense" is used to denote a nucleic acid molecule which is DNA or RNA with a complementary sequence to the tuf gene variable region of the gene.

According to the invention the tuf gene variable region is used to identify a target micro-organism in a test sample. The test sample may be any type of sample suspected of containing a target micro-organism. Consequently, test samples for analysis by the methods of the present invention may be obtained from numerous sources. Such sources include, but are not limited to, samples derived from animal subjects such as humans; flowers; seeds, vegetables; food; and samples derived from the environment. In some embodiments, the test sample is a "biological sample". Reference to a "biological sample" should be understood as a reference to any sample of biological material derived from an animal such as, but not limited to, blood, saliva, urine, tears, sweat, cerebrospinal fluid, lymph fluid, serum, plasma, mucus, sputum, faeces, and biopsy specimens.

The biological sample which is tested according to the methods of the present invention may be tested directly or may require some form of treatment prior to testing. For example, a biopsy sample may require homogenisation prior to testing. Further, to the extent that the biological sample is not in liquid form, (for example it may be a solid, semi-solid or dehydrated liquid sample) it may require the addition of a reagent, such as a buffer to mobilize the sample.

The test sample may also require processing to release any polynucleic acid prior to testing. For example, the polynucleic acid can be released using a lysis buffer, such as a commercially available lysis solution. A suitable commercially available lysis solution for bacteria is the Lyse-N-Go™ (Pierce Biotechnology Inc, Rockford Ill., USA) PCR reagent. Once released the polynucleic acid is available for testing by the methods of the invention.

Alternatively or in addition the test sample may be subjected to a purification step such that the polynucleic acid in the test sample is isolated, concentrated or separated.

An "isolated" polynucleic acid is one which has been released and/or separated and/or recovered from a component of its natural environment. Contaminant components of its natural environment are materials that would typically interfere with identification of a target micro-organism and may include enzymes, hormones, and other proteinaceous or non-proteinaceous solutes. In some embodiments, a polynucleic acid will be purified and/or concentrated (1) to a degree sufficient to obtain at least 30 to 45 bases of nucleotide sequence information, and/or (2) to homogeneity by gel electrophoresis.

In isolating the polynucleic acid the test sample may be subjected to a number of different processing steps, such as tissue homogenation, cell isolation and cytoplasmic extraction, nucleic acid extraction and the like. Methods of isolating nucleic acids from cells, tissues, organs or whole organisms are known to those of ordinary skill in the art and are described, for example, in Maniatis et al. (Molecular Cloning: A Laboratory Manual, Cold Spring Harbour Laboratory Press, 1989) and in Ausubel et al. (Current Protocols in Molecular Biology, John Wiley & Sons, Inc 1998), the content of each are incorporated herein by reference.

In some embodiments of the invention, a cell from a test sample may be used as a source of polynucleic acid for analysis, thereby obviating requirements for purified cultures. The polynucleic acid molecules may be either DNA, RNA or a combination of both. In some embodiments the polynucleic acid is DNA. Preferably, there is at least 100 micrograms of DNA available for analysis; however, considerably smaller amounts of DNA may be used in the methods of the invention. Nucleic acid amplification techniques, such as PCR, may be used to compensate when only low levels of polynucleic acid is available for analysis.

Based on sequence analysis of the target polynucleic acid, a multiplex PCR reaction may be employed with the use of several primers. Multiplex PCR is the term used when more than one pair of primers is used in a polymerase chain reaction. The goal of multiplex PCR is to amplify several segments of target polynucleic acid simultaneously and thereby to conserve template polynucleic acid, time and expense. Detailed protocols for multiplex PCR can be found in Molecular Cloning, A Laboratory Manual Sambrook and Russell Volume 2, third edition, Coldspring Harbour Laboratory Press. Since clinical samples often contain material that will interfere with PCR, a unique pre-processing method can be developed to obtain optimum amplification. The reaction conditions will be optimised for simultaneous amplification of all polynucleic acid regions of interest.

Other polynucleic acid amplification techniques include self-sustained sequence replication, Q beta replicase, ligation-based thermocycling approaches, real-time PCR, real-time strand displacement amplification (SDA), rolling-circle amplification (RCA) and multiple-displacement amplification (MDA).

Detailed protocols for amplification of polynucleic acid can be found in, among other places, Ausubel et al (Short Protocols in Molecular Biology, John Wiley & Sons (1995) volume 2, $5^{th}$ edition Chapter 15) and in Sambrook and Russell (Molecular Cloning, A Laboratory Manual, volume 2, third edition, Coldspring Harbour Laboratory Press). These publications also provide detailed guidance on how to design nucleic acid amplification primers.

In some embodiments of the present invention, the polynucleic acid is isolated and then amplified using PCR. Any amplification primers may be used to amplify tuf genes from target microorganisms as long as the primers specifically amplify the tuf gene variable region or a part thereof. Designing primers that are capable of amplifying a large number of tuf genes from different species of microorganism is well within the skill in the art. For example, tuf gene sequences for bacterial species are freely available from public databases such as GenBank™. There are a number of databases capable of multiple sequence alignments using the tuf gene sequences obtained. Once aligned, persons skilled in the art can determine conserved regions within the various microorganisms by analysing the multiple sequence alignment data. Table 1 shows the multiple sequence alignment of a number of tuf genes from various microorganisms.

In some embodiments, the primers used to amplify tuf genes from a number of microorganisms are selected from the group consisting of SEQ ID NOs:394-396, or equivalents thereof, provided said equivalents specifically amplify the tuf variable region or a part thereof of different species of microorganism at the same time.

The ability to design equivalents of SEQ ID NOs:394-395 is well within the skill in the art. For example, it is well appreciated that the 3' end of any amplification primer is the most important end of any primer as this needs to properly anneal to a DNA template, for example, for primer extension to take place. Accordingly, the 3' ends of SEQ ID NOs:394-395 need to be maintained. However, it is further appreciated that the 5' ends of most primers can be altered, extended and/or shortened without adversely affecting the primers ability to amplify a product. Persons skilled in the art are capable of determining changes that can be made in primers by routine experimentation.

As mentioned above, a polynucleic acid comprising a tuf gene or tuf gene variable region may be used to identify a target micro-organism in a test sample. Reference to "micro-organism" encompasses any organism that can only be observed with the aid of a microscope and includes

TABLE 1

| | | | |
|---|---|---|---|
| MPNE-HF2 | -------------ATGGCAAAACAAAAGTTTGATAGATCAAAAGCTCACGTTAATATTGG | 47 | SEQ ID NO: 397 |
| MPNE-M129 | -------------ATGGCAAGAGAGAAATTTGACCGATCTAAACCCCACGTTAATGTAGG | 47 | SEQ ID NO: 398 |
| LPNE-Paris | GGGAGACTTTCCGATGGCGAAGGAAAAATTTGAACGTAAGAAGCCGCACGTAAACGTGGG | 60 | SEQ ID NO: 399 |
| LPNE2-DAS | ------------------------------------------------------------ | | |
| LPNE-Philadelphia1 | -------------ATGGCGAAGGAAAAATTTGAACGTAAGAAGCCGCACGTAAACGTGGG | 47 | SEQ ID NO: 400 |
| LPNE-Lens | -------------ATGGCGAAGGAAAAATTTGAACGTAAGAAGCCGCACGTAAACGTGGG | 47 | SEQ ID NO: 401 |
| LLON-DAS | ------------------------------------------------------------ | | |
| FNUC-DAS | ------------------------------------------------------------ | | |
| CPNE-CWL029 | -------------ATGTCAAAAGAAACTTTTCAACGTAATAAGCCCCATATCAATATTGG | 47 | SEQ ID NO: 402 |
| EFAE-DAS | ------------------------------------------------------------ | | |
| EFAE-V583 | -------------ATGGCAAAAGAAAAATTTGACCGTTCTAAATCCCATGTTAACATTGG | 47 | SEQ ID NO: 403 |
| SAUR-Mu50 | -------------ATGGCAAAAGAAAAATTCGATCGTTCTAAAGAACATGCCAATATCGG | 47 | SEQ ID NO: 404 |
| SAUR-N315 | -------------ATGGCAAAAGAAAAATTCGATCGTTCTAAAGAACATGCCAATATCGG | 47 | SEQ ID NO: 405 |
| SAUR-MW2 | -------------ATGGCAAAAGAAAAATTCGATCGTTCTAAGAAACATGCCAATATCGG | 47 | SEQ ID NO: 406 |
| SAUR-MSSA476 | -------------ATGGCAAAAGAAAAATTCGATCGTTCTAAAGAACATGCCAATATCGG | 47 | SEQ ID NO: 407 |
| SAUR-MRSA252 | -------------ATGGCAAAAGAAAAATTTGATCGTTCTAAAGAACATGCCAATATCGG | 47 | SEQ ID NO: 408 |
| SEPI-12228 | -------------ATGGCAAAAGAAAAATTTGATCGCTCAAAAGAACATGCCAATATTGG | 47 | SEQ ID NO: 409 |
| SEPI-RP62A | -------------ATGGCAAAAGAAAAATTTGATCGCTCAAAAGAACATGCCAATATTGG | 47 | SEQ ID NO: 410 |
| SMIT-DAS | ------------------------------------------------------------ | | |
| SSAN-DAS | ------------------------------------------------------------ | | |
| SMIT-NCTC12261 | -------------ATGGCAAAAGAAAAATACGATCGTAGTAAACCACACGTTAACATTGG | 47 | SEQ ID NO: 411 |
| SPNE-R6 | -------------ATGGCAAAAGAAAAATACGATCGTAGTAAACCACACGTTAACATTGG | 47 | SEQ ID NO: 412 |
| SPYO-M1GAS | -------------ATGGCAAAAGAAAAATACGATCGTAGTAAACCCCACGTTAACATTGG | 47 | SEQ ID NO: 413 |
| SMUT-DAS | ------------------------------------------------------------ | | |
| SMUT-UA159 | -------------ATGGCAAAAGAAAAATACGATCGTAGTAAACCACACGTTAACATTGG | 47 | SEQ ID NO: 414 |
| HINF-RdKW20 | -------------ATGTCTAAAGAAAAATTTGAACGTACAAAACCGCACGTAAACGTGGG | 47 | SEQ ID NO: 415 |
| MCAT-DAS | ------------------------------------------------------------ | | |
| BPER-TohamaI | -------------ATGGCAAAAGGCAAGTTTGAACGTACCAACCCGCACGTGAACGTGGG | 47 | SEQ ID NO: 416 |
| BPAR-12822 | -------------ATGGCAAAAGGCAAGTTTGAACGTACCAAGCCGCACGTGAACGTGGG | 47 | SEQ ID NO: 417 |
| BCEP2-DAS | ------------------------------------------------------------ | | |
| EPSE-1710b | -------------ATGGCAAAAGAGAAGTTTGAGCGGACCAAGCCGCACGTGAACGTTGG | 47 | SEQ ID NO: 418 |
| SMAL-DAS | ------------------------------------------------------------ | | |
| PAER-PA01 | -------------GTGGCTAAGGAAAAATTCGAACGTAACAAACCGCACGTCAACGTCGG | 47 | SEQ ID NO: 419 |

TABLE 1-continued

| | | | |
|---|---|---|---|
| KPNE-DAS | ------------------------------------------------------------ | | |
| MAVI-K10 | -------------GTGGCGAAGGCGAAGTTCGAGCGGACGAAGCCGCACGTCAACATCGG | 47 | SEQ ID NO: 420 |
| MAVI-paratub | -------------GTGGCGAAGGCGAAGTTCGAGCGGACGAAGCCGCACGTCAACATCGG | 47 | SEQ ID NO: 421 |
| MAISpig-DAS | ------------------------------------------------------------ | | |
| MKAN-DAS | ------------------------------------------------------------ | | |
| MTUB-H37Rv | -------------GTGGCGAAGGCGAAGTTCCAGCGGACCAAGCCCCACGTCAACATCGG | 47 | SEQ ID NO: 422 |
| MTUE-CDC1551 | -------------GTGGCGAAGGCGAAGTTCCAGCGGACCAAGCCCCACGTCAACATCGG | 47 | SEQ ID NO: 423 |
| MAVI-DAS | ------------------------------------------------------------ | | |
| CIDP-NCTC13129 | -------------GTGGCAAAGGCTAAGTTCGAGCGTACCAAGCCGCACGTCAACATCGG | 47 | SEQ ID NO: 424 |
| NMEN-MC58 | -------------ATGGCTAAGGAAAAATTCGAACGTAGCAAACCGCACGTAAACGTTGG | 47 | SEQ ID NO: 425 |
| NMEN-Z2491 | -------------ATGGCTAAGGAAAAATTCGAACGTAGCAAACCGCACGTAAACGTTGG | 47 | SEQ ID NO: 426 |
| NMEN-DAS | ------------------------------------------------------------ | | |
| | | | |
| MPNE-HF2 | GACAATTGGACATATTGACCATGGTAAAACAACTTTAACAGCTGCAATCTGTACTTACCT | 107 | SEQ ID NO: 427 |
| MPNE-M129 | TACTATTGGCCACATTGACCACGGTAAAACAACTTTAACAGCAGCTATTTGTACTGTATT | 107 | SEQ ID NO: 428 |
| LPNE-Paris | CACGATTGGTCACGTAGACCATGGCAAGACGACATTGACAGCAGCTATTACAACGATTAT | 120 | SEQ ID NO: 429 |
| LPNE2-DAS | ------------------------------------------------------------ | | |
| LPNE-Philadeiphia1 | CACGATTGGTCACGTAGACCATGGTAAGACGACATTGACAGCAGCTATTACAACGATTAT | 107 | SEQ ID NO: 430 |
| LPNE-Lens | CACGATTGGTCACGTAGACCATGGTAAGACGACATTGACAGCAGCTATTACAACGATTAT | 107 | SEQ ID NO: 431 |
| LLON-DAS | ------------------------------------------------------------ | | |
| FNUC-DAS | ------------------------------------------------------------ | | |
| CPNE-CWL029 | GACGATCGGGCACGTTGACCATGGTAAAACTACGCTAACAGCGGCAATTACACGCGCGCT | 107 | SEQ ID NO: 432 |
| EFAE-DAS | ------------------------------------------------------------ | | |
| EFAE-V583 | TACTATCGGACACGTTGACCATGGTAAAACTACATTAACAGCTGCAATTGCTACTGTATT | 107 | SEQ ID NO: 433 |
| SAUR-Mu50 | TACTATCGGTCACGTTGACCATGGTAAAACAACATTAACAGCAGCAATCGCTACTGTATT | 107 | SEQ ID NO: 434 |
| SAUR-N315 | TACTATCGGTCACGTTGACCATGGTAAAACAACATTAACAGCAGCAATCGCTACTGTATT | 107 | SEQ ID NO: 435 |
| SAUR-MW2 | TACTATCGGTCACGTTGACCATGGTAAAACAACATTAACAGCAGCAATCGCTACTGTATT | 107 | SEQ ID NO: 436 |
| SAUR-MSSA476 | TACTATCGGTCACGTTGACCATGGTAAAACAACATTAACAGCAGCAATCGCTACTGTATT | 107 | SEQ ID NO: 437 |
| SAUR-MRSA252 | TACTATCGGTCACGTTGACCATGGTAAAACAACATTAACAGCAGCAATCGCTACTGTATT | 107 | SEQ ID NO: 438 |
| SEPI-12228 | TACTATCGGTCACGTTGACCATGGTAAAACAACTTTAACAGCTGCTATCGCAACTGTATT | 107 | SEQ ID NO: 439 |
| SEPI-RP62A | TACTATCGGTCACGTTGACCATGGTAAAACAACTTTAACAGCTGCTATCGCAACTGTATT | 107 | SEQ ID NO: 440 |
| SMIT-DAS | ------------------------------------------------------------ | | |
| SSAN-DAS | -----------------------------------------------------CTGTATT | 7 | SEQ ID NO: 441 |
| SMIT-NCTC12261 | TACTATCGGACACGTTGACCACGGTAAAACTACTTTGACAGCAGCTATCACAACTGTTTT | 107 | SEQ ID NO: 442 |
| SPNE-R6 | TACTATCGGACACGTTGACCACGGTAAAACTACCCTAACTGCAGCTATCACAACTGTTTT | 107 | SEQ ID NO: 443 |
| SPYO-M1GAS | TACAATCGGACACGTTGACCATGGTAAAACTACTTTAACAGCTGCAATCACAACTGTATT | 107 | SEQ ID NO: 444 |
| SMUT-DAS | -----------------------------------------------------CTGTACT | 7 | SEQ ID NO: 445 |
| SMUT-UA159 | TACTATCGGACACGTTGACCATGGTAAAACTACCTTAACTGCAGCTATCACAACTGTACT | 107 | SEQ ID NO: 446 |
| HINF-RdKW20 | TACAATCGGCCACGTTGACCACGGTAAAACAACTTTAACAGCAGCAATCACAACCGTATT | 107 | SEQ ID NO: 447 |
| MCAT-DAS | ------------------------------------------------------------ | | |
| BPER-TohamaI | TACGATTGGTCACGTTGACCACGGCAAAACGACGTTGACGGCGGCGATCACGACGGTGCT | 107 | SEQ ID NO: 448 |
| BPAR-12822 | TACGATTGGTCACGTTGACCACGGCAAAACGACGTTGACGGCGGCGATCACGACGGTGCT | 107 | SEQ ID NO: 449 |
| BCEP2-DAS | ------------------------------------------------------------ | | |
| BPSE-1710b | TACGATTGGTCACGTTGACCACGGCAAGACGACGCTGACGGCAGCGATCGCGACGGTGCT | 107 | SEQ ID NO: 450 |
| SMAL-DAS | -----------------------------------------------TGACAAGATCGGT | 13 | SEQ ID NO: 451 |
| PAER-PA01 | CACCATCGGTCACGTTGACCATGGCAAGACCACTCTGACCGCTGCACTGACCAAGGTCTG | 107 | SEQ ID NO: 452 |
| KPNE-DAS | ------------------------------------------------------------ | | |
| MAVI-K10 | GACCATCGGTCACGTTGACCACGGCAAGACCACGCTGACCGCGGCTATCACCAAGGTTCT | 107 | SEQ ID NO: 453 |
| MAVI-paratub | GACCATCGGTCACGTTGACCACGGCAAGACCACGCTGACCGCGGCTATCACCAAGGTTCT | 107 | SEQ ID NO: 454 |
| MAISpig-DAS | ----------------------------------------------------------CT | 2 | SEQ ID NO: 455 |
| MKAN-DAS | ----------------------------------------------------AAGGTCCT | 8 | SEQ ID NO: 456 |
| MTUB-H37Rv | GACCATCGGTCACGTTGACCACGGCAAGACCACCCTGACCGCGGCTATCACCAAGGTCCT | 107 | SEQ ID NO: 457 |
| MTUB-CDC1551 | GACCATCGGTCACGTTGACCACGGCAAGACCACCCTGACCGCGGCTATCACCAAGGTCCT | 107 | SEQ ID NO: 458 |
| MAVI-DAS | ------------------------------------------------------------ | | |
| NCTC13129 | CACCATCGGTCACGTTGACCACGGTAAGACCACCACCACCGCTGCTATCACCAAGGTTTT | 107 | SEQ ID NO: 459 |
| NMEN-MC58 | CACCATCGGTCACGTTGACCATGGTAAAACCACCCTGACTGCCGCTTTGACTACTATTTT | 107 | SEQ ID NO: 460 |
| NMEN-Z2491 | CACCATCGGTCACGTTGACCATGGTAAAACCACCCTGACTGCCGCTTTGACTACTATTTT | 107 | SEQ ID NO: 461 |
| NMEN-DAS | ------------------------------------------------------------ | | |
| | | | |
| MPNE-HF2 | TGCAAAAAAAGGTGGTGCTAAAG---------CAATGAAATATGATGAAATTGATAAAGC | 158 | SEQ ID NO: 462 |
| MPNE-M129 | AGCAAAAGAAGGTAAATCAGCTG---------CTACTCGTTACGACCAAATCGATAAGGC | 158 | SEQ ID NO: 463 |
| LPNE-Paris | GGCGAAGAAATATGGTGGTACAG---------CGAAGGCGTACGATCAAATTGATGCTGC | 171 | SEQ ID NO: 464 |
| LPNE2-DAS | ----------TATGGTGGTACAG---------CGAAGGCGTACGATCAAATTGATGCTGC | 41 | SEQ ID NO: 465 |
| LPNE-Philadelphia1 | GGCGAAGAAATATGGTGGTACAG---------CGAAGGCGTACGATCAAATTGATGCTGC | 158 | SEQ ID NO: 466 |
| LPNE-Lens | GGCGAAGAAATATGGTGGTACAG---------CGAAGGCGTACGATCAAATTGATGCTGC | 158 | SEQ ID NO: 467 |
| LLON-DAS | ---------GTTTGGTGGTATAG---------CAAAAGCATACGATCAGATCGATGCTGC | 42 | SEQ ID NO: 468 |
| FNUC-DAS | ---------------AGCTAAAA---------AAGTAGATTTTGACCAAATTGATGCTGC | 36 | SEQ ID NO: 469 |
| CPNE-CWL029 | ATCAGGGGATGGATTGGCCTCTT---------TCCGTGACTATAGTTCAATTGACAATAC | 158 | SEQ ID NO: 470 |
| EFAE-DAS | ----------------GGGAAAG---------CACAAAGCTACGATTCTATCGATAACGC | 35 | SEQ ID NO: 471 |
| EFAE-V583 | ATCAAAACACGGTGGCGGGGAAG---------CACAAAGCTACGATTCTATCGATAACGC | 158 | SEQ ID NO: 472 |
| SAUR-Mu50 | AGCAAAAAATGGTGACTCAGTTG---------CACAATCATATGACATGATTGACAACGC | 158 | SEQ ID NO: 473 |
| SAUR-N315 | AGCAAAAAATGGTGACTCAGTTG---------CACAATCATATGACATGATTGACAACGC | 158 | SEQ ID NO: 474 |
| SAUR-MW2 | AGCAAAAAATGGTGACTCAGTTG---------CACAATCATATGACATGATTGACAACGC | 158 | SEQ ID NO: 475 |
| SAUR-MSSA476 | AGCAAAAAATGGTGACTCAGTTG---------CACAATCATATGACATGATTGACAACGC | 158 | SEQ ID NO: 476 |
| SAUR-MRSA252 | AGCAAAAAATGGTGACTCAGTTG---------CACAATCATACGACATGATTGACAACGC | 158 | SEQ ID NO: 477 |
| SEPI-12228 | AGCTAAAAATGGTGACACTGTTG---------CACAATCATACGATATGATTGACAACGC | 158 | SEQ ID NO: 478 |
| SEPI-RP62A | AGCTAAAAATGGTGACACTGTTG---------CACAATCATACGATATGATTGACAACGC | 158 | SEQ ID NO: 479 |
| SMIT-DAS | ----------------------------------AAAGACTATGCGTCTATCGATGCTGC | 26 | SEQ ID NO: 480 |
| SSAN-DAS | GGCACGTCGCTTGCCTTCAGCAGTTAACCAACCTAAAGACTATGCGTCTATCGATGCTGC | 67 | SEQ ID NO: 481 |
| SMIT-NCTC12261 | GGCACGTCGCTTGCCTTCAGCTGTTAACCAACCTAAAGACTATGCGTCTATCGATGCTGC | 167 | SEQ ID NO: 482 |

TABLE 1-continued

| | | | |
|---|---|---|---|
| SPNE-R6 | GGCACGTCGCTTGCCTTCATCAGTTAACCAACCTAAAGACTATGCGTCTATCGATGCTGC | 167 | SEQ ID NO: 483 |
| SPYO-M1GAS | GGCACGTCGCTTGCCTTCATCAGTTAACCAACCAAAAGATTACGCTTCTATCGATGCTGC | 167 | SEQ ID NO: 484 |
| SMUT-DAS | GGCACGTCGTCTTCCAAGTGCAGTAAACCAACCAAAAGATTATTCATCTATTGATGCTGC | 67 | SEQ ID NO: 485 |
| SMUT-UA159 | GGCACGTCGTCTTCCAAGTGCAGTAAACCAACCAAAAGATTATTCATCTATTGATGCTGC | 167 | SEQ ID NO: 486 |
| HINF-RdKW20 | AGCAAAACACTACGGTGGTGCAG---------CGCGTGCATTTGACCAAATTGATAACGC | 158 | SEQ ID NO: 487 |
| MCAT-DAS | ---------------------------------------------------CGACTCTGC | 9 | SEQ ID NO: 488 |
| BPER-TohamaI | GTCGAACAAGTTCGGCGG---------CGAGGCTCGCGGCTACGACCAGATTGACGCGGC | 158 | SEQ ID NO: 489 |
| BPAR-12822 | GTCGAACAAGTTCGGCGG---------CGAGGCTCGCGGCTACGACCAGATTGACGCGGC | 158 | SEQ ID NO: 490 |
| BCEP2-DAS | ---------GTTCGGCGG---------CGAAGCGAAGAAGTACGACGAAATCGACGCGGC | 42 | SEQ ID NO: 491 |
| BPSE-1710b | GTCGGCGAAGTTCGGCGG---------CGAAGCGAAGAAGTACGACGAAATCGACGCGGC | 158 | SEQ ID NO: 492 |
| SMAL-DAS | GCCGAGCGC-TTCGGTGG---------CGAGTTCAAGGACTACTCCTCGATCGACGCCGC | 63 | SEQ ID NO: 493 |
| PAER-PA01 | CTCCGATACCTGGGGTGG---------TTCCGCTCGTGCTTTCGATCAGATCGACAACGC | 158 | SEQ ID NO: 494 |
| KPNE-DAS | ---------CTACGGTGG---------TTCCGCTCGCGCATTCGACCAGATCGATAACGC | 42 | SEQ ID NO: 495 |
| MAVI-K10 | GCACGACAAGTACCCGGACCTGA---ACGAGTCCCGCGCGTTCGACCAGATCGACAACGC | 164 | SEQ ID NO: 496 |
| MAVI-paratub | GCACGACAAGTACCCGGACCTGA---ACGAGTCCCGCGCGTTCGACCAGATCGACAACGC | 164 | SEQ ID NO: 497 |
| MAISpig-DAS | GCACGACAAGTACCCGGACCTGA---ACGAGTCCCGCGCGTTCGACCAGATCGACAACGC | 59 | SEQ ID NO: 498 |
| MKAN-DAS | GCATGACAAGTTCCCGGACCTGA---ACGAGTCGAAGGCGTTCGACCAGATCGACAACGC | 65 | SEQ ID NO: 499 |
| MTUB-H37Rv | GCACGACAAATTCCCCGATCTGA---ACGAGACGAAGGCATTCGACCAGATCGACAACGC | 164 | SEQ ID NO: 500 |
| MTUB-CDC1551 | GCACGACAAATTCCCCGATCTGA---ACGAGACGAAGGCATTCGACCAGATCGACAACGC | 164 | SEQ ID NO: 501 |
| MAVI-DAS | -------------------------------------------------------AACGC | 5 | SEQ ID NO: 502 |
| NCTC13129 | GGCAGACGCTTACCCAGAGCTGA---ACGAAGCTTTCGCTTTCGATGCCATCGATAAGGC | 164 | SEQ ID NO: 503 |
| NMEN-MC58 | GGCTAAAAAATTCGGCGG---------TGCTGCAAAAGCTTACGACCAAATCGACAACGC | 158 | SEQ ID NO: 504 |
| NMEN-Z2491 | GGCTAAAAAATTCGGCGG---------TGCTGCAAAAGCTTACGACCAAATCGACAACGC | 158 | SEQ ID NO: 505 |
| NMEN-DAS | ------------------------------------------------------------ | | |
| | | | |
| MPNE-HF2 | ACCTGAAGAAAAAGCTAGAGGTATTACTATTAATACTGCTCACGTTGAATATGAAACAGA | 218 | SEQ ID NO: 506 |
| MPNE-M129 | TCCGGAAGAAAAAGCACGGGGAATTACGATTAACTCCGCTCACGTGGAGTACTCCTCTGA | 218 | SEQ ID NO: 507 |
| LPNE-Paris | GCCAGAAGAAAGAGAGCGTGGTATTACTATTTCTACAGCACACGTTGAGTACGAATCAGC | 231 | SEQ ID NO: 508 |
| LPNE2-DAS | GCCAGAAGAAAGAGAGCGTGGGATTACTATTTCTACAGCACATGTTGAATACGAATCAGC | 101 | SEQ ID NO: 509 |
| LPNE-Philadelphia1 | GCCAGAAGAAAGAGAGCGTGGGATTACTATTTCTACAGCACATGTTGAATACGAATCAGC | 218 | SEQ ID NO: 510 |
| LPNE-Lens | GCCAGAAGAAAGAGAGCGTGGTATTACTATATCTACAGCCCATGTTGAATACGAATCAGC | 218 | SEQ ID NO: 511 |
| LLON-DAS | ACCAGAAGAAAGAGAGCGAGGCATCACAATCTCAACAGCGCACGTTGAATACGAATCAGC | 102 | SEQ ID NO: 512 |
| FNUC-DAS | TCCAGAAGAAAAAGAAAGAGGAATTACTATTAATACAGCTCATATTGAATATGAAACAGC | 96 | SEQ ID NO: 513 |
| CPNE-CWL029 | TCCAGAAGAAAAGGCTCGTGGAATTACTATCAACGCTTCTCACGTTGAATACGAAACCCC | 218 | SEQ ID NO: 514 |
| EFAE-DAS | TCCAGAAGAAAAAGAACGTGGAATCACAATCAACACTTCTCATATCGAATATGAAACTGA | 95 | SEQ ID NO: 515 |
| EFAE-V583 | TCCAGAAGAAAAAGAACGTGGAATCACAATCAACACTTCTCATATCGAATATGAAACTGA | 218 | SEQ ID NO: 516 |
| SAUR-Mu50 | TCCAGAAGAAAAAGAACGTGGTATCACAATCAATACTTCTCACATTGAGTACCAAACTGA | 218 | SEQ ID NO: 517 |
| SAUR-N315 | TCCAGAAGAAAAAGAACGTGGTATCACAATCAATACTTCTCACATTGAGTACCAAACTGA | 218 | SEQ ID NO: 518 |
| SAUR-MW2 | TCCAGAAGAAAAAGAACGTGGTATCACAATCAATACTTCTCACATTGAGTACCAAACTGA | 218 | SEQ ID NO: 519 |
| SAUR-MSSA476 | TCCAGAAGAAAAAGAACGTGGTATCACAATCAATACTTCTCACATTGAGTACCAAACTGA | 218 | SEQ ID NO: 520 |
| SAUR-MRSA252 | TCCAGAAGAAAAAGAACGTGGTATCACAATCAATACTTCACACATTGAGTACCAAACTGA | 218 | SEQ ID NO: 521 |
| SEPI-12228 | TCCAGAAGAAAAAGAACGTGGTATTACAATCAATACTGCACATATCGAATACCAAACTGA | 218 | SEQ ID NO: 522 |
| SEPI-RP62A | TCCAGAAGAAAAAGAACGTGGTATTACAATCAATACTGCACATATCGAATACCAAACTGA | 218 | SEQ ID NO: 523 |
| SMIT-DAS | TCCAGAAGAACGCGAACGCGGTATCACTATCAACACTGCGCACGTTGAGTACGAAACTGA | 86 | SEQ ID NO: 524 |
| SSAN-DAS | TCCAGAAGAACGCGAACGCGGAATCACTATCAACACTGCGCACGTTGAGTATGAAACTGC | 127 | SEQ ID NO: 525 |
| SMIT-NCTC12261 | TCCAGAAGAACGCGAACGTGGTATCACAATCAACACTGCGCACGTTGAGTACGAAACTGA | 227 | SEQ ID NO: 526 |
| SPNE-R6 | TCCAGAAGAACGCGAACGCGGTATCACTATCAACACTGCGCACGTTGAGTACGAAACTGA | 227 | SEQ ID NO: 527 |
| SPYO-M1GAS | TCCAGAAGAACGCGAACGCGGAATCACTATCAACACTGCACACGTTGAGTACGAAACTGC | 227 | SEQ ID NO: 528 |
| SMUT-DAS | TCCTGAAGAACGCGAACGCGGTATCACTATCAATACTGCGCACGTTGAGTATGAAACTGA | 127 | SEQ ID NO: 529 |
| SMUT-UA159 | TCCTGAAGAACGCGAACGCGGTATCACTATCAATACTGCGCACGTTGAGTATGAAACTGA | 227 | SEQ ID NO: 530 |
| HINF-RdKW20 | GCCAGAAGAAAAAGCGCGTGGTATTACCATCAACACTTCACACGTTGAATACGATACACC | 218 | SEQ ID NO: 531 |
| MCAT-DAS | ACCTGAAGAAAAAGCACGTGGTATTACTATTAACACATCTCACATCGAGTATGACACAGA | 69 | SEQ ID NO: 532 |
| BPER-TobamaI | GCCGGAAGAGAAGGCGCGTGGGATCACGATCAACACCTCGCACGTTGAGTACGAGACGGA | 218 | SEQ ID NO: 533 |
| BPAR-12822 | GCCGGAAGAGAAGGCGCGTGGGATCACGATCAACACCTCGCACGTTGAGTACGAGACGGA | 218 | SEQ ID NO: 534 |
| BCEP2-DAS | GCCGGAAGAAAAGGCACGCGGCATCACGATCAACACCGCGCACATCGAGTACGAAACGGC | 102 | SEQ ID NO: 535 |
| BPSE-1710b | GCCGGAAGAAAAGGCGCGCGGCATCACGATCAACACCGCGCACATCGAGTACGAAACGGC | 218 | SEQ ID NO: 536 |
| SMAL-DAS | GCCGGAAGAAAAGGCTCGTGGTATCACGATCTCGACCGCGCACGTCGAATACGAATCCCC | 123 | SEQ ID NO: 537 |
| PAER-PA01 | GCCGGAAGAAAAGGCCCGCGGTATCACCATCAACACCTCGCACGTTGAATACGATTCCGC | 218 | SEQ ID NO: 538 |
| KPNE-DAS | GCCGGAAGAAAAAGCTCGTGGTATCACCATCAACACCTCTCACGTTGAATATGACACCCC | 102 | SEQ ID NO: 539 |
| MAVI-K10 | GCCCGAGGAGCGTCAGCGCGGTATCACCATCAACATCTCCCACGTGGAGTACCAGACCGA | 224 | SEQ ID NO: 540 |
| MAVI-paratub | GCCCGAGGAGCGTCAGCGCGGTATCACCATCAACATCTCCCACGTGGAGTACCAGACCGA | 224 | SEQ ID NO: 541 |
| MAISpig-DAS | TCCCGAGGAGCGTCAGCGCGGTATCACGATCAACATCTCCCACGTGGAGTACCAGACCGA | 119 | SEQ ID NO: 542 |
| MKAN-DAS | TCCTGAGGAGCGCCAGCGCGGTATCACGATCAACATCGCGCACGTGGAGTACCAGACCGA | 125 | SEQ ID NO: 543 |
| MTUB-H37Rv | CCCCGAGGAGCGTCAGCGCGGTATCACCATCAACATCGCGCACGTGGAGTACCAGACCGA | 224 | SEQ ID NO: 544 |
| MTUB-CDC1551 | CCCCGAGGAGCGTCAGCGCGGTATCACCATCAACATCGCGCACGTGGAGTACCAGACCGA | 224 | SEQ ID NO: 545 |
| MAVI-DAS | GCCTGAAGAGCGTCAGCGCGGTATCACCATCAACATCTCGCATGTTGAGTACCAGACCGA | 65 | SEQ ID NO: 546 |
| CIDP-NCTC13129 | ACCGGAAGAGAAAGAGCGTGGTATTACCATCAACATCTCCCACGTGGAGTACCAGACCGA | 224 | SEQ ID NO: 547 |
| NMEN-MC58 | ACCCGAAGAAAAAGCACGCGGTATTACCATTAACACCTCGCACGTGGAATACGAAACCGA | 218 | SEQ ID NO: 548 |
| NMEN-Z2491 | ACCCGAAGAAAAAGCACGCGGTATTACCATTAACACCTCGCACGTGGAATACGAAACCGA | 218 | SEQ ID NO: 549 |
| NEEN-DAS | -CCCGAAGAAAAAGCACGCGGTATTACCATTAACACCTCGCACGTGGAATACGAAACCGA | 59 | SEQ ID NO: 550 |
| | | | |
| MPNE-MF2 | AAACAGACACTATGCTCACGTAGACTGTCCAGGTCACGCTGACTACGTTAAGAACATGAT | 278 | SEQ ID NO: 551 |
| MPNE-M129 | CAAGCGTCACTATGCTCACGTTGACTGTCCAGGACACGCTGACTACATTAAGAACATGAT | 278 | SEQ ID NO: 552 |
| LPNE-Paris | GAGCAGACATTATGCGCACGTAGACTGCCCGGGGCATGCTGACTATGTTAAGAACATGAT | 291 | SEQ ID NO: 553 |
| LPNE2-DAS | GAGCAGACATTATGCGCACGTAGACTGCCCGGGGCATGCTGACTATGTTAAGAACATGAT | 161 | SEQ ID NO: 554 |
| LPNE-Philadelphia1 | GAGCAGACATTATGCACACGTAGACTGCCCGGGACATGCTGACTATGTTAAGAACATGAT | 278 | SEQ ID NO: 555 |
| LPNE-Lens | GAGCAGACATTATGCACACGTAGACTGCCCGGGACATGCTGACTATGTTAAGAACATGAT | 278 | SEQ ID NO: 556 |
| LLON-DAS | GAACAGACACTATGCGCATGTTGATTGCCCAGGACATGCTGACTATGTGAAGAACATGAT | 162 | SEQ ID NO: 557 |
| FNUC-DAS | AAATAGACACTATGCTCACGTTGACTGTCCAGGGCATGCTGACTATGTTAAAAATATGAT | 156 | SEQ ID NO: 558 |
| CPNE-CWL029 | AAATCGTCACTACGCTCACGTAGACTGCCCTGGTCACGCTGACTATGTTAAAAATATGAT | 278 | SEQ ID NO: 559 |

TABLE 1-continued

| | | | |
|---|---|---|---|
| EFAE-DAS | AACTCGTCACTATGCACACGTTGACTGCCCAGGACACGCGGACTACGTTAAAAACATGAT | 155 | SEQ ID NO: 560 |
| EFAE-V583 | AACTCGTCACTATGCACACGTTGACTGCCCAGGACATGCGGACTACGTTAAAAACATGAT | 278 | SEQ ID NO: 561 |
| SAUR-Mu50 | CAAACGTCACTACGCTCACGTTGACTGCCCAGGACACGCTGACTACGTTAAAAACATGAT | 278 | SEQ ID NO: 562 |
| SAUR-N315 | CAAACGTCACTACGCTCACGTTGACTGCCCAGGACACGCTGACTACGTTAAAAACATGAT | 278 | SEQ ID NO: 563 |
| SAUR-MW2 | CAAACGTCACTACGCTCACGTTGACTGCCCAGGACACGCTGACTACGTTAAAAACATGAT | 278 | SEQ ID NO: 564 |
| SAUR-MSSA476 | CAAACGTCACTACGCTCACGTTGACTGCCCAGGACACGCTGACTACGTTAAAAACATGAT | 278 | SEQ ID NO: 565 |
| SAUR-MRSA252 | CAAACGTCACTACGCTCACGTTGACTGCCCAGGACACGCTGACTATGTTAAAAACATGAT | 278 | SEQ ID NO: 566 |
| SEPI-12228 | CAAACGTCACTATGCTCACGTTGACTGCCCAGGACACGCTGACTATGTTAAAAACATGAT | 278 | SEQ ID NO: 567 |
| SEPI-RP62A | CAAACGTCACTATGCTCACGTTGACTGCCCAGGACACGCTGACTATGTTAAAAACATGAT | 278 | SEQ ID NO: 568 |
| SMIT-DAS | AAAACGTCACTACGCTCACATCGACGCTCCAGGACACGCGGACTACGTTAAAAACATGAT | 146 | SEQ ID NO: 569 |
| SSAN-DAS | TAAGCGTCACTACGCTCACATCGACGCTCCAGGACACGCGGACTACGTTAAAAACATGAT | 187 | SEQ ID NO: 570 |
| SMIT-NCTC12261 | AAAACGTCACTACGCTCACATCGACGCTCCAGGACACGCGGACTATGTTAAAAACATGAT | 287 | SEQ ID NO: 571 |
| SPNE-R6 | AAAACGTCACTACGCTCACATCGACGCTCCAGGACACGCGGACTATGTTAAAAACATGAT | 287 | SEQ ID NO: 572 |
| SPYO-M1GAS | AACTCGTCACTATGCGCACATCGACGCTCCAGGACACGCGGACTACGTTAAAAACATGAT | 287 | SEQ ID NO: 573 |
| SMUT-DAS | AAAACGTCACTATGCTCACATTGACGCTCCAGGACACGCGGACTATGTTAAAAACATGAT | 187 | SEQ ID NO: 574 |
| SMUT-UA159 | AAAACGTCACTATGCTCACATTGATGCTCCAGGACACGCGGACTATGTTAAAAACATGAT | 287 | SEQ ID NO: 575 |
| HINF-RdKW20 | GACTCGCCACTACGCACACGTAGACTGTCCGGGACACGCCGACTATGTTAAAAATATGAT | 278 | SEQ ID NO: 576 |
| MCAT-DAS | AGCTCGTCACTACGCACATGTAGACTGCCCAGGCCACGCTGACTATGTTAAAAACATGAT | 129 | SEQ ID NO: 577 |
| BPER-TobamaI | GACGCGTCACTACGCGCACGTTGATTGCCCGGGTCACGCTGACTACGTGAAGAACATGAT | 278 | SEQ ID NO: 578 |
| BPAR-12822 | GACGCGTCACTACGCGCACGTTGATTGCCCGGGTCACGCTGACTACGTGAAGAACATGAT | 278 | SEQ ID NO: 579 |
| BCEP2-DAS | GAACCGCCACTACGCGCACGTCGACTGCCCGGGCCACGCCGACTACGTGAAGAACATGAT | 162 | SEQ ID NO: 580 |
| BPSE-1710b | GAACCGCCACTACGCACACGTGGACTGCCCGGGCCACGCCGACTACGTGAAGAACATGAT | 278 | SEQ ID NO: 581 |
| SMAL-DAS | GATCCGTCACTACGCCCACGTTGACTGCCCGGGCCACGCTGACTACGTCAAGAACATGAT | 183 | SEQ ID NO: 582 |
| PAER-PA01 | TGTTCGTCACTACGCCCACGTTGACTGCCCCGGTCACGCCGACTACGTGAAGAACATGAT | 278 | SEQ ID NO: 583 |
| KPNE-DAS | GACTCGCCACTACGCGCACGTAGACTGCCCGGGCCACGCCGACTATGTTAAAAACATGAT | 162 | SEQ ID NO: 584 |
| MAVI-K10 | CAAGCGGCACTACGCTCACGTCGACGCCCCGGGTCACGCCGACTACATCAAGAACATGAT | 284 | SEQ ID NO: 585 |
| MAVI-paratub | CAAGCGGCACTACGCTCACGTCGACGCCCCGGGTCACGCCGACTACATCAAGAACATGAT | 284 | SEQ ID NO: 586 |
| MAISpig-DAS | CAAGCGGCACTATGCCCACGTCGACGCCCCGGGTCACGCCGACTACATCAAGAACATGAT | 179 | SEQ ID NO: 587 |
| MKAN-DAS | GAAGCGGCACTATGCACACGTCGACGCGCCGGGCCACGCCGACTACATCAAGAACATGAT | 185 | SEQ ID NO: 588 |
| MTUB-H37Rv | CAAGCGGCACTACGCACACGTCGACGCCCCTGGCCACGCCGACTACATCAAGAACATGAT | 284 | SEQ ID NO: 589 |
| MTUB-CDC1551 | CAAGCGGCACTACGCACACGTCGACGCCCCTGGCCACGCCGACTACATCAAGAACATGAT | 284 | SEQ ID NO: 590 |
| MAVI-DAS | GAAGCGCCACTACGCACACGTGGACGCCCCCGGCCACGCGGACTACATCAAGAACATGAT | 125 | SEQ ID NO: 591 |
| CIDP-NCTC13129 | GAAGCGCCACTACGCACACGTTGACGCTCCAGGTCACGCTGACTACATCAAGAACATGAT | 284 | SEQ ID NO: 592 |
| NMEN-MC58 | AACCCGCCACTACGCACACGTAGACTGCCCGGGGCACGCCGACTACGTTAAAAACATGAT | 278 | SEQ ID NO: 593 |
| NNEN-Z2491 | AACCCGCCACTACGCACACGTAGACTGTCCGGGGCACGCCGACTACGTTAAAAACATGAT | 278 | SEQ ID NO: 594 |
| NMEN-DAS | AACCCGCCACTACGCACACGTAGACTGCCCGGGGCACGCCGACTACGTTAAAAACATGAT | 119 | SEQ ID NO: 595 |
| MPNE-HF2 | TACTGGTGCTGCTCAAATGGATGGTGCAATCTTAGTAGTTGCTGCATCTGATGGACCAAT | 338 | SEQ ID NO: 596 |
| MPNB-M129 | TACTGGTGCTGCACAAATGGATGGTGCCATTCTAGTAGTTTCAGCAACTGACAGTGTTAT | 338 | SEQ ID NO: 597 |
| LPNE-Paris | TACTGGTGCTGCGCAAATGGACGGAGCGATACTGGTTGTATCAGCAGCTGATGGTCCTAT | 351 | SEQ ID NO: 598 |
| LPNE2-DAB | TACTGGTGCTGCGCAAATGGACGGAGCGATACTGGTTGTATCAGCAGCTGATGGTCCTAT | 221 | SEQ ID NO: 599 |
| LPNE-Philadelphia1 | TACTGGTGCTGCGCAAATGGACGGAGCGATACTGGTTGTATCAGCAGCTGATGGTCCTAT | 338 | SEQ ID NO: 600 |
| LPNE-Lens | TACTGGTGCTGCGCAAATGGACGGAGCGATACTGGTTGTATCAGCAGCTGATGGTCCTAT | 338 | SEQ ID NO: 601 |
| LLON-DAS | TACAGGTGCTGCGCAAATGGACGGAGCGATACTGGTTGTATCAGCAGCTGATGGTCCTAT | 222 | SEQ ID NO: 602 |
| FNUC-DAS | AACTGGTGCTGCACAAATGGATGGAGCTATACTTGTTGTATCAGCTGCTGATGGTCCTAT | 216 | SEQ ID NO: 603 |
| CPNE-CWL029 | TACAGGCGCCGCTCAAATGGACGGAGCTATCCTAGTCGTTTCAGCTACAGACGGAGCTAT | 338 | SEQ ID NO: 604 |
| EFAE-DAS | CACTGGTGCTGCTCAAATGGACGGAGCTATCTTAGTAGTTTCTGCTGCTGATGGTCCTAT | 215 | SEQ ID NO: 605 |
| EFAE-V583 | CACTGGTGCTGCTCAAATGGACGGAGCTATCTTAGTAGTTTCTGCTGCTGATGGTCCTAT | 338 | SEQ ID NO: 606 |
| SAUR-Mu50 | CACTGGTGCTGCTCAAATGGACGGCGGTATCTTAGTAGTATCTGCTGCTGACGGTCCAAT | 338 | SEQ ID NO: 607 |
| SAUR-N315 | CACTGGTGCTGCTCAAATGGACGGCGGTATCTTAGTAGTATCTGCTGCTGACGGTCCAAT | 338 | SEQ ID NO: 608 |
| SAUR-MW2 | CACTGGTGCTGCTCAAATGGACGGCGGTATCTTAGTAGTATCTGCTGCTGACGGTCCAAT | 338 | SEQ ID NO: 609 |
| SAUR-MSSA476 | CACTGGTGCTGCTCAAATGGACGGCGGTATCTTAGTAGTATCTGCTGCTGACGGTCCAAT | 338 | SEQ ID NO: 610 |
| SAUR-MRSA252 | CACTGGTGCTGCTCAAATGGACGGTGGTATCTTAGTAGTATCTGCTGCTGACGGTCCAAT | 338 | SEQ ID NO: 611 |
| SEPI-12228 | CACTGGTGCAGCTCAAATGGACGGCGGTATCTTAGTTGTATCTGCTGCTGACGGTCCAAT | 338 | SEQ ID NO: 612 |
| SEPI-RP62A | CACTGGTGCAGCTCAAATGGACGGCGGTATCTTAGTTGTATCTGCTGCTGACGGTCCAAT | 338 | SEQ ID NO: 613 |
| SMIT-DAS | CACTGGTGCCGCTCAAATGGACGGAGCTATCCTTGTAGTAGCTTCAACTGACGGACCAAT | 206 | SEQ ID NO: 614 |
| SSAN-DAS | CACTGGTGCCGCTCAAATGGACGGAGCTATCCTTGTAGTAGCTTCAACTGACGGACCAAT | 247 | SEQ ID NO: 615 |
| SMIT-NCTC12261 | CACTGGTGCCGCTCAAATGGACGGAGCTATCCTTGTAGTAGCTTCAACTGACGGACCAAT | 347 | SEQ ID NO: 616 |
| SPNE-R6 | CACTGGTGCCGCTCAAATGGACGGAGCTATCCTTGTAGTAGCTTCAACTGACGGACCAAT | 347 | SEQ ID NO: 617 |
| SPYO-M1GAS | CACTGGTGCCGCTCAAATGGACGGAGCTATCCTTGTAGTTGCTTCAACTGATGGACCAAT | 347 | SEQ ID NO: 618 |
| SMUT-DAS | TACTGGTGCTGCCCAAATGGATGGTGCTATCCTTGTAGTAGCTTCAACTGATGGTCCAAT | 247 | SEQ ID NO: 619 |
| SMUT-UA159 | CACTGGTGCTGCCCAAATGGATGGTGCTATCCTTGTAGTAGCTTCAACTGATGGACCAAT | 347 | SEQ ID NO: 620 |
| HINF-RdKW20 | TACTGGTGCGGCACAAATGGATGGTGCTATTTTAGTAGTAGCAGCAACAGATGGTCCTAT | 338 | SEQ ID NO: 621 |
| MCAT-DAS | CACAGGTGCTGCACAGATGGACGGCGCAATCTTGGTTGTTTCTGCAACTGACGGCCCAAT | 189 | SEQ ID NO: 622 |
| BPER-TohamaI | CACGGGTGCTGCGCAGATGGACGGCGCGATCCTGGTGGTGTCGGCCGCAGACGGCCCGAT | 338 | SEQ ID NO: 623 |
| BPAR-12822 | CACGGGTGCTGCGCAGATGGACGGCGCGATCCTGGTGGTGTCGGCCGCAGACGGCCCGAT | 338 | SEQ ID NO: 624 |
| BCEP2-DAS | CACGGGTGCAGCGCAGATGGACGGCGCAATCCTGGTGTGCTCGGCCGCAGACGGCCCGAT | 222 | SEQ ID NO: 625 |
| BPSE-1710b | CACGGGCGCGGCGCAGATGGACGGCGCGATCCTGGTGTGCTCGGCCGCTGACGGCCCGAT | 338 | SEQ ID NO: 626 |
| SMAL-DAS | CACCGGTGCCGCCCAGATGGACGGCGCGATCCTGGTGTGCTCGGCCGCTGACGGCCCGAT | 243 | SEQ ID NO: 627 |
| PAER-PA01 | CACCGGTGCTGCCCAGATGGACGGCGCGATCCTGGTTTGCTCGGCTGCCGACGGCCCCAT | 338 | SEQ ID NO: 628 |
| KPNE-DAS | CACCGGTGCTGCGCAGATGGACGGCGCGATCCTGGTTGTTGCTGCGACTGACGGCCCGAT | 222 | SEQ ID NO: 629 |
| MAVI-K10 | CACCGGCGCCGCCCAGATGGACGGCGCGATCCTGGTGGTCGCCGCCACCGACGGCCCGAT | 344 | SEQ ID NO: 630 |
| MAVI-paratub | CACCGGCGCCGCCCAGATGGACGGCGCGATCCTGGTGGTCGCCGCCACCGACGGCCCGAT | 344 | SEQ ID NO: 631 |
| MAISpig-DAS | CACCGGTGCGGCCCAGATGGACGGCGCGATCCTGGTGGTTGCCGCCACCGACGGCCCGAT | 239 | SEQ ID NO: 632 |
| MKAN-DAS | CACCGGCGCCGCCCAGATGGACGGCGCGATCCTGGTGGTCGCCGCCACGGACGGCCCGAT | 245 | SEQ ID NO: 633 |
| MTUB-H37Rv | CACCGGCGCCGCGCAGATGGACGGTGCGATCCTGGTGGTCGCCGCCACCGACGGCCCGAT | 344 | SEQ ID NO: 634 |
| MTUB-CDC1551 | CACCGGCGCCGCGCAGATGGACGGTGCGATCCTGGTGGTCGCCGCCACCGACGGCCCGAT | 344 | SEQ ID NO: 635 |
| MAVI-DAS | CACCGGTGCCGCCCAGATGGACGGCGCGATCCTGGTGGTCGCCGCGACCGACGGCCCGAT | 185 | SEQ ID NO: 636 |
| NCTC13129 | CACCGGTGCTGCTCAGATGGACGGCGCAATCCTCGTTGTTGCTGCCACCGACGGCCCAAT | 344 | SEQ ID NO: 637 |
| NMEN-MC58 | TACCGGCGCCGCACAAATGGACGGTGCAATCCTGGTATGTTCCGCAGCCGACGGCCCTAT | 338 | SEQ ID NO: 638 |

TABLE 1-continued

| | | | |
|---|---|---|---|
| NMEN-Z2491 | TACCGGCGCAGCACAAATGGACGGTGCAATCCTGGTATGTTCCGCAGCCGACGGCCCTAT | 338 | SEQ ID NO: 639 |
| NMEN-DAS | TACCGGTGCCGCACAAATGGACGGTGCAATCCTGGTATGTTCCGCAGCCGACGGCCCTAT | 179 | SEQ ID NO: 640 |
| | | | |
| MPNE-HF2 | GCCACAAACAAGAGAACACATCTTATTAGCTAGACAAGTTGGTGTTCCTAAAATGGTAGT | 398 | SEQ ID NO: 641 |
| MPNE-M129 | GCCCCAAACCCGTGAACACATTTTGTTGGCCCGCCAAGTGGGTGTGCCACGCATGGTAGT | 398 | SEQ ID NO: 642 |
| LPNE-Paris | GCCACAAACGAGGGAACACATTCTATTGTCTCGCCAGGTAGGTGTTCCATATATTGTTGT | 411 | SEQ ID NO: 643 |
| LPNE2-DAS | GCCACAAACGAGGGAACACATTCTATTGTCTCGCCAGGTAGGTGTTCCATATATTGTTGT | 281 | SEQ ID NO: 644 |
| LPNE-Philadelphia1 | GCCACAAACGAGGGAACACATTCTATTGTCTCGCCAGGTAGGTGTTCCATATATTGTTGT | 398 | SEQ ID NO: 645 |
| LPNE-Lens | GCCACAAACGAGGGAACACATTCTATTGTCTCGCCAGGTAGGTGTTCCATATATTGTTGT | 398 | SEQ ID NO: 646 |
| LLON-DAS | GCCTCAAACTAGAGAACATATTCTATTGTCACGACAAGTAGGGGTGCCCTACATAGTAGT | 282 | SEQ ID NO: 647 |
| FNUC-DAS | GCCTCAAACAAGAGAACATATCTTACTTTCTAGACAAGTTGGAGTACCATATATTATTGT | 276 | SEQ ID NO: 648 |
| CPNE-CWL029 | GCCACAAACTAAAGAACATATCTTGCTAGCTCGCCAGGTTGGAGTTCCTTATATCGTTGT | 398 | SEQ ID NO: 649 |
| EFAE-DAS | GCCTCAAACACGTGAACATATCTTATTATCACGTAACGTTGGTGTACCATACATCGTTGT | 275 | SEQ ID NO: 650 |
| EFAE-V583 | GCCTCAAACACGTGAACATATCTTATTATCACGTAACGTTGGTGTACCATACATCGTTGT | 398 | SEQ ID NO: 651 |
| SAUR-Mu50 | GCCACAAACTCGTGAACACATTCTTTTATCACGTAACGTTGGTGTACCAGCATTAGTAGT | 398 | SEQ ID NO: 652 |
| SAUR-N315 | GCCACAAACTCGTGAACACATTCTTTTATCACGTAACGTTGGTGTACCAGCATTAGTAGT | 398 | SEQ ID NO: 653 |
| SAUR-MW2 | GCCACAAACTCGTGAACACATTCTTTTATCACGTAACGTTGGTGTACCAGCATTAGTAGT | 398 | SEQ ID NO: 654 |
| SAUR-MSSA476 | GCCACAAACTCGTGAACACATTCTTTTATCACGTAACGTTGGTGTACCAGCATTAGTAGT | 398 | SEQ ID NO: 655 |
| SAUR-MRSA252 | GCCACAAACTCGTGAACACATTCTTTTATCACGTAACGTTGGTGTACCAGCATTAGTAGT | 398 | SEQ ID NO: 656 |
| SEPI-12228 | GCCACAAACTCGTGAACACATCTTATTATCACGTAACGTTGGTGTACCAGCATTAGTTGT | 398 | SEQ ID NO: 657 |
| SEPI-RP62A | GCCACAAACTCGTGAACACATCTTATTATCACGTAACGTTGGTGTACCAGCATTAGTTGT | 398 | SEQ ID NO: 658 |
| SMIT-DAS | GCCACAAACTCGTGAGCACATCCTTCTTTCACGTCAGGTTGGTGTTAAACACTTGATCGT | 266 | SEQ ID NO: 659 |
| SSAN-DAS | GCCACAAACTCGTGAGCACATCTTGCTTTCACGTCAGGTTGGTGTTAAACACTTGATCGT | 307 | SEQ ID NO: 660 |
| SMIT-NCTC12261 | GCCACAAACTCGTGAGCACATCCTTCTTTCACGTCAGGTTGGTGTTAAACACCTTATCGT | 407 | SEQ ID NO: 661 |
| SPNE-R6 | GCCACAAACTCGTGAGCACATCCTTCTTTCACGTCAGGTTGGTGTTAAACACCTTATCGT | 407 | SEQ ID NO: 662 |
| SPYO-M1GAS | GCCACAAACTCGTGAGCACATCCTTCTTTCACGTCAGGTTGGTGTTAAACACCTTATCGT | 407 | SEQ ID NO: 663 |
| SMUT-DAS | GCCACAAACTCGTGAACACATTCTTCTTTCACGTCAAGTTGGTGTTAAATACCTTATTGT | 307 | SEQ ID NO: 664 |
| SMUT-UA159 | GCCACAAACTCGTGAACACATTCTTCTTTCACGTCAAGTTGGTGTTAAATACCTCATTGT | 407 | SEQ ID NO: 665 |
| HINF-RdKW20 | GCCACAAACTCGTGAACACATCTTATTAGGTCGCCAAGTAGGTGTTCCATACATCATCGT | 398 | SEQ ID NO: 666 |
| MCAT-DAS | GCCACAAACTCGTGAGCACATCCTACTGTCTCGTCAGGTTGGTGTACCATATATCATGGT | 249 | SEQ ID NO: 667 |
| BPER-TohamaI | GCCGCAGACGCGCGAGCACATTTTGCTGTCGCGCCAGGTTGGCGTGCCGTACATCATCGT | 398 | SEQ ID NO: 668 |
| BPAR-12822 | GCCGCAGACGCGCGAGCACATTTTGCTGTCGCGCCAGGTTGGCGTGCCGTACATCATCGT | 398 | SEQ ID NO: 669 |
| BCEP2-DAS | GCCGCAAACGCGTGAGCACATCCTGCTGGCGCGTCAGGTTGGCGTTCCGTACATCATCGT | 282 | SEQ ID NO: 670 |
| BPSE-1710b | GCCGCAAACGCGTGAGCACATCCTGCTGGCGCGTCAGGTCGGTGTGCCGTACATCATCGT | 398 | SEQ ID NO: 671 |
| SMAL-DAS | GCCGCAGACCCGTGAGCACATCCTGCTGTCGCGCCAGGTCGGCGTGCCGTACATCGTCGT | 303 | SEQ ID NO: 672 |
| PAER-PA01 | GCCGCAGACCCGCGAGCACATCCTGCTGTCCCGCCAGGTAGGCGTTCCCTACATCGTCGT | 398 | SEQ ID NO: 673 |
| KPNE-DAS | GCCGCAGACTCGTGAGCACATCCTGCTGGGTCGTCAGGTAGGCGTTCCGTACATCATCGT | 282 | SEQ ID NO: 674 |
| MAVI-K10 | GCCGCAGACCCGCGAGCACGTGCTGCTGGCCCGTCAGGTCGGTGTGCCCTACATCCTGGT | 404 | SEQ ID NO: 675 |
| MAVI-paratub | GCCGCAGACCCGCGAGCACGTGCTGCTGGCCCGTCAGGTCGGTGTGCCCTACATCCTGGT | 404 | SEQ ID NO: 676 |
| MAISpig-DAS | GCCGCAGACCCGTGAGCACGTGCTGCTCGCGCGTCAGGTCGGGGTGCCCTACATCCTGGT | 299 | SEQ ID NO: 677 |
| MKAN-DAS | GCCGCAGACCCGTGAGCACGTGCTGCTCGCACGTCAGGTGGGTGTGCCCTACATCCTGGT | 305 | SEQ ID NO: 678 |
| MTUB-H37Rv | GCCCCAGACCCGCGAGCACGTTCTGCTGGCGCGTCAAGTGGGTGTGCCCTACATCCTGGT | 404 | SEQ ID NO: 679 |
| MTUB-CDC1551 | GCCCCAGACCCGCGAGCACGTTCTGCTGGCGCGTCAAGTGGGTGTGCCCTACATCCTGGT | 404 | SEQ ID NO: 680 |
| MAVI-DAS | GCCGCAGACCCGCGAGCACGTGCTGCTCGGCCGTCAGGTGGGTGTGCCCTACATCCTCGT | 245 | SEQ ID NO: 681 |
| NCTC13129 | GCCTCAGACCCGTGAGCACGTTCTGCTCGCTCGCCAGGTCGGCGTTCCTTACATCCTCGT | 404 | SEQ ID NO: 682 |
| NMEN-MC58 | GCCGCAAACCCGCGAACACATCCTGCTGGCCCGCCAAGTAGGCGTACCTTACATCATCGT | 398 | SEQ ID NO: 683 |
| NMEN-Z2491 | GCCGCAAACCCGCGAACACATCCTGCTGGCCCGTCAAGTAGGCGTACCTTACATCATCGT | 398 | SEQ ID NO: 684 |
| NMEN-DAS | GCCGCAAACCCGCGAACACATCCTGCTGGCCCGTCAAGTAGGCGTACCTTACATCATCGT | 239 | SEQ ID NO: 685 |
| | | | |
| MPNE-HF2 | TTTCTTAAACAAATGTGATATGGTA------TCTGATGCTGAAATGCAAGACCTAGTAGA | 452 | SEQ ID NO: 686 |
| MPNE-M129 | GTTCCTAAACAAGTGTGACATTGCA------ACTGATGAAGAAGTGCAAGAGTTAGTAGC | 452 | SEQ ID NO: 687 |
| LPNE-Paris | GTTCATGAACAAAGCGGATATGGTT------GATGACCCTGAGTTATTAGAGTTAGTGGA | 465 | SEQ ID NO: 688 |
| LPNE2-DAB | GTTCATGAACAAAGCGGATATGGTT------GATGACCCTGAGTTATTAGAGTTAGTGGA | 335 | SEQ ID NO: 689 |
| LPNE-Philadelphia1 | GTTCATGAACAAAGCGGATATGGTT------GATGACCCTGAGTTATTAGAGTTAGTGGA | 452 | SEQ ID NO: 690 |
| LPNE-Lens | GTTCATGAACAAAGCGGATATGGTT------GATGACCCTGAGTTATTAGAGTTAGTGGA | 452 | SEQ ID NO: 691 |
| LLON-DAS | GTTTATGAATAAAGCGGACATGGTT------GATGATCCAGAGCTCTTAGAGCTTGTAGA | 336 | SEQ ID NO: 692 |
| FNUC-DAS | TTATTTAAATAAATCAGATATGGTT------GATGATGAAGAATTACTAGAATGGGTAGA | 330 | SEQ ID NO: 693 |
| CPNE-CWL029 | TTTCTTGAATAAAGTAGATATGATCTCTCAAGAAGATGCTGAACTTATTGACCTTGTTGA | 458 | SEQ ID NO: 694 |
| EFAE-DAS | ATTCTTAAACAAAATGGATATGGTT------GATGACGAAGAATTATTAGAATTAGTAGA | 329 | SEQ ID NO: 695 |
| EFAE-V583 | ATTCTTAAACAAAATGGATATGGTT------GATGACGAAGAATTATTAGAATTAGTAGA | 452 | SEQ ID NO: 696 |
| SAUR-Mu50 | ATTCTTAAACAAAGTTGACATGGTT------GACGATGAAGAATTATTAGAATTAGTAGA | 452 | SEQ ID NO: 697 |
| BAUR-N315 | ATTCTTAAACAAAGTTGACATGGTT------GACGATGAAGAATTATTAGAATTAGTAGA | 452 | SEQ ID NO: 698 |
| SAUR-MW2 | ATTCTTAAACAAAGTTGACATGGTT------GACGATGAAGAATTATTAGAATTAGTAGA | 452 | SEQ ID NO: 699 |
| SAUR-MSSA476 | ATTCTTAAACAAAGTTGACATGGTT------GACGATGAAGAATTATTAGAATTAGTAGA | 452 | SEQ ID NO: 700 |
| SAUR-MRBA252 | ATTCTTAAACAAAGTTGACATGGTT------GACGATGAAGAATTATTAGAATTAGTAGA | 452 | SEQ ID NO: 701 |
| SEPI-12228 | ATTCTTAAACAAAGTTGACATGGTA------GACGACGAAGAATTATTAGAATTAGTAGA | 452 | SEQ ID NO: 702 |
| SEPI-RP62A | ATTCTTAAACAAAGTTGACATGGTA------GACGACGAAGAATTATTAGAATTAGTAGA | 452 | SEQ ID NO: 703 |
| SMIT-DAS | CTTCATGAACAAAGTTGACTTGGTT------GACGATGAAGAATTGCTTGAATTGGTTGA | 320 | SEQ ID NO: 704 |
| SSAN-DAS | CTTCATGAACAAAGTTGACTTGGTT------GACGATGAAGAATTGCTTGAATTGGTTGA | 361 | SEQ ID NO: 705 |
| SMIT-NCTC12261 | CTTCATGAACAAAGTTGACTTGGTT------GACGACGAAGAATTGCTTGAATTGGTTGA | 461 | SEQ ID NO: 706 |
| SPNE-R6 | CTTCATGAACAAAGTTGACTTGGTT------GACGACGAAGAATTGCTTGAATTGGTTGA | 461 | SEQ ID NO: 707 |
| SPYO-M1GAS | GTTCATGAACAAAGTTGACCTTGTT------GATGACGAAGAGTTGCTTGAATTAGTTGA | 461 | SEQ ID NO: 708 |
| SMUT-DAS | CTTCATGAATAAGGTTGATTTGGTT------GATGATGAAGAACTGCTTGAATTGGTTGA | 361 | SEQ ID NO: 709 |
| SMUT-UA159 | CTTCATGAATAAAGTTGATTTGGTT------GACGATGAAGAATTGCTTGAATTGGTTGA | 461 | SEQ ID NO: 710 |
| HINF-RdKW20 | ATTCTTAAACAAATGCGACATGGTA------GATGACGAAGAGTTATTAGAATTAGTCGA | 452 | SEQ ID NO: 711 |
| MCAT-DAS | ATTCATGAACAAGTGCGACATGGTA------GATGATGAAGAGCTACTAGAATTGGTTGA | 303 | SEQ ID NO: 712 |
| BPER-TohamaI | GTTCCTGAACAAGGCGGACATGGTT------GATGACGCGGAGCTGCTCGAGCTGGTGGA | 452 | SEQ ID NO: 713 |
| BPAR-12822 | GTTCCTGAACAAGGCGGACATGGTT------GATGACGCGGAGCTGCTCGAGCTGGTGGA | 452 | SEQ ID NO: 714 |
| BCEP2-DAS | GTTCCTGAACAAGTGCGACATGGTG------GACGACGCTGAACTGCTCGAGCTGGTCGA | 336 | SEQ ID NO: 715 |
| BPSE-1710b | GTTCCTGAACAAGTGCGATATGGTG------GACGACGCGGAGCTGCTCGAGCTGGTCGA | 452 | SEQ ID NO: 716 |

TABLE 1-continued

| | | | |
|---|---|---|---|
| SMAL-DAS | GTTCCTGAACAAGGCCGACATGGTC------GACGACGCCGAGCTGCTCGAGCTGGTCGA | 357 | SEQ ID NO: 717 |
| PAER-PA01 | GTTCCTGAACAAGGCCGACATGGTC------GACGACGCCGAGCTGCTGGAACTGGTCGA | 452 | SEQ ID NO: 718 |
| KPNE-DAS | GTTCCTGAACAAATGCGACATGGTT------GATGACGAAGAGCTGCTGGAACTGGTTGA | 336 | SEQ ID NO: 719 |
| MAVI-K10 | CGCGCTGAACAAGGCCGACATGGTC------GACGACGAGGAGCTGCTCGAGCTCGTCGA | 458 | SEQ ID NO: 720 |
| MAVI-paratub | CGCGCTGAACAAGGCCGACATGGTC------GACGACGAGGAGCTGCTCGAGCTCGTCGA | 458 | SEQ ID NO: 721 |
| MAISpig-DAS | CGCCCTCAACAAGGCCGACATGGTC------GACGACGAGGAGCTCCTCGAGCTCGTCGA | 353 | SEQ ID NO: 722 |
| MKAN-DAS | CGCGCTGAACAAGGCCGACGCCGTC------GACGACGAGGAGTTGCTCGAACTCGTCGA | 359 | SEQ ID NO: 723 |
| MTUB-H37Rv | AGCGCTGAACAAGGCCGACGCAGTG------GACGACGAGGAGCTGCTCGAACTCGTCGA | 458 | SEQ ID NO: 724 |
| MTUB-CDC1551 | AGCGCTGAACAAGGCCGACGCAGTG------GACGACGAGGAGCTGCTCGAACTCGTCGA | 458 | SEQ ID NO: 725 |
| MAVI-DAS | GGCGCTGAACAAGTCGGACATGGTC------GACGACGAGGAGCTCCTCGAGCTCGTCGA | 299 | SEQ ID NO: 726 |
| NCTC13129 | TGCTCTGAACAAGTGCGACATGGTT------GATGATGAGGAAATCATCGAGCTCGTCGA | 458 | SEQ ID NO: 727 |
| NMEN-MC58 | GTTCATGAACAAATGCGACATGGTC------GACGATGCCGAGCTGTTGGAACTGGTTGA | 452 | SEQ ID NO: 728 |
| NMEN-Z2491 | GTTCATGAACAAATGCGACATGGTC------GACGATGCCGAGCTGTTGGAACTGGTTGA | 452 | SEQ ID NO: 729 |
| NMEN-DAS | GTTCATGAACAAATGCGACATGGTC------GACGATGCCGAGCTGTTGGAACTGGTTGA | 293 | SEQ ID NO: 730 |
| | | | |
| MPNE-HF2 | AATGGAAGTTAGAGAATTACTTTCTTCTTATGGTTTTGATGGAGATAACACTCCAGTTAT | 512 | SEQ ID NO: 731 |
| MPNE-M129 | AGAAGAGGTACGTGACTTATTAACTTCTTACGGCTTTGATGGCAAGAACACCCCTATTAT | 512 | SEQ ID NO: 732 |
| LPNE-Paris | AATGGAAGTGCGAGATTTATTAAGCAGTTACGATTTCCCAGGGGATGACATACCTATTGT | 525 | SEQ ID NO: 733 |
| LPNE2-DAS | AATGGAAGTGCGAGATTTATTAAGCAGTTACGATTTCCCAGGGGATGACATACCCATTGT | 395 | SEQ ID NO: 734 |
| LPNE-Philadelphia1 | AATGGAAGTGCGAGATTTATTAAGCAGTTACGATTTCCCAGGGGATGACATACCTATTGT | 512 | SEQ ID NO: 735 |
| LPNE-Lens | AATGGAAGTGCGAGATTTATTAAGCAGTTACGATTTCCCAGGGGATGATATACCTATTAT | 512 | SEQ ID NO: 736 |
| LLON-DAS | AATGGAAGTCCGTGATTTGTTGAGCAGTTATGATTTTCCTGGTGATGATATTCCAATTGT | 396 | SEQ ID NO: 737 |
| FNUC-DAS | AATGGAAGTTAGAGAATTATTAACTGAATATGGATTCCCAGGAGATGACATCCCTGTAAT | 390 | SEQ ID NO: 738 |
| CPNE-CWL0129 | GATGGAACTTAGTGAGCTTCTTGAAGAAAAAGGCT--ACAAAGGATG----CCCTATTAT | 512 | SEQ ID NO: 739 |
| EFAE-DAS | AATGGAAGTTCGTGACTTATTATCAGAATACGATTTCCCAGGCGATGATGTTCCAGTTAT | 389 | SEQ ID NO: 740 |
| EFAE-V583 | AATGGAAGTTCGTGACTTATTATCAGAATACGATTTCCCAGGCGATGATGTTCCAGTTAT | 512 | SEQ ID NO: 741 |
| SAUR-Mu50 | AATGGAAGTTCGTGACTTATTAAGCGAATATGACTTCCCAGGTGACGATGTACCTGTAAT | 512 | SEQ ID NO: 742 |
| SAUR-N315 | AATGGAAGTTCGTGACTTATTAAGCGAATATGACTTCCCAGGTGACGATGTACCTGTAAT | 512 | SEQ ID NO: 743 |
| SAUR-MW2 | AATGGAAGTTCGTGACTTATTAAGCGAATATGACTTCCCAGGTGACGATGTACCTGTAAT | 512 | SEQ ID NO: 744 |
| SAUR-MSSA476 | AATGGAAGTTCGTGACTTATTAAGCGAATATGACTTCCCAGGTGACGATGTACCTGTAAT | 512 | SEQ ID NO: 745 |
| SAUR-MRSA252 | AATGGAAGTTCGTGACTTATTAAGCGAATATGACTTCCCAGGTGACGATGTACCTGTAAT | 512 | SEQ ID NO: 746 |
| SEPI-12228 | AATGGAAGTTCGTGACTTATTAAGCGAATATGACTTCCCAGGTGACGATGTACCTGTAAT | 512 | SEQ ID NO: 747 |
| SEPI-RP62A | AATGGAAGTTCGTGACTTATTAAGCGAATATGACTTCCCAGGTGACGATGTACCTGTAAT | 512 | SEQ ID NO: 748 |
| SMIT-DAS | AATGGAAATCCGTGACCTTCTTTCAGAATACGATTTCCCAGGTGATGACCTTCCAGTTAT | 380 | SEQ ID NO: 749 |
| SSAN-DAS | AATGGAAATCCGTGACCTCTTGTCAGAATACGACTTCCCAGGTGACGATCTTCCAGTTAT | 421 | SEQ ID NO: 750 |
| SMIT-NCTC12261 | AATGGAAATCCGTGACCTATTGTCAGAATACGACTTCCCAGGTGACGATCTTCCAGTTAT | 521 | SEQ ID NO: 751 |
| SPNE-R6 | AATGGAAATCCGTGACCTATTGTCAGAATACGACTTCCCAGGTGACGATCTTCCAGTTAT | 521 | SEQ ID NO: 752 |
| SPYO-M1GAS | GATGGAAATTCGTGACCTTCTTTCAGAATACGATTTCCCAGGTGATGACCTTCCAGTTAT | 521 | SEQ ID NO: 753 |
| SMUT-DAS | AATGGAAATCCGTGATCTTCTTTCAGAATATGATTTCCCAGGTGATGATATTCCAGTTAT | 421 | SEQ ID NO: 754 |
| SMUT-UA159 | AATGGAAATCCGTGATCTTCTTTCAGAATATGATTTCCCAGGTGATGATATTCCAGTTAT | 521 | SEQ ID NO: 755 |
| HINF-RdKW20 | AATGGAAGTTCGTGAACTTCTATCTCAATATGACTTCCCAGGTGACGATACACCAATCGT | 512 | SEQ ID NO: 756 |
| MCAT-DAS | AATGGAAGTTCGTGAACTTCTATCTGACTATGACTTCCCAGGTGATGACACCCCAATCAT | 363 | SEQ ID NO: 757 |
| BPER-TohamaI | GATGGAAGTCCGCGAACTGCTGAGCAAGTACGATTTCCCGGGCGATGACACGCCGATCGT | 512 | SEQ ID NO: 758 |
| BPAR-12822 | GATGGAAGTCCGCGAACTGCTGAGCAAGTACGATTTCCCGGGCGATGACACGCCGATCGT | 512 | SEQ ID NO: 759 |
| BCEP2-DAS | GATGGAAGTTCGCGAACTGCTGTCGAAGTACGACTTCCCGGGCGACGACACGCCGATCAT | 396 | SEQ ID NO: 760 |
| BPSE-1710b | AATGGAAGTGCGCGAACTGCTGTCGAAGTACGACTTCCCGGGCGACGACACGCCGATCAT | 512 | SEQ ID NO: 761 |
| SMAL-DAS | GATGGAAGTGCGCGAACTGCTGAGCAAGTACGAGTTCCCGGGCGACGACACCCCGATCAT | 417 | SEQ ID NO: 762 |
| PAER-PA01 | GATGGAAGTTCGCGATCTGCTGAACACCTACGACTTCCCGGGCGACGACACTCCGATCAT | 512 | SEQ ID NO: 763 |
| KPNE-DAS | GATGGAAGTTCGTGAACTGCTGTCTCAGTACGATTTCCCGGGCGACGACACCCCGATCGT | 396 | SEQ ID NO: 764 |
| MAVI-K10 | GATGGAGGTCCGCGAGCTGCTGGCCGCCCAGGAGTTC---GACGAGGACGCCCCGGTGGT | 515 | SEQ ID NO: 765 |
| MAVI-paratub | GATGGAGGTCCGCGAGCTGCTGGCCGCCCAGGAGTTC---GACGAGGACGCCCCGGTGGT | 515 | SEQ ID NO: 766 |
| MAISpig-DAS | GATGGAGGTCCGCGAACTGCTGGCCGCCCAGGAGTTC---GACGAGGACGCCCCGGTGGT | 410 | SEQ ID NO: 767 |
| MKAN-DAS | GATGGAGGTCCGCGAGCTGCTGGCCGCCCAGGAGTTC---GACGAGGACGCCCCGGTGGT | 416 | SEQ ID NO: 768 |
| MTUB-H37Rv | GATGGAGGTCCGCGAGCTGCTGGCTGCCCAGGAATTC---GACGAGGACGCCCCGGTTGT | 515 | SEQ ID NO: 769 |
| MTUB-CDC1551 | GATGGAGGTCCGCGAGCTGCTGGCTGCCCAGGAATTC---GACGAGGACGCCCCGGTTGT | 515 | SEQ ID NO: 770 |
| MAVI-DAS | GATGGAGGTCCGCGAACTGCTGGCCGCCCAGGAGTTC---GACGAGGACGCCCCGGTCAT | 356 | SEQ ID NO: 771 |
| NCTC13129 | GATGGAGATCCGTGAGCTGCTCGCTGAGCAGGATTAC---GACGAAGAGGCTCCAATCAT | 515 | SEQ ID NO: 772 |
| NMEN-MC58 | AATGGAAATCCGCGACCTGCTGTCCAGCTACGACTTCCCCGGCGATGACTGCCCGATTGT | 512 | SEQ ID NO: 773 |
| NMEN-Z2491 | AATGGAAATCCGCGACCTGCTGTCCAGCTACGACTTCCCCGGCGACGACTGCCCGATCGT | 512 | SEQ ID NO: 774 |
| NMEN-DAS | AATGGAAATCCGCGACCTGCTGTCCAGCTACGACTTCCCCGGCGACGACTGCCCGATTGT | 353 | SEQ ID NO: 775 |
| | | | |
| MPNE-HF2 | TAGAGGTTCAGCTTTAAAAGCATTAGAAGGT---GAT----GCTACTTGAGAAGCTAAA- | 564 | SEQ ID NO: 776 |
| MPNE-M129 | TTATGGTTCTGCACTTAAAGCGCTTGAAGGT---GAT----CCTAAGTGGGAAGCTAAG- | 564 | SEQ ID NO: 777 |
| LPNE-Paris | TGTTGGTTCAGCTTTGAAAGCATTGGAAGGT---GAAGACAGTGATATAGGCGTTAAGGC | 582 | SEQ ID NO: 778 |
| LPNB2-DAS | TGTTGGTTCAGCTTTGAAAGCATTGGAAGGT---GAAGACAGTGATATAGGCGTTAAGGC | 452 | SEQ ID NO: 779 |
| LPNE-Philadelphia1 | TGTTGGTTCAGCTTTGAAAGCATTGGAAGGT---GAAGACAGTGATATAGGCGTTAAGGC | 569 | SEQ ID NO: 780 |
| LPNE-Lens | TGTTGGTTCAGCTTTGAAAGCATTGGAAGGT---GAAGACAGTGATATAGGTGTTAAGGC | 569 | SEQ ID NO: 781 |
| LLON-DAS | TGTTGGATCTGCATTGAAAGCATTAGAAGGT---GATACCAGTGATATTGGGGTGCCAGC | 453 | SEQ ID NO: 782 |
| FNDC-DAS | TAGAGGTTCATCATTAGGAGCTTTAAATGGT---GA----AGAAAAATGGATAGAAAAG- | 442 | SEQ ID NO: 783 |
| CPNE-CWL029 | CCGTGGTTCTGCTTTGAAAGCTCTTGAAGGT---GATGCAAATTATATCGA---AAAAG- | 565 | SEQ ID NO: 784 |
| EFAB-DAS | CGCAGGTTCTGCTTTGAAAGCTTTAGAAGGC---GAC----GAGTCTTATGAAGAAAAA- | 441 | SEQ ID NO: 785 |
| EFAE-V583 | CGCAGGTTCTGCTTTGAAAGCTTTAGAAGGC---GAC----GAGTCTTATGAAGAAAAA- | 564 | SEQ ID NO: 786 |
| SAUR-Mu50 | CGCTGGTTCAGCATTAAAAGCTTTAGAAGGC---GAT----GCTCAATACGAAGAAAAA- | 564 | SEQ ID NO: 787 |
| SAUR-N315 | CGCTGGTTCAGCATTAAAAGCTTTAGAAGGC---GAT----GCTCAATACGAAGAAAAA- | 564 | SEQ ID NO: 788 |
| SAUR-MW2 | CGCTGGTTCAGCATTAAAAGCTTTAGAAGGC---GAT----GCTCAATACGAAGAAAAA- | 564 | SEQ ID NO: 789 |
| SAUR-MSSA476 | CGCTGGTTCAGCATTAAAAGCTTTAGAAGGC---GAT----GCTCAATACGAAGAAAAA- | 564 | SEQ ID NO: 790 |
| SAUR-MRSA252 | CGCTGGTTCAGCATTAAAAGCTTTAGAAGGC---GAT----GCTCAATACGAAGAAAAA- | 564 | SEQ ID NO: 791 |
| SEPI-12228 | CGCTGGTTCTGCATTAAAAGCATTAGAAGGC---GAT----GCTGAATACGAACAAAAA- | 564 | SEQ ID NO: 792 |
| SEPI-RP62A | CGCTGGTTCTGCATTAAAAGCATTAGAAGGC---GAT----GCTGAATACGAACAAAAA- | 564 | SEQ ID NO: 793 |
| SMIT-DAS | CCAAGGTTCAGCTCTTAAAGCTCTTGAAGGT---GAT----GCTAAATACGAAGACATC- | 432 | SEQ ID NO: 794 |

TABLE 1-continued

| | | | |
|---|---|---|---|
| SSAN-DAS | CCAAGGTTCAGCTCTTAAAGCTCTTGAAGGT---GAC----TCTAAATATGAAGACATC- | 473 | SEQ ID NO: 795 |
| SMIT-NCTC12261 | CCAAGGTTCAGCTCTTAAAGCCCTTGAAGGT---GAC----ACTAAATACGAAGACATC- | 573 | SEQ ID NO: 796 |
| SPNE-R6 | CCAAGGTTCAGCACTTAAAGCTCTTGAAGGT---GAC----TCTAAATACGAAGACATC- | 573 | SEQ ID NO: 797 |
| SPYO-M1GAS | CCAAGGTTCAGCTCTTAAAGCTCTTGAAGGC---GAC----ACTAAATTTGAAGACATC- | 573 | SEQ ID NO: 798 |
| SMUT-DAS | TCAAGGTTCAGCTCTTAAAGCTCTTGAAGGT---GAT----ACTGCTCAAGAAGATATC- | 473 | SEQ ID NO: 799 |
| SMUT-UA159 | TCAAGGTTCAGCTCTTAAAGCTCTTGAAGGC---GAT----ACTGCTCAAGAAGATATC- | 573 | SEQ ID NO: 800 |
| HINF-RdXW20 | ACGTGGTTCAGCATTACAAGCGTTAAACGGC---GTA----GCAGAATGGGAAGAAAAA- | 564 | SEQ ID NO: 801 |
| MCAT-DAS | CAAAGGTTCAGCACTAGAAGCATTGAATGGT---TCTGACGGTAAATATGGTGAGCCTGC | 420 | SEQ ID NO: 802 |
| BPER-TohamaI | GAAGGGTTCGGCCAAGCTGGCGCTGGAAGGC---GACAAGGGCGAACTGGGCGAGCAGGC | 569 | SEQ ID NO: 803 |
| BPAR-12822 | GAAGGGTTCGGCCAAGCTGGCGCTGGAAGGC---GACAAGGGCGAACTGGGCGAGCAGGC | 569 | SEQ ID NO: 804 |
| BCEP2-DAS | CAAGGGTTCGGCAAAGCTGGCGCTGGAAGGC---GACAAGGGCGAGCTGGGCGAAACGGC | 453 | SEQ ID NO: 805 |
| BPSE-1710b | CAAGGGTTCGGCGAAGCTGGCGCTGGAAGGC---GACAAGGGCGAGCTGGGCGAAGTGGC | 569 | SEQ ID NO: 806 |
| SMAL-DAS | CGCCGGTTCGGCCCGCCTGGCGCTGGAAGGC---GACCAGAGCGACATCGGCGTGCCGGC | 474 | SEQ ID NO: 807 |
| PAER-PA01 | CATCGGTTCCGCGCTGATGGCGCTGGAAGGCAAGGATGACAACGGCATCGGCGTAAGCGC | 572 | SEQ ID NO: 808 |
| XPNE-DAS | TCGTGGTTCTGCTCTGAAAGCGCTGGAAGGC---GAC----GCAGAGTGGG--AAGCGAA | 447 | SEQ ID NO: 809 |
| MAVI-K10 | GCGGGTGTCGGCGCTCAAGGCGCTCGAGGGC---GAC----GCCAAGTGGGTGGAGT--C | 566 | SEQ ID NO: 810 |
| MAVI-paratub | GCGGGTGTCGGCGCTCAAGGCGCTCGAGGGC---GAC----GCCAAGTGGGTGGAGT--C | 566 | SEQ ID NO: 811 |
| MAISpig-DAS | GCGCGTCTCGGCGCTGAAGGCGCTCGAGGGC---GAC----GCCAAGTGGGTGGAGT--C | 461 | SEQ ID NO: 812 |
| MKAN-DAS | GCGGGTCTCGGCACTGAAGGCCCTCGAGGGC---GAC----CCCAAGTGGGTGGAGT--C | 467 | SEQ ID NO: 813 |
| MTUB-H37Rv | GCGGGTCTCGGCGCTCAAGGCGCTCGAGGGT---GAC----GCGAAGTGGGTTGCCT--C | 566 | SEQ ID NO: 814 |
| MTUB-CDC1551 | GCGGGTCTCGGCGCTCAAGGCGCTCGAGGGT---GAC----GCGAAGTGGGTTGCCT--C | 566 | SEQ ID NO: 815 |
| MAVI-DAS | CCGCGTCTCCGCGCTGAAGGCGCTGGAGGGT---GAC----CCGAAGTGGGTCAAGT--C | 407 | SEQ ID NO: 816 |
| CIDP-NCTC13129 | CCACATCTCCGCACTGAAGGCTCTTGAGGGC---GAC----GAGAAGTGGACCCAGT--C | 566 | SEQ ID NO: 817 |
| NMEN-MC58 | ACAAGGTTCCGCACTGAAAGCCTTGGAAGGC---GAT----GCCGCTTACGAAGAAA--A | 563 | SEQ ID NO: 818 |
| MMEN-Z2491 | ACAAGGTTCCGCACTGAAAGCCTTGGAAGGC---GAT----GCCGCTTACGAAGAAA--A | 563 | SEQ ID NO: 819 |
| NMEN-DAS | ACAAGGTTCTGCACTGAAAGCCTTGGAAGGC---GAT----GCCGCTTATGAAGAGA--A | 404 | SEQ ID NO: 820 |
| | | | |
| MPNE-HF2 | -ATTGATGAATTAATGGCTTCAGTAGATAGCTACATCCCAACTCCAACAAGAGATACAGA | 623 | SEQ ID NO: 821 |
| MPNE-M129 | -ATCCATGATTTAATGAATGCAGTTGATGAATGGATTCCAACTCCTGAACGTGAAGTGGA | 623 | SEQ ID NO: 822 |
| LPNE-Paris | TATAGAGAAATTGGTTGAAACAATGGATTCATACATTCCTGAGCCAGTTAGAAACATAGA | 642 | SEQ ID NO: 823 |
| LPNE2-DAS | TATTGAGAAATTGGTTGAAACAATGGATTCATACATTCCTGAGCCAGTTAGAAATATAGA | 512 | SEQ ID NO: 824 |
| LPNE-Philadelphia1 | TATTGAGAAATTGGTTGAAACAATGGATTCATACATTCCTGAGCCAGTTAGAAACATAGA | 629 | SEQ ID NO: 825 |
| LPNE-Lens | TATTGAGAAATTAGTTGAAACAATGGATTCATACATTCCTGAGCCAGTTAGAAACATAGA | 629 | SEQ ID NO: 826 |
| LLON-DAS | AATAGAGAAATTGGTAGAGACTATGGATTCTTATATTCCAGAGCCTGTAAGAAACATTGA | 513 | SEQ ID NO: 827 |
| FNUC-DAS | -ATAATGGAACTTATGGATGCAGTAGATAGCTATATCCCTACTCCTGAAAGAGCAGTAGA | 501 | SEQ ID NO: 828 |
| CPNE-CWL029 | --TTCGAGAACTTATGCAAGCTGTGGATGACAACATCCCTACACCAGAAAGAGAAATTGA | 623 | SEQ ID NO: 829 |
| EFAE-DAS | -ATCTTAGAATTAATGGCTGCAGTTGACGAATATATCCCAACTCCAGAACGTGATACTGA | 500 | SEQ ID NO: 830 |
| EFAE-V583 | -ATCTTAGAATTAATGGCTGCAGTTGACGAATATATCCCAACTCCAGAACGTGATACTGA | 623 | SEQ ID NO: 831 |
| SAUR-Mu50 | -ATCTTAGAATTAATGGAAGCTGTAGATACTTACATTCCAACTCCAGAACGTGATTCTGA | 623 | SEQ ID NO: 832 |
| SAUR-N315 | -ATCTTAGAATTAATGGAAGCTGTAGATACTTACATTCCAACTCCAGAACGTGATTCTGA | 623 | SEQ ID NO: 833 |
| SAUR-MW2 | -ATCTTAGAATTAATGGAAGCTGTAGATACTTACATTCCAACTCCAGAACGTGATTCTGA | 623 | SEQ ID NO: 834 |
| SAUR-MSSA476 | -ATCTTAGAATTAATGGAAGCTGTAGATACTTACATTCCAACTCCAGAACGTGATTCTGA | 623 | SEQ ID NO: 835 |
| SAUR-MRSA252 | -ATCTTAGAATTAATGGAAGCTGTAGATACTTACATTCCAACTCCAGAACGTGATTCTGA | 623 | SEQ ID NO: 836 |
| SEPI-12228 | -ATCTTAGACTTAATGCAAGCAGTTGATGATTACATTCCAACTCCAGAACGTGATTCTGA | 623 | SEQ ID NO: 837 |
| SEPI-RP62A | -ATCTTAGACTTAATGCAAGCAGTTGATGATTACATTCCAACTCCAGAACGTGATTCTGA | 623 | SEQ ID NO: 838 |
| SMIT-DAS | -ATCATGGACTTGATGAACACTGTTGATGAGTACATCCCAGAACCAGAACGCGATACTGA | 491 | SEQ ID NO: 839 |
| SSAN-DAS | -ATCATGGAATTGATGGACACTGTTGATGAGTACATCCCAGAACCAGAACGCGATACTGA | 532 | SEQ ID NO: 840 |
| SMIT-NCTC12261 | -GTTATGGAATTGATGAACACAGTTGATGAGTACATCCCAGAACCAGAACGTGACACTGA | 632 | SEQ ID NO: 841 |
| SPNE-R6 | -GTTATGGAATTGATGAACACAGTTGATGAGTATATCCCAGAACCAGAACGTGACACTGA | 632 | SEQ ID NO: 842 |
| SPYO-M1GAS | -ATCATGGAATTGATGGATACTGTTGATTCATACATTCCAGAACCAGAACGCGACACTGA | 632 | SEQ ID NO: 843 |
| SMUT-DAS | -ATCATGGAATTAATGCATACTGTTGATGACTACATTCCAGATCCAGAACGTGATACTGA | 532 | SEQ ID NO: 844 |
| SMUT-UA159 | -ATCATGGAATTAATGCATACTGTTGATGACTACATTCCAGATCCAGAACGTGATACTGA | 632 | SEQ ID NO: 845 |
| HINF-RdKW20 | -ATCCTTGAGTTAGCAAACCACTTAGATACTTACATCCCAGAACCAGAACGTGCGATTGA | 623 | SEQ ID NO: 846 |
| MCAT-DAS | TGTTCTAGAACTACTAGACACGCTAGATTCATACATCCCAGAGCCTGAGCGTGACATCGA | 480 | SEQ ID NO: 847 |
| BPER-TohamaI | GATTCTGTCGCTGGCGCAAGCGCTGGACACGTACATTCCGACGCCGGAGCGCGCGGTCGA | 629 | SEQ ID NO: 848 |
| BPAR-12822 | GATTCTGTCGCTGGCGCAAGCGCTGGACACGTACATTCCGACGCCGGAGCGCGCGGTCGA | 629 | SEQ ID NO: 849 |
| BCEP2-DAS | GATCATGAACCTGGCCGACGCGCTGGACACGTACATCCCGACGCCGGAGCGCGCGGTGGA | 513 | SEQ ID NO: 850 |
| BPSE-1710b | GATCATGAACCTGGCCGACGCGCTGGACACGTACATCCCGACGCCGGAGCGTGCGGTCGA | 629 | SEQ ID NO: 851 |
| SMAL-DAS | CATCCTGAAGCTGGTCGACGCGCTGGACAGCTGGATTCCGGAGCCGGAGCGTGCGATCGA | 534 | SEQ ID NO: 852 |
| PAER-PA01 | CGTGCAGAAGCTGGTAGAGACCCTGGACTCCTACATTCCGGAGCCGGTTCGTGCCATCGA | 632 | SEQ ID NO: 853 |
| KPNE-DAS | AATCATCGAACTGGCTGGCCACCTGGATACCTATATCCCGGAACCAGAGCGTGCGATTGA | 507 | SEQ ID NO: 854 |
| MAVI-K10 | CGTCGAGCAGCTGATGGAGGCCGTCGACGAGTCGATCCCGGACCCGGTCCGCGAGACGGA | 626 | SEQ ID NO: 855 |
| MAVI-paratub | CGTCGAGCAGCTGATGGAGGCCGTCGACGAGTCGATCCCGGACCCGGTCCGCGAGACGGA | 626 | SEQ ID NO: 856 |
| MAISpig-DAS | GGTCGAGCAGCTGATGGAGGCCGTCGACGAGTCGATCCCGGACCCCGTCCGTGAGACCGA | 521 | SEQ ID NO: 857 |
| MKAN-DAS | GGTGGAGCAGCTGATGGATGCGGTCGACGAGTCGATCCCCGACCCGGTCCGTGAGACCGA | 527 | SEQ ID NO: 858 |
| MTUB-H37Rv | TGTCGAGGAACTGATGAACGCGGTCGACGAGTCGATTCCGGACCCGGTCCGCGAGACCGA | 626 | SEQ ID NO: 859 |
| MTUB-CDC1551 | TGTCGAGGAACTGATGAACGCGGTCGACGAGTCGATTCCGGACCCGGTCCGCGAGACCGA | 626 | SEQ ID NO: 860 |
| MAVI-DAS | GGTTGAGGACCTCATGGAGGCCGTCGACGAGTCGATCCCGGATCCGGTTCGCGAGACCGA | 467 | SEQ ID NO: 861 |
| CIDP-NCTC13129 | CATCATCGACCTCATGCAGGCTTGCGATGATTCCATCCCAGACCCAGAGCGTGAGACCGA | 626 | SEQ ID NO: 862 |
| NMEN-MC58 | AATCTTCGAACTGGCTGCCGCATTGGACAGCTACATCCCGACTCCCGAGCGAGCCGTGGA | 623 | SEQ ID NO: 863 |
| NMEN-Z2491 | AATCTTCGAACTGGCTGCTGCATTGGACAGCTACATCCCGACTCCCGAGCGAGCCGTGGA | 623 | SEQ ID NO: 864 |
| NMEN-DAS | AATCTTCGAACTGGCTGCCGCATTGGACAGCTACATCCCGACTCCCGAGCGTGCCGTGGA | 464 | SEQ ID NO: 865 |
| | | | |
| MPNE-HF2 | CAAACCTTTCTTATTAGCGGTAGAAGACGTTATGACTATTACTGGTAGAGGTACTGTAGT | 683 | SEQ ID NO: 866 |
| MPNE-M129 | CAAACCCTTCTTGTTGGCAATCGAAGACACCATGACGATTACTGGCCGTGGTACCGTGGT | 683 | SEQ ID NO: 867 |
| LPNE-Paris | CAAGCCATTTTTGTTACCGATTGAAGACGTATTTTCAATTTCTGGACGCGGAACAGTGGT | 702 | SEQ ID NO: 868 |
| LPNE2-DAS | CAAGCCATTTTTGTTACCGATTGAAGACGTATTTTCAATTTCTGGACGCGGAACAGTGGT | 572 | SEQ ID NO: 869 |
| LPNE-Philadelphia1 | CAAGCCATTTTTGTTGCCGATTGAAGACGTATTTTCAATTTCTGGACGCGGAACAGTGGT | 689 | SEQ ID NO: 870 |
| LPNE-Lens | CAAGCCATTCTTGTTGCCGATTGAAGACGTGTTTTCAATTTCTGGACGCGGAACAGTGGT | 689 | SEQ ID NO: 871 |
| LLON-DAS | CAAATCGTTCTTATTACCGATTGAAGATGTATTTTCAATATCTGGCCGAGGAACAGTAGT | 573 | SEQ ID NO: 872 |

TABLE 1-continued

| | | | |
|---|---|---|---|
| FNUC-DAS | TCAACCATTCTTGATGCCAATAGAAGACGTTTTCACTATCACAGGAAGAGGAACAGTTGT | 561 | SEQ ID NO: 873 |
| CPNE-CWL0209 | TAAGCCTTTCTTAATGCCTATCGAAGACGTATTCTCAATCTCTGGTCGTGGTACTGTGGT | 683 | SEQ ID NO: 874 |
| EFAE-DAS | CAAACCATTCATGATGCCAGTCGAAGACGTATTCTCAATCACTGGACGTGGTACTGTTGC | 560 | SEQ ID NO: 875 |
| EFAE-V583 | CAAACCATTCATGATGCCAGTCGAAGACGTATTCTCAATCACTGGACGTGGTACTGTTGC | 683 | SEQ ID NO: 876 |
| SAUR-Mu50 | CAAACCATTCATGATGCCAGTTGAGGACGTATTCTCAATCACTGGTCGTGGTACTGTTGC | 683 | SEQ ID NO: 877 |
| SAUR-N315 | CAAACCATTCATGATGCCAGTCGAAGACGTATTCTCAATCACTGGACGTGGTACTGTTGC | 683 | SEQ ID NO: 878 |
| SAUR-MW2 | CAAACCATTCATGATGCCAGTTGAGGACGTATTCTCAATCACTGGTCGTGGTACTGTTGC | 683 | SEQ ID NO: 879 |
| SAUR-MSSA476 | CAAACCATTCATGATGCCAGTTGAGGACGTATTCTCAATCACTGGTCGTGGTACTGTTGC | 683 | SEQ ID NO: 880 |
| SAUR-MRSA252 | CAAACCATTCATGATGCCAGTTGAGGACGTATTCTCAATCACTGGTCGTGGTACTGTTGC | 683 | SEQ ID NO: 881 |
| SEPI-12228 | CAAACCATTCATGATGCCAGTTGAGGACGTATTCTCAATCACTGGTCGTGGTACTGTTGC | 683 | SEQ ID NO: 882 |
| SEPI-RP62A | CAAACCATTCATGATGCCAGTTGAGGACGTATTCTCAATCACTGGTCGTGGTACTGTTGC | 683 | SEQ ID NO: 883 |
| SMIT-DAS | CAAACCATTGCTTCTTCCAGTCGAAGACGTATTCTCAATCACTGGACGTGGTACTGTAGC | 551 | SEQ ID NO: 884 |
| SSAS-DAS | CAAGCCATTGCTTCTTCCAGTCGAAGACGTATTCTCAATCACTGGTCGTGGTACAGTTGC | 592 | SEQ ID NO: 885 |
| SMIT-NCTC12261 | CAAACCATTGCTTCTTCCAGTCGAAGACGTATTCTCAATCACTGGTCGTGGTACAGTTGC | 692 | SEQ ID NO: 886 |
| SPNE-R6 | CAAACCATTGCTTCTTCCAGTCGAGGACGTATTCTCAATCACTGGACGTGGTACAGTTGC | 692 | SEQ ID NO: 887 |
| SPYO-M1GAS | CAAACCATTGCTTCTTCCAGTCGAAGACGTATTCTCAATTACAGGTCGTGGTACAGTTGC | 692 | SEQ ID NO: 888 |
| SMUT-DAS | TAAGCCACTCCTTCTTCCAGTCGAAGATGTTTTCTCAATCACTGGTCGTGGTACTGTTGC | 592 | SEQ ID NO: 889 |
| SMUT-UA159 | CAAGCCGCTCCTTCTTCCAGTCGAAGATGTTTTCTCAATCACTGGTCGTGGTACTGTTGC | 692 | SEQ ID NO: 890 |
| HINF-RdKW20 | CCAACCGTTCCTTCTTCCAATCGAAGATGTGTTCTCAATCTCAGGTCGTGGTACTGTAGT | 683 | SEQ ID NO: 891 |
| MCAT-DAS | TAAGTCATTCCTAATGCCAATCGAAGATGTCTTCTCAATCTCAGGTCGTGGTACTGTTGT | 540 | SEQ ID NO: 892 |
| BPER-Tohama1 | CGGTGCGTTCCTGATGCCGGTGGAAGACGTGTTCTCGATCTCGGGCCGTGGCACGGTGGT | 689 | SEQ ID NO: 893 |
| BPAR-12822 | CGGTGCGTTCCTGATGCCGGTGGAAGACGTGTTCTCGATCTCGGGCCGTGGCACGGTGGT | 689 | SEQ ID NO: 894 |
| BCEP2-DAS | CGGTACGTTCCTGATGCCGGTGGAAGACGTGTTCTCGATCTCGGGCCGCGGTACGGTGGT | 573 | SEQ ID NO: 895 |
| BPSE-1710b | CGGCGCGTTCCTGATGCCGGTGGAAGACGTGTTCTCGATCTCGGGCCGTGGTACGGTGGT | 689 | SEQ ID NO: 896 |
| SMAL-DAS | CAAGCCGTTCCTGATGCCGGTGGAAGACGTGTTCTCGATCTCGGGCCGCGGCACCGTGGT | 594 | SEQ ID NO: 897 |
| PAER-PA01 | CCAGCCGTTCCTGATGCCGATCGAAGACGTGTTCTCGATCTCCGGCCGCGGTACCGTGGT | 692 | SEQ ID NO: 898 |
| KPNE-DAS | CAAGCCGTTCCTGCTGCCGATCGAAGACGTATTCTCCATCTCCGGTCGTGGTACCGTTGT | 567 | SEQ ID NO: 899 |
| MAVI-K10 | CAAGCCGTTCCTGATGCCGGTGGAAGACGTCTTCACCATCACCGGTCGTGGCACGGTGGT | 686 | SEQ ID NO: 900 |
| MAVI-paratub | CAAGCCGTTCCTGATGCCGGTGGAGGACGTCTTCACCATCACCGGTCGTGGCACGGTGGT | 686 | SEQ ID NO: 901 |
| MAISPig-DAS | GAAGCCGTTCCTGATGCCGGTGGAGGACGTCTTCACGATCACCGGTCGTGGCACCGTGGT | 581 | SEQ ID NO: 902 |
| MKAN-DAS | CAAGCCGTTCCTGATGCCCGTCGAGGACGTCTTCACGATCACCGGCCGCGGCACCGTGGT | 587 | SEQ ID NO: 903 |
| MTUB-H37Rv | CAAGCCGTTCCTGATGCCGGTCGAGGACGTCTTCACCATTACCGGCCGCGGAACCGTGGT | 686 | SEQ ID NO: 904 |
| MTUB-CDC1551 | CAAGCCGTTCCTGATGCCGGTCGAGGACGTCTTCACCATTACCGGCCGCGGAACCGTGGT | 686 | SEQ ID NO: 905 |
| MAVI-DAS | CAAGCCGTTCCTGATGCCCGTCGAGGACGTCTTCACCATCACCGGTCGTGGCACCGTGGT | 527 | SEQ ID NO: 906 |
| CIDP-NCTC13129 | CAAGCCATTCCTCATGCCTATCGAGGACATCTTCACCATCACCGGCCGCGGTACCGTTGT | 686 | SEQ ID NO: 907 |
| NMEN-MC58 | CAAACCGTTCCTGCTGCCTATCGAAGACGTGTTCTCCATTTCCGGCCGCGGTACAGTAGT | 683 | SEQ ID NO: 908 |
| NMEN-Z2491 | CAAACCTTTCTTGTTGCCTATCGAAGACGTATTCTCTATTTCCGGTCGTGGTACAGTAGT | 683 | SEQ ID NO: 909 |
| NMEN-DAS | CAAACCTTTCCTGCTGCCTATCGAAGACGTGTTCTCCATTTCCGGCCGAGGTACAGTAGT | 524 | SEQ ID NO: 910 |
| MPNE-HF2 | AACTGGTAGAGTTGAAAGAGGTACTTTAAAATTAAACGATGAAGTTGAAATCGTTGGTAT | 743 | SEQ ID NO: 911 |
| MPNE-M129 | TACCGGTCGGGTTGAACGTGGTGAATTGAAAGTAGGTCAAGAAATTGAAATCGTTGGTTT | 743 | SEQ ID NO: 912 |
| LPNE-Paris | AACTGGTCGTGTTGAGAGTGGAATTGTTAAAGTTGGTGAGGAAGTTGAAATTGTTGGAAT | 762 | SEQ ID NO: 913 |
| LPNE2-DAS | AACTGGTCGTGTTGAGAGTGGAATTGTTAAAGTTGGTGAGGAAGTTGAAATTGTTGGAAT | 632 | SEQ ID NO: 914 |
| LPNE-Philadelphia1 | AACTGGTCGTGTAGAGAGTGGAATTGTTAAAGTTGGTGAGGAAGTTGAAATTGTTGGAAT | 749 | SEQ ID NO: 915 |
| LPNE-Lens | AACTGGTCGTGTTGAGAGTGGAATTGTTAAAGTTGGTGAGGAAGTTGAAATTGTTGGAAT | 749 | SEQ ID NO: 916 |
| LLON-DAS | AACAGGACGTATCGAAAGCGGAATTATCAAAGTTGGCGAAGAGATCGAAATTGTAGGAAT | 633 | SEQ ID NO: 917 |
| FNUC-DAS | TACAGGAAGAGTTGAAAGAGGAATCATCAAAGTTGGAGAAGAAATTGAAATAGTTGGAAT | 621 | SEQ ID NO: 918 |
| CPNE-CWL029 | TACAGGAAGAATCGAGCGTGGAATCGTTAAAGTTTCTGATAAAGTTCAGCTCGTGGGATT | 743 | SEQ ID NO: 919 |
| EFAE-DAS | TACAGGACGTGTTGAACGTGGTGAAGTTCGCGTTGGTGACGAAGTTGAAATCGTTGGTAT | 620 | SEQ ID NO: 920 |
| EFAE-V583 | TACAGGCCGTGTTGAACGTGGTGAAGTTCGCGTTGGTGACGAAGTTGAAATCGTTGGTAT | 743 | SEQ ID NO: 921 |
| SAUR-Mu50 | TACAGGCCGTGTTGAACGTGGTCAAATCAAAGTTGGTGAAGAAGUTGAAATCATCGGTTT | 743 | SEQ ID NO: 922 |
| SAUR-N315 | TACAGGCCGTGTTGAACGTGGTCAAATCAAAGTTGGTGAAGAAGTTGAAATCATCGGTTT | 743 | SEQ ID NO: 923 |
| SAUR-MW2 | TACAGGCCGTGTTGAACGTGGTCAAATCAAAGTTGGTGAAGAAGTTGAAATCATCGGTTT | 743 | SEQ ID NO: 924 |
| SAUR-MSSA476 | TACAGGCCGTGTTGAACGTGGTCAAATCAAAGTTGGTGAAGAAGTTGAAATCATCGGTTT | 743 | SEQ ID NO: 925 |
| SAUR-MRSA252 | TACAGGCCGTGTTTAACGTGCTCAAATCAAAGTTGGTGAAGAAGTTGAAATCATCGGTTT | 743 | SEQ ID NO: 926 |
| SEPI-12228 | TACAGGCCGTGTTGAACGTGGTCAAATCAAAGTTGGTGAAGAAGTTGAAATCATCGGTAT | 743 | SEQ ID NO: 927 |
| SEPI-RP62A | TACAGGCCGTGTTGAACGTGGTCAAATCAAAGTTGGTGAAGAAGTTGAAATCATCGGTAT | 743 | SEQ ID NO: 928 |
| SMIT-DAS | ATCAGGACGTATCGACCGTGGTATCGTTAAAGTCAACGACGAAATCGAAATCGTTGGTAT | 611 | SEQ ID NO: 929 |
| SSAN-DAS | TTCAGGACGTATCGACCGTGGTATCGTTAAAGTCAACGACGAAATCGAAATCGTTGGTAT | 652 | SEQ ID NO: 930 |
| SMIT-NCTC12261 | TTCAGGACGTATCGACCGTGGTATCGTTAAAGTCAACGACGAAATCGAAATCGTTGGTAT | 752 | SEQ ID NO: 931 |
| SPNE-R6 | TTCAGGACGTATCGACCGTGGTATCGTTAAAGTCAACGACGAAATCGAAATCGTTGGTAT | 752 | SEQ ID NO: 932 |
| SPYO-M1GAS | TTCAGGACGTATCGACCGTGGTACTGTTCGTGTCAACGACGAAATCGAAATCGTTGGTAT | 752 | SEQ ID NO: 933 |
| SMUT-DAS | TTCAGGACGTATTGATCGTGGTACTGTTAAAGTTAACGATGAAGTTGAAATCGTTGGTAT | 652 | SEQ ID NO: 934 |
| SMUT-UA159 | TTCAGGACGTATTGATCGTGGTACTGTTAAAGTTAACGATGAAGTTGAAATCGTTGGTAT | 752 | SEQ ID NO: 935 |
| HINF-RdKW20 | AACAGGTCGTGTAGAACGAGGTATTATCCGTACAGGTGATGAAGTAGAAATCGTCGGTAT | 743 | SEQ ID NO: 936 |
| MCAT-DAS | AACTGGCCGTGTTGAATCAGGCATTATTAAAGTTGGTGATGAAATTGAAATCATCGGTAT | 600 | SEQ ID NO: 937 |
| BPER-TohamaI | GACTGGCCGTATCGAGCGCGGCGTGGTGAAGGTTGGCGAGGAAATCGAAATCGTGGGCAT | 749 | SEQ ID NO: 938 |
| BPAR-12822 | GACTGGCCGTATCGAGCGCGGCGTGGTGAAGGTTGGCGAGGAAATCGAAATCGTGGGTAT | 749 | SEQ ID NO: 939 |
| BCEP2-DAS | GACGGGTCGTGTGGAGCGCGGCGTGGTGAAGGTCGGTGAGGAAATCGAAATCGTCGGTAT | 633 | SEQ ID NO: 940 |
| BPSE-1710b | GACGGGTCGTGTCGAGCGCGGCGTGATCAAGGTTGGCGAGGAAATCGAAATCGTCGGTAT | 149 | SEQ ID NO: 941 |
| SMAL-DAS | GACCGGTCGTATCGAGCGCGGCGTGATCAAGGTTGGCGACGAAATCGAAATCGTCGGCAT | 654 | SEQ ID NO: 942 |
| PAER-PA01 | AACCGGTCGTGTAGAGCGCGGCATCATCAAGGTCCAGGAAGAAGTGGAAATCGTCGGCAT | 752 | SEQ ID NO: 943 |
| KPNE-DAS | TACCGGTCGTGTAGAGCGCGGTATCATCAAAGTAGGTGAAGAAGTTGAAATCGTTGGTAT | 627 | SEQ ID NO: 944 |
| MAVI-K10 | CACCGGCCGTGTCGAGCGCGGCGTGATCAACGTGAACGAGGAAGTCGAGATCGTCGGCAT | 746 | SEQ ID NO: 945 |
| MAVI-paratub | CACCGGCCGTGTCGAGCGCGGCGTGATCAACGTGAACGAGGAAGTCGAGATCGTCGGCAT | 746 | SEQ ID NO: 946 |
| MAISpig-DAS | CACCGGTCGTGTCGAGCGCGGTGTGATCAACGTGAACGAGGAAGTCGAGATCGTCGGTAT | 641 | SEQ ID NO: 947 |
| MKAN-DAS | CACCGGTCGTGGCGAGCGCGGCGTGGTCAACGTGAACGAGGAAGTCGAGATCGTCGGCAT | 647 | SEQ ID NO: 948 |
| MTUB-H37Rv | CACCGGTCGTGGCGAGCGCGGCGTGATCAACGTGAACGAGGAAGTTGAGATCGTCGGCAT | 746 | SEQ ID NO: 949 |
| MTUB-CDC1551 | CACCGGTCGTGGCGAGCGCGGCGTGATCAACGTGAACGAGGAAGTTGAGATCGTCGGCAT | 746 | SEQ ID NO: 950 |
| MAVI-DAS | GACCGGTCGCGTCGAGCGTGGCGTGATCAACGTCAACGAAGAGGTCGAGATCGTCGGCAT | 587 | SEQ ID NO: 951 |

TABLE 1-continued

| | | | |
|---|---|---|---|
| NCTC13129 | TACCGGCCGTGTTGAGCGTGGCTCCCTGAAGGTCAACGAGGACGTCGAGATCATCGGTAT | 746 | SEQ ID NO: 952 |
| NMEN-MC58 | AACCGGCCGTGTAGAGCGCGGTATCATCCACGTTGGTGACGAGATTGAAATCGTCGGTCT | 743 | SEQ ID NO: 953 |
| NMEN-Z2491 | AACCGGTCGTGTAGAGCGCGGTATCATCCACGTCGGTGACGAGATCGAAATCGTCGGTCT | 743 | SEQ ID NO: 954 |
| NMEN-DAS | AACCGGCCGTGTAGAGCGCGGTATCATCCACGTTGGTGACGAGATTGAAATCGTCGGTCT | 584 | SEQ ID NO: 955 |
| | | | |
| MPNE-HF2 | ---CCATGATACTAGAAAAGCAGTTGTTACTGGTATGGAAATGTTAAGAAAAACATTAGA | 800 | SEQ ID NO: 956 |
| MPNE-M129 | ---ACGTCCAATCCGTAAAGCAGTTGTTACCGGAATCGAAATGTTCAAAAAGGAACTTGA | 800 | SEQ ID NO: 957 |
| LPNE-Paris | ---AAGAGACACTCAAAAGACGACTTGTACGGGTGTTGAGATGTTCCGTAAATTACTTGA | 819 | SEQ ID NO: 958 |
| LPNE2-DAS | ---AAGAGACACCCAAAAGACGACTTGTACGGGTGTTGAGATGTTCCGTAAATTACTTGA | 689 | SEQ ID NO: 959 |
| LPNE-Philadelphia1 | ---AAGAGACACCCAAAAGACGACTTGTACGGGTGTTGAGATGTTCCGTAAATTACTTGA | 806 | SEQ ID NO: 960 |
| LPNE-Lens | ---AAGAGACACCCAAAAGACGACTTGTACTGGTGTTGAGATGTTCCGTAAATTACTTGA | 806 | SEQ ID NO: 961 |
| LLON-DAS | ---TCGTGATACTGCAAAGACTACCTGTACTGGTGTTGAGATGTTCCGTAAGTTATTAGA | 690 | SEQ ID NO: 962 |
| FNUC-DAS | ---TAAACCTACAACTAAAACAACTTGTACAGGGGTTGAAATGTTTAGAAAACTTCTTGA | 678 | SEQ ID NO: 963 |
| CPNE-CWL029 | ---AGGAGAGACTAAAGAAACAATCGTTACTGGAGTCGAAATGTTCAGGAAAGAACTTCC | 800 | SEQ ID NO: 964 |
| EFAE-DAS | TAAAGACGAAACATCTAAAACAACTGTTACAGGTGTTGAAATGTTCCGTAAATTATTAGA | 680 | SEQ ID NO: 965 |
| EPAE-V583 | TAAAGACGAAACATCTAAAACAACTGTTACAGGTGTTGAAATGTTCCGTAAATTATTAGA | 803 | SEQ ID NO: 966 |
| SAUR-Mu50 | ---ACATGACACATCTAAAACAACTGTTACAGGTGTTGAAATGTTCCGTAAATTATTAGA | 800 | SEQ ID NO: 967 |
| SAUR-N315 | ---ACATGACACATCTAAAACAACTGTTACAGGTGTTGAAATGTTCCGTAAATTATTAGA | 800 | SEQ ID NO: 968 |
| SAUR-MW2 | ---ACATGACACATCTAAAACAACTGTTACAGGTGTTGAAATGTTCCGTAAATTATTAGA | 800 | SEQ ID NO: 969 |
| SAUR-MSSA476 | ---ACATGACACATCTAAAACAACTGTTACAGGTGTTGAAATGTTCCGTAAATTATTAGA | 800 | SEQ ID NO: 970 |
| SAUR-MRSA252 | ---ACATGACACATCTAAAACAACTGTTACAGGTGTTGAAATGTTCCGTAAATTATTAGA | 800 | SEQ ID NO: 971 |
| SEPI-12228 | ---GCACGAAACTTCTAAAACAACTGTTACTGGTGTAGAAATGTTCCGTAAATTATTAGA | 800 | SEQ ID NO: 972 |
| SEPI-RP62A | ---GCACGAAACTTCTAAAACAACTGTTACTGGTGTAGAAATGTTCCGTAAATTATTAGA | 800 | SEQ ID NO: 973 |
| SMIT-DAS | TAAAGAAGAAATCCAAAAAGCGGTTGTTACTGGTGTTGAAATGTTCCGTAAACAACTTGA | 671 | SEQ ID NO: 974 |
| SSAN-DAS | CAAAGAAGAAATCCAAAAAGCAGTTGTTACTGGTGTTGAAATGTTCCGTAAACAGCTTGA | 712 | SEQ ID NO: 975 |
| SMIT-NCTC12261 | CAAAGAAGAAACTCAAAAAGCAGTTGTTACTGGTGTTGAAATGTTCCGTAAACAACTTGA | 812 | SEQ ID NO: 976 |
| SPNE-R6 | CAAAGAAGAAACTCAAAAAGCAGTTGTTACTGGTGTTGAAATGTTCCGTAAACAACTTGA | 812 | SEQ ID NO: 977 |
| SPYO-M1GAS | CAAAGAAGAAACTAAAAAAGCTGTTGTTACTGGTGTTGAAATGTTCCGTAAACAACTTGA | 812 | SEQ ID NO: 978 |
| SMUT-DAS | CCGTGATGACATTCAAAAAGCTGTTGTTACTGGTGTTGAAATGTTCCGTAAACAATTGGA | 712 | SEQ ID NO: 979 |
| SMUT-DA159 | CCGTGATGACATTCAAAAAGCTGTTGTTACTGGTGTTGAAATGTTCCGTAAACAATTGGA | 812 | SEQ ID NO: 980 |
| HINF-RdKW20 | ---CAAAGATACAGCGAAAACTACTGTAACGGGTGTTGAAATGTTCCGTAAATTACTTGA | 800 | SEQ ID NO: 981 |
| MCAT-DAS | ---CAAACCAACTACTAAAACCACTTGTACTGGTGTTGAAATGTTCCGTAAGCTGCTAGA | 657 | SEQ ID NO: 982 |
| BPER-TohamaI | CAAGCCGACGG---TGAAGACGACCTGCACGGGCGTGGAGATGTTCCGCAAGCTGCTGGA | 806 | SEQ ID NO: 983 |
| BPAR-12822 | CAAGCCGACGG---TGAAGACGACCTGCACGGGCGTGGAGATGTTCCGCAAGCTGCTGGA | 806 | SEQ ID NO: 984 |
| BCEP2-DAS | CAAGCCGACGG---TGAAGACGACCTGCACGGGCGTTGAAATGTTCCGCAAGCTGCTGGA | 690 | SEQ ID NO: 985 |
| BPSE-1710b | CAAGGCGACGG---CGAAGACGACCTGCACGGGCGTGGAAATGTTCCGCAAGCTGCTGGA | 806 | SEQ ID NO: 986 |
| SMAL-DAS | CCGTCCGGTGC---AGAAGACCACCGTGACCGGCGTTGAAATGTTCCGCAAGCTGCTGGA | 711 | SEQ ID NO: 987 |
| PAER-PA01 | CAAGGCGACCA---CCAAGACTACCTGCACCGGCGTTGAAATGTTCCGCAAGCTGCTCGA | 809 | SEQ ID NO: 988 |
| KPNE-DAS | CAAAGAAACCG---CGAAAACCACCTGTACTGGCGTTGAAATGTTCCGCAAACTGCTGGA | 684 | SEQ ID NO: 989 |
| MAVI-K10 | CCGCCCGTCCAGCACCAAGACCACGGTCACCGGTGTGGAGATGTTCCGCAAGCTGCTCGA | 806 | SEQ ID NO: 990 |
| MAVI-paratub | CCGCCCGTCCAGCACCAAGACCACGGTCACCGGTGTGGAGATGTTCCGCAAGCTGCTCGA | 806 | SEQ ID NO: 991 |
| MAISpig-DAS | CAAGCCGACCAGCACCAAGACCACCGTCACCGGTGTGGAGATGTTCCGCAAGCTGCTCGA | 701 | SEQ ID NO: 992 |
| MKAN-DAS | CCGTCCGACCACCACCAAGACCACGGTCACCGGTGTGGAGATGTTCCGCAAGCTGCTCGA | 707 | SEQ ID NO: 993 |
| MTUB-H37Rv | TCGCCCATCGACCACCAAGACCACCGTCACCGGTGTGGAGATGTTCCGCAAGCTGCTCGA | 806 | SEQ ID NO: 994 |
| MTUB-CDC1551 | TCGCCCATCGACCACCAAGACCACCGTCACCGGTGTGGAGATGTTCCGCAAGCTGCTCGA | 806 | SEQ ID NO: 995 |
| MAVI-DAS | CCGCCCGACCACGACCAAGACCACCGTCACCGGTGTGGAAATGTTCCGCAAGCTGCTCGA | 647 | SEQ ID NO: 996 |
| CIDP-NCTC13129 | CCGCGAGAAGGCTACCACCACCACCGTTACCGGTATCGAGATGTTCCGTAAGCTTCTCGA | 806 | SEQ ID NO: 997 |
| NMEN-MC58 | GAAAGAAACCC---AAAAAACCACTTGTACCGGTGTTGAAATGTTCCGCAAACTGCTGGA | 800 | SEQ ID NO: 998 |
| NMEN-Z2491 | GAAAGAAACTC---AAAAAACCACTTGTACCGGTGTTGAAATGTTCCGCAAACTGCTGGA | 800 | SEQ ID NO: 999 |
| NMEN-DAS | GAAAGAAACCC---AAAAAACCACCTGTACCGGTGTTGAAATGTTCCGCAAACTGCTGGA | 641 | SEQ ID NO: 1000 |
| | | | |
| MPNE-HF2 | CGAAGTAAAAGCTGGGGATAACGCTGGTATCTTATTAAGAGGTATTGATAGAAAAGATGT | 860 | SEQ ID NO: 1001 |
| MPNE-M129 | TTCAGCAATGGCTGGGGACAACGCTGGGGTATTACTCCGTGGTGTGGACCGTAAAGAAGT | 860 | SEQ ID NO: 1002 |
| LPNE-Paris | TGAAGGTCGAGCTGGTGATAACGTTGGAGTGTTATTACGAGGTACGAAGCGAGATGAAGT | 879 | SEQ ID NO: 1003 |
| LPNE2-DAS | TGAAGGTCGAGCTGGTGATAACGTTGGTGTGTTATTACGAGGTACGAAGCGAGATGAAGT | 749 | SEQ ID NO: 1004 |
| LPNE-Philadelphia1 | TGAAGGTCGAGCTGGTGATAACGTTGGTGTGTTATTACGAGGTACGAAGCGAGATGAAGT | 866 | SEQ ID NO: 1005 |
| LPNE-Lens | TGAAGGTCGAGCTGGTGATAACGTTGGTGTGTTATTACGCGGTACGAAGCGAGATGAAGT | 866 | SEQ ID NO: 1006 |
| LLON-DAS | CGAAGGACGTGCAGGTGATAACGTTGGTATATTACTCCGTGGAACAAAACGAGACGAAGT | 750 | SEQ ID NO: 1007 |
| FNUC-DAS | TCAAGGTCAAGCAGGAGATAATATCGGAGTATTATTAAGAGGAACTAAGAAAGAAGAAGT | 738 | SEQ ID NO: 1008 |
| CPNE-CWL028 | TGAAGGTCGTGCAGGAGAAAACGTTGGTTTACTCCTCAGAGGTATTGGAAAGAACGATGT | 860 | SEQ ID NO: 1009 |
| EFAE-DAS | CTACGCTGAAGCAGGCGACAACATCGGTGCTTTATTACGTGGTGTAGCACGTGAAGATAT | 740 | SEQ ID NO: 1010 |
| EFAE-V583 | CTACGCTGAAGCAGGCGACAACATCGGTGCTTTATTACGTGGTGTAGCACGTGAAGATAT | 863 | SEQ ID NO: 1011 |
| SAUR-Mu50 | CTACGCTGAAGCTGGTGACAACATTGGTGCATTATTACGTGGTGTTGCTCGTGAAGACGT | 860 | SEQ ID NO: 1012 |
| SAUR-N315 | CTACGCTGAAGCTGGTGACAACATTGGTGCATTATTACGTGGTGTTGCTCGTGAAGACGT | 860 | SEQ ID NO: 1013 |
| SAUR-MW2 | CTACGCTGAAGCTGGTGACAACATTGGTGCATTATTACGTGGTGTTGCTCGTGAAGACGT | 860 | SEQ ID NO: 1014 |
| SAUR-MSSA476 | CTACGCTGAAGCTGGTGACAACATTGGTGCATTATTACGTGGTGTTGCTCGTGAAGACGT | 860 | SEQ ID NO: 1015 |
| SAUR-MRSA252 | CTACGCTGAAGCTGGTGACAACATTGGTGCATTATTACGTGGTGTTGCTCGTGAAGACGT | 860 | SEQ ID NO: 1016 |
| SEPI-12228 | CTACGCTGAAGCTGGTGACAACATCGGTGCTTTATTACGTGGTGTTGCACGTGAAGACGT | 860 | SEQ ID NO: 1017 |
| SEPI-RP62A | CTACGCTGAAGCTGGTGACAACATCGGTGCTTTATTACGTGGTGTTGCACGTGAAGACGT | 860 | SEQ ID NO: 1018 |
| SMIT-DAS | CGAATGTCTTGCAGGGGACAACGTTGGTGTGCTTCTTCGTGGTATCCAACGTGATGAAAT | 731 | SEQ ID NO: 1019 |
| SSAN-DAS | CGAAGGTCTTGCAGGGGACAACGTAGGTGTGCTTCTCCGTGGTATCCAACGTGATGAAAT | 772 | SEQ ID NO: 1020 |
| SMIT-NCTC12261 | CGAAGGTCTTGCCGGAGATAATGTAGGTGTCCTTCTTCGTGGTGTTCAACGTGATGAAAT | 872 | SEQ ID NO: 1021 |
| SPNE-R6 | CGAAGGTCTTGCTGGAGATAACGTAGGTGTCCTTCTTCGTGGTGTTCAACGTGATGAAAT | 872 | SEQ ID NO: 1022 |
| SPYO-M1GAS | CGAAGGTCTTGCAGGAGACAACGTAGGTATCCTTCTTCGTGGTGTTCAACGTGACGAAAT | 872 | SEQ ID NO: 1023 |
| SMUT-DAS | TGAAGGTATTGCAGGGGATAATGTTGGTGTTCTCCTTCGTGGTATCCAACGTGATGAAAT | 772 | SEQ ID NO: 1024 |
| SMUT-UA159 | TGAAGGTATTGCAGGGGATAATGTTGGTGTTCTCCTTCGTGGTATCCAACGTGATGAAAT | 872 | SEQ ID NO: 1025 |
| HINF-RdKW20 | CGAAGGTCGTGCAGGTGAAAACATCGGTGCATTATTACGTGGTACCAAACGTGAAGAAAT | 860 | SEQ ID NO: 1026 |
| MCAT-DAS | CGAAGGTCGTGCAGGTGAGAACTGTGGTATCCTACTACGTGGTACTAAGCGTGAAGAAGT | 717 | SEQ ID NO: 1027 |
| BPER-TohamaI | CCAGGGCCAGGCGGGCGACAACGTGGGTATCTTGCTGCGCGGCACCAAGCGTGAAGACGT | 866 | SEQ ID NO: 1028 |
| BPAR-12822 | CCAGGGCCAGGCGGGCGACAACGTGGGTATCTTGCTGCGCGGCACCAAGCGTGAAGACGT | 866 | SEQ ID NO: 1029 |

TABLE 1-continued

| | | | |
|---|---|---|---|
| BCEP2-DAS | CCAGGGTCAGGCAGGCGACAACGTCGGTATCCTGCTGCGCGGCACGAAGCGTGAAGACGT | 750 | SEQ ID NO: 1030 |
| BPSE-1710b | TCAGGGTCAGGCGGGCGACAACGTCGGTATCCTGCTGCGCGGCACGAAGCGTGAAGACGT | 866 | SEQ ID NO: 1031 |
| SMAL-DAS | CCAGGGTCAGGCAGGCGACAACGCTGGCCTGCTGCTGCGCGGCACCAAGCGTGACGACGT | 771 | SEQ ID NO: 1032 |
| PAER-PA01 | CGAAGGTCGTGCTGGTGAGAACGTTGGTATCCTGCTGCGTGGCACCAAGCGTGAAGACGT | 869 | SEQ ID NO: 1033 |
| KPNE-DAS | CGAAGGCCGTGCTGGTGAGAACGTAGGTGTTCTGCTGCGTGGTATCAAACGTGAAGAAAT | 744 | SEQ ID NO: 1034 |
| MAVI-K10 | CCAGGGCCAGGCCGGTGACAACGTCGGTCTGCTGCTGCGTGGTATCAAGCGTGAGGACGT | 866 | SEQ ID NO: 1035 |
| MAVI-paratub | CCAGGGCCAGGCCGGTGACAACGTCGGTCTGCTGCTGCGTGGTATCAAGCGTGAGGACGT | 866 | SEQ ID NO: 1036 |
| MAISpig-DAS | CCAGGGACAGGCCGGCGACAACGTCGGACTGTTGCTGCGTGGCATCAAGCGCGAGGACGT | 761 | SEQ ID NO: 1037 |
| MKAN-DAS | CCAGGGTCAGGCCGGTGACAACGTCGGGCTGTTGCTGCGTGGTGTCAAGCGTGAGGACGT | 767 | SEQ ID NO: 1038 |
| MTUB-H37Rv | CCAGGGCCAGGCGGGCGACAACGTTGGTTTGCTGCTGCGGGGCGTCAAGCGCGAGGACGT | 866 | SEQ ID NO: 1039 |
| MTUB-CDC1551 | CCAGGGCCAGGCGGGCGACAACGTTGGTTTGCTGCTGCGGGGCGTCAAGCGCGAGGACGT | 866 | SEQ ID NO: 1040 |
| MAVI-DAS | CCAGGGCCAGGCCGGCGACAACGTCGGTCTGCTGGTTCGTGGCATCAAGCGCGAGGACGT | 707 | SEQ ID NO: 1041 |
| NCTC13129 | CTACACCGAGGCTGGCGACAACTGTGGTCTGCTTCTCCGTGGCGTTAAGCGCGAAGACGT | 866 | SEQ ID NO: 1042 |
| NMEN-MC58 | CGAAGGTCAGGCGGGCGACAACGTAGGCGTATTGCTGCGCGGTACCAAACGTGAAGACGT | 860 | SEQ ID NO: 1043 |
| NMEN-Z2491 | CGAAGGTCAAGCAGGCGACAACGTAGGCGTATTGCTGCGCGGTACCAAACGTGAAGACGT | 860 | SEQ ID NO: 1044 |
| NMEN-DAS | CGAAGGTCAGGCGGGCGACAACGTACGCGTATTGCTGCGCGGTACCAAACGTGAAGACGT | 701 | SEQ ID NO: 1045 |
| MPNE-HF2 | TGAACGTGGACAAGTATTAGCTAAACC-TGGTTCAATTAAACCTCACAAACAATTTGAAG | 919 | SEQ ID NO: 1046 |
| MPNE-M129 | GGAACGTGGTCAAGTGTTAGCTAAACC-AGGTTCGATTAAACCGCACAAGAAATTTAAAG | 919 | SEQ ID NO: 1047 |
| LPNE-Paris | GGAGCGTGGACAGGTATTGGCAAAGCC-AGGTACCATCAAGCCACACACCAAGTTTGAAG | 938 | SEQ ID NO: 1048 |
| LPNE2-DAS | GGAGCGTGGACAGGTATTGGCTAAGCC-AGGTACCATCAAGCCACACACCAAGTTTGAAG | 808 | SEQ ID NO: 1049 |
| LPNE-Philadelphia1 | GGAGCGTGGACAGGTATTGGCGAAGCC-AGGAACCATCAAGCCACACACCAAGTTTGAAG | 925 | SEQ ID NO: 1050 |
| LPNE-Lens | GGAGCGCGGACAGGTATTGGCTAAGCC-AGGAACCATCAAGCCACACACCAAGTTTGAAG | 925 | SEQ ID NO: 1051 |
| LLON-DAS | TGAGCGTGGTCAGGTATTAGCCAAACC-AGGTACAATTAAGCCTCACACTAAATTTGAAG | 809 | SEQ ID NO: 1052 |
| FNUC-DAS | TGAAAGAGGACAAGTTCTTGCTAAACC-AGGAAGTATCCACCCTCATACAAACTTTAAAG | 797 | SEQ ID NO: 1053 |
| CPNE-CWL029 | TGAAAGAGGTATGGTGGTTTGTCAGCC-TAACAGCGTGAAGCCTCATACGAAATTTAAGT | 919 | SEQ ID NO: 1054 |
| EFAE-DAS | CGAACGTGGACAAGTATTAGCTAAACC-AGCTACAATCACTCCACACACAAAATTCAAAG | 799 | SEQ ID NO: 1055 |
| EFAE-V583 | CGAACGTGGACAAGTATTAGCTAAACC-AGCTACAATCACTCCACACACAAAATTCAAAG | 922 | SEQ ID NO: 1056 |
| SAUR-Mu50 | ACAACGTGGTCAAGTATTAGCTGCTCC-TGGTTCAATTACACCACATACTGAATTTAAAG | 919 | SEQ ID NO: 1057 |
| SAUR-N315 | ACAACGTGGTCAAGTATTAGCTGCTCC-TGGTTCAATTACACCACATACTGAATTTAAAG | 919 | SEQ ID NO: 1058 |
| SAUR-MW2 | ACAACGTGGTCAAGTATTAGCTGCTCC-TGGTTCAATTACACCACATACTGAATTTAAAG | 919 | SEQ ID NO: 1059 |
| SAUR-MSSA476 | ACAACGTGGTCAAGTATTAGCTGCTCC-TGGTTCAATTACACCACATACTGAATTTAAAG | 919 | SEQ ID NO: 1060 |
| SAUR-MRSA252 | ACAACGTGGTCAAGTATTAGCTGCTCC-TGGTTCAATTACACCACATACTGAATTTAAAG | 919 | SEQ ID NO: 1061 |
| SEPI-12228 | ACAACGTGGTCAAGTATTAGCTGCTCC-TGGTTCTATTACACCACACAAAATTCAAAG | 919 | SEQ ID NO: 1062 |
| SEPI-RP62A | ACAACGTGGTCAAGTATTAGCTGCTCC-TGGTTCTATTACACCACACACAAAATTCAAAG | 919 | SEQ ID NO: 1063 |
| SMIT-DAS | CGAACGTGGACAAGTTATCGCTAAACC-AGGTTCAATCAACCCACACACTAAATTCAAAG | 790 | SEQ ID NO: 1064 |
| SSAN-DAS | CGAACGTGGACAAGTTATCGCTAAACC-AGGTTCAATCAACCCACACACTAAATTCAAAG | 831 | SEQ ID NO: 1065 |
| SMIT-NCTC12261 | CGAACGTGGACAAGTTATTGCTAAACC-AGGTTCAATCAACCCACACACTAAATTCAAAG | 931 | SEQ ID NO: 1066 |
| SPNE-R6 | CGAACGTGGACAAGTTATCGCTAAACC-AGGTTCAATCAACCCACACACTAAATTCAAAG | 931 | SEQ ID NO: 1067 |
| SPYO-M1GAS | CGAACGTGGTCAAGTTATTGCTAAACC-AGGTTCAATCAACCCACACACTAAATTCAAAG | 931 | SEQ ID NO: 1068 |
| SMUT-DAS | CGAACGTGGTCAAGTTCTTGCTAAACC-AGGTTCAATTCACCCACATACTAAATTCAAAG | 831 | SEQ ID NO: 1069 |
| SMUT-UA159 | CGAACGTGGTCAAGTTCTTGCTAAACC-AGGTTCAATTCACCCACATACTAAATTCAAAG | 931 | SEQ ID NO: 1070 |
| HINF-RdKW20 | CGAACGTGGTCAAGTATTAGCGAAACC-AGGTTCAATTCACACCACACACTGACTTGAAT | 919 | SEQ ID NO: 1071 |
| MCAT-DAS | TCAACGTGGTCAAGTATTGGCTAAGCC-AGGTTCAATCACCCCACACACCAAGTTTGATG | 776 | SEQ ID NO: 1072 |
| BPER-TohamaI | CGAGCGTGGCCAGGTGCTGGCCAAGCC-GGGTTCGATCAACCCGCACACGGACTTCACGG | 925 | SEQ ID NO: 1073 |
| BPAR-12822 | CGAGCGTGGCCAGGTGCTGGCCAAGCC-GGGTTCGATCAACCCGCACACGGACTTCACGG | 925 | SEQ ID NO: 1074 |
| BCEP2-DAS | GGAGCGCGGTCAGGTTCTGGCGAAGCC-GGGTTCGATCACGCCGCACACGCACTTCACGG | 809 | SEQ ID NO: 1075 |
| BPSE-1710b | GGAGCGCGGCCAGGTTCTGGCGAAGCC-GGGTTCGATCACGCCGCACACGCACTTCACGG | 925 | SEQ ID NO: 1076 |
| SMAL-DAS | CGAGCGTGGCCAGGTGCTGGCCAAGCC-GGGCACGATCAAGCCGCACACCAAGTTCGAAG | 830 | SEQ ID NO: 1077 |
| PAER-PA01 | AGAGCGTGGCCAGGTACTGGCCAAGCC-GGGCACCATCAAGCCGCACACCAAGTTCGAGT | 928 | SEQ ID NO: 1078 |
| KPNE-DAS | CGAACGTGGTCAGGTACTGGCTAAGCC-GGGCACCATCAACCCGCACACCAAGTTCGAAT | 803 | SEQ ID NO: 1079 |
| MAVI-K10 | CGAGCGCGGTCAGGTCGTCACCAAGCC-CGGCACCACCACGCCGCACACCGAGTTCGAGG | 925 | SEQ ID NO: 1080 |
| MAVI-paratub | CGAGCGCGGTCAGGTCGTCACCAAGCC-CGGCACCACCACGCCGCACACCGAGTTCGAGG | 925 | SEQ ID NO: 1081 |
| MAISpig-DAS | CGAGCGCGGTCAGGTCGTCGTGAAGCC-CGGCACCACCACGCCGCACACCGAGTTCGAGG | 820 | SEQ ID NO: 1082 |
| MKAN-DAS | CGAGCGCGGCCAGGTCGTCATCAAGCC-CGGCACCACAACCCCGCACACCGAGTTCGAGG | 826 | SEQ ID NO: 1083 |
| MTUB-H37Rv | CGAGCGTGGCCAGGTTGTCACCAAGCC-CGGCACCACCACGCCGCACACCGAGTTCGAAG | 925 | SEQ ID NO: 1084 |
| MTUB-CDC1551 | CGAGCGTGGCCAGGTTGTCACCAAGCC-CGGCACCACCACGCCGCACACCGAGTTCGAAG | 925 | SEQ ID NO: 1085 |
| MAVI-DAS | CGAGCGTGGCCAGGTTGTGGTCAAGCC-CGGCACCACCACCCCGCACACCGAGTTCGAGG | 766 | SEQ ID NO: 1086 |
| NCTC13129 | TGAGCGTGGCCAGGTTGTTGTTAAGCC-AGGCGCTTACACCCCTCACACCGAGTTCGAGG | 925 | SEQ ID NO: 1087 |
| NMEN-MC58 | GGAACGCGGTCAGGTATTGGCTAAACC-GGGTACTATCACTCCTCACACCAAATTCAAAG | 919 | SEQ ID NO: 1088 |
| NMEN-Z2491 | AGAGCGTGGTCAAGTATTGGCTAAACC-GGGTACAATCACTCCTCACACCAAGTTCAAAG | 919 | SEQ ID NO: 1089 |
| NMEN-DAS | GGAACGCGGTCAGGTATTGGCCAAACCCGGGTACTATCACTCCTCACACCAAGTTCAAAG | 761 | SEQ ID NO: 1090 |
| MPNE-HF2 | CAGAAATCTAGTCTCTTAAAAAAGAAGAAGGTGGAAGACATACTCCAGTATTAAATGGAT | 979 | SEQ ID NO: 1091 |
| MPNE-M129 | CGGAAATCTATGCTTTAAAGAAGGAAGAAGGTGGTCGTCACACCGGTTTCTTAAACGGTT | 979 | SEQ ID NO: 1092 |
| LPNE-Paris | CAGAAGTGTATGTGTTATCCAAGGAAGAAGGCGGACGTCACACACCATTCTTTAATGGAT | 998 | SEQ ID NO: 1093 |
| LPNE2-DAS | CAGAAGTGTATGTATTATCCAAGGAAGAAGGCGGACGTCACACACCATTCTTTAATGGAT | 868 | SEQ ID NO: 1094 |
| LPNE-Philadelphia1 | CAGAAGTGTATGTATTATCCAAGGAAGAAGGCGGACGTCACACTCCATTCTTTAATGGAT | 985 | SEQ ID NO: 1095 |
| LPNE-Lens | CAGAAGTGTATGTATTATCGAAGGAAGAAGGCGGACGTCACACTCCATTCTTTAATGGAT | 985 | SEQ ID NO: 1096 |
| LLON-DAS | CAGAAGTGTATGTATTATCGAAGGAAGAAGGCGGACGTCACACTCCATTCTTTAATGGAT | 869 | SEQ ID NO: 1097 |
| FNUC-DAS | GTGAAGTCTATGTATTAACTAAAGATGAAGGAGGAAGACACACTCCATTTTTCACAGGAT | 857 | SEQ ID NO: 1098 |
| CPNE-CWL029 | CAGCTGTTTACGTTCTTCAGAAAGAAGAAGGCGGACGTCATAAGCCTTTCTTCAGCGGAT | 979 | SEQ ID NO: 1099 |
| EFAE-DAS | CTGAAGTATACGTATTATCAAAAGAAGAAGGCGGACGTCACACTCCATTCTTCACTAACT | 859 | SEQ ID NO: 1100 |
| EFAE-V583 | CTGAAGTATACGTATTATCAAAAGAAGAACGCGGACGTCACACTCCATTCTTCACTAACT | 982 | SEQ ID NO: 1101 |
| SAUR-Mu50 | CAGAAGTATACGTATTATCAAAAGACGAAGGTGGACGTCACACTCCATTCTTCTCAAACT | 979 | SEQ ID NO: 1102 |
| SAUR-N315 | CAGAAGTATACGTATTATCAAAAGACGAAGGTGGACGTCACACTCCATTCTTCTCAAACT | 979 | SEQ ID NO: 1103 |
| SAUR-MW2 | CAGAAGTATACGTATTATCAAAAGACGAAGGTGGACGTCACACTCCATTCTTCTCAAACT | 979 | SEQ ID NO: 1104 |
| SAUR-MSSA476 | CAGAAGTATACGTATTATCAAAAGACGAAGGTGGACGTCACACTCCATTCTTCTCAAACT | 979 | SEQ ID NO: 1105 |
| SAUR-MRSA252 | CAGAAGTATACGTATTATCAAAAGACGAAGGTGGACGTCACACTCCATTCTTCTCAAACT | 979 | SEQ ID NO: 1106 |
| SEPI-12228 | CTGAAGTATACGTATTATCTAAAGATGAAGGTGGACGTCACACTCCATTCTTCACTAACT | 979 | SEQ ID NO: 1107 |

TABLE 1-continued

| | | | |
|---|---|---|---|
| SEPI-RP62A | CTGAAGTATACGTATTATCTAAAGATGAAGGTGGACGTCACACTCCATTCTTCACTAACT | 979 | SEQ ID NO: 1108 |
| SMIT-DAS | GTGAAGTTTACATCCTTACTAAAGAAGAAGGTGGACGTCATACTCCATTCTTCAACAACT | 850 | SEQ ID NO: 1109 |
| SSAN-DAS | GTGAAGTTTATATCCTTACTAAAGAAGAAGGCGGACGTCACACTCCATTCTTCAACAACT | 891 | SEQ ID NO: 1110 |
| SMIT-NCTC12261 | GTGAAGTTTACATCCTTACTAAAGAAGAAGGTGGACGTCACACTCCATTCTTCAACAACT | 991 | SEQ ID NO: 1111 |
| SPNE-R6 | GTGAAGTCTACATCCTTACTAAAGAAGAAGGTGGACGTCACACTCCATTCTTCAACAACT | 991 | SEQ ID NO: 1112 |
| SPYO-M1GAS | GTGAAGTATATATCCTTTCTAAAGACGAAGGTGGACGTCACACTCCATTCTTCAACAACT | 991 | SEQ ID NO: 1113 |
| SMUT-DAS | GTGAAGTTTATATCCTTACTAAAGAAGAAGGTGGACGTCATACACCATTCTTCAATAACT | 891 | SEQ ID NO: 1114 |
| SMUT-UA159 | GTGAAGTTTATATCCTTACTAAAGAAGAAGGTGGACGTCATACACCATTCTTCAATAACT | 991 | SEQ ID NO: 1115 |
| HINF-RdKW20 | CAGAAGTGTACGTATTATCAAAAGATGAAGGTGGTCGTCATACTCCATTCTTCAAAGGTT | 979 | SEQ ID NO: 1116 |
| MCAT-DAS | CAGAAGTATACGTGCTATCAAAAGAAGAAGGTGGTCGTCATACCCCATTCCTAAATGGCT | 836 | SEQ ID NO: 1117 |
| BPER-TohamaI | CCGAGGTGTACATTCTGTCCAAGGAAGAGGGTGGCCGTCACACGCCGTTCTTCAACGGCT | 985 | SEQ ID NO: 1118 |
| BPAR-12822 | CCGAGGTGTACATTCTGTCCAAGGAAGAGGGTGGCCGTCACACGCCGTTCTTCAACGGCT | 985 | SEQ ID NO: 1119 |
| BCEP2-DAS | CCGAAGTGTACGTGCTGAGCAAGGACGAAGGCGGCCGTCACACGCCGTTCTTCAACAACT | 869 | SEQ ID NO: 1120 |
| BPSE-1710b | CTGAAGTGTACGTGCTGAGCAAGGACGAAGGCGGCCGCCACACGCCGTTCTTCAACAACT | 985 | SEQ ID NO: 1121 |
| SMAL-DAS | GCGAAGTGTACGTCCTGTCGAAGGACGAAGGCGGCCGCCACACCCCGTTCTTCAACGGCT | 890 | SEQ ID NO: 1122 |
| PAER-PA01 | GCGAAGTGTACGTGCTGTCCAAGGAAGAAGGTGGTCGTCACACCCCGTTCTTCAAGGGCT | 988 | SEQ ID NO: 1123 |
| KPNE-DAS | CTGAAGTGTACATCCTGTCCAAAGACGAAGGCGGCCGTCATACTCCGTTCTTCAAAGGCT | 863 | SEQ ID NO: 1124 |
| MAVI-K10 | GCCAGGTCTACATCCTGTCCAAGGACGAGGGCGGCCGGCACACGCCGTTCTTCAACAACT | 985 | SEQ ID NO: 1125 |
| MAVI-paratub | GCCAGGTCTACATCCTGTCCAAGGACGAGGGCGGCCGGCACACGCCGTTCTTCAACAACT | 985 | SEQ ID NO: 1126 |
| MAISpig-DAS | GCAGCGTCTACATCCTGTCCAAGGACGAGGGCGGCCGGCACACGCCGTTCTTCAACAACT | 880 | SEQ ID NO: 1127 |
| MKAN-DAS | GCCAGGTTTACATCCTGTCCAAGGACGAGGGTGGCCGGCACACGCCGTTCTTCAACAACT | 886 | SEQ ID NO: 1128 |
| MTUB-H37Rv | GCCAGGTCTACATCCTGTCCAAGGACGAGGGCGGCCGGCACACGCCGTTCTTCAACAACT | 985 | SEQ ID NO: 1129 |
| MTUB-CDC1551 | GCCAGGTCTACATCCTGTCCAAGGACGAGGGCGGCCGGCACACGCCGTTCTTCAACAACT | 985 | SEQ ID NO: 1130 |
| MAVI-DAS | GCAGCGTCTACATCCTGTCCAAGGACGAGGGCGGCCGCCACACGCCGTTCTTCAACAACT | 826 | SEQ ID NO: 1131 |
| NCTC13129 | GCTCTGTCTACGTTCTGTCCAAGGACGAGGGTGGCCGCCACACCCCATTCTTCGACAACT | 985 | SEQ ID NO: 1132 |
| NMEN-MC58 | CAGAAGTATACGTACTGAGCAAAGAAGAGGGTGGTCGTCACACTCCGTTCTTCGCCAACT | 979 | SEQ ID NO: 1133 |
| NMEN-Z2491 | CAGAAGTATACGTACTGAGCAAAGAAGAGGGCGGCCGCCATACCCCGTTCTTCGCCAACT | 979 | SEQ ID NO: 1134 |
| NMEN-DAS | CAGACGTGTACGTACTGAGCAAAGAAGAGGGCGGCCGCCATACTCCGTTCTTCGCCAACT | 821 | SEQ ID NO: 1135 |
| MPNE-HF2 | ATAGACCACAATTCTACTTCAGAACTACTGATGTTACTGGACAAATCACACTTGATAAAG | 1039 | SEQ ID NO: 1136 |
| MPNE-M129 | ACCGTCCCCAATTCTACTTCCGTACTACAGACGTTACTGGTTCGATTTCCCTACCAGAAA | 1039 | SEQ ID NO: 1137 |
| LPNE-Paris | ACCGTCCACAATTCTATTTCAGAACCACTGACGTGACAGGTACTTGTGACTTGCCATCAG | 1058 | SEQ ID NO: 1138 |
| LPNE2-DAS | ACCGTCCACAATTCTATTTCAGAACCACTGACGTAACA---------------------- | 906 | SEQ ID NO: 1139 |
| LPEN-Philadelphia1 | ACCGTCCACAATTCTATTTCAGAACCACTGACGTGACAGGTACTTGTGACTTGCCATCAG | 1045 | SEQ ID NO: 1140 |
| LPNE-Lens | ACCGTCCACAATTCTATTTCAGAACCACTGACGTGACAGGTACTTGTGACTTGCCATCAG | 1045 | SEQ ID NO: 1141 |
| LLON-DAS | ATAGACCACAGTTTATTTTAGAACAACAGACGTAACAGGAACTTGTGATTTACCATCTG | 929 | SEQ ID NO: 1142 |
| FNUC-DAS | ACAGACCTCAATTCTATTTTAGAACTACTGATATCACTGGTGCAGTAACTTTACCAGATG | 917 | SEQ ID NO: 1143 |
| CPNE-CWL029 | ACAGACCTCAGTTCTTCTTCCGTACTACAGACGTGACAGGAGTCGTAACTCTTCCTGAAG | 1039 | SEQ ID NO: 1144 |
| EFAE-DAS | ACCGTCCTCAATTCTACTTCCGTACAACAGACGTTACTGGTGTTGTAGAATTGCCAGAAG | 919 | SEQ ID NO: 1145 |
| EFAE-V583 | ACCGTCCTCAATTCTACTTCCGTACAACAGACGTTACTGGTGTTGTAGAATTGCCAGAAG | 1042 | SEQ ID NO: 1146 |
| SAUR-Mu50 | ATCGTCCACAATTCTATTTCCGTACTACTGACGTAACTGGTGTTGTTCACTTACCAGAAG | 1039 | SEQ ID NO: 1147 |
| SAUR-N315 | ATCGTCCACAATTCTATTTCCGTACTACTGACGTAACTGGTGTTGTTCACTTACCAGAAG | 1039 | SEQ ID NO: 1148 |
| SAUR-MW2 | ATCGTCCACAATTCTATTTCCGTACTACTGACGTAACTGGTGTTGTTCACTTACCAGAAG | 1039 | SEQ ID NO: 1149 |
| SAUR-MSSA476 | ATCGTCCACAATTCTATTTCCGTACTACTGACGTAACTGGTGTTGTTCACTTACCAGAAG | 1039 | SEQ ID NO: 1150 |
| SAUR-MRSA252 | ATCGTCCACAATTCTATTTCCGTACTACTGACGTAACTGGTGTTGTTCACTTACCAGAAG | 1039 | SEQ ID NO: 1151 |
| SEPI-12228 | ATCGCCCACAATTCTATTTCCGTACTACTGACGTAACTGGTGTTGTAAACTTACCAGAAG | 1039 | SEQ ID NO: 1152 |
| SEPI-RP62A | ATCGCCCACAATTCTATTTCCGTACTACTGACGTAACTGGTGTTGTAAACTTACCAGAAG | 1039 | SEQ ID NO: 1153 |
| SMIT-DAS | ACCGTCCACAGTTCTACTTCCGTACAACTGACGTAACTGGATCTATCGAACTTCCAGCTG | 910 | SEQ ID NO: 1154 |
| SSAN-DAS | ACCGTCCACAGTTCTACTTCCGTACAACTGACGTTACAGGTTCAATCGAACTTCCAGCAG | 951 | SEQ ID NO: 1155 |
| SMIT-NCTC12261 | ACCGTCCACAATTCTACTTCCGTACTACTGACGTTACAGGTTCAATCGAACTTCCAGCAG | 1051 | SEQ ID NO: 1156 |
| SPNE-R6 | ACCGTCCACAATTCTACTTCCGTACTACTGACGTTACAGGTTCAATCGAACTTCCAGCAG | 1051 | SEQ ID NO: 1157 |
| SPYO-M1GAS | ACCGTCCACAATTCTACTTCCGTACAACTGACGTTACAGGTTCAATCGAACTTCCAGCAG | 1051 | SEQ ID NO: 1158 |
| SMUT-DAS | ATCGTCCACAATTCTACTTCCGTACAACTGACGTAACTGGTTCAATTGAGTTGCCAGCAG | 951 | SEQ ID NO: 1159 |
| SMUT-UA159 | ATCGTCCACAATTCTACTTCCGTACAACTGACGTAACTGGTTCAATTGAGTTGCCAGCAG | 1051 | SEQ ID NO: 1160 |
| HINF-RdKW20 | ACCGTCCACAATTCTATTTCCGTACAACAGACGTGACTGGTACAATCGAATTACCAGAAG | 1039 | SEQ ID NO: 1161 |
| MCAT-DAS | ATCGTCCACAGTTCTACTTCCGTACCACAGACGTAACTGGTGCCATCACCCTACAAGAAG | 896 | SEQ ID NO: 1162 |
| BPER-TohamaI | ATCGTCCGCAGTTCTACTTCCGCACGACGGACGTGACCGGCACGATCGACCTGCCGGCGG | 1045 | SEQ ID NO: 1163 |
| BPAR-12822 | ATCGTCCGCAGTTCTACTTCCGCACGACGGACGTGACCGGCACGATCGACCTGCCGGCGG | 1045 | SEQ ID NO: 1164 |
| BCEP2-DAS | ACCGTCCGCAGTT----------------------------------------------- | 882 | SEQ ID NO: 1165 |
| BPSE-1710b | ACCGTCCGCAGTTCTACTTCCGTACGACGGACGTGACGGGCTCGATCGAGCTGCCGAAGG | 1045 | SEQ ID NO: 1166 |
| SMAL-DAS | ACCGTCCGCAGTTCTACTTCCGCACCACCGACATCACCGGCGCAGCTGCGCTGCCGGAAG | 950 | SEQ ID NO: 1167 |
| PAER-PA01 | ACCGTCCGCAGTTCTACTTCCGTACCACCGATGTGACCGGTAACTGCGAACTGCCGGAAG | 1048 | SEQ ID NO: 1168 |
| KPNE-DAS | ACCGTCCGCAGTTCTACTTCCGTACTACTGACGTGACTGGCACCATCGAACTGCCGGAAG | 923 | SEQ ID NO: 1169 |
| MACI-K10 | ACCGCCCGCAGTTCTACTTCCGCACCACCGACGTGACCGGTGTGGTGACGCTGCCGGAGG | 1045 | SEQ ID NO: 1170 |
| MAVI-paratub | ACCGCCCGCAGTTCTACTTCCGCACCACCGACGTGACCGGTGTGGTGACGCTGCCGGAGG | 1045 | SEQ ID NO: 1171 |
| MAISpig-DAS | ACCGTCCGCAGTTCTACTTCCGCACCACCGACGTGACCGGTGTGGTGACGCTGCCGGAGG | 940 | SEQ ID NO: 1172 |
| MKAN-DAS | ACCGTCCGCAGTTCTACTTCCGCACCACCGACGTGACCGGTGTGGTGACGCTGCCGGAGG | 946 | SEQ ID NO: 1173 |
| MTUB-H37Rv | ACCGTCCGCAGTTCTACTTCCGCACCACCGACGTGACCGGTGTGGTGACGCTGCCGGAGG | 1045 | SEQ ID NO: 1174 |
| MTUB-CDC1551 | ACCGTCCGCAGTTCTACTTCCGCACCACCGACGTGACCGGTGTGGTGACGCTGCCGGAGG | 1045 | SEQ ID NO: 1175 |
| MAVI-DAS | ACCGCCCGCAGTTCTACTTCCGTACCACGGACGTGACCGGCGTGGTGACCCTCCCCGAG- | 885 | SEQ ID NO: 1176 |
| NCTC13129 | ACCGCCCACAGTTCTACTTCCGCACCACCGACGTTACCGGTGTTGTGAAGCTTCCTGAGG | 1045 | SEQ ID NO: 1177 |
| NMEN-MC58 | ACCGTCCGCAATTCTACTTCCGTACCACCGACGTAACCGGCGCGGTTACTTTGGAAGAAG | 1039 | SEQ ID NO: 1178 |
| NMEN-Z2491 | ACCGTCCCCAATTCTACTTCCGTACCACCGACGTAACCGGCGCGGTTACTTTGGAAGAAG | 1039 | SEQ ID NO: 1179 |
| NMEN-DAS | ACCGTCCGCA-TTCTACTTCCGTACCACCGACGTAACCGGCGCGGTTACTTTGGAAGAAG | 880 | SEQ ID NO: 1180 |
| MPNE-HF2 | GTGTTGAAATGATTAACCCAGGAGATAACACTAAGATTACTGTTGAACTTATTTCTCCAA | 1099 | SEQ ID NO: 1181 |
| MPNE-M129 | ACACCGAAATGGTGCTACCAGGTGACAATACCTCGATTACAGTTGAACTAATTGCACCAA | 1099 | SEQ ID NO: 1182 |
| LPNE-Paris | GAGTTGAAATGGTAATGCCTGGAGATAATGTGCAATTAGTTGTTAGCTTGCATGCTCCGA | 1118 | SEQ ID NO: 1183 |
| LPNE2-DAS | ------------------------------------------------------------ | | |
| LPNE-Philadelphia1 | GAGTTGAAATGGTAATGCCTGGAGATAATGTGCAATTAGTTGTTAGCTTGCATGCTCCGA | 1105 | SEQ ID NO: 1184 |

TABLE 1-continued

| | | | |
|---|---|---|---|
| LPNE-Lens | GAGTTGAAATGGTAATGCCTGGAGATAATGTGCAATTAGTTGTTAGCTTGCATGCTCCGA | 1105 | SEQ ID NO: 1185 |
| LLON-DAS | GAGTTGAAATGGTAATGCCTGGAGATAACGTACAGTTG---------------------- | 967 | SEQ ID NO: 1186 |
| FNUC-DAS | GAGTAGAAATGGTTATGCCAG--------------------------------------- | 938 | SEQ ID NO: 1187 |
| CPNE-CWL029 | GAACTGAAATGGTAATGCCTGGAGATAACGTTGAGCTTGATGTTGAGCTCATTGGAACAG | 1099 | SEQ ID NO: 1188 |
| EFAE-DAS | GTACTGAAATGGTAATGCCTGGTGATAACGT----------------------------- | 950 | SEQ ID NO: 1199 |
| EFAE-V583 | GTACTGAAATGGTAATGCCTGGTGATAACGTTGCTATGGACGTTGAATTAATTCACCCAA | 1102 | SEQ ID NO: 1190 |
| SAUR-Mu50 | GTACTGAAATGGTAATGCCTGGTGATAACGTTGAAATGACAGTAGAATTAATCGCTCCAA | 1099 | SEQ ID NO: 1191 |
| SAUR-N315 | GTACTGAAATGGTAATGCCTGGTGATAACGTTGAAATGACAGTAGAATTAATCGCTCCAA | 1099 | SEQ ID NO: 1192 |
| SAUR-MW2 | GTACTGAAATGGTAATGCCTGGTGATAACGTTGAAATGACAGTAGAATTAATCGCTCCAA | 1099 | SEQ ID NO: 1193 |
| SAUR-MSSA476 | GTACTGAAATGGTAATGCCTGGTGATAACGTTGAAATGACAGTAGAATTAATCGCTCCAA | 1099 | SEQ ID NO: 1194 |
| SAUR-MRSA252 | GTACTGAAATGGTAATGCCTGGTGATAACGTTGAAATGACAGTAGAATTAATCGCTCCAA | 1099 | SEQ ID NO: 1195 |
| SEPI-12228 | GTACAGAAATGGTTATGCCTGGCGACAACGTTGAAATGACAGTTGAATTAATCGCTCCAA | 1099 | SEQ ID NO: 1196 |
| SEPI-RP62A | GTACAGAAATGGTTATGCCTGGCGACAACGTTGAAATGACAGTTGAATTAATCGCTCCAA | 1099 | SEQ ID NO: 1197 |
| SMIT-DAS | GAACTGAAATGGTAATGCCTGGTGATAACGTGACTATCGACGTT---------------- | 954 | SEQ ID NO: 1198 |
| SSAN-DAS | GTACTGAAATGGTAATGCCTGGTGATAACGTAACAATCGACGTTGAGT------------ | 999 | SEQ ID NO: 1199 |
| SMIT-NCTC12261 | GTACTGAAATGGTAATGCCTGGTGATAACGTGACAATCGACGTTGAGTTGATCCACCCAA | 1111 | SEQ ID NO: 1200 |
| SPNE-R6 | GTACTGAAATGGTAATGCCTGGTGATAACGTGACAATCGACGTTGAGTTGATTCACCCAA | 1111 | SEQ ID NO: 1201 |
| SPYO-M1GAS | GTACAGAAATGGTTATGCCTGGTGATAACGTGACAATCGACGTTGAGTTGATCCACCCAA | 1111 | SEQ ID NO: 1202 |
| SMUT-DAS | GTACTGAAATGGTTATGCCTGGTGATA--------------------------------- | 978 | SEQ ID NO: 1203 |
| SMUT-UA159 | GTACTGAAATGGTAATGCCTGGTGATAACGTGACAATCGACGTTGAGTTGATCCACCCAA | 1111 | SEQ ID NO: 1204 |
| HINF-RdKW20 | GCGTGGAAATGGTAATGCCAGGCGATAACATCAAGATGACAGTAAGCTTAATCCACCCAA | 1099 | SEQ ID NO: 1205 |
| MCAT-DAS | GCACTGAAATGGTTATGCCAGGTGATAACGTTGAGATGAGCGTTGAGCTAATC-ACCCAA | 955 | SEQ ID NO: 1206 |
| BPER-TohamaI | ACAAGGAAATGGTGCTGCCGGGCGACAACGTGTCGATGACCGTCAAGCTGCTGGCCCCGA | 1105 | SEQ ID NO: 1207 |
| BPAR-12822 | ACAAGGAAATGGTGCTGCCGGGCGACAACGTGTCGATGACCGTCAAGCTGCTGGCCCCGA | 1105 | SEQ ID NO: 1208 |
| BCEP2-DAS | ------------------------------------------------------------ | | |
| BPSE-1710b | ACAAGGAAATGGTGATGCCGGGCGACAACGTGTCGATCACGGTGAAGCTGATCGCGCCGA | 1105 | SEQ ID NO: 1209 |
| SMAL-DAS | GCGTCGAAATGGTGATGCCGGGTGACAACGTCAAGATGGTCGTCAC-------------- | 996 | SEQ ID NO: 1210 |
| PAER-PA01 | GCGTAGAGATGGTAATGCCGGGCGACAACATCAAGATGGTTGTCACCCTGATCGCTCCGA | 1108 | SEQ ID NO: 1211 |
| KPNE-DAS | GCGTAGAGATGGTAATGCCGGGCGACAACATCAAAATGG--------------------- | 962 | SEQ ID NO: 1212 |
| MAVI-K10 | GCACCGAGATGGTGATGCCCGGTGACAACACCAACATCTCGGTGAAGCTGATCCAGCCCG | 1105 | SEQ ID NO: 1213 |
| MAVI-Paratub | GCACCGAGATGGTGATGCCCGGTGACAACACCAACATCTCGGTGAAGCTGATCCAGCCCG | 1105 | SEQ ID NO: 1214 |
| MAISpig-DAS | GCACCGAGATGGTGATGCCCGGTGACAACACCAACATCTCGGTGAAGCTGATCCAGC--- | 997 | SEQ ID NO: 1215 |
| MKAN-DAS | GCACCGAGATGGTGATGCCCGGTGACA--------------------------------- | 973 | SEQ ID NO: 1216 |
| MTUB-H37Rv | GCACCGAGATGGTGATGCCCGGTGACAACACCAACATCTCGGTGAAGTTGATCCAGCCCG | 1105 | SEQ ID NO: 1217 |
| MTUB-CDC1551 | GCACCGAGATGGTGATGCCCGGTGACAACACCAACATCTCGGTGAAGTTGATCCAGCCCG | 1105 | SEQ ID NO: 1218 |
| MAVI-DAS | ------------------------------------------------------------ | | |
| NCTC13129 | GCACCGAGATGGTGATGCCCGGTGACAACACCAACATCTCGGTGAAGCTGATCCAGCCCG | 1105 | SEQ ID NO: 1219 |
| NMEN-MC58 | GTGTAGAAATGGTAATGCCGGGTGAAAACGTAACCATCACCGTAGAACTGATTGCGCCTA | 1099 | SEQ ID NO: 1220 |
| NMEN-Z2491 | GTGTGGAAATGGTAATGCCGGGCGAGAACGTAACCATCACCGTAGAACTGATTGCGCCTA | 1099 | SEQ ID NO: 1221 |
| NMEN-DAS | GAGTGGAAATGGTAATGCCTGGTGAGAACGTAACCATCACCGTAGA-CTGATTGCGTCTA | 939 | SEQ ID NO: 1222 |
| | | | |
| MPNE-HF2 | TTGCTGTTGAAGAAGGAAGTAAATTCTCAATCCG-TGAAGGTGGAAGAACAGTAGGTGCT | 1158 | SEQ ID NO: 1223 |
| MPNE-M129 | TTGCTTGTGAAAAAGGTAGTAAGTTCTCCATCCG-TGAAGGTGGTCGAACGGTTGGTGCT | 1158 | SEQ ID NO: 1224 |
| LPNE-Paris | TTGCGATGGATGAAGGTTTAAGATTCGCAATTAG-AGAGGGTGGCCGAACTGTTGGCGCC | 1177 | SEQ ID NO: 1225 |
| LPNE2-DAS | ------------------------------------------------------------ | | |
| LPNE-Philadelphia1 | TTGCGATGGATGAAGGTTTAAGATTCGCAATTAG-AGAGGGTGGCCGAACTGTTGGCGCC | 1164 | SEQ ID NO: 1226 |
| LPNE-Lens | TTGCGATGGATGAGGGTTTAAGATTCGCAATTAG-AGAGGGTGGCCGAACTGTTGGCGCC | 1164 | SEQ ID NO: 1227 |
| LLON-DAS | ------------------------------------------------------------ | | |
| FNUC-DAS | ------------------------------------------------------------ | | |
| CPNE-CWL029 | TTGCTCTTGAAGAAGGAATGAGATTTGCAATTCG-TGAAGGTGGTCGTACTATCGGCGCT | 1158 | SEQ ID NO: 1228 |
| EFAE-DAS | ------------------------------------------------------------ | | |
| EFAE-V583 | TCGCTATCGAAGACGGAACTCGTTTCTCTATTCG-TGAAGGCGGACGTACTGTAGGTTCA | 1161 | SEQ ID NO: 1229 |
| SAUR-Mu50 | TCGCGATTGAAGACGGTACTCGTTTCTCAATCCG-CGAAGGTGGACGTACTGTAGGATCA | 1158 | SEQ ID NO: 1230 |
| SAUR-N315 | TCGCGATTGAAGACGGTACTCGTTTCTCAATCCG-CGAAGGTGGACGTACTGTAGGATCA | 1158 | SEQ ID NO: 1231 |
| SAUR-MW2 | TCGCGATTGAAGACGGTACTCGTTTCTCAATCCG-TGAAGGTGGACGTACTGTAGGATCA | 1158 | SEQ ID NO: 1232 |
| SAUR-MSSA476 | TCGCGATTGAAGACGGTACTCGTTTCTCAATCCG-TGAAGGTGGACGTACTGTAGGATCA | 1158 | SEQ ID NO: 1233 |
| SAUR-MRSA252 | TCGCGATTGAAGACGGTACTCGTTTCTCAATCCG-TGAAGGTGGACGTACTGTAGGATCA | 1158 | SEQ ID NO: 1234 |
| SEPI-12228 | TCGCTATCGAAGACGGAACTCGTTTCTCAATTCG-TGAAGGTGGACGTACTGTTGGATCA | 1158 | SEQ ID NO: 1235 |
| SEPI-RP62A | TCGCTATCGAAGACGGAACTCGTTTCTCAATTCG-TGAAGGTGGACGTACTGTTGGATCA | 1158 | SEQ ID NO: 1236 |
| SMIT-DAS | ------------------------------------------------------------ | | |
| SSAN-DAS | ------------------------------------------------------------ | | |
| SMIT-NCTC12261 | TCGCCGTAGAACAAGGTACTACATTCTCTATCCG-TGAGGGTGGACGTACTGTTGGTTCA | 1170 | SEQ ID NO: 1237 |
| SPNE-R6 | TCGCCGTAGAACAAGGTACTACATTCTCTATCCG-TGAGGGTGGACGTACTGTTGGTTCA | 1170 | SEQ ID NO: 1238 |
| SPYO-M1GAS | TCGCCGTAGAACAAGGTACTACTTTCTCAATCCG-TGAAGGTGGACGTACTGTTGGTTCA | 1170 | SEQ ID NO: 1239 |
| SMUT-DAS | ------------------------------------------------------------ | | |
| SMUT-UA159 | TCGCTGTTGAACAAGGTACTACTTTCTCTATTCG-TGAAGGTGGACGTACTGTTGGTTCT | 1170 | SEQ ID NO: 1240 |
| HINF-RdKW20 | TTGCGATGGATCAAGGTTTACGTTTCGCAATCCG-TGAAGGTGGCCGTACAGTAGGTGCA | 1158 | SEQ ID NO: 1241 |
| MCAT-DAS | TCGCATGGACA------------------------------------------------- | 966 | SEQ ID NO: 1242 |
| BPER-TohamaI | TCGCCATGGAAGAAGGTCTGCGTTTCGCCATCCG-TGAAGGCGGTCGTACCGTCGGCGCC | 1164 | SEQ ID NO: 1243 |
| BPAR-12822 | TCGCCATGGAAGAAGGTCTGCGTTTCGCCATCCG-TGAAGGCGGTCGTACCGTCGGCGCC | 1164 | SEQ ID NO: 1244 |
| BCEP2-DAS | ------------------------------------------------------------ | | |
| BPSE-1710b | TCGCGATGGAAGAAGGTCTGCGCTTCGCGATCCG-CGAAGGCGGTCGCACCGTCGGCGCC | 1164 | SEQ ID NO: 1245 |
| SMAL-DAS | ------------------------------------------------------------ | | |
| PAER-PA01 | TCGCCATGGAAGATGGCCTGCGCTTCGCGATCCG-CGAAGGCGGCCGTACCGTTGGCGCC | 1167 | SEQ ID NO: 1246 |
| KPNE-DAS | ------------------------------------------------------------ | | SEQ ID NO: 1247 |
| MAVI-K10 | TCGCCATGGACGAGGGTCTGCGGTTCGCCATCCG-CGAGGGTGGTCGCACCGTCGGCGCC | 1164 | SEQ ID NO: 1248 |
| MAVI-paratub | TCGCCATGGACGAGGGTCTGCGGTTCGCCATCCG-CGAGGGTGGTCGCACCGTCGGCGCC | 1164 | SEQ ID NO: 1249 |
| MAISpig-DAS | ------------------------------------------------------------ | | |
| MKAN-DAS | ------------------------------------------------------------ | | |
| MTUB-H37Rv | TCGCCATGGACGAAGGTCTGCGTTTCGCGATCCG-CGAGGGTGGCCGCACCGTGGGCGCC | 1164 | SEQ ID NO: 1250 |

TABLE 1-continued

| | | | |
|---|---|---|---|
| MTUB-CDC1551 | TCGCCATGGACGAAGGTCTGCGTTTCGCGATCCG-CGAGGGTGGCCGCACCGTGGGCGCC | 1164 | SEQ ID NO: 1251 |
| MAVI-DAS | ------------------------------------------------------------ | | |
| NCTC13129 | TCGCTATGGATGAGGGCCTGCGCTTCGCTATCCG-CGAGGGCTCCCGCACCGTCGGCGCT | 1164 | SEQ ID NO: 1252 |
| NMEN-MC58 | TCGCTATGGAAGAAGGCCTGCGCTTTGCGATTCG-CGAAGGCGGCCGTACCGTGGGTGCC | 1158 | SEQ ID NO: 1253 |
| NMEN-Z2491 | TCGCTATGGAAGAAGGTTTGCGCTTTGCGATTCG-CGAAGGCGGCCGTACCGTGGGTGCC | 1158 | SEQ ID NO: 1254 |
| NMEN-DAS | TCGCTATGGAAGAG---CTGCGCTT-GCGTCGTGTCGCGCGTGTCCAT------------ | 983 | SEQ ID NO: 1255 |
| | | | |
| MPNE-HF2 | GGTACAGTAACTAAAGTTATTAAGTAA | 1185 | SEQ ID NO: 1256 |
| MPNE-M129 | GGTTCAGTCACGGAAGTGCTTGAATAG | 1185 | SEQ ID NO: 1257 |
| LPNE-Paris | GGTGTAGTCGCTAAAATAATCGAGTAA | 1204 | SEQ ID NO: 1258 |
| LPNE2-DAS | --------------------------- | | |
| LPNE-Philadelphia1 | GGTGTAGTCGCTAAAATAATCGAGTAA | 1191 | SEQ ID NO: 1259 |
| LPNE-Lens | GGTGTAGTCGCTAAAATAATCGAGTAA | 1191 | SEQ ID NO: 1260 |
| LLON-DAS | --------------------------- | | |
| FNUC-DAS | --------------------------- | | |
| CPNE-CWL029 | GGAACGATTTCAAAGATCAATGCTTAA | 1185 | SEQ ID NO: 1261 |
| EFAE-DAS | --------------------------- | | |
| EFAE-V583 | GGCGTTGTTACTGAAATCGTTAAATAA | 1188 | SEQ ID NO: 1262 |
| SAUR-Mu50 | GGCGTTGTTACTGAAATCATTAAATAA | 1185 | SEQ ID NO: 1263 |
| SAUR-N315 | GGCGTTGTTACTGAAATCATTAAATAA | 1185 | SEQ ID NO: 1264 |
| SAUR-MW2 | GGCGTTGTTACTGAAATCATTAAATAA | 1185 | SEQ ID NO: 1265 |
| SAUR-MSSA476 | GGCGTTGTTACTGAAATCATTAAATAA | 1185 | SEQ ID NO: 1266 |
| SAUR-MRSA252 | GGCGTTGTTACTGAAATCATTAAATAA | 1185 | SEQ ID NO: 1267 |
| SEPI-12228 | GGCGTTGTAACTGAAATCTTTGAATAA | 1185 | SEQ ID NO: 1268 |
| SEPI-RP62A | GGCGTTGTAACTGAAATCTTTGAATAA | 1185 | SEQ ID NO: 1269 |
| SMIT-DAS | --------------------------- | | |
| SSAN-DAS | --------------------------- | | |
| SMIT-NCTC12261 | GGTATGGTTACAGAAATCGAAGCTTAA | 1197 | SEQ ID NO: 1270 |
| SPNE-R6 | GGTATGGTTACAGAAATCGAAGCTTAA | 1197 | SEQ ID NO: 1271 |
| SPYO-M1GAS | GGTATCGTTTCAGAAATCGAAGCTTAA | 1197 | SEQ ID NO: 1272 |
| SMUT-DAS | --------------------------- | | |
| SMUT-UA159 | GGTATCGTTTCAGAAATCGAAGCTTAA | 1197 | SEQ ID NO: 1273 |
| HINF-RdKW20 | GGCGTTGTTGCGAAAATCATCAAATAA | 1185 | SEQ ID NO: 1274 |
| MCAT-DAS | --------------------------- | | |
| BPAR-TohamaI | GGCGTCGTCGCCAAGATCATCAAGTAA | 1191 | SEQ ID NO: 1275 |
| SPAR-12822 | GGCGTCGTCGCTAAGATCATCAAGTAA | 1191 | SEQ ID NO: 1276 |
| BCBP2-DAS | --------------------------- | | |
| BPSE-1710b | GGCGTCGTCGCCAAGATCATCGAGTAA | 1191 | SEQ ID NO: 1277 |
| SMAL-DAS | --------------------------- | | |
| PAER-PA01 | GGCGTGGTTGCCAAGATCATCGAGTAA | 1194 | SEQ ID NO: 1278 |
| KPNE-DAS | --------------------------- | | SEQ ID NO: 1279 |
| MAVI-K10 | GGCCGGGTCGTCAAGATCATCAAGTAG | 1191 | SEQ ID NO: 1280 |
| MAVI-paratub | GGCCGGGTCGTCAAGATCATCAAGTAG | 1191 | SEQ ID NO: 1281 |
| MAISpig-DAS | --------------------------- | | |
| MKAN-DAS | --------------------------- | | |
| MTUB-H37Rv | GGCCGGGTCACCAAGATCATCAAGTAG | 1191 | SEQ ID NO: 1282 |
| MTUB-CDC1551 | GGCCGGGTCACCAAGATCATCAAGTAG | 1191 | SEQ ID NO: 1283 |
| MAVI-DAS | --------------------------- | | |
| NCTC13129 | GGTCGCGTTACCAAGATCATCAAGTAA | 1191 | SEQ ID NO: 1284 |
| NMEN-MC58 | GGCGTGGTTTCTTCTGTTATCGCTTAA | 1185 | SEQ ID NO: 1285 |
| NMEN-Z2491 | GGCGTGGTTTCTTCTGTTATCGCTTAA | 1185 | SEQ ID NO: 1286 |
| NMEN-DAS | --------------------------- | | |

Abbreviations used in Table 1
MPNE - *Mycoplasma pneumoniae*
LPNE - *Legionella pneumophila*
LLON - *Legionella longbeachiae*
FNUC - *Fusobacterium nucleatum*
CPNE - *Chlamydophila pneumoniae*
EFAE - *Enterococcus faecalis*
SAUR - *Staphylococcus aureus*
SEPI - *Staphylococcus epidermidis*
SMIT - *Streptococcus mitis*
SSAN - *Streptococcus sanguis*
SPNE - *Streptococcus pneumoniae*
SPYO - *Streptococcus pyogenes*
SMUT - *Streptococcus mutans*
HINF - *Haemophilus influenzae*
MCAT - *Moraxella catarrhalis*
BPER - *Bordetella pertussis*
BPAR - *Bordetella parapertussis*
BCEP - *Burkholderia cepacia*
BPSE - *Burkholderia pseudomallei*
SMAL - *Stenotrophomonas maltophilia*
PAER - *Pseudomonas aeruginosa*
KPNE - *Klebsiella pneumoniae*
MAVI - *Mycobacterium avium*
MAIS - *Mycobacterium intracellulare*
MKAN - *Mycobacterium kansasii*
MTUB - *Mycobacterium tuberculosis*

TABLE 1-continued

CDIP - *Corynebacterium diphtheriae*
NMEN - *Neisseria meningitidis* bacteria, intestinal flora, monerans, monerons, microbes, pathogens, pilus, protists, protistans, protoctists, viruses, rickettsieae, protozoans, algae spirillum and fungi.

In some embodiments, the target micro-organism is a prokaryotic micro-organism. Examples of prokaryotic microorganisms include *Bordotella pertussis, Haemophilus influenzae, Legionella pneumophila, Mycoplasma pneumoniae, Staphylococcus aureus, Myobacterium tuberculosis, Escherichia coli, Streptococcus pyogenes, Burkholderia cepacia, Corynebacterium, Chlamydophila pneumoniae, Enterococcus faecalis, Fusobacterium nucleatum, Klebsiella pneumoniae, Legionella longbeachiae, Moraxella catarrhalis, Neisseria meningitidis, Pseudomonas aeruginosa, Staphylococcus epidermidis, Stenotrophomonas maltophilia, Streptococcus pneumoniae, Streptococcus mutans, Streptococcus sanguis*, and *Serratia marcescens.*

As shown in Table 2, the bacteria referred to above display a range of characteristics.

TABLE 2

| Gram positive bacterial species | Gram negative bacterial species |
|---|---|
| Aerobic bacilli | Aerobic bacilli |
| *Corynebacterium diphtheriae* | *Bordetella pertussis*<br>*Chlamydophila pneumoniae*<br>*Haemophilus influenzae*<br>*Serratia marcescens*<br>*Moraxella catarrhalis*<br>*Legionella pneumophila*<br>*Legionella longbeachiae*<br>*Mycoplasma pneumoniae*<br>*Klebsiella pneumoniae*<br>*Burkholderia cepacia*<br>*Stenotrophomonas maltophilia*<br>*Pseudomonas aeruginosa* |
| Aerobic cocci | Aerobic cocci |
| *Staphylocuccus aureus*<br>*Staphylococcus epidermidis*<br>*Streptococcus pneumoniae*<br>*Streptococcus pyogenes*<br>*Streptpcoccus mutans*<br>*Streptococcus sanguis*<br>*Enterococcus faecalis* | *Neisseria meningitidis* |
| | Anaerobic bacilli |
| | *Fusobacterium nucleatum*<br>*Mycobacterium tuberculosis* |

The methods of the invention for identifying micro-organisms may be used in a variety of fields including, but not limited to, human medicine, epidemiology, drug development, veterinary medicine, agriculture, the environment, food science, and industrial microbiology. For example, micro-organism identification may be used to determine the identity of a micro-organism found in a patient suffering from an infectious disease. Micro-organism identification may also be used to monitor food safety by testing for pathogens. Similarly, plants may be checked to determine if they harbour phytopathogenic bacteria. Further, the methods of the present invention may be used to identify drug resistant bacteria including antibiotic resistant strains of bacteria.

One method of the present invention for identifying a target microorganism in a test sample comprises contacting the test sample or a product of the amplification process described supra, with a probe derived from the tuf gene variable region for a time and under conditions sufficient for hybridization to take place.

The term "probe" as used herein is interchangeably used with the terms "oligonucleotide probe" or "hybridization probe" and refers to a short span of contiguous nucleotides, preferably between 10 and 50 nucleotides, that are complementary to at least a part of a tuf gene variable region from target microorganism, such that it is capable of specifically binding to a polynucleic acid as defined herein from the target microorganism. The design, use and labelling of probes is described in Keller et al., *DNA Probes*, pp. 149-213 (Stockton Press, 1989).

The terms "specific binding" or "specifically binding" refers to that interaction between a probe of the present invention and the corresponding polynucleic acid from a target microorganism.

As used herein the term "contacting" means to bring the test sample or amplification product into physical proximity with a probe derived from the tuf gene variable region such that, if other conditions are suitable, hybridization can take place. The contacting may be direct or indirect. For example, the test sample may directly contact the probe such that hybridisation can take place. Alternatively, the sample may hybridise with another molecule (eg another nucleic acid molecule) which in turn hybridises with the probe derived from a tuf gene variable region.

"Hybridisation" is used herein to denote the pairing of complementary nucleotide sequences to produce a DNA-DNA hybrid or a DNA-RNA hybrid. Complementary base sequences are those sequences that are related by the base pairing rules. In DNA, A pairs with T and C pairs with G. In RNA U pairs with A and C pairs with G. In this regard, the terms "match" and "mismatch" as used herein refer to the hybridisation potential of paired nucleotides in complementary nucleic acid strands. Matched nucleotides hybridise efficiently, such as the classical A-T and G-C pair mentioned above. Mismatches are combinations of nucleotides that do not hybridise efficiently.

Defining appropriate hybridisation conditions is within the skill of the art. See eg., Sambrook et al., supra. However, ordinarily, "stringent conditions" for hybridisation or annealing of probes are those that (1) employ low ionic strength and high temperature for washing, for example, 0.015M NaCl/0.0015M sodium citrate/0.1% sodium dodecyl sulfate (SDS) at 50° C., or (2) employ during hybridisation a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

An example of medium stringency conditions for hybridisation is the use of 50% formamide, 5×SSC (0.75M NaCl, 0.075M sodium citrate), 50 mM sodium phosphate (pH 6.8), 0.1 sodium pyrophosphate, 5×Denhardt's solution, sonicated salmon sperm DNA (50 μg/mL), 0.1% SDS, and 10% dextran sulfate at 42° C., with washes at 42° C. in 0.2×SSC and 0.1% SDS.

Suitable hybridisation and washing conditions depend on specific applications. The higher the degree of similarity between two micro-organisms that need to be differentiated, the higher the stringency of hybridisation and washing conditions should be. For example, when an application requires differentiating micro-organisms on the genus level, hybridisation and washing conditions of relatively low stringency may be all that is necessary. However, when differentiating between micro-organisms on the species level, wherein the micro-organism share a higher degree of similarity, hybridisation and washing conditions of higher stringency are required. Further, when differentiating between micro-organisms on the strain level wherein the micro-organisms share an even higher degree of similarity, hybridisation and washing conditions of even higher stringency are required.

In some embodiments, the step of contacting the test sample comprises hybridization with at least a portion of a tuf gene variable region with a set of probes comprising at least one probe selected from the group consisting of SEQ ID NOs:12 to 57, 208 to 209 and 210.

In other embodiments, the at least one probe is selected from the group consisting of SEQ ID NOs:12 to 79, 208 to 209 and 210. In other embodiments, the at least one probe is selected from the group consisting of SEQ ID NOs:12 to 392 and 393.

In some embodiments, the target microorganism is selected from the group consisting of *Bordetella* species, *Chlamydophila* species, *Haemophilus* species, *Legionella* species, *Mycoplasma* species, *Mycobacterium* species, *Staphylococcus* species, *Streptococcus* species, *Pseudomonas* species, *Moraxella* species and *Fusobacterium* species, *Stenotrophomonas* species, *Burkholderi* species, *Enterococcus* species, *Corynebacterium* species and *Neisseria* species, wherein the probe is selected from the group consisting of:

for *Haemophilus influenzae*:

```
TATTATCCGTACAGGTGATGAAGTAGAAA;   (SEQ ID NO.: 12)
AAAGATACAGCGAAAACTACTGTAACG;     (SEQ ID NO.: 13)
CATCGGTGCATTATTACGTGGTAC;        (SEQ ID NO.: 14)
CATACTCCATTCTTCAAAGGTTACCG;      (SEQ ID NO.: 15)
TGACTGGTACAATCGAATTACCAGAA;      (SEQ ID NO.: 16)
CCGTAAATTACTTGACGAAGGTCG;        (SEQ ID NO.: 17)
ACTTCGAATC AGAAGTGTAC;           (SEQ ID NO.: 64)
CAAACGTGAA GAAATCGAAC;           (SEQ ID NO.: 65)
CGATAACATC AAGATGACAG T;         (SEQ ID NO.: 66)
```

for *Moraxella catarrhalis*:

```
TGAGCGTGACATCGATAAGTCA;          (SEQ ID NO.: 18)
CAGGCATTATTAAAGTTGGTGATGAAATT;   (SEQ ID NO.: 19)
AAACCAACTACTAAAACCACTTGTACTG;    (SEQ ID NO.: 20)
CGTAAGCTGCTAGACGAAGGT;           (SEQ ID NO.: 21)
TACCCCATTCCTAAATGGCTATCG;        (SEQ ID NO.: 22)
TAACTGGTGCCATCACCCTAC;           (SEQ ID NO.: 23)
AGTTTGATGCAGAAGTATACG            (SEQ ID NO.: 208)
```

-continued

```
TATCCTACTACGTGGTACTAA            (SEQ ID NO.: 209)
ATAACGTTGAGATGAGCG               (SEQ ID NO.: 210)
```

for *Enterococcus faecalis*:

```
AAGGCGACGAGTCTTATGAAGA;          (SEQ ID NO.: 24)
AATTAATGGCTGCAGTTGACGAAT;        (SEQ ID NO.: 25)
GAAGTTCGCGTTGGTGACG;             (SEQ ID NO.: 26)
GACGAAACATCTAAAACAACTGTTACAG;    (SEQ ID NO.: 27)
TGGTGTTGTAGAATTGCCAGAAG;         (SEQ ID NO.: 28)
TAAACCAGCTACAATCACTCCACA;        (SEQ ID NO.: 29)
```

for *Staphylococcus aureus*:

```
GTTGACATGGTTGACGATGAAGAATTA;     (SEQ ID NO.: 30)
CTTAGAATTAATGGAAGCTGTAGATACTTACA; (SEQ ID NO.: 31)
ATCATCGGTTTACATGACACATCTAAAA;    (SEQ ID NO.: 32)
CACCACATACTGAATTTAAAGCAGAAGTA;   (SEQ ID NO.: 33)
CATTCTTCTCAAACTATCGTCCACAA;      (SEQ ID NO.: 34)
CTGGTGTTGTTCACTTACCAGAAG;        (SEQ ID NO.: 35)
TACTGAAATGGTAATGCCTGGTGATA;      (SEQ ID NO.: 36)
CCAATCGCGATTGAAGACGG;            (SEQ ID NO.: 37)
CTGGTTCAGCATTAAAAGCTTTAGAAG;     (SEQ ID NO.: 38)
TGACAACATTGGTGCATTATTACGT;       (SEQ ID NO.: 39)
TGTTACAGGTGTTGAAATGTTCCG;        (SEQ ID NO.: 40)
GTATTATCAAAAGACGAAGGTGGACG;      (SEQ ID NO.: 41)
GCGATGCTCAATACGAAGAAAAAATC;      (SEQ ID NO.: 42)
TGAATTCAAA GCAGAAGTAT AC;        (SEQ ID NO.: 76)
ATTATTACGT GGTGTTGCTC;           (SEQ ID NO.: 77)
GTGATAACGT TGAAATGACA G;         (SEQ ID NO.: 78)
```

for *Staphylococcus epidermidis*:

```
TAGACTTAATGCAAGCAGTTGATGATTAC;   (SEQ ID NO.: 43)
CCACACACAAAATTCAAAGCTGAAG;       (SEQ ID NO.: 44)
CTGGTGTTGTAAACTTACCAGAAGG;       (SEQ ID NO.: 45)
GAAATGGTTATGCCTGGCGAC;           (SEQ ID NO.: 46)
CTGGTTCTGCATTAAAAGCATTAGAAG;     (SEQ ID NO.: 47)
TGACAACATCGGTGCTTTATTACG;        (SEQ ID NO.: 48)
CTGTTACTGGTGTAGAAATGTTCCG;       (SEQ ID NO.: 49)
CGTATTATCTAAGATGAAGGTGGCG;       (SEQ ID NO.: 50)
```

for *Pseudomonas aeruginosa*:

```
AAGTTCGAGTGCGAAGT;              (SEQ ID NO.: 51)
AAGGCGTAGAGATGGTAAT;            (SEQ ID NO.: 52)
TTCTTCAAGGGCTACCG;              (SEQ ID NO.: 53)
ATCATCAAGGTCCAGGAAGAAGT;        (SEQ ID NO.: 54)
ACCAAGACTACCTGCACCG;            (SEQ ID NO.: 55)
TGTACGTGCTGTCCAAGGAA;           (SEQ ID NO.: 56)
CCGGTAACTGCGAACTGC;             (SEQ ID NO.: 57)
CACGTTGACTGCCCCGGTCACGC;        (SEQ ID NO.: 85)
ACGCCTTCCGGCAGTTCGCAGTTAC;      (SEQ ID NO.: 86)
ATCGGTCACGTTGACCATGGCA;         (SEQ ID NO.: 87)
GCCGCCTTCGCGGATCGCGAA;          (SEQ ID NO.: 88)
```

for *Bordetella pertussis*:

```
GTACATTCTG TCCAAGGAAG;    (SEQ ID NO.: 58)
GACAACGTGG GTATCTTG;      (SEQ ID NO.: 59)
GACAAGGAAA TGGTGCT;       (SEQ ID NO.: 60)
```

for *Chlamydophila pneumoniae*:

```
AATTTAAGTC AGCTGTTTAC G;  (SEQ ID NO.: 61)
GAGGTATTGG AAAGAACGAT;    (SEQ ID NO.: 62)
ATAACGTTGA GCTTGATGTT;    (SEQ ID NO.: 63)
```

for *Legionella pneumophila*:

```
AGTTTGAAGC AGAAGTGTAT;          (SEQ ID NO.: 67)
TGTTATTACG AGGTACGAAG;          (SEQ ID NO.: 68)
AGATAATGTG CAATTAGTTG TTA;      (SEQ ID NO.: 69)
```

for *Mycoplasma pneumoniae*:

```
GAAATTTAAA GCGGAAATCT ATG;      (SEQ ID NO.: 70)
GAACGTGGTC AAGTGTTAG;           (SEQ ID NO.: 71)
GACAATACCT CGATTACAGT;          (SEQ ID NO.: 72)
```

for *Mycobacterium tuberculosis*

```
AACATCTCGG TGAAGTTGAT;    (SEQ ID NO.: 73)
TGACAACACC AACATCTC;      (SEQ ID NO.: 74)
ACGAAGGTCT GCGTTT;        (SEQ ID NO.: 75)
```

for *Streptococcus pneumoniae*

```
AATTCAAAGG TGAAGTCTAC A;  (SEQ ID NO.: 79)
CAACGTGATG AAATCGAAC;     (SEQ ID NO.: 80)
GACAATCGAC GTTGAGTT;      (SEQ ID NO.: 81)
```

for *Streptococcus pyogenes*

```
CAAAGGTGAA GTATATATCC TTTC;   (SEQ ID NO.: 82)
CAACGTGACG AAATCGAA;          (SEQ ID NO.: 83)
CGTGACAATC AACGTTGA;          (SEQ ID NO.: 84)
```

and combinations thereof.

Once hybridization is believed to have taken place then any hybrids formed are detected. The person skilled in the art would be readily able to detect hybridisation between the probes of the invention and the polynucleic acid of the invention. For example, where neither the polynucleic acid or probe is labelled, hybridisation can be detected using a DNA intercalating dye such as ethidium bromide, SYBR®Green (Applied Biosystems, Scoresby VIC, Australia), or SYTOX Orange (Invitrogen, Mount Waverley VIC, Australia). These dyes bind efficiently to double stranded DNA. Therefore when hybrids between the target polynucleic acid and the probe nucleotide sequence are formed, staining with a dye as described above will facilitate detection of the resulting hybrids.

In some preferred embodiments of the present invention, a polynucleic acid derived from a test sample or a probe is labelled to facilitate hybridisation detection. Methods and materials that can be used to label DNA or RNA molecules are known in the art. In the examples below, a method of labelling the DNA with Cy3 or Cy5 is described. However, other known labelling materials and methods may also be used. For example, other Cy dyes such as Cy3.5 and Cy5.5, Alexa fluorescent dyes and radioactive isotopes such as $^{32}P$ and $^{35}S$ and the like can also be used to label the whole genomic DNA to facilitate the detection of hybridisation. Furthermore, a two-colour fluorescent labelling strategy may be used in the present invention. The strategy is described in Ramsay, 1998, *Nat. Biotech.*, 16:40-44) and Shalon et al., 1996, *Genome Res.*, 6:639-645, both of which are incorporated by reference in their entirety. Such multiple-colour hybridisation detection strategy minimises variations resulting from inconsistent experimental conditions and allows direct and quantitative comparison of target abundance among different samples (see Ramsay, 1998, supra and Shalon et al., 1996, supra). The label is one that preferably does not provide a variable signal, but instead provides a constant and reproducible signal over a given period of time.

In some embodiments, the preferred method of contacting probes and test samples and detecting microorganisms is by using a microarray. A "microarray" is typically a 2-dimensional array upon which two or more probes of the invention have been deposited. In some embodiments there are at least 3 positions on the microarray containing a probe each having a different sequence of the invention. This has the advantage of minimising false positives.

Another method of detecting the presence of polynucleic acid from target microorganisms is specific nucleic acid microarrays and microchip technology. A microarray is a tool for detecting gene or nucleic acid sequence presence and typically consists of a small membrane or glass slide onto which samples of many probes have been arranged in a regular pattern.

For example, oligonucleotide probes for microorganism polynucleic acid disclosed herein can be deposited at predetermined locations on a glass slide. Test samples or polynucleic acid isolated therefrom can be added to the probes under conditions which allow hybridization or binding between the probes and polynucleic acid if present in the test sample. Alternatively, polynucleic acid from a test sample may be applied to the slide before adding probes for polynucleic acid disclosed herein. Binding between the probes and polynucleic acid can be detected by any means known in the art and specific binding between the polynucleic acid and a probe indicates the polynucleic acid is present in the test sample.

The methodology of hybridisation of polynucleic acids and microarray technology is well known in the art. For example, the specific preparation of polynucleic acids for hybridisation and probes, slides, and hybridisation conditions are provided in PCT/US01/10482, herein incorporated by reference.

Microarray technology allows for the measurement of thousands of genes or polynucleic acids simultaneously thereby presenting a powerful tool for identifying the presence of microorganisms. Two microarray technologies are currently in wide use. The first are cDNA arrays and the second are oligonucleotide arrays. Although differences exist in the construction of these chips, essentially all downstream data analysis and output are the same. The product of these analyses are typically measurements of the intensity of the signal received from a labelled probe used to detect a polynucleic acid from the test sample that hybridizes to a polynucleic acid at a known location on the microarray. Typically, the signal intensity is proportional to the polynucleic acid quantity. A large number of such techniques are available and useful. Preferred methods can be found in U.S. Pat. No. 6,271,002 to Linsley et al.; U.S. Pat. No. 6,218,122 to Friend et al.; U.S. Pat. No. 6,218,114 to Peck et al.; and U.S. Pat. No. 6,004,755 to Wang et al., the disclosure of each of which is incorporated herein by reference.

In a preferred method, biotinylated probes are prepared and hybridized to a microarray such as Affymetrix HG-U133A oligonucleotide microarrays (Affymetrix, Santa Clara, Calif.) by methods such as those described in Hoffmann et al., 2005, *Mol. Biotechnol.,* 29:31-8. Array images can then be reduced to intensity values for each probe (CEL files) using, for example, Affymetrix MAS 5.0 software. Expression measures are extracted using robust multi-array analysis (RMA) for example as described in Irizarry et al., 2003, *Nucleic Acids Res.,* 31:e15 and Dallas et al., 2005, *BMC Genomics.,* 6:59.

Once a microorganism(s) has been detected using the invention described herein, an appropriate diagnosis, prognosis or treatment might be effected. Accordingly, the invention further provides a method for the prognosis, diagnosis, prevention, or treatment in a subject of a disease, comprising the detection of hybridisation between a polynucleic acid in a test sample and a probe derived from a tuf gene variable region. Detecting hybridisation between a nucleic acid molecule in a sample and variable region of a gene enables identification of a micro-organism in the sample. This information can be used to determine whether the disease is caused by a pathogenic micro-organism, and hence the prognosis, diagnosis, prevention, or treatment for the disease.

As used herein "prognosis" means a prediction of the course and outcome of a disease or the likelihood of a subject developing a disease.

As used herein "diagnosis" means the process of identifying a disease, such as by its symptoms, laboratory tests (including genotypic tests), and physical findings.

As used herein "prevention" means any prevention of a disease in a subject and includes preventing the disease from occurring in a subject that may be predisposed to the disease, but has not yet been diagnosed as having it. The effect may be prophylactic in terms of completely or partially preventing the disease or sign or symptom thereof.

As used herein "treatment" or "treating" means any treatment of a disease in a subject by administering a medicament to the subject following the detection of a particular microorganism. "Treatment" and "treating" includes: (a) inhibiting the disease, i.e., arresting its development; or (b) relieving or ameliorating the symptoms of the disease, i.e., cause regression of the symptoms of the disease. The effect may be therapeutic in terms of a partial or complete cure of the disease.

Methods of the invention can be used in the prognosis, diagnosis, prevention, or treatment of any subject, such as an animal or plant, as all animals and plants are infected by micro-organisms and are subject to diseases and disorders caused by micro-organisms.

As used herein an "animal" means any animal, such as a human or a mammal of economical importance and/or social importance to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, eg., poultry, such as turkeys, chickens, ducks, geese, guinea fowl, and the like, as they are also of economical importance to humans. Thus, provided is the treatment of livestock, including, but not limited to, domesticated swine (pigs and hogs), ruminants, horses, poultry, and the like. The term does not denote a particular age. Thus, both adult and newborn subjects are intended to be covered.

As used herein a "plant" includes any member of the plant kingdom including, but not limited to, eukaryotic algae, mosses, club mosses, ferns, angiosperms, gymnosperms, and lichens (which contain algae) including any parts (eg pollen, seeds, cells, tubers, stems) thereof, and any cellular components (eg plasmids, ribosomes, etc.) thereof.

"Disease" as used herein is a general term used to refer to any departure from health in which a subject suffers.

In some embodiments the disease is one associated with pathogens (including animal pathogens) and in particular infectious diseases, respiratory infections, including, pneumonia (including community acquired pneumonia), whooping cough, meningitis, typhus, tuberculosis, diptheria, typhoid fever and bacterial diarrhea; gastrointestinal tract infections, including gastroenteritis; dermal infections; genital tract infections; urinary tract infections; nosocomial infections; typhoid fever; botulism; strep throat; rheumatic fever; syphilis, cystitis; kidney infection; folliculitis; furunculosis (boils); impetigo (school sore); methicillin resistant *Staphylococcus aureus*; staphylococcal scalded skin syndrome; toxic shock syndrome; cellulitis, erysipelas; necrotising fascilitis; scarlet fever; wound infections ie. dermatitis and scabies.

A medical or veterinary practitioner, after being provided with the results of the above method may prescribe appropriate treatment according to his or her knowledge and skill. However, in an alternative embodiment, a computer software program may be provided to advise on the appropriate treatment of the patient, once the identification of the microorganism has taken place.

Embodiments of the present invention may also be conveniently provided in kits. The kits of the invention may comprise reagents such as probes or primers, reference polynucleic acids, buffers, enzymes and the like. The kits of the invention may also comprise instructions for carrying out the methods of the present invention. Such instructions may take the form of package inserts, or labels, or referrals to other sources such as books, journals, websites, and compact discs.

The invention will now be further described by way of reference only to the following non-limiting examples. It should be understood, however, that the examples following are illustrative only, and should not be taken in any way as a restriction on the generality of the invention described above.

EXAMPLE 1

Identification of Microorganisms from Sputum Sample

Sputum samples were obtained from pathology laboratories and diluted with water. Two microliters of these samples were used to amplify a specific conserved sequence found in eubacterial species by polymerase chain reaction (PCR). The PCR product was then used as a template for direct incorporation of the fluorescent analogue Cy5 by randomly primed polymerisation reactions Dorell et al, 2001 (Genome Res. 11, 1706-15) or by post-PCR labelling.

Oligonucleotide probes were designed containing unique signature sequences chosen from conserved sequences in eubacterial species and printed on micro-array slides.

The labelled PCR product was then hybridised to the microarray slide. The hybridisation took place under a glass cover slip in a humidified chamber submerged in a 53° C. water bath for 30 mins. The slides were washed, dried and scanned for fluorescence by using a laser-activated, confocal scanner.

Background was subtracted for each spot on the scanned array and analysed by the software to give the species present in the clinical sample and to advise on the appropriate treatment of the patient.

Materials and Methods

Slides: CodeLink™ activated slides (GE Healthcare).

Oligonucleotide probes: Oligonucleotides ranging from 17 to 24 nucleotides with a 5' amino modification and 10 T attachment at 5' end were designed. Oligonucleotides were designed containing unique signature sequences in the eubacterial species' tuf gene.

Spotting solution: 1M sodium phosphate buffer. Oligonucleotides dissolved in Milli-Q water at a concentration of 100 μM. Final concentration of oligonucleotides in spotting solution was 25 μM and that of sodium phosphate buffer was 250 mM.

Printing: Printing of Epoxy slides was performed using MicroGrid II Compact Microarrayer (BioRobotics).

Target DNA: A fragment of the tuf gene was amplified using the primer pair MAtuf-F4 (forward primer, 5' KYACIGGHGTBGARATGTTC 3', SEQ ID NO.:396) and MAtuf-R5 (reverse primer, 5' GTDCGDCCRCCYTCWCGRAT 3', SEQ ID No.395). A second fragment of the tuf gene was amplified using the primers MAtuf-F1 (SEQ ID No. 394) and MAtuf-R5 (SEQ ID No. 395). The primers were designed using conserved regions found in the tuf gene. The PCR conditions were 1×94° C., 1 min initial denaturation, 35×94° C., 30 secs/50° C., 30 secs/72° C., 30 secs, 1×72° C., 7 mins final extension. PCR products were purified using the Wizard PCR Preps DNA Purification kit (Promega) prior to labelling.

Labelling: Labelling was performed using the labelling mixture 2 mM dATP, dCTP, dGTP, 1.5 mM dTTP and 0.5 mM biotin-dUTP. Labelling was performed overnight at 37° C. for the product obtained using the primers MAtuf-F4 and MAtuf-R5. Direct labelling during the PCR reaction using Cy5-dUTP (GE Healthcare) was performed for the tuf fragment amplified using the MAtuf-F1 and MAtuf-R5 primers.

Hybridisation: Hybridisation was performed in a hybridisation chamber at 53° C. for 30 minutes. This was followed by 4 wash steps, 5 minutes each as follows: wash 1, 2×SSC/0.1% SDS; wash 2, 0.5×SSC/0.1% SDS; wash 3, 2×SSC; wash 4, 4×SSC/0.2% Tween 20. After hybridisation, the arrays were scanned using a GenePix 4000B scanner (Affymetrix).

Results

PCR amplification of the tuf gene fragment. The size of the amplified PCR product using the primers MAtuf-F4 and MAtuf-R5 was approximately 381 base pairs (FIG. 1). The primers MAtuf-F1 and MAtuf-R5 primers produced a PCR amplification product of approximately 1.1 kb.

Scanner outputs. The microarray successfully detected and differentiated organisms tested in this study; namely (a) *Streptococcus pneumoniae*; (b) *Moraxella catarrhalis*; (c) *Legionella pneumophila*; (d) *Staphylococcus aureus*; (e) *Haemophilus influenzae* (FIGS. 2, 3, 4, 5 and 6)

DISCUSSION

DNA microarrays combine high-precision technology with advanced molecular biology to acquire high-throughput screening of DNA fragments. In this study, the potential of the DNA microarray technique to identify and differentiate PCR derived amplicons from five pathogenic bacteria was investigated; namely, *Streptococcus pneumoniae, Moraxella catarrhalis, Legionella pneumophila, Staphylococcus aureus* and *Haemophilus influenzae.*

A fragment from the tuf gene was chosen for amplification. This gene is universally present in all bacterial species. Parts of this gene are highly conserved (conserved regions) whereas the rest exhibit high variation (variable regions). The conserved and variable regions were determined via multiple sequence alignment of the gene using the tuf DNA sequences obtained from several different bacterial species. The conserved regions were used to design primers in order to obtain amplicons containing variable regions. These amplicons were used on a DNA microarray to detect and differentiate aforementioned bacterial species.

This indicates that microarray technology can be used as a method for identifying and discriminating bacterial species. The method has been proven to be highly sensitive and specific. This investigation demonstrates that bacterial tuf gene sequences amplified via PCR technique could be successfully coupled with DNA microarrays to serve the above purpose in a clinical diagnostic setup. If current demands can be met, nucleic acid microarray technology will give competitive advantages over other molecular based identification methods. The rapid development in this area will improve the technology and reduce the cost at the same time, making the microarray methodology attractive and competitive.

Sequences

Nucleotide sequences of tuf genes from various microorganisms are provided in SEQ ID NOs.:1 to 11. SEQ ID NOs.:12 to 393 are signature (probe) sequences from various microorganisms, in which:

ABAU—*Acinetobacter baumanii*
BCEP—*Burkholderia cepacia*
BPER—*Bordetella pertussis*
CABO—*Chlamydophila abortus*
CDIP—*Corynebacterium diphtheriae*
CJEJ—*Campylobacter jejuni*
CPER—*Clostridium perfringens*
CPNE—*Chlamydophila pneumoniae*
CTET—*Clostridium tetani*
EFAE—*Enterococcus faecalis*
FNUC—*Fusobacterium nucleatum*
HPYL—*Helicobacter pylori*
HHEP—*Helicobacter hepaticus*

HINF—*Haemophilus influenzae*
KPNE—*Klebsiella pneumoniae*
LLON—*Legionella longbeachiae*
LMON—*Listeria monocytogenes*
LPNE—*Legionella pneumophila*
MCAT—*Moraxella catarrhalis*
MTUB—*Mycobacterium tuberculosis*
MPNE—*Mycoplasma pneumoniae*
NGON—*Neisseria gonorrhoeae*
NMEN—*Neisseria meningitidis*
PAER—*Pseudomonas aeruginosa*
SAUR—*Staphylococcus aureus*
SEPI—*Staphylococcus epidermidis*
SSAP—*Staphylococcus saprophyticus*
SMAL—*Stenotrophomonas maltophilia*
SPNE—*Streptococcus pneumoniae*
SPYO—*Streptococcus pyogenes*
SMUT—*Streptococcus mutans*
SSAN—*Streptococcus sanguis*
SMAR—*Serratia marcescens*
VVUL—*Vibrio vulnificus*
VPAR—*Vibrio parahaemolyticus*
VCHO—*Vibrio cholerae*
YPES—*Yersinia pestis*
YPSE—*Yersinia pseudotuberculosis*

Sequences 394 and 395 are oligonucleotide primers designed against the conserved regions of tuf genes of various micro-organisms.

Sequences may also contain alternative bases. These are shown as follows:

R—A or G
Y—C or T
M—A or C
K—G or T
S—G or C
W—A or T
H—A or C or T
B—G or C or T
V—A or G or C
D—A or G or T
I—A base that binds to A, G, C or T

The invention claimed is:

1. A method for detecting at least one microorganism in a clinical sample comprising:

(a) providing a clinical sample suspected of containing one or more microorganisms;

(b) releasing, isolating and/or concentrating polynucleic acids from said at least one microorganism(s) from said clinical sample, if present in the clinical sample;

(c) amplifying a portion of said polynucleic acids with the primer pair of SEQ ID NO: 394 and SEQ ID NO: 395, which primer pair amplifies the variable region or a part thereof of the tuf gene from *Bordetella pertussis, Chlamydophila pneumoniae, Haemophilus influenza, Legionella pneumophila, Mycoplasma pneumonia, Mycobacterium tuberculosis, Staphylococcus aureus, Staphylococcus epidermis, Streptococcus pneumoniae, Streptococcus pyogenes, Streptococcus mutans, Pseudomonas aureginosa, Enterococcus feacalis* or *Neisseria meningitides* to produce a first detectable amplified product;

(d) contacting said first detectable amplified product with at least one probe or combination thereof selected from the group consisting of SEQ ID Nos: 12 to 393 for a time and under conditions sufficient for hybridization to take place; and (e) detecting any hybridization which has taken place in step (d);

wherein the presence or absence of hybridization is indicative of the presence or absence of said one or more microorganisms in said clinical sample.

2. The method of claim 1, wherein the clinical sample is a sputum sample.

* * * * *

SEQUENCE LISTING

```
<160> NUMBER OF SEQ ID NOS: 1286

<210> SEQ ID NO 1
<211> LENGTH: 1191
<212> TYPE: DNA
<213> ORGANISM: Mycobacterium tuberculosis

<400> SEQUENCE: 1

gtggcgaagg cgaagttcca gcggaccaag ccccacgtca acatcgggac catcggtcac      60

gttgaccacg gcaagaccac cctgaccgcg gctatcacca aggtcctgca cgacaaattc     120

cccgatctga acgagacgaa ggcattcgac cagatcgaca acgcccccga ggagcgtcag     180

cgcggtatca ccatcaacat cgcgcacgtg gagtaccaga ccgacaagcg gcactacgca     240

cacgtcgacg cccctggcca cgccgactac atcaagaaca tgatcaccgg cgccgcgcag     300

atggacggtg cgatcctggt ggtcgccgcc accgacggcc cgatgcccca gacccgcgag     360

cacgttctgc tggcgcgtca agtgggtgtg ccctacatcc tggtagcgct gaacaaggcc     420

gacgcagtgg acgacgagga gctgctcgaa ctcgtcgaga tggaggtccg cgagctgctg     480

gctgcccagg aattcgacga ggacgccccg gttgtgcggg tctcggcgct caaggcgctc     540

gagggtgacg cgaagtgggt tgcctctgtc gaggaactga tgaacgcggt cgacgagtcg     600

attccggacc cggtccgcga gaccgacaag ccgttcctga tgccggtcga ggacgtcttc     660

accattaccg gccgcggaac cgtggtcacc ggacgtgtgg agcgcggcgt gatcaacgtg     720

aacgaggaag ttgagatcgt cggcattcgc ccatcgacca ccaagaccac cgtcaccggt     780

gtggagatgt tccgcaagct gctcgaccag ggccaggcgg gcgacaacgt tggtttgctg     840

ctgcggggcg tcaagcgcga ggacgtcgag cgtggccagg ttgtcaccaa gcccggcacc     900

accacgccgc acaccgagtt cgaaggccag gtctacatcc tgtccaagga cgagggcggc     960

cggcacacgc cgttcttcaa caactaccgt ccgcagttct acttccgcac caccgacgtg    1020

accggtgtgg tgacactgcc ggagggcacc gagatggtga tgcccggtga caacaccaac    1080

atctcggtga agttgatcca gcccgtcgcc atggacgaag gtctgcgttt cgcgatccgc    1140

gagggtggcc gcaccgtggg cgccggccgg gtcaccaaga tcatcaagta g             1191
```

<210> SEQ ID NO 2
<211> LENGTH: 953
<212> TYPE: DNA
<213> ORGANISM: Legionella longbeachiae

<400> SEQUENCE: 2

```
gtttggtggt atagcaaaag catacgatca gatcgatgct gcaccagaag aaagagagcg     60
aggcatcaca atctcaacag cgcacgttga atacgaatca gcgaacagac actatgcgca    120
tgttgatccc aggacatgct gactatgtga agaacatgat tacaggtgct gcacaaatgg    180
acggagcgat acttgtagta tctgcagcag atggtcctat gcctcaaact agagaacata    240
ttctattgtc acgcagtagg ggtgccctac atagtagtgt ttatgaataa agcggacatg    300
gttgatgatc cagagctctt agagcttgta gaaatggaag tccgtgattt gttgagcagt    360
tatgattttc ctggtgatgt atccaattgt tgttggatct gcattgaaag cattagaagg    420
tgataccagt gatattgggg tgccagcaat agagaaattg gtagagacta tggattctta    480
tattccagag cctgtaagaa acattacaat cgttcttatt accgattgaa gatgtatttt    540
caatatctgg ccgaggaaca gtagtaacag gacgtatcga aagcggaatt atcaaagttg    600
gcgaagagat cgaaattgta ggaattcgtg aactgaaaga ctacctgtac tggtgttgag    660
atgttccgta agttattaga cgaaggacgt gcaggtgata acgttggtat attactccgt    720
ggaacaaaac gagacgaagt tgagcgtggt caggtatagc caaccaggta caattaagcc    780
tcacactaaa tttgaagcgg aagtatacgt gttatctaaa gaagaaggtg gacgacatac    840
cccgtttttc aatggatata gaccacagtt ttattttaga acacagacga acaggaactt    900
gtgatttacc atctggagtt gaaatggtaa tgcctggaga taacgtacag ttg          953
```

<210> SEQ ID NO 3
<211> LENGTH: 924
<212> TYPE: DNA
<213> ORGANISM: Fusobacterium nucleatum

<400> SEQUENCE: 3

```
agctaaaaaa gtagattttg accaaattga tgctgctcca gaagaaaaag aaagaggaat     60
tactattaat acagctcata ttgaatatga aacagcaaat agacactatg ctcacgttga    120
ctgtccagca tgctgactat gttaaaaata tgataactgg tgctgcacaa atggatggag    180
ctatacttgt tgtatcagct gctgatggtc ctatgcctca aacaagagaa catatcttac    240
tttctagaca agtgagtacc atatattatt gtttatttaa ataaatcaga tatggttgat    300
gatgaagaat tactagaatt ggtagaaatg gaagttagag aattattaac tgaatatgga    360
ttcccaggag atgacatcct gaattagagg ttcatcatta ggagctttaa atggtgaaga    420
aaaatggata gaaaagataa tggaacttat ggatgcagta gatagctata tccctactcc    480
tgaaagagca gtagatcaac cattctgagc caatagaaga cgttttcact atcacaggaa    540
gaggaacagt tgttacagga agagttgaaa gaggaatcat caaagttgga gaagaaattg    600
aaatagttgg aattaaacct acaactaaaa cactttacag gggttgaaat gtttagaaaa    660
cttcttgatc aaggtcaagc aggagataat atcggagtat tattaagagg aactaagaaa    720
gaagaagttg aaagaggaca agttcttgct aaaccagaag taccaccctc atacaaactt    780
taaaggtgaa gtctatgtat taactaaaga tgaaggagga agacacactc catttttcac    840
aggatacaga cctcaattct attttagaac tactgatatc actgtgcaga actttaccag    900
atggagtaga aatggttatg ccag                                           924
```

<210> SEQ ID NO 4
<211> LENGTH: 909
<212> TYPE: DNA
<213> ORGANISM: Moraxella catarrhalis

<400> SEQUENCE: 4
agaaaaagca cgtggtatta ctattaacac atctcacatc gagtatgaca cagaagctcg 60
tcactacgca catgtagact gcccaggcca cgctgactat gttaaaaaca tgatcacagg 120
tgctgcagat ggacggcgca atcttggttg tttctgcaac tgacggccca atgccacaaa 180
ctcgtgagca catcctactg tctcgtcagg ttggtgtacc atatatcatg gtattcatga 240
acaagtgcga catgagatga tgaagagcta ctagaattgg ttgaaatgga agttcgtgaa 300
cttctatctg actatgactt cccaggtgat gacaccccaa tcatcaaagg ttcagcacta 360
gaagcattga atggttctgc gtaaatatgg tgagcctgct gttctagaac tactagacac 420
gctagattca tacatcccag agcctgagcg tgacatcgat aagtcattcc taatgccaat 480
cgaagatgtc ttctcaatct caggtgtgta ctgttgtaac tggccgtgtt gaatcaggca 540
ttattaaagt tggtgatgaa attgaaatca tcggtatcaa accaactact aaaaccactt 600
gtactggtgt tgaaatgttc cgtaagctgc tgacgaggtc gtgcaggtga gaactgtggt 660
atcctactac gtggtactaa gcgtgaagaa gttcaacgtg gtcaagtatt ggctaagcca 720
ggttcaatca ccccacacac caagtttgat gcagaagata cggctatcaa aagaagaagg 780
tggtcgtcat accccattcc taaatggcta tcgtccacag ttctacttcc gtaccacaga 840
cgtaactggt gccatcaccc tacaagaagg cactgaaatg gtttgccagt gataacgttg 900
agatgagcg 909

<210> SEQ ID NO 5
<211> LENGTH: 982
<212> TYPE: DNA
<213> ORGANISM: Stenotrophomonas maltophilia

<400> SEQUENCE: 5
tgacaagatc ggtgccgagc gcttcggtgg cgagttcaag gactactcct cgatcgacgc 60
cgcgccggaa gaaaaggctc gtggtatcac gatctcgacc gcgcacgtcg aatacgaatc 120
cccgatctca ctacgcccac gttgactgcc cgggccacgc tgactacgtc aagaacatga 180
tcaccggtgc cgcccagatg gacggcgcga tcctggtgtg ctcggccgct gacggcccga 240
tgccgcagac ccgggcacat cctgctgtcg cgccaggtcg gcgtgccgta catcgtcgtg 300
ttcctgaaca aggccgacat ggtcgacgac gccgagctgc tcgagctggt cgagatggaa 360
gtgcgcgaac tgctgagcag tcgagttccc gggcgacgac accccgatca tcgccggttc 420
ggcccgcctg gcgctggaag gcgaccagag cgacatcggc gtgccggcca tcctgaagct 480
ggtcgacgcg ctggacagct ggattcgggc cggagcgtgc gatcgacaag ccgttcctga 540
tgccggtgga agacgtgttc tcgatctcgg gccgcggcac cgtggtgacc ggtcgtatcg 600
agcgcggcgt gatcaaggtt ggcgacgaaa tcgaaatcgt cggcatccgt ccggtgcaga 660
agaccaccgt ccggcgttga aatgttccgc aagctgctgg accagggtca ggcaggcgac 720
aacgctggcc tgctgctgcg cggcaccaag cgtgacgacg tcgagcgtgg ccaggtgctg 780
gccaagccgg gcacgacagc cgcacaccaa gttcgaaggc gaagtgtacg tcctgtcgaa 840
ggacgaaggc ggccgccaca ccccgttctt caacggctac cgtccgcagt tctacttccg 900
caccaccgac atcaccggcg cactcgctgc cggaaggcgt cgaaatggtg atgccgggtg 960
acaacgtcaa gatggtcgtc ac 982

<210> SEQ ID NO 6
<211> LENGTH: 984
<212> TYPE: DNA
<213> ORGANISM: Streptococcus sanguis

<400> SEQUENCE: 6

```
ctgtattggc acgtcgcttg ccttcagcag ttaaccaacc taaagactat gcgtctatcg      60
atgctgctcc agaagaacgc gaacgcggaa tcactatcaa cactgcgcac gttgagtatg     120
aaactgcagc gtcactacgc tcacatcgac gctccaggac acgcggacta cgttaaaaac     180
atgatcactg gtgccgctca aatggacgga gctatccttg tagtagcttc aactgacgga     240
ccaatgccac aaatgtgagc acatcttgct ttcacgtcag gttggtgtta aacacttgat     300
cgtcttcatg aacaaagttg acttggttga cgatgaagaa ttgcttgaat tggttgaaat     360
ggaaatccgt gacctcttgt cagaatacga cttcccaggt gacgatcttc cagttatcca     420
aggttcagct taaagctctt gaaggtgact ctaaatatga agacatcatc atggaattga     480
tggacactgt tgatgagtac atcccagaac cagaacgcga tactgacaag ccattgcttc     540
ttccagtcga agacgttctc aatcactggt cgtggtacag ttgcttcagg acgtatcgac     600
cgtggtatcg ttaaagtcaa cgacgaaatc gaaatcgttg gtatcaaaga agaaatccaa     660
aaagcagttg ttactggtgt tgaagttccg taaacagctt gacgaaggtc ttgcagggac     720
aacgtaggtg tgcttctccg tggtatccaa cgtgatgaaa tcgaacgtgg acaagttatc     780
gctaaaccag gttcaatcaa cccacacata attcaagggt gaagtttata tccttactaa     840
agaagaaggc ggacgtcaca ctccattctt caacaactac cgtccacagt tctacttccg     900
tacaactgac gttacaggtt caatcgaact tccacaggac tgaaatggta atgcctggtg     960
ataacgtaac aatcgacgtt gagt                                            984
```

<210> SEQ ID NO 7
<211> LENGTH: 964
<212> TYPE: DNA
<213> ORGANISM: Streptococcus mutans

<400> SEQUENCE: 7

```
ctgtactggc acgtcgtctt ccaagtgcag taaaccaacc aaaagattat tcatctattg      60
atgctgctcc tgaagaacgc gaacgcggta tcactatcaa tactgcgcac gttgagtatg     120
aaactgaaac gtcactatgc tcacattgac gctccaggac acgcggacta tgttaaaaac     180
atgattactg gtgctgccca aatggatggt gctatccttg tagtagcttc aactgatggt     240
ccaatgccac aaatgtgaac acattcttct ttcacgtcaa gttggtgtta aataccttat     300
tgtcttcatg aataaggttg atttggttga tgatgaagaa ctgcttgaat tggttgaaat     360
ggaaatccgt gatcttcttc aaatatgatt tcccaggtga tgatattcca gttattcaag     420
gttcagctct taaagctctt gaaggtgata ctgctcaaga agatatcatc atggaattaa     480
tgcatactgt tgatgactac attccgatca gaacgtgata ctgataagcc actccttctt     540
ccagtcgaag atgttttctc aatcactggt cgtggtactg ttgcttcagg acgtattgat     600
cgtggtactg ttaaagttaa cgatgaagtt gaatcttggt atccgtgatg acattcaaaa     660
agctgttgtt actggtgttg aaatgttccg taaacaattg gatgaaggta ttgcagggga     720
taatgttggt gttctccttc gtggtatcca acgtgataaa tcaacgtggt caagttcttg     780
ctaaaccagg ttcaattcac ccacatacta aattcaaagg tgaagtttat atccttacta     840
aagaagaagg tggacgtcat acaccattct tcaataacta tcgccacaat ctacttccgt     900
```

acaactgacg taactggttc aattgagttg ccagcaggta ctgaaatggt tatgcctggt 960
gata 964

<210> SEQ ID NO 8
<211> LENGTH: 870
<212> TYPE: DNA
<213> ORGANISM: Burkholderia cepacia

<400> SEQUENCE: 8
gttcggcggc gaagcgaaga agtacgacga aatcgacgcg gcgccggaag aaaaggcacg 60
cggcatcacg atcaacaccg cgcacatcga gtacgaaacg gcgaaccgcc actacgcgca 120
cgtcgacccc gggccacgcc gactacgtga agaacatgat cacgggtgca gcgcagatgg 180
acggcgcaat cctggtgtgc tcggccgcag acggcccgat gccgcaaacg cgtgagcaca 240
tcctgctggc gcgcggttgg cgttccgtac atcatcgtgt tcctgaacaa gtgcgacatg 300
gtggacgacg ctgaactgct cgagctggtc gagatggaag ttcgcgaact gctgtcgaag 360
tacgacttcc cgggcgacgc agccgatcat caagggttcg gcaaagctgg cgctggaagg 420
cgacaagggc gagctgggcg aaacggcgat catgaacctg gccgacgcgc tggacacgta 480
catcccgacg ccggagcgcg cggtgacgta cgttcctgat gccggtggaa gacgtgttct 540
cgatctcggg ccgcggtacg gtggtgacgg gtcgtgtgga gcgcggcgtg gtgaaggtcg 600
gtgaggaaat cgaaatcgtc ggtatcaagc cacgggaaga cgacctgcac gggcgttgaa 660
atgttccgca agctgctgga ccagggtcag gcaggcgaca acgtcggtat cctgctgcgc 720
ggcacgaagc gtgaagacgt ggagcgcggt caggttcggc gagccgggtt cgatcacgcc 780
gcacacgcac ttcacggccg aagtgtacgt gctgagcaag gacgaaggcg gccgtcacac 840
gccgttcttc aacaactacc gtccgcagtt 870

<210> SEQ ID NO 9
<211> LENGTH: 936
<212> TYPE: DNA
<213> ORGANISM: Enterococcus faecalis

<400> SEQUENCE: 9
gggaaagcac aaagctacga ttctatcgat aacgctccag aagaaaaaga acgtggaatc 60
acaatcaaca cttctcatat cgaatatgaa actgaaactc gtcactatgc acacgttgac 120
tgcccagcac gcggactacg ttaaaaacat gatcactggt gctgctcaaa tggacggagc 180
tatcttagta gtttctgctg ctgatggtcc tatgcctcaa acacgtgaac atatcttatt 240
atcacgtaac gttggtacca tacatcgttg tattcttaaa caaaatggat atggttgatg 300
acgaagaatt attagaatta gtagaaatgg aagttcgtga cttattatca gaatacgatt 360
tcccaggcga tgatgttccg tatcgcaggt tctgctttga aagctttaga aggcgacgag 420
tcttatgaag aaaaaatctt agaattaatg gctgcagttg acgaatatat cccaactcca 480
gaacgtgata ctgacaaacc attcagatcc agtcgaagac gtattctcaa tcactggacg 540
tggtactgtt gctacaggac gtgttgaacg tggtgaagtt cgcgttggtg acgaagttga 600
aatcgttggt attaaagacg aaacatctaa acaacgttac aggtgttgaa atgttccgta 660
aattattaga ctacgctgaa gcaggcgaca acatcggtgc tttattacgt ggtgtagcac 720
gtgaagatat cgaacgtgga caagtattag ctaaaccgct acatcactcc acacacaaaa 780
ttcaaagctg aagtatacgt attatcaaaa gaagaaggcg gacgtcacac tccattcttc 840
actaactacc gtcctcaatt ctacttccgt acaacagacg ttatggtgtg tagaattgcc 900
agaaggtact gaaatggtaa tgcctggtga taacgt 936

<210> SEQ ID NO 10
<211> LENGTH: 945
<212> TYPE: DNA
<213> ORGANISM: Corynebacterium diphtheriae

<400> SEQUENCE: 10
tgcacaatca tacgacatga ttgacaacgc accagaagaa aaagaacgtg gtattacaat 60
caatactgca cacatcgaat atcaaactga caaacgtcac tatgctcacg ttgactgccc 120
aggacactga ctatgttaaa aacatgatca ctggtgctgc gcaaatggac ggcggtatct 180
tagttgtatc tgcagctgat ggtccaatgc cacaaactcg tgaacacatt cttttatcac 240
gtaacgttgg tgtcagcttt agttgtattc ttaaacaaag ttgatatggt agacgacgaa 300
gaattattag aattagtaga aatggaagtt cgtgacttac tatctgaata cgacttccca 360
ggtgacgacg tacctgtaac gtggttcagc attaaaagct ttagaaggcg acgaaaaata 420
cgaagaaaaa atcttagaat taatgcaagc agttgatgac tacatcccaa ctccagaacg 480
tgattctgac aaaccattca tgatgcagtg aggacgtatt ctcaatcact ggtcgtggta 540
ctgttgctac aggccgtgtt gaacgtggtc aaatcaaagt tggtgaagaa gttgaaatca 600
tcggtttaca tgacacttct aaaacaactg tactgtgtag aaatgttccg taagttatta 660
gactacgctg aagctggtga caacattggt gctttattac gtggtgttgc tcgtgaagac 720
gtacaacgtg gtcaagtatt agctgctcct ggttcaatac acacatacaa aattcaaagc 780
ggaagtttac gttttatcta aagacgaagg tggacgtcac actccattct tcagtaacta 840
ccgcccacaa ttctatttcc gtactactga cgtaactggc gttttcaata ccagaaggta 900
ctgaaatggt tatgcctggt gacaacgttg aaatgacagt agaat 945

<210> SEQ ID NO 11
<211> LENGTH: 969
<212> TYPE: DNA
<213> ORGANISM: Neisseria meningitidis

<400> SEQUENCE: 11
cccgaagaaa aagcacgcgg tattaccatt aacacctcgc acgtggaata cgaaaccgaa 60
acccgccact acgcacacgt agactgcccg gggcacgccg actacgttaa aaacatgatt 120
accggtggca caaatggacg gtgcaatcct ggtatgttcc gcagccgacg gccctatgcc 180
gcaaacccgc gaacacatcc tgctggcccg tcaagtaggc gtaccttaca tcatcgtgtt 240
catgaacaaa tgcaatggtc gacgatgccg agctgttgga actggttgaa atggaaatcc 300
gcgacctgct gtccagctac gacttccccg gcgacgactg cccgattgta caaggttctg 360
cactgaaagc cttggaaggg agccgcttat gaagagaaaa tcttcgaact ggctgccgca 420
ttggacagct acatcccgac tcccgagcgt gccgtggaca aacctttcct gctgcctatc 480
gaagacgtgt tctccatttc cggccaggac agtagtaacc ggccgtgtag agcgcggtat 540
catccacgtt ggtgacgaga ttgaaatcgt cggtctgaaa gaaacccaaa aaaccacctg 600
taccggtgtt gaaatgttcc gcaaactgct gacgaggtca ggcgggcgac aacgtacgcg 660
tattgctgcg cggtaccaaa cgtgaagacg tggaacgcgg tcaggtattg gccaaacccg 720
ggtactatca ctcctcacac caagttcaaa gcagacggta cgactgagca aagaagaggg 780
cggccgccat actccgttct tcgccaacta ccgtccgcat tctacttccg taccaccgac 840
gtaaccggcg cggttacttt ggaagaagga gtggaaatgg taagcctggg agaacgtaac 900
catcaccgta gactgattgc gtctatcgct atggaagagc tgcgcttgcg tcgtgtcgcg 960
cgtgtccat 969

<210> SEQ ID NO 12
<211> LENGTH: 29
<212> TYPE: DNA
<213> ORGANISM: Haemophilus influenzae

<400> SEQUENCE: 12
tattatccgt acaggtgatg aagtagaaa 29

<210> SEQ ID NO 13
<211> LENGTH: 27
<212> TYPE: DNA
<213> ORGANISM: Haemophilus influenzae

<400> SEQUENCE: 13
aaagatacag cgaaaactac tgtaacg 27

<210> SEQ ID NO 14
<211> LENGTH: 24
<212> TYPE: DNA
<213> ORGANISM: haemophilus influenzae

<400> SEQUENCE: 14
catcggtgca ttattacgtg gtac 24

<210> SEQ ID NO 15
<211> LENGTH: 26
<212> TYPE: DNA
<213> ORGANISM: haemophilus influenzae

<400> SEQUENCE: 15
catactccat tcttcaaagg ttaccg 26

<210> SEQ ID NO 16
<211> LENGTH: 26
<212> TYPE: DNA
<213> ORGANISM: Haemophilus influenzae

<400> SEQUENCE: 16
tgactggtac aatcgaatta ccagaa 26

<210> SEQ ID NO 17
<211> LENGTH: 24
<212> TYPE: DNA
<213> ORGANISM: Haemophilus influenzae

<400> SEQUENCE: 17
ccgtaaatta cttgacgaag gtcg 24

<210> SEQ ID NO 18
<211> LENGTH: 22
<212> TYPE: DNA
<213> ORGANISM: Moraxella catarrhalis

<400> SEQUENCE: 18
tgagcgtgac atcgataagt ca 22

<210> SEQ ID NO 19
<211> LENGTH: 29
<212> TYPE: DNA
<213> ORGANISM: Moraxella catarrhalis

<400> SEQUENCE: 19
caggcattat taaagttggt gatgaaatt 29

<210> SEQ ID NO 20
<211> LENGTH: 28
<212> TYPE: DNA
<213> ORGANISM: Moraxella catarrhalis

<400> SEQUENCE: 20
aaaccaacta ctaaaaccac ttgtactg 28

<210> SEQ ID NO 21
<211> LENGTH: 21
<212> TYPE: DNA
<213> ORGANISM: Moraxella catarrhalis

<400> SEQUENCE: 21
cgtaagctgc tagacgaagg t 21

<210> SEQ ID NO 22
<211> LENGTH: 24
<212> TYPE: DNA
<213> ORGANISM: Moraxella catarrhalis

<400> SEQUENCE: 22
taccccattc ctaaatggct atcg 24

<210> SEQ ID NO 23
<211> LENGTH: 21
<212> TYPE: DNA
<213> ORGANISM: Moraxella catarrhalis

<400> SEQUENCE: 23
taactggtgc catcacccta c 21

<210> SEQ ID NO 24
<211> LENGTH: 22
<212> TYPE: DNA
<213> ORGANISM: Enterococcus faecalis

<400> SEQUENCE: 24
aaggcgacga gtcttatgaa ga 22

<210> SEQ ID NO 25
<211> LENGTH: 24
<212> TYPE: DNA
<213> ORGANISM: Enterococcus faecalis

<400> SEQUENCE: 25
aattaatggc tgcagttgac gaat 24

<210> SEQ ID NO 26
<211> LENGTH: 19
<212> TYPE: DNA
<213> ORGANISM: Enterococcus faecalis

<400> SEQUENCE: 26
gaagttcgcg ttggtgacg 19

<210> SEQ ID NO 27
<211> LENGTH: 28
<212> TYPE: DNA
<213> ORGANISM: Enterococcus faecalis

<400> SEQUENCE: 27
gacgaaacat ctaaaacaac tgttacag 28

<210> SEQ ID NO 28
<211> LENGTH: 23
<212> TYPE: DNA
<213> ORGANISM: Enterococcus faecalis

<400> SEQUENCE: 28
tggtgttgta gaattgccag aag 23

<210> SEQ ID NO 29
<211> LENGTH: 24
<212> TYPE: DNA
<213> ORGANISM: Enterococcus faecalis

<400> SEQUENCE: 29
taaaccagct acaatcactc caca 24

<210> SEQ ID NO 30
<211> LENGTH: 27
<212> TYPE: DNA
<213> ORGANISM: Staphylococcus aureus

<400> SEQUENCE: 30
gttgacatgg ttgacgatga agaatta 27

<210> SEQ ID NO 31
<211> LENGTH: 32
<212> TYPE: DNA
<213> ORGANISM: Staphylococcus aureus

<400> SEQUENCE: 31
cttagaatta atggaagctg tagatactta ca 32

<210> SEQ ID NO 32
<211> LENGTH: 28
<212> TYPE: DNA
<213> ORGANISM: Staphylococcus aureus

<400> SEQUENCE: 32
atcatcggtt tacatgacac atctaaaa 28

<210> SEQ ID NO 33
<211> LENGTH: 29
<212> TYPE: DNA
<213> ORGANISM: Staphylococcus aureus

<400> SEQUENCE: 33
caccacatac tgaatttaaa gcagaagta 29

<210> SEQ ID NO 34
<211> LENGTH: 26
<212> TYPE: DNA
<213> ORGANISM: Staphylococcus aureus

<400> SEQUENCE: 34
cattcttctc aaactatcgt ccacaa 26

<210> SEQ ID NO 35
<211> LENGTH: 24
<212> TYPE: DNA
<213> ORGANISM: Staphylococcus aureus

<400> SEQUENCE: 35
ctggtgttgt tcacttacca gaag 24

<210> SEQ ID NO 36
<211> LENGTH: 26
<212> TYPE: DNA
<213> ORGANISM: Staphylococcus aureus

<400> SEQUENCE: 36
tactgaaatg gtaatgcctg gtgata 26

<210> SEQ ID NO 37
<211> LENGTH: 20
<212> TYPE: DNA
<213> ORGANISM: Staphylococcus aureus

<400> SEQUENCE: 37
ccaatcgcga ttgaagacgg 20

<210> SEQ ID NO 38
<211> LENGTH: 27
<212> TYPE: DNA
<213> ORGANISM: Staphylococcus aureus

<400> SEQUENCE: 38
ctggttcagc attaaaagct ttagaag 27

<210> SEQ ID NO 39
<211> LENGTH: 25
<212> TYPE: DNA
<213> ORGANISM: Staphylococcus aureus

<400> SEQUENCE: 39
tgacaacatt ggtgcattat tacgt 25

<210> SEQ ID NO 40
<211> LENGTH: 24
<212> TYPE: DNA
<213> ORGANISM: Staphylococcus aureus

<400> SEQUENCE: 40
tgttacaggt gttgaaatgt tccg 24

<210> SEQ ID NO 41
<211> LENGTH: 26
<212> TYPE: DNA
<213> ORGANISM: Staphylococcus aureus

<400> SEQUENCE: 41
gtattatcaa aagacgaagg tggacg 26

<210> SEQ ID NO 42
<211> LENGTH: 26
<212> TYPE: DNA
<213> ORGANISM: Staphylococcus aureus

<400> SEQUENCE: 42
gcgatgctca atacgaagaa aaaatc 26

<210> SEQ ID NO 43
<211> LENGTH: 29
<212> TYPE: DNA
<213> ORGANISM: Staphylococcus epidermidis

<400> SEQUENCE: 43
tagacttaat gcaagcagtt gatgattac 29

<210> SEQ ID NO 44
<211> LENGTH: 25
<212> TYPE: DNA
<213> ORGANISM: Staphylococcus epidermidis

<400> SEQUENCE: 44
ccacacacaa aattcaaagc tgaag 25

<210> SEQ ID NO 45
<211> LENGTH: 25
<212> TYPE: DNA
<213> ORGANISM: Staphylococcus epidermidis

<400> SEQUENCE: 45
ctggtgttgt aaacttacca gaagg 25

<210> SEQ ID NO 46
<211> LENGTH: 21
<212> TYPE: DNA
<213> ORGANISM: Staphylococcus epidermidis

<400> SEQUENCE: 46
gaaatggtta tgcctggcga c 21

<210> SEQ ID NO 47
<211> LENGTH: 27
<212> TYPE: DNA
<213> ORGANISM: Staphylococcus epidermidis

<400> SEQUENCE: 47
ctggttctgc attaaaagca ttagaag 27

<210> SEQ ID NO 48
<211> LENGTH: 24
<212> TYPE: DNA
<213> ORGANISM: Staphylococcus epidermidis

<400> SEQUENCE: 48
tgacaacatc ggtgctttat tacg 24

<210> SEQ ID NO 49
<211> LENGTH: 25
<212> TYPE: DNA
<213> ORGANISM: Staphylococcus epidermidis

<400> SEQUENCE: 49
ctgttactgg tgtagaaatg ttccg 25

<210> SEQ ID NO 50
<211> LENGTH: 27
<212> TYPE: DNA
<213> ORGANISM: Staphylococcus epidermidis

<400> SEQUENCE: 50
cgtattatct aaagatgaag gtggacg 27

<210> SEQ ID NO 51
<211> LENGTH: 17
<212> TYPE: DNA
<213> ORGANISM: Pseudomonas aeruginosa

<400> SEQUENCE: 51
aagttcgagt gcgaagt 17

<210> SEQ ID NO 52
<211> LENGTH: 19
<212> TYPE: DNA
<213> ORGANISM: Pseudomonas aeruginosa

<400> SEQUENCE: 52
aaggcgtaga gatggtaat 19

<210> SEQ ID NO 53
<211> LENGTH: 17
<212> TYPE: DNA
<213> ORGANISM: Pseudomonas aeruginosa

<400> SEQUENCE: 53
ttcttcaagg gctaccg 17

<210> SEQ ID NO 54
<211> LENGTH: 23
<212> TYPE: DNA
<213> ORGANISM: Pseudomonas aeruginosa

<400> SEQUENCE: 54
atcatcaagg tccaggaaga agt 23

<210> SEQ ID NO 55
<211> LENGTH: 19
<212> TYPE: DNA
<213> ORGANISM: Pseudomonas aeruginosa

<400> SEQUENCE: 55
accaagacta cctgcaccg 19

<210> SEQ ID NO 56
<211> LENGTH: 20
<212> TYPE: DNA
<213> ORGANISM: Pseudomonas aeruginosa

<400> SEQUENCE: 56
tgtacgtgct gtccaaggaa 20

<210> SEQ ID NO 57
<211> LENGTH: 18
<212> TYPE: DNA
<213> ORGANISM: Pseudomonas aeruginosa

<400> SEQUENCE: 57
ccggtaactg cgaactgc 18

<210> SEQ ID NO 58
<211> LENGTH: 20
<212> TYPE: DNA
<213> ORGANISM: Bordetella pertussis

<400> SEQUENCE: 58
gtacattctg tccaaggaag 20

<210> SEQ ID NO 59
<211> LENGTH: 18
<212> TYPE: DNA
<213> ORGANISM: Bordetella pertussis

<400> SEQUENCE: 59
gacaacgtgg gtatcttg 18

<210> SEQ ID NO 60
<211> LENGTH: 17
<212> TYPE: DNA
<213> ORGANISM: Bordetella pertussis

<400> SEQUENCE: 60
gacaaggaaa tggtgct 17

<210> SEQ ID NO 61
<211> LENGTH: 21
<212> TYPE: DNA
<213> ORGANISM: Chlamydia pneumoniae

<400> SEQUENCE: 61
aatttaagtc agctgtttac g 21

<210> SEQ ID NO 62
<211> LENGTH: 20
<212> TYPE: DNA
<213> ORGANISM: Chlamydia pneumoniae

<400> SEQUENCE: 62
gaggtattgg aaagaacgat 20

<210> SEQ ID NO 63
<211> LENGTH: 20
<212> TYPE: DNA
<213> ORGANISM: Chlamydia pneumoniae

<400> SEQUENCE: 63
ataacgttga gcttgatgtt 20

<210> SEQ ID NO 64
<211> LENGTH: 20
<212> TYPE: DNA
<213> ORGANISM: Haemophilus influenzae

<400> SEQUENCE: 64
acttcgaatc agaagtgtac 20

<210> SEQ ID NO 65
<211> LENGTH: 20
<212> TYPE: DNA
<213> ORGANISM: Haemophilus influenzae

<400> SEQUENCE: 65
caaacgtgaa gaaatcgaac 20

<210> SEQ ID NO 66
<211> LENGTH: 21
<212> TYPE: DNA
<213> ORGANISM: Haemophilus influenzae

<400> SEQUENCE: 66
cgataacatc aagatgacag t 21

<210> SEQ ID NO 67
<211> LENGTH: 20
<212> TYPE: DNA
<213> ORGANISM: Legionella pneumophila

<400> SEQUENCE: 67
agtttgaagc agaagtgtat 20

<210> SEQ ID NO 68
<211> LENGTH: 20
<212> TYPE: DNA
<213> ORGANISM: Legionella pneumophila

<400> SEQUENCE: 68
tgttattacg aggtacgaag 20

<210> SEQ ID NO 69
<211> LENGTH: 23
<212> TYPE: DNA
<213> ORGANISM: Legionella pneumophila

<400> SEQUENCE: 69
agataatgtg caattagttg tta 23

<210> SEQ ID NO 70
<211> LENGTH: 23
<212> TYPE: DNA
<213> ORGANISM: Mycoplasma pneumoniae

<400> SEQUENCE: 70
gaaatttaaa gcggaaatct atg 23

<210> SEQ ID NO 71
<211> LENGTH: 19
<212> TYPE: DNA
<213> ORGANISM: Mycoplasma pneumoniae

<400> SEQUENCE: 71
gaacgtggtc aagtgttag 19

<210> SEQ ID NO 72
<211> LENGTH: 20
<212> TYPE: DNA
<213> ORGANISM: Mycoplasma pneumoniae

<400> SEQUENCE: 72
gacaatacct cgattacagt 20

<210> SEQ ID NO 73
<211> LENGTH: 20
<212> TYPE: DNA
<213> ORGANISM: Mycobacterium tuberculosis

<400> SEQUENCE: 73
aacatctcgg tgaagttgat 20

<210> SEQ ID NO 74
<211> LENGTH: 18
<212> TYPE: DNA
<213> ORGANISM: Mycobacterium tuberculosis

<400> SEQUENCE: 74
tgacaacacc aacatctc 18

<210> SEQ ID NO 75
<211> LENGTH: 16
<212> TYPE: DNA
<213> ORGANISM: Mycobacterium tuberculosis

<400> SEQUENCE: 75
acgaaggtct gcgttt 16

<210> SEQ ID NO 76
<211> LENGTH: 22
<212> TYPE: DNA
<213> ORGANISM: Staphylococcus aureus

<400> SEQUENCE: 76
tgaattcaaa gcagaagtat ac 22

<210> SEQ ID NO 77
<211> LENGTH: 20
<212> TYPE: DNA
<213> ORGANISM: Staphylococcus aureus

<400> SEQUENCE: 77
attattacgt ggtgttgctc 20

<210> SEQ ID NO 78
<211> LENGTH: 21
<212> TYPE: DNA
<213> ORGANISM: Staphylococcus aureus

<400> SEQUENCE: 78
gtgataacgt tgaaatgaca g 21

<210> SEQ ID NO 79
<211> LENGTH: 21
<212> TYPE: DNA
<213> ORGANISM: Streptococcus pneumoniae

<400> SEQUENCE: 79
aattcaaagg tgaagtctac a 21

<210> SEQ ID NO 80
<211> LENGTH: 19
<212> TYPE: DNA
<213> ORGANISM: Streptococcus pneumoniae

<400> SEQUENCE: 80
caacgtgatg aaatcgaac 19

<210> SEQ ID NO 81
<211> LENGTH: 18
<212> TYPE: DNA
<213> ORGANISM: Streptococcus pneumoniae

<400> SEQUENCE: 81
gacaatcgac gttgagtt 18

<210> SEQ ID NO 82
<211> LENGTH: 24
<212> TYPE: DNA
<213> ORGANISM: Streptococcus pyogenes

<400> SEQUENCE: 82
caaaggtgaa gtatatatcc tttc 24

<210> SEQ ID NO 83
<211> LENGTH: 18
<212> TYPE: DNA
<213> ORGANISM: Streptococcus pyogenes

<400> SEQUENCE: 83
caacgtgacg aaatcgaa 18

<210> SEQ ID NO 84
<211> LENGTH: 18
<212> TYPE: DNA
<213> ORGANISM: Streptococcus pyogenes

<400> SEQUENCE: 84
cgtgacaatc aacgttga 18

<210> SEQ ID NO 85
<211> LENGTH: 23
<212> TYPE: DNA
<213> ORGANISM: Pseudomonas aeruginosa

<400> SEQUENCE: 85
cacgttgact gccccggtca cgc 23

<210> SEQ ID NO 86
<211> LENGTH: 25
<212> TYPE: DNA
<213> ORGANISM: Pseudomonas aeruginosa

<400> SEQUENCE: 86
acgccttccg gcagttcgca gttac 25

<210> SEQ ID NO 87
<211> LENGTH: 22
<212> TYPE: DNA
<213> ORGANISM: Pseudomonas aeruginosa

<400> SEQUENCE: 87
atcggtcacg ttgaccatgg ca 22

<210> SEQ ID NO 88
<211> LENGTH: 21
<212> TYPE: DNA
<213> ORGANISM: Pseudomonas aeruginosa

<400> SEQUENCE: 88
gccgccttcg cggatcgcga a 21

<210> SEQ ID NO 89
<211> LENGTH: 24
<212> TYPE: DNA
<213> ORGANISM: Neisseria gonorrhoeae

<400> SEQUENCE: 89
caccctgact gctgctttga ctac 24

<210> SEQ ID NO 90
<211> LENGTH: 22
<212> TYPE: DNA
<213> ORGANISM: Neisseria gonorrhoeae

<400> SEQUENCE: 90
ccacctgtac cggcgttgaa at 22

<210> SEQ ID NO 91
<211> LENGTH: 26
<212> TYPE: DNA
<213> ORGANISM: Neisseria gonorrhoeae

<400> SEQUENCE: 91
gtattggcca aaccgggtac tatcac 26

<210> SEQ ID NO 92
<211> LENGTH: 17
<212> TYPE: DNA
<213> ORGANISM: Neisseria gonorrhoeae

<400> SEQUENCE: 92
gagggcggcc gccatac 17

<210> SEQ ID NO 93
<211> LENGTH: 27
<212> TYPE: DNA
<213> ORGANISM: Neisseria gonorrhoeae

<400> SEQUENCE: 93
ccattaacac ctcgcacgta gaatacg 27

<210> SEQ ID NO 94
<211> LENGTH: 26
<212> TYPE: DNA
<213> ORGANISM: Neisseria gonorrhoeae

<400> SEQUENCE: 94
attttagcta aaaaattcgg cggcgc 26

<210> SEQ ID NO 95
<211> LENGTH: 22
<212> TYPE: DNA
<213> ORGANISM: Helicobacter pylori

<400> SEQUENCE: 95
agcgatttca gcggtgcttt ct 22

<210> SEQ ID NO 96
<211> LENGTH: 25
<212> TYPE: DNA
<213> ORGANISM: Helicobacter pylori

<400> SEQUENCE: 96
gagactgaaa ccagacacta tgcgc 25

<210> SEQ ID NO 97
<211> LENGTH: 25
<212> TYPE: DNA
<213> ORGANISM: Helicobacter pylori

<400> SEQUENCE: 97
ggatggagcg atcttggttg tttct 25

<210> SEQ ID NO 98
<211> LENGTH: 26
<212> TYPE: DNA
<213> ORGANISM: Helicobacter pylori

<400> SEQUENCE: 98
gcgtgcctca cattgttgtt ttctta 26

<210> SEQ ID NO 99
<211> LENGTH: 33
<212> TYPE: DNA
<213> ORGANISM: Helicobacter pylori

<400> SEQUENCE: 99
atggtagatg accaagaatt gttagagctt gta 33

<210> SEQ ID NO 100
<211> LENGTH: 24
<212> TYPE: DNA
<213> ORGANISM: Helicobacter pylori

<400> SEQUENCE: 100
gttgagcgcg tatgaatttc ctgg 24

<210> SEQ ID NO 101
<211> LENGTH: 24
<212> TYPE: DNA
<213> ORGANISM: Helicobacter pylori

<400> SEQUENCE: 101
cctatcgtag cgggttcagc ttta 24

<210> SEQ ID NO 102
<211> LENGTH: 26
<212> TYPE: DNA
<213> ORGANISM: Helicobacter pylori

<400> SEQUENCE: 102
gtgaatgggg cgaaaaagtg cttaaa 26

<210> SEQ ID NO 103
<211> LENGTH: 28
<212> TYPE: DNA
<213> ORGANISM: Helicobacter pylori

<400> SEQUENCE: 103
tcatggctga agtggattcc tatatccc 28

<210> SEQ ID NO 104
<211> LENGTH: 21
<212> TYPE: DNA
<213> ORGANISM: Helicobacter pylori

<400> SEQUENCE: 104
tgggcgtgct tttgagagga a 21

<210> SEQ ID NO 105
<211> LENGTH: 28
<212> TYPE: DNA
<213> ORGANISM: Helicobacter pylori

<400> SEQUENCE: 105
atggttctat gcaaaccagg ttctatca 28

<210> SEQ ID NO 106
<211> LENGTH: 29
<212> TYPE: DNA
<213> ORGANISM: Helicobacter pylori

<400> SEQUENCE: 106
gttaggaacc aaatttgcga ttcgtgaag 29

<210> SEQ ID NO 107
<211> LENGTH: 23
<212> TYPE: DNA
<213> ORGANISM: Helicobacter hepaticus

<400> SEQUENCE: 107
gcagctattt ctgctgtgtt ggc 23

<210> SEQ ID NO 108
<211> LENGTH: 25
<212> TYPE: DNA
<213> ORGANISM: Helicobacter hepaticus

<400> SEQUENCE: 108
cggagcaatt cttgttgttt ctgcc 25

<210> SEQ ID NO 109
<211> LENGTH: 30
<212> TYPE: DNA
<213> ORGANISM: Helicobacter hepaticus

<400> SEQUENCE: 109
gatgctgaat tacttgagct tgtggaaatg 30

<210> SEQ ID NO 110
<211> LENGTH: 33
<212> TYPE: DNA
<213> ORGANISM: Helicobacter hepaticus

<400> SEQUENCE: 110
ttgcttagtc aatatgattt ccctggagat gat 33

<210> SEQ ID NO 111
<211> LENGTH: 34
<212> TYPE: DNA
<213> ORGANISM: Helicobacter hepaticus

<400> SEQUENCE: 111
taatgtaggt gaatggggtg aaaaagtatt aaaa 34

<210> SEQ ID NO 112
<211> LENGTH: 27
<212> TYPE: DNA
<213> ORGANISM: Helicobacter hepaticus

<400> SEQUENCE: 112
gtagaaagag gtgttgtgca agtaggc 27

<210> SEQ ID NO 113
<211> LENGTH: 34
<212> TYPE: DNA
<213> ORGANISM: Helicobacter hepaticus

<400> SEQUENCE: 113
ggtattttgt tgcgaggaac aaaaaaagaa gaag 34

<210> SEQ ID NO 114
<211> LENGTH: 23
<212> TYPE: DNA
<213> ORGANISM: Helicobacter hepaticus

<400> SEQUENCE: 114
atggttcttt gtaagcccgg ctc 23

<210> SEQ ID NO 115
<211> LENGTH: 25
<212> TYPE: DNA
<213> ORGANISM: Helicobacter hepaticus

<400> SEQUENCE: 115
ggaacttatt gctcctgtgg cactt 25

<210> SEQ ID NO 116
<211> LENGTH: 33
<212> TYPE: DNA
<213> ORGANISM: Campylobacter jejuni

<400> SEQUENCE: 116
agcgtggtat tactattgct acttctcata ttg 33

<210> SEQ ID NO 117
<211> LENGTH: 28
<212> TYPE: DNA
<213> ORGANISM: Campylobacter jejuni

<400> SEQUENCE: 117
cacattcttc tttctcgtca agtaggcg 28

<210> SEQ ID NO 118
<211> LENGTH: 34
<212> TYPE: DNA
<213> ORGANISM: Campylobacter jejuni

<400> SEQUENCE: 118
gatgatgctg aacttttaga gttagttgaa atgg 34

<210> SEQ ID NO 119
<211> LENGTH: 34
<212> TYPE: DNA
<213> ORGANISM: Campylobacter jejuni

<400> SEQUENCE: 119
ttattaagct cttatgattt cccaggcgat gata 34

<210> SEQ ID NO 120
<211> LENGTH: 31
<212> TYPE: DNA
<213> ORGANISM: Campylobacter jejuni

<400> SEQUENCE: 120
ggcgatgata cacctattat ttctggttct g 31

<210> SEQ ID NO 121
<211> LENGTH: 27
<212> TYPE: DNA
<213> ORGANISM: Campylobacter jejuni

<400> SEQUENCE: 121
gctcttgaag aagctaaagc tggacaa 27

<210> SEQ ID NO 122
<211> LENGTH: 32
<212> TYPE: DNA
<213> ORGANISM: Campylobacter jejuni

<400> SEQUENCE: 122
cttatggctg cagttgatag ctatattcca ac 32

<210> SEQ ID NO 123
<211> LENGTH: 32
<212> TYPE: DNA
<213> ORGANISM: Campylobacter jejuni

<400> SEQUENCE: 123
cgtggtacta aaaaagaaga agttatccgt gg 32

<210> SEQ ID NO 124
<211> LENGTH: 34
<212> TYPE: DNA
<213> ORGANISM: Campylobacter jejuni

<400> SEQUENCE: 124
gatgttacag gttcgattaa attagctgat ggtg 34

<210> SEQ ID NO 125
<211> LENGTH: 25
<212> TYPE: DNA
<213> ORGANISM: Campylobacter jejuni

<400> SEQUENCE: 125
ctgtaagctt gatcgctcca gtagc 25

<210> SEQ ID NO 126
<211> LENGTH: 22
<212> TYPE: DNA
<213> ORGANISM: Chlamydophila abortus

<400> SEQUENCE: 126
gcaattacac gcgcactgtc ag 22

<210> SEQ ID NO 127
<211> LENGTH: 27
<212> TYPE: DNA
<213> ORGANISM: Chlamydophila abortus

<400> SEQUENCE: 127
gttgaatacg aaacccctaa ccgtcac 27

<210> SEQ ID NO 128
<211> LENGTH: 21
<212> TYPE: DNA
<213> ORGANISM: Chlamydophila abortus

<400> SEQUENCE: 128
ccgctactga cggtgctatg c 21

<210> SEQ ID NO 129
<211> LENGTH: 22
<212> TYPE: DNA
<213> ORGANISM: Chlamydophila abortus

<400> SEQUENCE: 129
ctgttggcaa gacaggtagg gg 22

<210> SEQ ID NO 130
<211> LENGTH: 20
<212> TYPE: DNA
<213> ORGANISM: Chlamydophila abortus

<400> SEQUENCE: 130
aggatgccga gcttgtcgac 20

<210> SEQ ID NO 131
<211> LENGTH: 29
<212> TYPE: DNA
<213> ORGANISM: Chlamydophila abortus

<400> SEQUENCE: 131
gaagaaaaag gttacaaagg ctgccctat 29

<210> SEQ ID NO 132
<211> LENGTH: 33
<212> TYPE: DNA
<213> ORGANISM: Chlamydophila abortus

<400> SEQUENCE: 132
gaaatgttta gaaaagaact tccagaaggt cag 33

<210> SEQ ID NO 133
<211> LENGTH: 24
<212> TYPE: DNA
<213> ORGANISM: Chlamydophila abortus

<400> SEQUENCE: 133
atggtgattt gccaacctaa cagc 24

<210> SEQ ID NO 134
<211> LENGTH: 28
<212> TYPE: DNA
<213> ORGANISM: Chlamydophila abortus

<400> SEQUENCE: 134
gatatgattt ctcaagagga tgccgagc 28

<210> SEQ ID NO 135
<211> LENGTH: 29
<212> TYPE: DNA
<213> ORGANISM: Clostridium perfringens

<400> SEQUENCE: 135
agcagctata acaacagttt tagcacaag 29

<210> SEQ ID NO 136
<211> LENGTH: 33
<212> TYPE: DNA
<213> ORGANISM: Clostridium perfringens

<400> SEQUENCE: 136
ggtggagcag aagcattcaa atatgatgaa ata 33

<210> SEQ ID NO 137
<211> LENGTH: 29
<212> TYPE: DNA
<213> ORGANISM: Clostridium perfringens

<400> SEQUENCE: 137
gttgagtacg aaacagctaa cagacacta 29

<210> SEQ ID NO 138
<211> LENGTH: 30
<212> TYPE: DNA
<213> ORGANISM: Clostridium perfringens

<400> SEQUENCE: 138
ggagctatat tagtttgttc agcagctgat 30

<210> SEQ ID NO 139
<211> LENGTH: 34
<212> TYPE: DNA
<213> ORGANISM: Clostridium perfringens

<400> SEQUENCE: 139
cttattatca tcaagagttg gagttgacca catc 34

<210> SEQ ID NO 140
<211> LENGTH: 22
<212> TYPE: DNA
<213> ORGANISM: Clostridium perfringens

<400> SEQUENCE: 140
aacccaactg acgaagctgc aa 22

<210> SEQ ID NO 141
<211> LENGTH: 28
<212> TYPE: DNA
<213> ORGANISM: Clostridium perfringens

<400> SEQUENCE: 141
agaggagttc tacatgtagg agacgaag 28

<210> SEQ ID NO 142
<211> LENGTH: 30
<212> TYPE: DNA
<213> ORGANISM: Clostridium perfringens

<400> SEQUENCE: 142
ggtatccaaa gaactgatat cgaaagaggt 30

<210> SEQ ID NO 143
<211> LENGTH: 31
<212> TYPE: DNA
<213> ORGANISM: Clostridium perfringens

<400> SEQUENCE: 143
caagttttag ctcaagttgg aacaatcaac c 31

<210> SEQ ID NO 144
<211> LENGTH: 33
<212> TYPE: DNA
<213> ORGANISM: Clostridium perfringens

<400> SEQUENCE: 144
ggaagttgaa ttaatcacag aaatcgctat gga 33

<210> SEQ ID NO 145
<211> LENGTH: 28
<212> TYPE: DNA
<213> ORGANISM: Clostridium tetani

<400> SEQUENCE: 145
gggtttgcga aagcattcaa atatgacg 28

<210> SEQ ID NO 146
<211> LENGTH: 28
<212> TYPE: DNA
<213> ORGANISM: Clostridium tetani

<400> SEQUENCE: 146
atcctagtag taagtgcagc agatggtc 28

<210> SEQ ID NO 147
<211> LENGTH: 31
<212> TYPE: DNA
<213> ORGANISM: Clostridium tetani

<400> SEQUENCE: 147
cacatactat tagcatccag agttggagtt g 31

<210> SEQ ID NO 148
<211> LENGTH: 28
<212> TYPE: DNA
<213> ORGANISM: Clostridium tetani

<400> SEQUENCE: 148
gaccaagtag atgacgcaga gttaatcg 28

<210> SEQ ID NO 149
<211> LENGTH: 24
<212> TYPE: DNA
<213> ORGANISM: Clostridium tetani

<400> SEQUENCE: 149
acgcaccagt agtagtagga tccg 24

<210> SEQ ID NO 150
<211> LENGTH: 28
<212> TYPE: DNA
<213> ORGANISM: Clostridium tetani

<400> SEQUENCE: 150
gaaaatccag aagatgatgc agcaacac 28

<210> SEQ ID NO 151
<211> LENGTH: 33
<212> TYPE: DNA
<213> ORGANISM: Clostridium tetani

<400> SEQUENCE: 151
gacgaaatag aaatcgtagg attaagtgat gaa 33

<210> SEQ ID NO 152
<211> LENGTH: 33
<212> TYPE: DNA
<213> ORGANISM: Clostridium tetani

<400> SEQUENCE: 152
agcaagaaat cagtaatcac aggaatagaa atg 33

<210> SEQ ID NO 153
<211> LENGTH: 29
<212> TYPE: DNA
<213> ORGANISM: Clostridium tetani

<400> SEQUENCE: 153
attagcagca acaggatcag taaaaccac 29

<210> SEQ ID NO 154
<211> LENGTH: 35
<212> TYPE: DNA
<213> ORGANISM: Clostridium tetani

<400> SEQUENCE: 154
atgaaggtag aattaataac aagagtagca atgga 35

<210> SEQ ID NO 155
<211> LENGTH: 26
<212> TYPE: DNA
<213> ORGANISM: Listeria monocytogenes

<400> SEQUENCE: 155
ggctatgctg atgcacaagc ttatga 26

<210> SEQ ID NO 156
<211> LENGTH: 31
<212> TYPE: DNA
<213> ORGANISM: Staphylococcus saprophyticus

<400> SEQUENCE: 156
ggtgactctg tagcacaatc atatgacatg a 31

<210> SEQ ID NO 157
<211> LENGTH: 33
<212> TYPE: DNA
<213> ORGANISM: Staphylococcus saprophyticus

<400> SEQUENCE: 157
acttcacaca tcgagtatac tactgacaaa cgt 33

<210> SEQ ID NO 158
<211> LENGTH: 30
<212> TYPE: DNA
<213> ORGANISM: Staphylococcus saprophyticus

<400> SEQUENCE: 158
cggagctatc ttagtagtat ctgctgctga 30

<210> SEQ ID NO 159
<211> LENGTH: 26
<212> TYPE: DNA
<213> ORGANISM: Staphylococcus saprophyticus

<400> SEQUENCE: 159
acaaggtgac aaggaagctc aagacc 26

<210> SEQ ID NO 160
<211> LENGTH: 29
<212> TYPE: DNA
<213> ORGANISM: Staphylococcus saprophyticus

<400> SEQUENCE: 160
ttaatgcaag ctgttgatga cttcattcc 29

<210> SEQ ID NO 161
<211> LENGTH: 32
<212> TYPE: DNA
<213> ORGANISM: Staphylococcus saprophyticus

<400> SEQUENCE: 161
gtatgcaaga agaatcaagc aaaacaactg tt 32

<210> SEQ ID NO 162
<211> LENGTH: 26
<212> TYPE: DNA
<213> ORGANISM: Staphylococcus saprophyticus

<400> SEQUENCE: 162
ggtgtttcac gtgatgatgt acaacg 26

<210> SEQ ID NO 163
<211> LENGTH: 38
<212> TYPE: DNA
<213> ORGANISM: Staphylococcus saprophyticus

<400> SEQUENCE: 163
gaaatggatg ttgaattaat ttctccaatc gctattga 38

<210> SEQ ID NO 164
<211> LENGTH: 20
<212> TYPE: DNA
<213> ORGANISM: Vibrio vulnificus

<400> SEQUENCE: 164
tacggcggta cagctcgtga 20

<210> SEQ ID NO 165
<211> LENGTH: 33
<212> TYPE: DNA
<213> ORGANISM: Vibrio vulnificus

<400> SEQUENCE: 165
ggtatcacaa tctctacttc tcacgtagag tac 33

<210> SEQ ID NO 166
<211> LENGTH: 24
<212> TYPE: DNA
<213> ORGANISM: Vibrio vulnificus

<400> SEQUENCE: 166
tacgacactc catctcgcca ctac 24

<210> SEQ ID NO 167
<211> LENGTH: 31
<212> TYPE: DNA
<213> ORGANISM: Vibrio vulnificus

<400> SEQUENCE: 167
gatgatgaag agcttctaga gctagtagaa a 31

<210> SEQ ID NO 168
<211> LENGTH: 24
<212> TYPE: DNA
<213> ORGANISM: Vibrio vulnificus

<400> SEQUENCE: 168
ctagcagaag cgctagacag ctac 24

<210> SEQ ID NO 169
<211> LENGTH: 26
<212> TYPE: DNA
<213> ORGANISM: Vibrio vulnificus

<400> SEQUENCE: 169
gttgttgagc taatctctcc aatcgc 26

<210> SEQ ID NO 170
<211> LENGTH: 30
<212> TYPE: DNA
<213> ORGANISM: Vibrio parahaemolyticus

<400> SEQUENCE: 170
gctgctatct gtactactct agctaaagtg 30

<210> SEQ ID NO 171
<211> LENGTH: 22
<212> TYPE: DNA
<213> ORGANISM: Vibrio parahaemolyticus

<400> SEQUENCE: 171
ggcggtgaag cgaaagactt cg 22

<210> SEQ ID NO 172
<211> LENGTH: 28
<212> TYPE: DNA
<213> ORGANISM: Vibrio parahaemolyticus

<400> SEQUENCE: 172
ggtatcacaa tcgcaacttc tcacgtag 28

<210> SEQ ID NO 173
<211> LENGTH: 23
<212> TYPE: DNA
<213> ORGANISM: Vibrio parahaemolyticus

<400> SEQUENCE: 173
gtacgacact ccaagccgtc act 23

<210> SEQ ID NO 174
<211> LENGTH: 33
<212> TYPE: DNA
<213> ORGANISM: Vibrio parahaemolyticus

<400> SEQUENCE: 174
acgatgaaga gctactagaa ctagtagaaa tgg 33

<210> SEQ ID NO 175
<211> LENGTH: 33
<212> TYPE: DNA
<213> ORGANISM: Vibrio parahaemolyticus

<400> SEQUENCE: 175
ctagctgaag ctctagatac ttacatccct gag 33

<210> SEQ ID NO 176
<211> LENGTH: 20
<212> TYPE: DNA
<213> ORGANISM: Vibrio parahaemolyticus

<400> SEQUENCE: 176
agagcgtgcg gtagatcagc 20

<210> SEQ ID NO 177
<211> LENGTH: 25
<212> TYPE: DNA
<213> ORGANISM: Vibrio parahaemolyticus

<400> SEQUENCE: 177
gcgtggtatc ctaacagttg gtgac 25

<210> SEQ ID NO 178
<211> LENGTH: 27
<212> TYPE: DNA
<213> ORGANISM: Vibrio parahaemolyticus

<400> SEQUENCE: 178
gttgagctaa ttgcaccaat cgcaatg 27

<210> SEQ ID NO 179
<211> LENGTH: 34
<212> TYPE: DNA
<213> ORGANISM: Vibrio cholerae

<400> SEQUENCE: 179
acaatcaata cttctcacgt agagtacgat actc 34

<210> SEQ ID NO 180
<211> LENGTH: 26
<212> TYPE: DNA
<213> ORGANISM: Vibrio cholerae

<400> SEQUENCE: 180
tgtccaggac acgcggatta tgttaa 26

<210> SEQ ID NO 181
<211> LENGTH: 23
<212> TYPE: DNA
<213> ORGANISM: Vibrio cholerae

<400> SEQUENCE: 181
tagttgtagc ggcaactgac ggt 23

<210> SEQ ID NO 182
<211> LENGTH: 30
<212> TYPE: DNA
<213> ORGANISM: Vibrio cholerae

<400> SEQUENCE: 182
gcactggata cttatattcc agagccagag 30

<210> SEQ ID NO 183
<211> LENGTH: 32
<212> TYPE: DNA
<213> ORGANISM: Vibrio cholerae

<400> SEQUENCE: 183
acagtaaaaa cgacctgtac aggtgtagag at 32

<210> SEQ ID NO 184
<211> LENGTH: 24
<212> TYPE: DNA
<213> ORGANISM: Vibrio cholerae

<400> SEQUENCE: 184
gacgtaacag gcagcatcga gcta 24

<210> SEQ ID NO 185
<211> LENGTH: 28
<212> TYPE: DNA
<213> ORGANISM: Vibrio cholerae

<400> SEQUENCE: 185
gtgaagatgg ttgtagacct gattgcac 28

<210> SEQ ID NO 186
<211> LENGTH: 24
<212> TYPE: DNA
<213> ORGANISM: Acinetobacter baumanii

<400> SEQUENCE: 186
cgatcgcaac aatctgtgcg aaaa 24

<210> SEQ ID NO 187
<211> LENGTH: 32
<212> TYPE: DNA
<213> ORGANISM: Acinetobacter baumanii

<400> SEQUENCE: 187
gaaagattac tcacaaatcg actcagctcc ag 32

<210> SEQ ID NO 188
<211> LENGTH: 30
<212> TYPE: DNA
<213> ORGANISM: Acinetobacter baumanii

<400> SEQUENCE: 188
cacgtagaat acgactctcc aattcgtcac 30

<210> SEQ ID NO 189
<211> LENGTH: 27
<212> TYPE: DNA
<213> ORGANISM: Acinetobacter baumanii

<400> SEQUENCE: 189
gacgacgaag agcttcttga gcttgta 27

<210> SEQ ID NO 190
<211> LENGTH: 28
<212> TYPE: DNA
<213> ORGANISM: Acinetobacter baumanii

<400> SEQUENCE: 190
tggtcaatat ggcgagtctt cagttctt 28

<210> SEQ ID NO 191
<211> LENGTH: 19
<212> TYPE: DNA
<213> ORGANISM: Acinetobacter baumanii

<400> SEQUENCE: 191
aaccagagcg cgcaatcga 19

<210> SEQ ID NO 192
<211> LENGTH: 23
<212> TYPE: DNA
<213> ORGANISM: Acinetobacter baumanii

<400> SEQUENCE: 192
aagctggtat cgtgaaagtg ggc 23

<210> SEQ ID NO 193
<211> LENGTH: 25
<212> TYPE: DNA
<213> ORGANISM: Acinetobacter baumanii

<400> SEQUENCE: 193
tgcaatccag ttgaaagaag gcgtt 25

<210> SEQ ID NO 194
<211> LENGTH: 33
<212> TYPE: DNA
<213> ORGANISM: Acinetobacter baumanii

<400> SEQUENCE: 194
cgttgaaatg tcagtagaat tgatccaccc aat 33

<210> SEQ ID NO 195
<211> LENGTH: 25
<212> TYPE: DNA
<213> ORGANISM: Yersinia pestis

<400> SEQUENCE: 195
atggatggtg caatcctggt tgttg 25

<210> SEQ ID NO 196
<211> LENGTH: 19
<212> TYPE: DNA
<213> ORGANISM: Yersinia pestis

<400> SEQUENCE: 196
ttgggtcgtc aggttggcg 19

<210> SEQ ID NO 197
<211> LENGTH: 23
<212> TYPE: DNA
<213> ORGANISM: Yersinia pestis

<400> SEQUENCE: 197
ctggcgatga tctgccagtt gtt 23

<210> SEQ ID NO 198
<211> LENGTH: 30
<212> TYPE: DNA
<213> ORGANISM: Yersinia pestis

<400> SEQUENCE: 198
gctggttacc tggattctta tatcccagaa 30

<210> SEQ ID NO 199
<211> LENGTH: 33
<212> TYPE: DNA
<213> ORGANISM: Yersinia pestis

<400> SEQUENCE: 199
actgttaaat ctacttgtac tggcgttgaa atg 33

<210> SEQ ID NO 200
<211> LENGTH: 31
<212> TYPE: DNA
<213> ORGANISM: Yersinia pestis

<400> SEQUENCE: 200
aaccacacac tacctttgaa tcagaagttt a 31

<210> SEQ ID NO 201
<211> LENGTH: 33
<212> TYPE: DNA
<213> ORGANISM: Yersinia pseudotuberculosis

<400> SEQUENCE: 201
ggtcatgctg actacgttaa aaatatgatc acc 33

<210> SEQ ID NO 202
<211> LENGTH: 24
<212> TYPE: DNA
<213> ORGANISM: Yersinia pseudotuberculosis

<400> SEQUENCE: 202
atggatggag cgatcttggt tgtt 24

<210> SEQ ID NO 203
<211> LENGTH: 29
<212> TYPE: DNA
<213> ORGANISM: Yersinia pseudotuberculosis

<400> SEQUENCE: 203
acgctgagtg ggaagctaaa attatcgag 29

<210> SEQ ID NO 204
<211> LENGTH: 28
<212> TYPE: DNA
<213> ORGANISM: Yersinia pseudotuberculosis

<400> SEQUENCE: 204
ttggcagaag ctctggatag ctatattc 28

<210> SEQ ID NO 205
<211> LENGTH: 30
<212> TYPE: DNA
<213> ORGANISM: Yersinia pseudotuberculosis

<400> SEQUENCE: 205
acgattaaaa caacttgtac tggcgttgaa 30

<210> SEQ ID NO 206
<211> LENGTH: 25
<212> TYPE: DNA
<213> ORGANISM: Yersinia pseudotuberculosis

<400> SEQUENCE: 206
ggtactaagc gtgacgatgt tcagc 25

<210> SEQ ID NO 207
<211> LENGTH: 32
<212> TYPE: DNA
<213> ORGANISM: Yersinia pseudotuberculosis

<400> SEQUENCE: 207
gttgttaacc taattgctcc tatcgcaatg ga 32

<210> SEQ ID NO 208
<211> LENGTH: 21
<212> TYPE: DNA
<213> ORGANISM: Moraxella catarrhalis

<400> SEQUENCE: 208
agtttgatgc agaagtatac g 21

<210> SEQ ID NO 209
<211> LENGTH: 21
<212> TYPE: DNA
<213> ORGANISM: Moraxella catarrhalis

<400> SEQUENCE: 209
tatcctacta cgtggtacta a 21

<210> SEQ ID NO 210
<211> LENGTH: 18
<212> TYPE: DNA
<213> ORGANISM: Moraxella catarrhalis

<400> SEQUENCE: 210
ataacgttga gatgagcg 18

<210> SEQ ID NO 211
<211> LENGTH: 23
<212> TYPE: DNA
<213> ORGANISM: Streptococcus pyogenes

<400> SEQUENCE: 211
accttgttga tgacgaagag ttg 23

<210> SEQ ID NO 212
<211> LENGTH: 27
<212> TYPE: DNA
<213> ORGANISM: Streptococcus pyogenes

<400> SEQUENCE: 212
aattagttga gatggaaatt cgtgacc 27

<210> SEQ ID NO 213
<211> LENGTH: 26
<212> TYPE: DNA
<213> ORGANISM: Streptococcus pyogenes

<400> SEQUENCE: 213
gtattctcaa ttacaggtcg tggtac 26

<210> SEQ ID NO 214
<211> LENGTH: 21
<212> TYPE: DNA
<213> ORGANISM: Streptococcus pyogenes

<400> SEQUENCE: 214
gtggtactgt tcgtgtcaac g 21

<210> SEQ ID NO 215
<211> LENGTH: 23
<212> TYPE: DNA
<213> ORGANISM: Streptococcus pyogenes

<400> SEQUENCE: 215
aacgtaggta tccttcttcg tgg 23

<210> SEQ ID NO 216
<211> LENGTH: 21
<212> TYPE: DNA
<213> ORGANISM: Streptococcus pyogenes

<400> SEQUENCE: 216
cttcgtggtg ttcaacgtga c 21

<210> SEQ ID NO 217
<211> LENGTH: 22
<212> TYPE: DNA
<213> ORGANISM: Streptococcus pyogenes

<400> SEQUENCE: 217
ttcaacgtga cgaaatcgaa cg 22

<210> SEQ ID NO 218
<211> LENGTH: 31
<212> TYPE: DNA
<213> ORGANISM: Streptococcus pyogenes

<400> SEQUENCE: 218
gtgaagtata tatcctttct aaagacgaag g 31

<210> SEQ ID NO 219
<211> LENGTH: 22
<212> TYPE: DNA
<213> ORGANISM: Streptococcus pyogenes

<400> SEQUENCE: 219
tccagcaggt acagaaatgg tt 22

<210> SEQ ID NO 220
<211> LENGTH: 23
<212> TYPE: DNA
<213> ORGANISM: Streptococcus pyogenes

<400> SEQUENCE: 220
cgtgacaatc aacgttgagt tga 23

<210> SEQ ID NO 221
<211> LENGTH: 20
<212> TYPE: DNA
<213> ORGANISM: Streptococcus pneumoniae

<400> SEQUENCE: 221
cactggtgct gctcaaatgg 20

<210> SEQ ID NO 222
<211> LENGTH: 24
<212> TYPE: DNA
<213> ORGANISM: Streptococcus pneumoniae

<400> SEQUENCE: 222
caaggttcag cacttaaagc tctt 24

<210> SEQ ID NO 223
<211> LENGTH: 27
<212> TYPE: DNA
<213> ORGANISM: Streptococcus pneumoniae

<400> SEQUENCE: 223
tcttgaaggt gactctaaat acgaaga 27

<210> SEQ ID NO 224
<211> LENGTH: 26
<212> TYPE: DNA
<213> ORGANISM: Streptococcus pneumoniae

<400> SEQUENCE: 224
gttgatgagt atatcccaga accaga 26

<210> SEQ ID NO 225
<211> LENGTH: 22
<212> TYPE: DNA
<213> ORGANISM: Streptococcus pneumoniae

<400> SEQUENCE: 225
ttccagtcga ggacgtattc tc 22

<210> SEQ ID NO 226
<211> LENGTH: 21
<212> TYPE: DNA
<213> ORGANISM: Streptococcus pneumoniae

<400> SEQUENCE: 226
aatcactgga cgtggtacag t 21

<210> SEQ ID NO 227
<211> LENGTH: 24
<212> TYPE: DNA
<213> ORGANISM: Streptococcus mutans

<400> SEQUENCE: 227
ttcccaggtg atgatattcc agtt 24

<210> SEQ ID NO 228
<211> LENGTH: 28
<212> TYPE: DNA
<213> ORGANISM: Streptococcus mutans

<400> SEQUENCE: 228
gatactgctc aagaagatat catcatgg 28

<210> SEQ ID NO 229
<211> LENGTH: 23
<212> TYPE: DNA
<213> ORGANISM: Streptococcus mutans

<400> SEQUENCE: 229
cgttggtatc cgtgatgaca ttc 23

<210> SEQ ID NO 230
<211> LENGTH: 27
<212> TYPE: DNA
<213> ORGANISM: Streptococcus mutans

<400> SEQUENCE: 230
gtaaacaatt ggatgaaggt attgcag 27

<210> SEQ ID NO 231
<211> LENGTH: 24
<212> TYPE: DNA
<213> ORGANISM: Streptococcus mutans

<400> SEQUENCE: 231
ggataatgtt ggtgttctcc ttcg 24

<210> SEQ ID NO 232
<211> LENGTH: 28
<212> TYPE: DNA
<213> ORGANISM: Streptococcus mutans

<400> SEQUENCE: 232
ggttcaattc acccacatac taaattca 28

<210> SEQ ID NO 233
<211> LENGTH: 22
<212> TYPE: DNA
<213> ORGANISM: Streptococcus mutans

<400> SEQUENCE: 233
gttcaattga gttgccagca gg 22

<210> SEQ ID NO 234
<211> LENGTH: 29
<212> TYPE: DNA
<213> ORGANISM: Streptococcus mutans

<400> SEQUENCE: 234
tcatacacca ttcttcaata actatcgtc 29

<210> SEQ ID NO 235
<211> LENGTH: 23
<212> TYPE: DNA
<213> ORGANISM: Streptococcus mutans

<400> SEQUENCE: 235
tcaggacgta ttgatcgtgg tac 23

<210> SEQ ID NO 236
<211> LENGTH: 25
<212> TYPE: DNA
<213> ORGANISM: Streptococcus sanguis

<400> SEQUENCE: 236
ggtgttaaac acttgatcgt cttca 25

<210> SEQ ID NO 237
<211> LENGTH: 21
<212> TYPE: DNA
<213> ORGANISM: Streptococcus sanguis

<400> SEQUENCE: 237
ccgtaaacag cttgacgaag g 21

<210> SEQ ID NO 238
<211> LENGTH: 20
<212> TYPE: DNA
<213> ORGANISM: Streptococcus sanguis

<400> SEQUENCE: 238
tgtgcttctc cgtggtatcc 20

<210> SEQ ID NO 239
<211> LENGTH: 30
<212> TYPE: DNA
<213> ORGANISM: Streptococcus sanguis

<400> SEQUENCE: 239
acactaaatt caagggtgaa gtttatatcc 30

<210> SEQ ID NO 240
<211> LENGTH: 18
<212> TYPE: DNA
<213> ORGANISM: Streptococcus sanguis

<400> SEQUENCE: 240
aagaaggcgg acgtcaca 18

<210> SEQ ID NO 241
<211> LENGTH: 27
<212> TYPE: DNA
<213> ORGANISM: Staphylococcus aureus

<400> SEQUENCE: 241
gttgacatgg ttgacgatga agaatta 27

<210> SEQ ID NO 242
<211> LENGTH: 21
<212> TYPE: DNA
<213> ORGANISM: Neisseria meningitidis

<400> SEQUENCE: 242
cgcggttact ttggaagaag g 21

<210> SEQ ID NO 243
<211> LENGTH: 20
<212> TYPE: DNA
<213> ORGANISM: Neisseria meningitidis

<400> SEQUENCE: 243
aaactgctgg acgaaggtca 20

<210> SEQ ID NO 244
<211> LENGTH: 23
<212> TYPE: DNA
<213> ORGANISM: Neisseria meningitidis

<400> SEQUENCE: 244
tacgtactga gcaaagaaga ggg 23

<210> SEQ ID NO 245
<211> LENGTH: 19
<212> TYPE: DNA
<213> ORGANISM: Neisseria meningitidis

<400> SEQUENCE: 245
tcttcgccaa ctaccgtcc 19

<210> SEQ ID NO 246
<211> LENGTH: 19
<212> TYPE: DNA
<213> ORGANISM: Bordetella pertussis

<400> SEQUENCE: 246
caagccgggt tcgatcaac 19

<210> SEQ ID NO 247
<211> LENGTH: 23
<212> TYPE: DNA
<213> ORGANISM: Bordetella pertussis

<400> SEQUENCE: 247
gaggtgtaca ttctgtccaa gga 23

<210> SEQ ID NO 248
<211> LENGTH: 21
<212> TYPE: DNA
<213> ORGANISM: Bordetella pertussis

<400> SEQUENCE: 248
cgttcttcaa cggctatcgt c 21

<210> SEQ ID NO 249
<211> LENGTH: 20
<212> TYPE: DNA
<213> ORGANISM: Bordetella pertussis

<400> SEQUENCE: 249
gacaaggaaa tggtgctgcc 20

<210> SEQ ID NO 250
<211> LENGTH: 20
<212> TYPE: DNA
<213> ORGANISM: Bordetella pertussis

<400> SEQUENCE: 250
caacgtgggt atcttgctgc 20

<210> SEQ ID NO 251
<211> LENGTH: 18
<212> TYPE: DNA
<213> ORGANISM: Bordetella pertussis

<400> SEQUENCE: 251
tgactggccg tatcgagc 18

<210> SEQ ID NO 252
<211> LENGTH: 30
<212> TYPE: DNA
<213> ORGANISM: Enterococcus faecalis

<400> SEQUENCE: 252
tggatatggt tgatgacgaa gaattattag 30

<210> SEQ ID NO 253
<211> LENGTH: 29
<212> TYPE: DNA
<213> ORGANISM: Enterococcus faecalis

<400> SEQUENCE: 253
gtgacttatt atcagaatac gatttccca 29

<210> SEQ ID NO 254
<211> LENGTH: 25
<212> TYPE: DNA
<213> ORGANISM: Fusobacterium nucleatum

<400> SEQUENCE: 254
actgaatatg gattcccagg agatg 25

<210> SEQ ID NO 255
<211> LENGTH: 26
<212> TYPE: DNA
<213> ORGANISM: Fusobacterium nucleatum

<400> SEQUENCE: 255
acatccctgt aattagaggt tcatca 26

<210> SEQ ID NO 256
<211> LENGTH: 31
<212> TYPE: DNA
<213> ORGANISM: Fusobacterium nucleatum

<400> SEQUENCE: 256
ggtgaagaaa aatggataga aaagataatg g 31

<210> SEQ ID NO 257
<211> LENGTH: 29
<212> TYPE: DNA
<213> ORGANISM: Fusobacterium nucleatum

<400> SEQUENCE: 257
acttatggat gcagtagata gctatatcc 29

<210> SEQ ID NO 258
<211> LENGTH: 26
<212> TYPE: DNA
<213> ORGANISM: Fusobacterium nucleatum

<400> SEQUENCE: 258
gaaagagcag tagatcaacc attctt 26

<210> SEQ ID NO 259
<211> LENGTH: 28
<212> TYPE: DNA
<213> ORGANISM: Fusobacterium nucleatum

<400> SEQUENCE: 259
aggaatcatc aaagttggag aagaaatt 28

<210> SEQ ID NO 260
<211> LENGTH: 30
<212> TYPE: DNA
<213> ORGANISM: Fusobacterium nucleatum

<400> SEQUENCE: 260
taaacctaca actaaaacaa cttgtacagg 30

<210> SEQ ID NO 261
<211> LENGTH: 23
<212> TYPE: DNA
<213> ORGANISM: Fusobacterium nucleatum

<400> SEQUENCE: 261
cttcttgatc aaggtcaagc agg 23

<210> SEQ ID NO 262
<211> LENGTH: 30
<212> TYPE: DNA
<213> ORGANISM: Fusobacterium nucleatum

<400> SEQUENCE: 262
aagaggaact aagaaagaag aagttgaaag 30

<210> SEQ ID NO 263
<211> LENGTH: 24
<212> TYPE: DNA
<213> ORGANISM: Fusobacterium nucleatum

<400> SEQUENCE: 263
cttgctaaac caggaagtat ccac 24

<210> SEQ ID NO 264
<211> LENGTH: 21
<212> TYPE: DNA
<213> ORGANISM: Stenotrophomonas maltophilia

<400> SEQUENCE: 264
aatacgaatc cccgatccgt c 21

<210> SEQ ID NO 265
<211> LENGTH: 21
<212> TYPE: DNA
<213> ORGANISM: Stenotrophomonas maltophilia

<400> SEQUENCE: 265
actgctgagc aagtacgagt t 21

<210> SEQ ID NO 266
<211> LENGTH: 19
<212> TYPE: DNA
<213> ORGANISM: Stenotrophomonas maltophilia

<400> SEQUENCE: 266
atcctgaagc tggtcgacg 19

<210> SEQ ID NO 267
<211> LENGTH: 21
<212> TYPE: DNA
<213> ORGANISM: Stenotrophomonas maltophilia

<400> SEQUENCE: 267
gatcaaggtt ggcgacgaaa t 21

<210> SEQ ID NO 268
<211> LENGTH: 20
<212> TYPE: DNA
<213> ORGANISM: Stenotrophomonas maltophilia

<400> SEQUENCE: 268
tgtacgtcct gtcgaaggac 20

<210> SEQ ID NO 269
<211> LENGTH: 19
<212> TYPE: DNA
<213> ORGANISM: Burkholderia cepacia

<400> SEQUENCE: 269
acgccgatca tcaagggtt 19

<210> SEQ ID NO 270
<211> LENGTH: 19
<212> TYPE: DNA
<213> ORGANISM: Burkholderia cepacia

<400> SEQUENCE: 270
cgatcatgaa cctggccga 19

<210> SEQ ID NO 271
<211> LENGTH: 18
<212> TYPE: DNA
<213> ORGANISM: Burkholderia cepacia

<400> SEQUENCE: 271
acgtcggtat cctgctgc 18

<210> SEQ ID NO 272
<211> LENGTH: 18
<212> TYPE: DNA
<213> ORGANISM: Burkholderia cepacia

<400> SEQUENCE: 272
gaagccgggt tcgatcac 18

<210> SEQ ID NO 273
<211> LENGTH: 22
<212> TYPE: DNA
<213> ORGANISM: Burkholderia cepacia

<400> SEQUENCE: 273
cgttcttcaa caactaccgt cc 22

<210> SEQ ID NO 274
<211> LENGTH: 17
<212> TYPE: DNA
<213> ORGANISM: Burkholderia cepacia

<400> SEQUENCE: 274
gtggtgacgg gtcgtgt 17

<210> SEQ ID NO 275
<211> LENGTH: 17
<212> TYPE: DNA
<213> ORGANISM: Burkholderia cepacia

<400> SEQUENCE: 275
cgtacatccc gacgccg 17

<210> SEQ ID NO 276
<211> LENGTH: 22
<212> TYPE: DNA
<213> ORGANISM: Corynebacterium diphtheriae

<400> SEQUENCE: 276
aacaagtgcg acatggttga tg 22

<210> SEQ ID NO 277
<211> LENGTH: 22
<212> TYPE: DNA
<213> ORGANISM: Corynebacterium diphtheriae

<400> SEQUENCE: 277
aagaggctcc aatcatccac at 22

<210> SEQ ID NO 278
<211> LENGTH: 20
<212> TYPE: DNA
<213> ORGANISM: Corynebacterium diphtheriae

<400> SEQUENCE: 278
gaagtggacc cagtccatca 20

<210> SEQ ID NO 279
<211> LENGTH: 20
<212> TYPE: DNA
<213> ORGANISM: Corynebacterium diphtheriae

<400> SEQUENCE: 279
ctgaaggtca acgaggacgt 20

<210> SEQ ID NO 280
<211> LENGTH: 19
<212> TYPE: DNA
<213> ORGANISM: Corynebacterium diphtheriae

<400> SEQUENCE: 280
ttctcgacta caccgaggc 19

<210> SEQ ID NO 281
<211> LENGTH: 22
<212> TYPE: DNA
<213> ORGANISM: Corynebacterium diphtheriae

<400> SEQUENCE: 281
gttgttgtta agccaggcgc tt 22

<210> SEQ ID NO 282
<211> LENGTH: 21
<212> TYPE: DNA
<213> ORGANISM: Corynebacterium diphtheriae

<400> SEQUENCE: 282
gagttcgagg gctctgtcta c 21

<210> SEQ ID NO 283
<211> LENGTH: 23
<212> TYPE: DNA
<213> ORGANISM: Chlamydophila pneumoniae

<400> SEQUENCE: 283
cgcttctcac gttgaatacg aaa 23

<210> SEQ ID NO 284
<211> LENGTH: 21
<212> TYPE: DNA
<213> ORGANISM: Chlamydophila pneumoniae

<400> SEQUENCE: 284
acatatcttg ctagctcgcc a 21

<210> SEQ ID NO 285
<211> LENGTH: 29
<212> TYPE: DNA
<213> ORGANISM: Chlamydophila pneumoniae

<400> SEQUENCE: 285
tagatatgat ctctcaagaa gatgctgaa 29

<210> SEQ ID NO 286
<211> LENGTH: 24
<212> TYPE: DNA
<213> ORGANISM: Chlamydophila pneumoniae

<400> SEQUENCE: 286
aagaaaaagg ctacaaagga tgcc 24

<210> SEQ ID NO 287
<211> LENGTH: 30
<212> TYPE: DNA
<213> ORGANISM: Chlamydophila pneumoniae

<400> SEQUENCE: 287
ttgaaggtga tgcaaattat atcgaaaaag 30

<210> SEQ ID NO 288
<211> LENGTH: 23
<212> TYPE: DNA
<213> ORGANISM: Chlamydophila pneumoniae

<400> SEQUENCE: 288
ttcgagaact tatgcaagct gtg 23

<210> SEQ ID NO 289
<211> LENGTH: 30
<212> TYPE: DNA
<213> ORGANISM: Chlamydophila pneumoniae

<400> SEQUENCE: 289
tggaatcgtt aaagtttctg ataaagttca 30

<210> SEQ ID NO 290
<211> LENGTH: 28
<212> TYPE: DNA
<213> ORGANISM: Chlamydophila pneumoniae

<400> SEQUENCE: 290
ggagagacta aagaaacaat cgttactg 28

<210> SEQ ID NO 291
<211> LENGTH: 26
<212> TYPE: DNA
<213> ORGANISM: Chlamydophila pneumoniae

<400> SEQUENCE: 291
gaaaacgttg gtttactcct cagagg 26

<210> SEQ ID NO 292
<211> LENGTH: 24
<212> TYPE: DNA
<213> ORGANISM: Chlamydophila pneumoniae

<400> SEQUENCE: 292
ttgaaagagg tatggtggtt tgtc 24

<210> SEQ ID NO 293
<211> LENGTH: 26
<212> TYPE: DNA
<213> ORGANISM: Chlamydophila pneumoniae

<400> SEQUENCE: 293
cagctgttta cgttcttcag aaagaa 26

<210> SEQ ID NO 294
<211> LENGTH: 23
<212> TYPE: DNA
<213> ORGANISM: Chlamydophila pneumoniae

<400> SEQUENCE: 294
caggagtcgt aactcttcct gaa 23

<210> SEQ ID NO 295
<211> LENGTH: 27
<212> TYPE: DNA
<213> ORGANISM: Legionella pneumophila

<400> SEQUENCE: 295
atgaccctga gttattagag ttagtgg 27

<210> SEQ ID NO 296
<211> LENGTH: 26
<212> TYPE: DNA
<213> ORGANISM: Legionella pneumophila

<400> SEQUENCE: 296
gtgcgagatt tattaagcag ttacga 26

<210> SEQ ID NO 297
<211> LENGTH: 22
<212> TYPE: DNA
<213> ORGANISM: Legionella pneumophila

<400> SEQUENCE: 297
tgttggttca gctttgaaag ca 22

<210> SEQ ID NO 298
<211> LENGTH: 26
<212> TYPE: DNA
<213> ORGANISM: legionella pneumophila

<400> SEQUENCE: 298
ttggaaggtg aagacagtga tatagg 26

<210> SEQ ID NO 299
<211> LENGTH: 26
<212> TYPE: DNA
<213> ORGANISM: Legionella pneumophila

<400> SEQUENCE: 299
ttcatacatt cctgagccag ttagaa 26

<210> SEQ ID NO 300
<211> LENGTH: 19
<212> TYPE: DNA
<213> ORGANISM: Legionella pneumophila

<400> SEQUENCE: 300
tttctggacg cggaacagt 19

<210> SEQ ID NO 301
<211> LENGTH: 26
<212> TYPE: DNA
<213> ORGANISM: Legionella pneumophila

<400> SEQUENCE: 301
aagttggtga ggaagttgaa attgtt 26

<210> SEQ ID NO 302
<211> LENGTH: 20
<212> TYPE: DNA
<213> ORGANISM: Legionella pneumophila

<400> SEQUENCE: 302
gatgaaggtc gagctggtga 20

<210> SEQ ID NO 303
<211> LENGTH: 26
<212> TYPE: DNA
<213> ORGANISM: Legionella pneumophila

<400> SEQUENCE: 303
ggataccgtc cacaattcta tttcag 26

<210> SEQ ID NO 304
<211> LENGTH: 22
<212> TYPE: DNA
<213> ORGANISM: Legionella pneumophila

<400> SEQUENCE: 304
catcaagcca cacaccaagt tt 22

<210> SEQ ID NO 305
<211> LENGTH: 28
<212> TYPE: DNA
<213> ORGANISM: Legionella longbeachiae

<400> SEQUENCE: 305
aggtacaatt aagcctcaca ctaaattt 28

<210> SEQ ID NO 306
<211> LENGTH: 30
<212> TYPE: DNA
<213> ORGANISM: Legionella longbeachiae

<400> SEQUENCE: 306
cggaagtata cgtgttatct aaagaagaag 30

<210> SEQ ID NO 307
<211> LENGTH: 31
<212> TYPE: DNA
<213> ORGANISM: Legionella longbeachiae

<400> SEQUENCE: 307
atagaccaca gttttatttt agaacaacag a 31

<210> SEQ ID NO 308
<211> LENGTH: 26
<212> TYPE: DNA
<213> ORGANISM: Legionella longbeachiae

<400> SEQUENCE: 308
tatagcaaaa gcatacgatc agatcg 26

<210> SEQ ID NO 309
<211> LENGTH: 22
<212> TYPE: DNA
<213> ORGANISM: Legionella longbeachiae

<400> SEQUENCE: 309
gaggcatcac aatctcaaca gc 22

<210> SEQ ID NO 310
<211> LENGTH: 21
<212> TYPE: DNA
<213> ORGANISM: Legionella longbeachiae

<400> SEQUENCE: 310
tattggggtg ccagcaatag a 21

<210> SEQ ID NO 311
<211> LENGTH: 29
<212> TYPE: DNA
<213> ORGANISM: Legionella longbeachiae

<400> SEQUENCE: 311
attcttatat tccagagcct gtaagaaac 29

<210> SEQ ID NO 312
<211> LENGTH: 29
<212> TYPE: DNA
<213> ORGANISM: Legionella longbeachiae

<400> SEQUENCE: 312
attgacaaat cgttcttatt accgattga 29

<210> SEQ ID NO 313
<211> LENGTH: 25
<212> TYPE: DNA
<213> ORGANISM: Legionella longbeachiae

<400> SEQUENCE: 313
aattcgtgat actgcaaaga ctacc 25

<210> SEQ ID NO 314
<211> LENGTH: 26
<212> TYPE: DNA
<213> ORGANISM: Legionella longbeachiae

<400> SEQUENCE: 314
ggtatattac tccgtggaac aaaacg 26

<210> SEQ ID NO 315
<211> LENGTH: 23
<212> TYPE: DNA
<213> ORGANISM: Legionella longbeachiae

<400> SEQUENCE: 315
agttattaga cgaaggacgt gca 23

<210> SEQ ID NO 316
<211> LENGTH: 24
<212> TYPE: DNA
<213> ORGANISM: Haemophilus influenzae

<400> SEQUENCE: 316
tagtagtagc agcaacagat ggtc 24

<210> SEQ ID NO 317
<211> LENGTH: 25
<212> TYPE: DNA
<213> ORGANISM: Haemophilus influenzae

<400> SEQUENCE: 317
atcttattag gtcgccaagt aggtg 25

<210> SEQ ID NO 318
<211> LENGTH: 30
<212> TYPE: DNA
<213> ORGANISM: Haemophilus influenzae

<400> SEQUENCE: 318
ccatacatca tcgtattctt aaacaaatgc 30

<210> SEQ ID NO 319
<211> LENGTH: 21
<212> TYPE: DNA
<213> ORGANISM: Haemophilus influenzae

<400> SEQUENCE: 319
cgttaaacgg cgtagcagaa t 21

<210> SEQ ID NO 320
<211> LENGTH: 27
<212> TYPE: DNA
<213> ORGANISM: Haemophilus influenzae

<400> SEQUENCE: 320
aaatccttga gttagcaaac cacttag 27

<210> SEQ ID NO 321
<211> LENGTH: 20
<212> TYPE: DNA
<213> ORGANISM: Haemophilus influenzae

<400> SEQUENCE: 321
aaccagaacg tgcgattgac 20

<210> SEQ ID NO 322
<211> LENGTH: 23
<212> TYPE: DNA
<213> ORGANISM: Moraxella catarrhalis

<400> SEQUENCE: 322
cgactctgca cctgaagaaa aag 23

<210> SEQ ID NO 323
<211> LENGTH: 30
<212> TYPE: DNA
<213> ORGANISM: Moraxella catarrhalis

<400> SEQUENCE: 323
ggtattacta ttaacacatc tcacatcgag 30

<210> SEQ ID NO 324
<211> LENGTH: 24
<212> TYPE: DNA
<213> ORGANISM: Moraxella catarrhalis

<400> SEQUENCE: 324
tatgacacag aagctcgtca ctac 24

<210> SEQ ID NO 325
<211> LENGTH: 21
<212> TYPE: DNA
<213> ORGANISM: Moraxella catarrhalis

<400> SEQUENCE: 325
tggttgtttc tgcaactgac g 21

<210> SEQ ID NO 326
<211> LENGTH: 22
<212> TYPE: DNA
<213> ORGANISM: Moraxella catarrhalis

<400> SEQUENCE: 326
atcctactgt ctcgtcaggt tg 22

<210> SEQ ID NO 327
<211> LENGTH: 29
<212> TYPE: DNA
<213> ORGANISM: Moraxella catarrhalis

<400> SEQUENCE: 327
atatatcatg gtattcatga acaagtgcg 29

<210> SEQ ID NO 328
<211> LENGTH: 26
<212> TYPE: DNA
<213> ORGANISM: Moraxella catarrhalis

<400> SEQUENCE: 328
gcattgaatg gttctgacgg taaata 26

<210> SEQ ID NO 329
<211> LENGTH: 25
<212> TYPE: DNA
<213> ORGANISM: Moraxella catarrhalis

<400> SEQUENCE: 329
tgctgttcta gaactactag acacg 25

<210> SEQ ID NO 330
<211> LENGTH: 20
<212> TYPE: DNA
<213> ORGANISM: Mycoplasma pneumoniae

<400> SEQUENCE: 330
attaactccg ctcacgtgga 20

<210> SEQ ID NO 331
<211> LENGTH: 26
<212> TYPE: DNA
<213> ORGANISM: Mycoplasma pneumoniae

<400> SEQUENCE: 331
ttctagtagt ttcagcaact gacagt 26

<210> SEQ ID NO 332
<211> LENGTH: 24
<212> TYPE: DNA
<213> ORGANISM: Mycoplasma pneumoniae

<400> SEQUENCE: 332
ttcctaaaca agtgtgacat tgca 24

<210> SEQ ID NO 333
<211> LENGTH: 27
<212> TYPE: DNA
<213> ORGANISM: Mycoplasma pneumoniae

<400> SEQUENCE: 333
actgatgaag aagtgcaaga gttagta 27

<210> SEQ ID NO 334
<211> LENGTH: 22
<212> TYPE: DNA
<213> ORGANISM: Mycoplasma pneumoniae

<400> SEQUENCE: 334
ttacggcttt gatggcaaga ac 22

<210> SEQ ID NO 335
<211> LENGTH: 23
<212> TYPE: DNA
<213> ORGANISM: Mycoplasma pneumoniae

<400> SEQUENCE: 335
ttatggttct gcacttaaag cgc 23

<210> SEQ ID NO 336
<211> LENGTH: 25
<212> TYPE: DNA
<213> ORGANISM: Mycoplasma pneumoniae

<400> SEQUENCE: 336
tgatcctaag tgggaagcta agatc 25

<210> SEQ ID NO 337
<211> LENGTH: 30
<212> TYPE: DNA
<213> ORGANISM: Mycoplasma pneumoniae

<400> SEQUENCE: 337
gatttaatga atgcagttga tgaatggatt 30

<210> SEQ ID NO 338
<211> LENGTH: 24
<212> TYPE: DNA
<213> ORGANISM: Mycoplasma pneumoniae

<400> SEQUENCE: 338
gaacgtggtg aattgaaagt aggt 24

<210> SEQ ID NO 339
<211> LENGTH: 24
<212> TYPE: DNA
<213> ORGANISM: Mycoplasma pneumoniae

<400> SEQUENCE: 339
gtccaatccg taaagcagtt gtta 24

<210> SEQ ID NO 340
<211> LENGTH: 23
<212> TYPE: DNA
<213> ORGANISM: Mycoplasma pneumoniae

<400> SEQUENCE: 340
aaggaacttg attcagcaat ggc 23

<210> SEQ ID NO 341
<211> LENGTH: 22
<212> TYPE: DNA
<213> ORGANISM: Mycoplasma pneumoniae

<400> SEQUENCE: 341
gtggaccgta aagaagtgga ac 22

<210> SEQ ID NO 342
<211> LENGTH: 23
<212> TYPE: DNA
<213> ORGANISM: Mycoplasma pneumoniae

<400> SEQUENCE: 342
taaaccaggt tcgattaaac cgc 23

<210> SEQ ID NO 343
<211> LENGTH: 25
<212> TYPE: DNA
<213> ORGANISM: Mycoplasma pneumoniae

<400> SEQUENCE: 343
tactacagac gttactggtt cgatt 25

<210> SEQ ID NO 344
<211> LENGTH: 20
<212> TYPE: DNA
<213> ORGANISM: Mycoplasma pneumoniae

<400> SEQUENCE: 344
gctgctactc gttacgacca 20

<210> SEQ ID NO 345
<211> LENGTH: 15
<212> TYPE: DNA
<213> ORGANISM: Mycobacterium tuberculosis

<400> SEQUENCE: 345
acaacgcccc cgagg 15

<210> SEQ ID NO 346
<211> LENGTH: 14
<212> TYPE: DNA
<213> ORGANISM: Mycobacterium tuberculosis

<400> SEQUENCE: 346
acgcccctgg ccac 14

<210> SEQ ID NO 347
<211> LENGTH: 18
<212> TYPE: DNA
<213> ORGANISM: Mycobacterium tuberculosis

<400> SEQUENCE: 347
gatggacggt gcgatcct 18

<210> SEQ ID NO 348
<211> LENGTH: 16
<212> TYPE: DNA
<213> ORGANISM: Mycobacterium tuberculosis

<400> SEQUENCE: 348
cccgatgccc cagacc 16

<210> SEQ ID NO 349
<211> LENGTH: 17
<212> TYPE: DNA
<213> ORGANISM: Mycobacterium tuberculosis

<400> SEQUENCE: 349
gagcacgttc tgctggc 17

<210> SEQ ID NO 350
<211> LENGTH: 19
<212> TYPE: DNA
<213> ORGANISM: Mycobacterium tuberculosis

<400> SEQUENCE: 350
atcctggtag cgctgaaca 19

<210> SEQ ID NO 351
<211> LENGTH: 17
<212> TYPE: DNA
<213> ORGANISM: Mycobacterium tuberculosis

<400> SEQUENCE: 351
gacgcagtgg acgacga 17

<210> SEQ ID NO 352
<211> LENGTH: 18
<212> TYPE: DNA
<213> ORGANISM: Mycobacterium tuberculosis

<400> SEQUENCE: 352
ggctgcccag gaattcga 18

<210> SEQ ID NO 353
<211> LENGTH: 15
<212> TYPE: DNA
<213> ORGANISM: Mycobacterium tuberculosis

<400> SEQUENCE: 353
ccccggttgt gcggg 15

<210> SEQ ID NO 354
<211> LENGTH: 18
<212> TYPE: DNA
<213> ORGANISM: Mycobacterium tuberculosis

<400> SEQUENCE: 354
tgggttgcct ctgtcgag 18

<210> SEQ ID NO 355
<211> LENGTH: 19
<212> TYPE: DNA
<213> ORGANISM: Mycobacterium tuberculosis

<400> SEQUENCE: 355
aggaactgat gaacgcggt 19

<210> SEQ ID NO 356
<211> LENGTH: 18
<212> TYPE: DNA
<213> ORGANISM: Mycobacterium tuberculosis

<400> SEQUENCE: 356
cgagtcgatt ccggaccc 18

<210> SEQ ID NO 357
<211> LENGTH: 17
<212> TYPE: DNA
<213> ORGANISM: Mycobacterium tuberculosis

<400> SEQUENCE: 357
cattaccggc cgcggaa 17

<210> SEQ ID NO 358
<211> LENGTH: 17
<212> TYPE: DNA
<213> ORGANISM: Mycobacterium tuberculosis

<400> SEQUENCE: 358
gtcaccggac gtgtgga 17

<210> SEQ ID NO 359
<211> LENGTH: 21
<212> TYPE: DNA
<213> ORGANISM: Mycobacterium tuberculosis

<400> SEQUENCE: 359
acgaggaagt tgagatcgtc g 21

<210> SEQ ID NO 360
<211> LENGTH: 17
<212> TYPE: DNA
<213> ORGANISM: Mycobacterium tuberculosis

<400> SEQUENCE: 360
ttcgcccatc gaccacc 17

<210> SEQ ID NO 361
<211> LENGTH: 19
<212> TYPE: DNA
<213> ORGANISM: Mycobacterium tuberculosis

<400> SEQUENCE: 361
acaacgttgg tttgctgct 19

<210> SEQ ID NO 362
<211> LENGTH: 18
<212> TYPE: DNA
<213> ORGANISM: Mycobacterium tuberculosis

<400> SEQUENCE: 362
cgagttcgaa ggccaggt 18

<210> SEQ ID NO 363
<211> LENGTH: 17
<212> TYPE: DNA
<213> ORGANISM: Mycobacterium tuberculosis

<400> SEQUENCE: 363
gtggtgacac tgccgga 17

<210> SEQ ID NO 364
<211> LENGTH: 22
<212> TYPE: DNA
<213> ORGANISM: Mycobacterium tuberculosis

<400> SEQUENCE: 364
gacaaattcc ccgatctgaa cg 22

<210> SEQ ID NO 365
<211> LENGTH: 20
<212> TYPE: DNA
<213> ORGANISM: Mycobacterium tuberculosis

<400> SEQUENCE: 365
aacgagacga aggcattcga 20

<210> SEQ ID NO 366
<211> LENGTH: 17
<212> TYPE: DNA
<213> ORGANISM: Serratia marcescens

<400> SEQUENCE: 366
gttctgcacg tgctttc 17

<210> SEQ ID NO 367
<211> LENGTH: 18
<212> TYPE: DNA
<213> ORGANISM: Serratia marcescens

<400> SEQUENCE: 367
ggttggcgtt cctttcat 18

<210> SEQ ID NO 368
<211> LENGTH: 16
<212> TYPE: DNA
<213> ORGANISM: Serratia marcescens

<400> SEQUENCE: 368
acctgccagt gatccg 16

<210> SEQ ID NO 369
<211> LENGTH: 17
<212> TYPE: DNA
<213> ORGANISM: Serratia marcescens

<400> SEQUENCE: 369
tggacagcta catccca 17

<210> SEQ ID NO 370
<211> LENGTH: 20
<212> TYPE: DNA
<213> ORGANISM: Serratia marcescens

<400> SEQUENCE: 370
agacaccgtt aagtctacct 20

<210> SEQ ID NO 371
<211> LENGTH: 19
<212> TYPE: DNA
<213> ORGANISM: Serratia marcescens

<400> SEQUENCE: 371
taaaccaggc tccatcaag 19

<210> SEQ ID NO 372
<211> LENGTH: 19
<212> TYPE: DNA
<213> ORGANISM: Serratia marcescens

<400> SEQUENCE: 372
tcctgagcaa agatgaagg 19

<210> SEQ ID NO 373
<211> LENGTH: 17
<212> TYPE: DNA
<213> ORGANISM: Serratia marcescens

<400> SEQUENCE: 373
gaaggtggtc gtcacac 17

<210> SEQ ID NO 374
<211> LENGTH: 19
<212> TYPE: DNA
<213> ORGANISM: Serratia marcescens

<400> SEQUENCE: 374
gacaacgtga acatggttg 19

<210> SEQ ID NO 375
<211> LENGTH: 16
<212> TYPE: DNA
<213> ORGANISM: Serratia marcescens

<400> SEQUENCE: 375
acgtgaccgg taccat 16

<210> SEQ ID NO 376
<211> LENGTH: 17
<212> TYPE: DNA
<213> ORGANISM: Serratia marcescens

<400> SEQUENCE: 376
tcctggtagt agctgcg 17

<210> SEQ ID NO 377
<211> LENGTH: 19
<212> TYPE: DNA
<213> ORGANISM: Serratia marcescens

<400> SEQUENCE: 377
caaagttggc gaagaagtt 19

<210> SEQ ID NO 378
<211> LENGTH: 17
<212> TYPE: DNA
<213> ORGANISM: Klebsiella pneumoniae

<400> SEQUENCE: 378
atcctggttg ttgctgc 17

<210> SEQ ID NO 379
<211> LENGTH: 18
<212> TYPE: DNA
<213> ORGANISM: Klebsiella pneumoniae

<400> SEQUENCE: 379
gtaggcgttc cgtacatc 18

<210> SEQ ID NO 380
<211> LENGTH: 16
<212> TYPE: DNA
<213> ORGANISM: Klebsiella pneumoniae

<400> SEQUENCE: 380
acaccccgat cgttcg 16

<210> SEQ ID NO 381
<211> LENGTH: 20
<212> TYPE: DNA
<213> ORGANISM: Klebsiella pneumoniae

<400> SEQUENCE: 381
cctggatacc tatatcccgg 20

<210> SEQ ID NO 382
<211> LENGTH: 22
<212> TYPE: DNA
<213> ORGANISM: Klebsiella pneumoniae

<400> SEQUENCE: 382
atcaaagtag gtgaagaagt tg 22

<210> SEQ ID NO 383
<211> LENGTH: 16
<212> TYPE: DNA
<213> ORGANISM: Klebsiella pneumoniae

<400> SEQUENCE: 383
accgcgaaaa ccacct 16

<210> SEQ ID NO 384
<211> LENGTH: 16
<212> TYPE: DNA
<213> ORGANISM: Klebsiella pneumoniae

<400> SEQUENCE: 384
taagccgggc accatc 16

<210> SEQ ID NO 385
<211> LENGTH: 18
<212> TYPE: DNA
<213> ORGANISM: Klebsiella pneumoniae

<400> SEQUENCE: 385
tcctgtccaa agacgaag 18

<210> SEQ ID NO 386
<211> LENGTH: 16
<212> TYPE: DNA
<213> ORGANISM: Klebsiella pneumoniae

<400> SEQUENCE: 386
gaaggcggcc gtcata 16

<210> SEQ ID NO 387
<211> LENGTH: 19
<212> TYPE: DNA
<213> ORGANISM: Klebsiella pneumoniae

<400> SEQUENCE: 387
ggcgacaaca tcaaaatgg 19

<210> SEQ ID NO 388
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: variation
<222> LOCATION: (3)..(3)
<223> OTHER INFORMATION: R can be A or G
<220> FEATURE:
<221> NAME/KEY: variation
<222> LOCATION: (8)..(8)
<223> OTHER INFORMATION: W can be A or T
<220> FEATURE:
<221> NAME/KEY: variation
<222> LOCATION: (9)..(9)
<223> OTHER INFORMATION: Y can be C or T
<220> FEATURE:
<221> NAME/KEY: variation
<222> LOCATION: (13)..(13)
<223> OTHER INFORMATION: M can be A or C
<220> FEATURE:
<221> NAME/KEY: variation
<222> LOCATION: (15)..(15)
<223> OTHER INFORMATION: H can be A or C or T

<400> SEQUENCE: 388
carttctwyt tcmghac 17

<210> SEQ ID NO 389
<211> LENGTH: 20
<212> TYPE: DNA
<213> ORGANISM: ARTIFICIAL SEQUENCE
<220> FEATURE:
<223> OTHER INFORMATION: Primer
<220> FEATURE:
<221> NAME/KEY: variation
<222> LOCATION: (3)..(3)
<223> OTHER INFORMATION: R can be A or G
<220> FEATURE:
<221> NAME/KEY: variation
<222> LOCATION: (6)..(6)
<223> OTHER INFORMATION: H can be A or C or T
<220> FEATURE:
<221> NAME/KEY: variation
<222> LOCATION: (9)..(9)
<223> OTHER INFORMATION: R can be A or G
<220> FEATURE:
<221> NAME/KEY: variation
<222> LOCATION: (12)..(12)
<223> OTHER INFORMATION: Y can be C or T
<220> FEATURE:
<221> NAME/KEY: variation
<222> LOCATION: (15)..(15)
<223> OTHER INFORMATION: H can be A or C or T
<220> FEATURE:
<221> NAME/KEY: variation
<222> LOCATION: (18)..(18)
<223> OTHER INFORMATION: K can be G or T

<400> SEQUENCE: 389
aargahgarg gygghcgkca 20

<210> SEQ ID NO 390
<211> LENGTH: 17
<212> TYPE: DNA
<213> ORGANISM: ARTIFICIAL SEQUENCE
<220> FEATURE:
<223> OTHER INFORMATION: Primer
<220> FEATURE:
<221> NAME/KEY: variation
<222> LOCATION: (3)..(3)
<223> OTHER INFORMATION: R can be A or G
<220> FEATURE:
<221> NAME/KEY: variation
<222> LOCATION: (9)..(9)
<223> OTHER INFORMATION: N can be A or C or G or T
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: variation
<222> LOCATION: (10)..(10)
<223> OTHER INFORMATION: M can be A or C
<220> FEATURE:
<221> NAME/KEY: variation
<222> LOCATION: (12)..(12)
<223> OTHER INFORMATION: R can be A or G
<220> FEATURE:
<221> NAME/KEY: variation
<222> LOCATION: (15)..(15)
<223> OTHER INFORMATION: N can be A or G or C or T
<220> FEATURE:
<221> NAME/KEY: misc_feature
<222> LOCATION: (15)..(15)
<223> OTHER INFORMATION: n is a, c, g, or t

<400> SEQUENCE: 390
garatggtnm trccngg 17

<210> SEQ ID NO 391
<211> LENGTH: 21
<212> TYPE: DNA
<213> ORGANISM: ARTIFICIAL SEQUENCE
<220> FEATURE:
<223> OTHER INFORMATION: Primer

<400> SEQUENCE: 391
agtttgatgc agaagtatac g 21

<210> SEQ ID NO 392
<211> LENGTH: 21
<212> TYPE: DNA
<213> ORGANISM: ARTIFICIAL SEQUENCE
<220> FEATURE:
<223> OTHER INFORMATION: Primer

<400> SEQUENCE: 392
tatcctacta cgtggtacta a 21

<210> SEQ ID NO 393
<211> LENGTH: 18
<212> TYPE: DNA
<213> ORGANISM: ARTIFICIAL SEQUENCE
<220> FEATURE:
<223> OTHER INFORMATION: Primer

<400> SEQUENCE: 393
ataacgttga gatgagcg 18

<210> SEQ ID NO 394
<211> LENGTH: 20
<212> TYPE: DNA
<213> ORGANISM: artificial
<220> FEATURE:
<223> OTHER INFORMATION: Primer directed at all tuf genes
<220> FEATURE:
<221> NAME/KEY: variation
<222> LOCATION: (12)..(12)
<223> OTHER INFORMATION: Y can be C or T
<220> FEATURE:
<221> NAME/KEY: variation
<222> LOCATION: (15)..(15)
<223> OTHER INFORMATION: Y can be C or T
<220> FEATURE:
<221> NAME/KEY: variation
<222> LOCATION: (18)..(18)
<223> OTHER INFORMATION: R can be A or G

<400> SEQUENCE: 394
cacgttgacc ayggyaarac 20

<210> SEQ ID NO 395
<211> LENGTH: 20
<212> TYPE: DNA
<213> ORGANISM: artificial
<220> FEATURE:
<223> OTHER INFORMATION: Primer directed at all tuf genes
<220> FEATURE:
<221> NAME/KEY: variation
<222> LOCATION: (3)..(3)
<223> OTHER INFORMATION: D can be A or G or T
<220> FEATURE:
<221> NAME/KEY: variation
<222> LOCATION: (6)..(6)
<223> OTHER INFORMATION: D can be A or G or T
<220> FEATURE:
<221> NAME/KEY: variation
<222> LOCATION: (9)..(9)
<223> OTHER INFORMATION: R can be A or G
<220> FEATURE:
<221> NAME/KEY: variation
<222> LOCATION: (12)..(12)
<223> OTHER INFORMATION: Y can be C or T
<220> FEATURE:
<221> NAME/KEY: variation
<222> LOCATION: (15)..(15)
<223> OTHER INFORMATION: W can be A or T
<220> FEATURE:
<221> NAME/KEY: variation
<222> LOCATION: (18)..(18)
<223> OTHER INFORMATION: R can be A or G
<220> FEATURE:
<221> NAME/KEY: variation
<222> LOCATION: (18)..(18)
<223> OTHER INFORMATION: r can be a or g

<400> SEQUENCE: 395
gtdcgdccrc cytcwcgrat 20

<210> SEQ ID NO 396
<211> LENGTH: 20
<212> TYPE: DNA
<213> ORGANISM: ARTIFICIAL
<220> FEATURE:
<223> OTHER INFORMATION: Primer directed at all tuf genes
<220> FEATURE:
<221> NAME/KEY: misc_feature
<222> LOCATION: (1)..(1)
<223> OTHER INFORMATION: k can be g or t
<220> FEATURE:
<221> NAME/KEY: misc_feature
<222> LOCATION: (2)..(2)
<223> OTHER INFORMATION: y can be c or t
<220> FEATURE:
<221> NAME/KEY: misc_feature
<222> LOCATION: (5)..(5)
<223> OTHER INFORMATION: n stands for deoxyinosine - a base that binds
to a, g, c or t
<220> FEATURE:
<221> NAME/KEY: misc_feature
<222> LOCATION: (8)..(8)
<223> OTHER INFORMATION: h can be a, c or t
<220> FEATURE:
<221> NAME/KEY: misc_feature
<222> LOCATION: (11)..(11)

<223> OTHER INFORMATION: b can be g, c or t
<220> FEATURE:
<221> NAME/KEY: misc_feature
<222> LOCATION: (14)..(14)
<223> OTHER INFORMATION: r can be a or g

<400> SEQUENCE: 396
kyacngghgt bgaratgttc 20

<210> SEQ ID NO 397
<211> LENGTH: 47
<212> TYPE: DNA
<213> ORGANISM: Mycoplasma pneumoniae

<400> SEQUENCE: 397
atggcaaaac aaaagtttga tagatcaaaa gctcacgtta atattgg 47

<210> SEQ ID NO 398
<211> LENGTH: 47
<212> TYPE: DNA
<213> ORGANISM: Mycoplasma pneumoniae

<400> SEQUENCE: 398
atggcaagag agaaatttga ccgatctaaa ccccacgtta atgtagg 47

<210> SEQ ID NO 399
<211> LENGTH: 60
<212> TYPE: DNA
<213> ORGANISM: Legionella pneumophila

<400> SEQUENCE: 399
gggagacttt ccgatggcga aggaaaaatt tgaacgtaag aagccgcacg taaacgtggg 60

<210> SEQ ID NO 400
<211> LENGTH: 47
<212> TYPE: DNA
<213> ORGANISM: Legionella pneumophila

<400> SEQUENCE: 400
atggcgaagg aaaaatttga acgtaagaag ccgcacgtaa acgtggg 47

<210> SEQ ID NO 401
<211> LENGTH: 47
<212> TYPE: DNA
<213> ORGANISM: Legionella pneumophila

<400> SEQUENCE: 401
atggcgaagg aaaaatttga acgtaagaag ccgcacgtaa acgtggg 47

<210> SEQ ID NO 402
<211> LENGTH: 47
<212> TYPE: DNA
<213> ORGANISM: Chlamydophila pneumoniae

<400> SEQUENCE: 402
atgtcaaaag aaacttttca acgtaataag ccccatatca atattgg 47

<210> SEQ ID NO 403
<211> LENGTH: 47
<212> TYPE: DNA
<213> ORGANISM: Enterococcus faecalis

<400> SEQUENCE: 403
atggcaaaag aaaaatttga ccgttctaaa tcccatgtta acattgg 47

<210> SEQ ID NO 404
<211> LENGTH: 47
<212> TYPE: DNA
<213> ORGANISM: Staphylococcus aureus

<400> SEQUENCE: 404
atggcaaaag aaaaattcga tcgttctaaa gaacatgcca atatcgg 47

<210> SEQ ID NO 405
<211> LENGTH: 47
<212> TYPE: DNA
<213> ORGANISM: Staphylococcus aureus

<400> SEQUENCE: 405
atggcaaaag aaaaattcga tcgttctaaa gaacatgcca atatcgg 47

<210> SEQ ID NO 406
<211> LENGTH: 47
<212> TYPE: DNA
<213> ORGANISM: Staphylococcus aureus

<400> SEQUENCE: 406
atggcaaaag aaaaattcga tcgttctaaa gaacatgcca atatcgg 47

<210> SEQ ID NO 407
<211> LENGTH: 47
<212> TYPE: DNA
<213> ORGANISM: Staphylococcus aureus

<400> SEQUENCE: 407
atggcaaaag aaaaattcga tcgttctaaa gaacatgcca atatcgg 47

<210> SEQ ID NO 408
<211> LENGTH: 47
<212> TYPE: DNA
<213> ORGANISM: Staphylococcus aureus

<400> SEQUENCE: 408
atggcaaaag aaaaatttga tcgttctaaa gaacatgcca atatcgg 47

<210> SEQ ID NO 409
<211> LENGTH: 47
<212> TYPE: DNA
<213> ORGANISM: Staphylococcus epidermidis

<400> SEQUENCE: 409
atggcaaaag aaaaatttga tcgctcaaaa gaacatgcca atattgg 47

<210> SEQ ID NO 410
<211> LENGTH: 47
<212> TYPE: DNA
<213> ORGANISM: Staphylococcus epidermidis

<400> SEQUENCE: 410
atggcaaaag aaaaatttga tcgctcaaaa gaacatgcca atattgg 47

<210> SEQ ID NO 411
<211> LENGTH: 47
<212> TYPE: DNA
<213> ORGANISM: Streptococcus mitis

<400> SEQUENCE: 411
atggcaaaag aaaaatacga tcgtagtaaa ccacacgtta acattgg 47

<210> SEQ ID NO 412
<211> LENGTH: 47
<212> TYPE: DNA
<213> ORGANISM: Streptococcus pneumoniae

<400> SEQUENCE: 412
atggcaaaag aaaaatacga tcgtagtaaa ccacacgtta acattgg 47

<210> SEQ ID NO 413
<211> LENGTH: 47
<212> TYPE: DNA
<213> ORGANISM: Streptococcus pyogenes

<400> SEQUENCE: 413
atggcaaaag aaaaatacga tcgtagtaaa ccccacgtta acattgg 47

<210> SEQ ID NO 414
<211> LENGTH: 47
<212> TYPE: DNA
<213> ORGANISM: Streptococcus mutans

<400> SEQUENCE: 414
atggcaaaag aaaaatacga tcgtagtaaa ccacacgtta acattgg 47

<210> SEQ ID NO 415
<211> LENGTH: 47
<212> TYPE: DNA
<213> ORGANISM: Haemophilus influenzae

<400> SEQUENCE: 415
atgtctaaag aaaaatttga acgtacaaaa ccgcacgtaa acgtggg 47

<210> SEQ ID NO 416
<211> LENGTH: 47
<212> TYPE: DNA
<213> ORGANISM: Bordetella pertussis

<400> SEQUENCE: 416
atggcaaaag gcaagtttga acgtaccaag ccgcacgtga acgtggg 47

<210> SEQ ID NO 417
<211> LENGTH: 47
<212> TYPE: DNA
<213> ORGANISM: Bordetella parapertussis

<400> SEQUENCE: 417
atggcaaaag gcaagtttga acgtaccaag ccgcacgtga acgtggg 47

<210> SEQ ID NO 418
<211> LENGTH: 47
<212> TYPE: DNA
<213> ORGANISM: Burkholderia pseudomallei

<400> SEQUENCE: 418
atggcaaaag agaagtttga gcggaccaag ccgcacgtga acgttgg 47

<210> SEQ ID NO 419
<211> LENGTH: 47
<212> TYPE: DNA
<213> ORGANISM: Pseudomonas aeruginosa

<400> SEQUENCE: 419
gtggctaagg aaaaattcga acgtaacaaa ccgcacgtca acgtcgg 47

<210> SEQ ID NO 420
<211> LENGTH: 47
<212> TYPE: DNA
<213> ORGANISM: Mycobacterium avium

<400> SEQUENCE: 420
gtggcgaagg cgaagttcga gcggacgaag ccgcacgtca acatcgg 47

<210> SEQ ID NO 421
<211> LENGTH: 47
<212> TYPE: DNA
<213> ORGANISM: Mycobacterium avium

<400> SEQUENCE: 421
gtggcgaagg cgaagttcga gcggacgaag ccgcacgtca acatcgg 47

<210> SEQ ID NO 422
<211> LENGTH: 47
<212> TYPE: DNA
<213> ORGANISM: Mycobacterium tuberculosis

<400> SEQUENCE: 422
gtggcgaagg cgaagttcca gcggaccaag ccccacgtca acatcgg 47

<210> SEQ ID NO 423
<211> LENGTH: 47
<212> TYPE: DNA
<213> ORGANISM: Mycobacterium tuberculosis

<400> SEQUENCE: 423
gtggcgaagg cgaagttcca gcggaccaag ccccacgtca acatcgg 47

<210> SEQ ID NO 424
<211> LENGTH: 47
<212> TYPE: DNA
<213> ORGANISM: Corynebacterium diphtheriae

<400> SEQUENCE: 424
gtggcaaagg ctaagttcga gcgtaccaag ccgcacgtca acatcgg 47

<210> SEQ ID NO 425
<211> LENGTH: 47
<212> TYPE: DNA
<213> ORGANISM: Neisseria meningitidis

<400> SEQUENCE: 425
atggctaagg aaaaattcga acgtagcaaa ccgcacgtaa acgttgg 47

<210> SEQ ID NO 426
<211> LENGTH: 47
<212> TYPE: DNA
<213> ORGANISM: Neisseria meningitidis

<400> SEQUENCE: 426
atggctaagg aaaaattcga acgtagcaaa ccgcacgtaa acgttgg 47

<210> SEQ ID NO 427
<211> LENGTH: 60
<212> TYPE: DNA
<213> ORGANISM: Mycoplasma pneumoniae

<400> SEQUENCE: 427
gacaattgga catattgacc atggtaaaac aactttaaca gctgcaatct gtacttacct 60

<210> SEQ ID NO 428
<211> LENGTH: 60
<212> TYPE: DNA
<213> ORGANISM: Mycoplasma pneumoniae

<400> SEQUENCE: 428
tactattggc cacattgacc acggtaaaac aactttaaca gcagctattt gtactgtatt 60

<210> SEQ ID NO 429
<211> LENGTH: 60
<212> TYPE: DNA
<213> ORGANISM: Legionella pneumophila

<400> SEQUENCE: 429
cacgattggt cacgtagacc atggcaagac gacattgaca gcagctatta caacgattat 60

<210> SEQ ID NO 430
<211> LENGTH: 60
<212> TYPE: DNA
<213> ORGANISM: Legionella pneumophila

<400> SEQUENCE: 430
cacgattggt cacgtagacc atggtaagac gacattgaca gcagctatta caacgattat 60

<210> SEQ ID NO 431
<211> LENGTH: 60
<212> TYPE: DNA
<213> ORGANISM: Legionella pneumophila

<400> SEQUENCE: 431
cacgattggt cacgtagacc atggtaagac gacattgaca gcagctatta caacgattat 60

<210> SEQ ID NO 432
<211> LENGTH: 60
<212> TYPE: DNA
<213> ORGANISM: Chlamydophila pneumoniae

<400> SEQUENCE: 432
gacgatcggg cacgttgacc atggtaaaac tacgctaaca gcggcaatta cacgcgcgct 60

<210> SEQ ID NO 433
<211> LENGTH: 60
<212> TYPE: DNA
<213> ORGANISM: Enterococcus faecalis

<400> SEQUENCE: 433
tactatcgga cacgttgacc atggtaaaac tacattaaca gctgcaattg ctactgtatt 60

<210> SEQ ID NO 434
<211> LENGTH: 60
<212> TYPE: DNA
<213> ORGANISM: Staphylococcus aureus

<400> SEQUENCE: 434
tactatcggt cacgttgacc atggtaaaac aacattaaca gcagcaatcg ctactgtatt 60

<210> SEQ ID NO 435
<211> LENGTH: 60
<212> TYPE: DNA
<213> ORGANISM: Staphylococcus aureus

<400> SEQUENCE: 435
tactatcggt cacgttgacc atggtaaaac aacattaaca gcagcaatcg ctactgtatt 60

<210> SEQ ID NO 436
<211> LENGTH: 60
<212> TYPE: DNA
<213> ORGANISM: Staphylococcus aureus

<400> SEQUENCE: 436
tactatcggt cacgttgacc atggtaaaac aacattaaca gcagcaatcg ctactgtatt 60

<210> SEQ ID NO 437
<211> LENGTH: 60
<212> TYPE: DNA
<213> ORGANISM: Staphylococcus aureus

<400> SEQUENCE: 437
tactatcggt cacgttgacc atggtaaaac aacattaaca gcagcaatcg ctactgtatt 60

<210> SEQ ID NO 438
<211> LENGTH: 60
<212> TYPE: DNA
<213> ORGANISM: Staphylococcus aureus

<400> SEQUENCE: 438
tactatcggt cacgttgacc atggtaaaac aacattaaca gcagcaatcg ctactgtatt 60

<210> SEQ ID NO 439
<211> LENGTH: 60
<212> TYPE: DNA
<213> ORGANISM: Staphylococcus epidermidis

<400> SEQUENCE: 439
tactatcggt cacgttgacc atggtaaaac aactttaaca gctgctatcg caactgtatt 60

<210> SEQ ID NO 440
<211> LENGTH: 60
<212> TYPE: DNA
<213> ORGANISM: Staphylococcus epidermidis

<400> SEQUENCE: 440
tactatcggt cacgttgacc atggtaaaac aactttaaca gctgctatcg caactgtatt 60

<210> SEQ ID NO 441
<211> LENGTH: 10
<212> TYPE: DNA
<213> ORGANISM: Streptococcus sanguis

<400> SEQUENCE: 441
cccctgtatt 10

<210> SEQ ID NO 442
<211> LENGTH: 60
<212> TYPE: DNA
<213> ORGANISM: Streptococcus mitis

<400> SEQUENCE: 442
tactatcgga cacgttgacc acggtaaaac tactttgaca gcagctatca caactgtttt 60

<210> SEQ ID NO 443
<211> LENGTH: 60
<212> TYPE: DNA
<213> ORGANISM: Streptococcus pneumoniae

<400> SEQUENCE: 443
tactatcgga cacgttgacc acggtaaaac taccctaact gcagctatca caactgtttt 60

<210> SEQ ID NO 444
<211> LENGTH: 60
<212> TYPE: DNA
<213> ORGANISM: Streptococcus pyogenes

<400> SEQUENCE: 444
tacaatcgga cacgttgacc atggtaaaac tactttaaca gctgcaatca caactgtatt 60

<210> SEQ ID NO 445
<211> LENGTH: 10
<212> TYPE: DNA
<213> ORGANISM: Streptococcus mutans

<400> SEQUENCE: 445
cccctgtact 10

<210> SEQ ID NO 446
<211> LENGTH: 60
<212> TYPE: DNA
<213> ORGANISM: Streptococcus mutans

<400> SEQUENCE: 446
tactatcgga cacgttgacc atggtaaaac taccttaact gcagctatca caactgtact 60

<210> SEQ ID NO 447
<211> LENGTH: 60
<212> TYPE: DNA
<213> ORGANISM: Haemophilus influenzae

<400> SEQUENCE: 447
tacaatcggc cacgttgacc acggtaaaac aactttaaca gcagcaatca caaccgtatt 60

<210> SEQ ID NO 448
<211> LENGTH: 60
<212> TYPE: DNA
<213> ORGANISM: Bordetella pertussis

<400> SEQUENCE: 448
tacgattggt cacgttgacc acggcaaaac gacgttgacg gcggcgatca cgacggtgct 60

<210> SEQ ID NO 449
<211> LENGTH: 60
<212> TYPE: DNA
<213> ORGANISM: Bordetella parapertussis

<400> SEQUENCE: 449
tacgattggt cacgttgacc acggcaaaac gacgttgacg gcggcgatca cgacggtgct 60

<210> SEQ ID NO 450
<211> LENGTH: 60
<212> TYPE: DNA
<213> ORGANISM: Burkholderia pseudomallei

<400> SEQUENCE: 450
tacgattggt cacgttgacc acggcaagac gacgctgacg gcagcgatcg cgacggtgct 60

<210> SEQ ID NO 451
<211> LENGTH: 13
<212> TYPE: DNA
<213> ORGANISM: Stenotrophomonas maltophilia

<400> SEQUENCE: 451
tgacaagatc ggt 13

<210> SEQ ID NO 452
<211> LENGTH: 60
<212> TYPE: DNA
<213> ORGANISM: Pseudomonas aeruginosa

<400> SEQUENCE: 452
caccatcggt cacgttgacc atggcaagac cactctgacc gctgcactga ccaaggtctg 60

<210> SEQ ID NO 453
<211> LENGTH: 60
<212> TYPE: DNA
<213> ORGANISM: Mycobacterium avium

<400> SEQUENCE: 453
gaccatcggt cacgttgacc acggcaagac cacgctgacc gcggctatca ccaaggttct 60

<210> SEQ ID NO 454
<211> LENGTH: 60
<212> TYPE: DNA
<213> ORGANISM: Mycobacterium avium

<400> SEQUENCE: 454
gaccatcggt cacgttgacc acggcaagac cacgctgacc gcggctatca ccaaggttct 60

<210> SEQ ID NO 455
<211> LENGTH: 10
<212> TYPE: DNA
<213> ORGANISM: Mycobacterium intracellulare

<400> SEQUENCE: 455
ccccccccct 10

<210> SEQ ID NO 456
<211> LENGTH: 10
<212> TYPE: DNA
<213> ORGANISM: Mycobacterium kansasii

<400> SEQUENCE: 456
ccaaggtcct 10

<210> SEQ ID NO 457
<211> LENGTH: 60
<212> TYPE: DNA
<213> ORGANISM: Mycobacterium tuberculosis

<400> SEQUENCE: 457
gaccatcggt cacgttgacc acggcaagac caccctgacc gcggctatca ccaaggtcct 60

<210> SEQ ID NO 458
<211> LENGTH: 60
<212> TYPE: DNA
<213> ORGANISM: Mycobacterium tuberculosis

<400> SEQUENCE: 458
gaccatcggt cacgttgacc acggcaagac caccctgacc gcggctatca ccaaggtcct 60

<210> SEQ ID NO 459
<211> LENGTH: 60
<212> TYPE: DNA
<213> ORGANISM: Corynebacterium diphtheriae

<400> SEQUENCE: 459
caccatcggt cacgttgacc acggtaagac caccaccacc gctgctatca ccaaggtttt 60

<210> SEQ ID NO 460
<211> LENGTH: 60
<212> TYPE: DNA
<213> ORGANISM: Neisseria meningitidis

<400> SEQUENCE: 460
caccatcggt cacgttgacc atggtaaaac caccctgact gccgctttga ctactatttt 60

<210> SEQ ID NO 461
<211> LENGTH: 60
<212> TYPE: DNA
<213> ORGANISM: Neisseria meningitidis

<400> SEQUENCE: 461
caccatcggt cacgttgacc atggtaaaac caccctgact gccgctttga ctactatttt 60

<210> SEQ ID NO 462
<211> LENGTH: 51
<212> TYPE: DNA
<213> ORGANISM: Mycoplasma pneumoniae

<400> SEQUENCE: 462
tgcaaaaaaa ggtggtgcta aagcaatgaa atatgatgaa attgataaag c 51

<210> SEQ ID NO 463
<211> LENGTH: 51
<212> TYPE: DNA
<213> ORGANISM: Mycoplasma pneumoniae

<400> SEQUENCE: 463
agcaaaagaa ggtaaatcag ctgctactcg ttacgaccaa atcgataagg c 51

<210> SEQ ID NO 464
<211> LENGTH: 51
<212> TYPE: DNA
<213> ORGANISM: Legionella pneumophila

<400> SEQUENCE: 464
ggcgaagaaa tatggtggta cagcgaaggc gtacgatcaa attgatgctg c 51

<210> SEQ ID NO 465
<211> LENGTH: 41
<212> TYPE: DNA
<213> ORGANISM: Legionella pneumophila

<400> SEQUENCE: 465
tatggtggta cagcgaaggc gtacgatcaa attgatgctg c 41

<210> SEQ ID NO 466
<211> LENGTH: 51
<212> TYPE: DNA
<213> ORGANISM: Legionella pneumophila

<400> SEQUENCE: 466
ggcgaagaaa tatggtggta cagcgaaggc gtacgatcaa attgatgctg c 51

<210> SEQ ID NO 467
<211> LENGTH: 51
<212> TYPE: DNA
<213> ORGANISM: Legionella pneumophila

<400> SEQUENCE: 467
ggcgaagaaa tatggtggta cagcgaaggc gtacgatcaa attgatgctg c 51

<210> SEQ ID NO 468
<211> LENGTH: 42
<212> TYPE: DNA
<213> ORGANISM: Legionella longbeachae

<400> SEQUENCE: 468
gtttggtggt atagcaaaag catacgatca gatcgatgct gc 42

<210> SEQ ID NO 469
<211> LENGTH: 36
<212> TYPE: DNA
<213> ORGANISM: Fusobacterium nucleatum

<400> SEQUENCE: 469
agctaaaaaa gtagattttg accaaattga tgctgc 36

<210> SEQ ID NO 470
<211> LENGTH: 51
<212> TYPE: DNA
<213> ORGANISM: Chlamydophila pneumoniae

<400> SEQUENCE: 470
atcaggggat ggattggcct ctttccgtga ctatagttca attgacaata c 51

<210> SEQ ID NO 471
<211> LENGTH: 35
<212> TYPE: DNA
<213> ORGANISM: Enterococcus faecalis

<400> SEQUENCE: 471
gggaaagcac aaagctacga ttctatcgat aacgc 35

<210> SEQ ID NO 472
<211> LENGTH: 51
<212> TYPE: DNA
<213> ORGANISM: Enterococcus faecalis

<400> SEQUENCE: 472
atcaaaacac ggtggcgggg aagcacaaag ctacgattct atcgataacg c 51

<210> SEQ ID NO 473
<211> LENGTH: 51
<212> TYPE: DNA
<213> ORGANISM: Staphylococcus aureus

<400> SEQUENCE: 473
agcaaaaaat ggtgactcag ttgcacaatc atatgacatg attgacaacg c 51

<210> SEQ ID NO 474
<211> LENGTH: 51
<212> TYPE: DNA
<213> ORGANISM: Staphylococcus aureus

<400> SEQUENCE: 474
agcaaaaaat ggtgactcag ttgcacaatc atatgacatg attgacaacg c 51

<210> SEQ ID NO 475
<211> LENGTH: 51
<212> TYPE: DNA
<213> ORGANISM: Staphylococcus aureus

<400> SEQUENCE: 475
agcaaaaaat ggtgactcag ttgcacaatc atatgacatg attgacaacg c 51

<210> SEQ ID NO 476
<211> LENGTH: 51
<212> TYPE: DNA
<213> ORGANISM: Staphylococcus aureus

<400> SEQUENCE: 476
agcaaaaaat ggtgactcag ttgcacaatc atatgacatg attgacaacg c 51

<210> SEQ ID NO 477
<211> LENGTH: 51
<212> TYPE: DNA
<213> ORGANISM: Staphylococcus aureus

<400> SEQUENCE: 477
agcaaaaaat ggtgactcag ttgcacaatc atacgacatg attgacaacg c 51

<210> SEQ ID NO 478
<211> LENGTH: 51
<212> TYPE: DNA
<213> ORGANISM: Staphylococcus epidermidis

<400> SEQUENCE: 478
agctaaaaat ggtgacactg ttgcacaatc atacgatatg attgacaacg c 51

<210> SEQ ID NO 479
<211> LENGTH: 51
<212> TYPE: DNA
<213> ORGANISM: Staphylococcus epidermidis

<400> SEQUENCE: 479
agctaaaaat ggtgacactg ttgcacaatc atacgatatg attgacaacg c 51

<210> SEQ ID NO 480
<211> LENGTH: 26
<212> TYPE: DNA
<213> ORGANISM: Streptococcus mitis

<400> SEQUENCE: 480
aaagactatg cgtctatcga tgctgc 26

<210> SEQ ID NO 481
<211> LENGTH: 60
<212> TYPE: DNA
<213> ORGANISM: Streptococcus sanguis

<400> SEQUENCE: 481
ggcacgtcgc ttgccttcag cagttaacca acctaaagac tatgcgtcta tcgatgctgc 60

<210> SEQ ID NO 482
<211> LENGTH: 60
<212> TYPE: DNA
<213> ORGANISM: Streptococcus mitis

<400> SEQUENCE: 482
ggcacgtcgc ttgccttcag ctgttaacca acctaaagac tatgcgtcta tcgatgctgc 60

<210> SEQ ID NO 483
<211> LENGTH: 60
<212> TYPE: DNA
<213> ORGANISM: Streptococcus pneumoniae

<400> SEQUENCE: 483
ggcacgtcgc ttgccttcat cagttaacca acctaaagac tatgcgtcta tcgatgctgc 60

<210> SEQ ID NO 484
<211> LENGTH: 60
<212> TYPE: DNA
<213> ORGANISM: Streptococcus pyogenes

<400> SEQUENCE: 484
ggcacgtcgc ttgccttcat cagttaacca accaaaagat tacgcttcta tcgatgctgc 60

<210> SEQ ID NO 485
<211> LENGTH: 60
<212> TYPE: DNA
<213> ORGANISM: Streptococcus mutans

<400> SEQUENCE: 485
ggcacgtcgt cttccaagtg cagtaaacca accaaaagat tattcatcta ttgatgctgc 60

<210> SEQ ID NO 486
<211> LENGTH: 60
<212> TYPE: DNA
<213> ORGANISM: Streptococcus mutans

<400> SEQUENCE: 486
ggcacgtcgt cttccaagtg cagtaaacca accaaaagat tattcatcta ttgatgctgc 60

<210> SEQ ID NO 487
<211> LENGTH: 51
<212> TYPE: DNA
<213> ORGANISM: Haemophilus influenzae

<400> SEQUENCE: 487
agcaaaacac tacggtggtg cagcgcgtgc atttgaccaa attgataacg c 51

<210> SEQ ID NO 488
<211> LENGTH: 10
<212> TYPE: DNA
<213> ORGANISM: Moraxella catarrhalis

<400> SEQUENCE: 488
cgactctgcc 10

<210> SEQ ID NO 489
<211> LENGTH: 51
<212> TYPE: DNA
<213> ORGANISM: Bordetella pertussis

<400> SEQUENCE: 489
gtcgaacaag ttcggcggcg aggctcgcgg ctacgaccag attgacgcgg c 51

<210> SEQ ID NO 490
<211> LENGTH: 51
<212> TYPE: DNA
<213> ORGANISM: Bordetella parapertussis

<400> SEQUENCE: 490
gtcgaacaag ttcggcggcg aggctcgcgg ctacgaccag attgacgcgg c 51

<210> SEQ ID NO 491
<211> LENGTH: 42
<212> TYPE: DNA
<213> ORGANISM: Burkholderia cepacia

<400> SEQUENCE: 491
gttcggcggc gaagcgaaga agtacgacga aatcgacgcg gc 42

<210> SEQ ID NO 492
<211> LENGTH: 51
<212> TYPE: DNA
<213> ORGANISM: Burkholderia pseudomallei

<400> SEQUENCE: 492
gtcggcgaag ttcggcggcg aagcgaagaa gtacgacgaa atcgacgcgg c 51

<210> SEQ ID NO 493
<211> LENGTH: 50
<212> TYPE: DNA
<213> ORGANISM: Stenotrophomonas maltophilia

<400> SEQUENCE: 493
gccgagcgct tcggtggcga gttcaaggac tactcctcga tcgacgccgc 50

<210> SEQ ID NO 494
<211> LENGTH: 51
<212> TYPE: DNA
<213> ORGANISM: Pseudomonas aeruginosa

<400> SEQUENCE: 494
ctccgatacc tggggtggtt ccgctcgtgc tttcgatcag atcgacaacg c 51

<210> SEQ ID NO 495
<211> LENGTH: 42
<212> TYPE: DNA
<213> ORGANISM: Klebsiella pneumoniae

<400> SEQUENCE: 495
ctacggtggt tccgctcgcg cattcgacca gatcgataac gc 42

<210> SEQ ID NO 496
<211> LENGTH: 57
<212> TYPE: DNA
<213> ORGANISM: Mycobacterium avium

<400> SEQUENCE: 496
gcacgacaag tacccggacc tgaacgagtc ccgcgcgttc gaccagatcg acaacgc 57

<210> SEQ ID NO 497
<211> LENGTH: 57
<212> TYPE: DNA
<213> ORGANISM: Mycobacterium avium

<400> SEQUENCE: 497
gcacgacaag tacccggacc tgaacgagtc ccgcgcgttc gaccagatcg acaacgc 57

<210> SEQ ID NO 498
<211> LENGTH: 57
<212> TYPE: DNA
<213> ORGANISM: Mycobacterium intracellulare

<400> SEQUENCE: 498
gcacgacaag tacccggacc tgaacgagtc ccgcgcgttc gaccagatcg acaacgc 57

<210> SEQ ID NO 499
<211> LENGTH: 57
<212> TYPE: DNA
<213> ORGANISM: Mycobacterium kansasii

<400> SEQUENCE: 499
gcatgacaag ttcccggacc tgaacgagtc gaaggcgttc gaccagatcg acaacgc 57

<210> SEQ ID NO 500
<211> LENGTH: 57
<212> TYPE: DNA
<213> ORGANISM: Mycobacterium tuberculosis

<400> SEQUENCE: 500
gcacgacaaa ttccccgatc tgaacgagac gaaggcattc gaccagatcg acaacgc 57

<210> SEQ ID NO 501
<211> LENGTH: 57
<212> TYPE: DNA
<213> ORGANISM: Mycobacterium tuberculosis

<400> SEQUENCE: 501
gcacgacaaa ttccccgatc tgaacgagac gaaggcattc gaccagatcg acaacgc 57

<210> SEQ ID NO 502
<211> LENGTH: 10
<212> TYPE: DNA
<213> ORGANISM: Mycobacterium avium

<400> SEQUENCE: 502
aaaaaaacgc 10

<210> SEQ ID NO 503
<211> LENGTH: 57
<212> TYPE: DNA
<213> ORGANISM: Corynebacterium diphtheriae

<400> SEQUENCE: 503
ggcagacgct tacccagagc tgaacgaagc tttcgctttc gatgccatcg ataaggc 57

<210> SEQ ID NO 504
<211> LENGTH: 51
<212> TYPE: DNA
<213> ORGANISM: Neisseria meningitidis

<400> SEQUENCE: 504
ggctaaaaaa ttcggcggtg ctgcaaaagc ttacgaccaa atcgacaacg c 51

<210> SEQ ID NO 505
<211> LENGTH: 51
<212> TYPE: DNA
<213> ORGANISM: Neisseria meningitidis

<400> SEQUENCE: 505
ggctaaaaaa ttcggcggtg ctgcaaaagc ttacgaccaa atcgacaacg c 51

<210> SEQ ID NO 506
<211> LENGTH: 60
<212> TYPE: DNA
<213> ORGANISM: Mycoplasma pneumoniae

<400> SEQUENCE: 506
acctgaagaa aaagctagag gtattactat taatactgct cacgttgaat atgaaacaga 60

<210> SEQ ID NO 507
<211> LENGTH: 60
<212> TYPE: DNA
<213> ORGANISM: Mycoplasma pneumoniae

<400> SEQUENCE: 507
tccggaagaa aaagcacggg gaattacgat taactccgct cacgtggagt actcctctga 60

<210> SEQ ID NO 508
<211> LENGTH: 60
<212> TYPE: DNA
<213> ORGANISM: Legionella pneumophila

<400> SEQUENCE: 508
gccagaagaa agagagcgtg gtattactat ttctacagca cacgttgagt acgaatcagc 60

<210> SEQ ID NO 509
<211> LENGTH: 60
<212> TYPE: DNA
<213> ORGANISM: Legionella pneumophila

<400> SEQUENCE: 509
gccagaagaa agagagcgtg ggattactat ttctacagca catgttgaat acgaatcagc 60

<210> SEQ ID NO 510
<211> LENGTH: 60
<212> TYPE: DNA
<213> ORGANISM: Legionella pneumophila

<400> SEQUENCE: 510
gccagaagaa agagagcgtg ggattactat ttctacagca catgttgaat acgaatcagc 60

<210> SEQ ID NO 511
<211> LENGTH: 60
<212> TYPE: DNA
<213> ORGANISM: Legionella pneumophila

<400> SEQUENCE: 511
gccagaagaa agagagcgtg gtattactat atctacagcc catgttgaat acgaatcagc 60

<210> SEQ ID NO 512
<211> LENGTH: 60
<212> TYPE: DNA
<213> ORGANISM: Legionella longbeachiae

<400> SEQUENCE: 512
accagaagaa agagagcgag gcatcacaat ctcaacagcg cacgttgaat acgaatcagc 60

<210> SEQ ID NO 513
<211> LENGTH: 60
<212> TYPE: DNA
<213> ORGANISM: Fusobacterium nucleatum

<400> SEQUENCE: 513
tccagaagaa aaagaaagag gaattactat taatacagct catattgaat atgaaacagc 60

<210> SEQ ID NO 514
<211> LENGTH: 60
<212> TYPE: DNA
<213> ORGANISM: Chlamydophila pneumoniae

<400> SEQUENCE: 514
tccagaagaa aaggctcgtg gaattactat caacgcttct cacgttgaat acgaaacccc 60

<210> SEQ ID NO 515
<211> LENGTH: 60
<212> TYPE: DNA
<213> ORGANISM: Enterococcus faecalis

<400> SEQUENCE: 515
tccagaagaa aaagaacgtg gaatcacaat caacacttct catatcgaat atgaaactga 60

<210> SEQ ID NO 516
<211> LENGTH: 60
<212> TYPE: DNA
<213> ORGANISM: Enterococcus faecalis

<400> SEQUENCE: 516
tccagaagaa aaagaacgtg gaatcacaat caacacttct catatcgaat atgaaactga 60

<210> SEQ ID NO 517
<211> LENGTH: 60
<212> TYPE: DNA
<213> ORGANISM: Staphylococcus aureus

<400> SEQUENCE: 517
tccagaagaa aaagaacgtg gtatcacaat caatacttct cacattgagt accaaactga 60

<210> SEQ ID NO 518
<211> LENGTH: 60
<212> TYPE: DNA
<213> ORGANISM: Staphylococcus aureus

<400> SEQUENCE: 518
tccagaagaa aaagaacgtg gtatcacaat caatacttct cacattgagt accaaactga 60

<210> SEQ ID NO 519
<211> LENGTH: 60
<212> TYPE: DNA
<213> ORGANISM: Staphylococcus aureus

<400> SEQUENCE: 519
tccagaagaa aaagaacgtg gtatcacaat caatacttct cacattgagt accaaactga 60

<210> SEQ ID NO 520
<211> LENGTH: 60
<212> TYPE: DNA
<213> ORGANISM: Staphylococcus aureus

<400> SEQUENCE: 520
tccagaagaa aaagaacgtg gtatcacaat caatacttct cacattgagt accaaactga 60

<210> SEQ ID NO 521
<211> LENGTH: 60
<212> TYPE: DNA
<213> ORGANISM: Staphylococcus aureus

<400> SEQUENCE: 521
tccagaagaa aaagaacgtg gtatcacaat caatacttca cacattgagt accaaactga 60

<210> SEQ ID NO 522
<211> LENGTH: 60
<212> TYPE: DNA
<213> ORGANISM: Staphylococcus epidermidis

<400> SEQUENCE: 522
tccagaagaa aaagaacgtg gtattacaat caatactgca catatcgaat accaaactga 60

<210> SEQ ID NO 523
<211> LENGTH: 60
<212> TYPE: DNA
<213> ORGANISM: Staphylococcus epidermidis

<400> SEQUENCE: 523
tccagaagaa aaagaacgtg gtattacaat caatactgca catatcgaat accaaactga 60

<210> SEQ ID NO 524
<211> LENGTH: 60
<212> TYPE: DNA
<213> ORGANISM: Streptococcus mitis

<400> SEQUENCE: 524
tccagaagaa cgcgaacgcg gtatcactat caacactgcg cacgttgagt acgaaactga 60

<210> SEQ ID NO 525
<211> LENGTH: 60
<212> TYPE: DNA
<213> ORGANISM: Streptococcus sanguis

<400> SEQUENCE: 525
tccagaagaa cgcgaacgcg gaatcactat caacactgcg cacgttgagt atgaaactgc 60

<210> SEQ ID NO 526
<211> LENGTH: 60
<212> TYPE: DNA
<213> ORGANISM: Streptococcus mitis

<400> SEQUENCE: 526
tccagaagaa cgcgaacgtg gtatcacaat caacactgcg cacgttgagt acgaaactga 60

<210> SEQ ID NO 527
<211> LENGTH: 60
<212> TYPE: DNA
<213> ORGANISM: Streptococcus pneumoniae

<400> SEQUENCE: 527
tccagaagaa cgcgaacgcg gtatcactat caacactgcg cacgttgagt acgaaactga 60

<210> SEQ ID NO 528
<211> LENGTH: 60
<212> TYPE: DNA
<213> ORGANISM: Streptococcus pyogenes

<400> SEQUENCE: 528
tccagaagaa cgcgaacgcg gaatcactat caacactgca cacgttgagt acgaaactgc 60

<210> SEQ ID NO 529
<211> LENGTH: 60
<212> TYPE: DNA
<213> ORGANISM: Streptococcus mutans

<400> SEQUENCE: 529
tcctgaagaa cgcgaacgcg gtatcactat caatactgcg cacgttgagt atgaaactga 60

<210> SEQ ID NO 530
<211> LENGTH: 60
<212> TYPE: DNA
<213> ORGANISM: Streptococcus mutans

<400> SEQUENCE: 530
tcctgaagaa cgcgaacgcg gtatcactat caatactgcg cacgttgagt atgaaactga 60

<210> SEQ ID NO 531
<211> LENGTH: 60
<212> TYPE: DNA
<213> ORGANISM: Haemophilus influenzae

<400> SEQUENCE: 531
gccagaagaa aaagcgcgtg gtattaccat caacacttca cacgttgaat acgatacacc 60

<210> SEQ ID NO 532
<211> LENGTH: 60
<212> TYPE: DNA
<213> ORGANISM: Moraxella catarrhalis

<400> SEQUENCE: 532
acctgaagaa aaagcacgtg gtattactat taacacatct cacatcgagt atgacacaga 60

<210> SEQ ID NO 533
<211> LENGTH: 60
<212> TYPE: DNA
<213> ORGANISM: Bordetella pertussis

<400> SEQUENCE: 533
gccggaagag aaggcgcgtg ggatcacgat caacacctcg cacgttgagt acgagacgga 60

<210> SEQ ID NO 534
<211> LENGTH: 60
<212> TYPE: DNA
<213> ORGANISM: Bordetella parapertussis

<400> SEQUENCE: 534
gccggaagag aaggcgcgtg ggatcacgat caacacctcg cacgttgagt acgagacgga 60

<210> SEQ ID NO 535
<211> LENGTH: 60
<212> TYPE: DNA
<213> ORGANISM: Burkholderia cepacia

<400> SEQUENCE: 535
gccggaagaa aaggcacgcg gcatcacgat caacaccgcg cacatcgagt acgaaacggc 60

<210> SEQ ID NO 536
<211> LENGTH: 60
<212> TYPE: DNA
<213> ORGANISM: Burkholderia pseudomallei

<400> SEQUENCE: 536
gccggaagaa aaggcgcgcg gcatcacgat caacaccgcg cacatcgagt acgaaacggc 60

<210> SEQ ID NO 537
<211> LENGTH: 60
<212> TYPE: DNA
<213> ORGANISM: Stenotrophomonas maltophilia

<400> SEQUENCE: 537
gccggaagaa aaggctcgtg gtatcacgat ctcgaccgcg cacgtcgaat acgaatcccc 60

<210> SEQ ID NO 538
<211> LENGTH: 60
<212> TYPE: DNA
<213> ORGANISM: Pseudomonas aeruginosa

<400> SEQUENCE: 538
gccggaagaa aaggcccgcg gtatcaccat caacacctcg cacgttgaat acgattccgc 60

<210> SEQ ID NO 539
<211> LENGTH: 60
<212> TYPE: DNA
<213> ORGANISM: Klebsiella pneumoniae

<400> SEQUENCE: 539
gccggaagaa aaagctcgtg gtatcaccat caacacctct cacgttgaat atgacacccc 60

<210> SEQ ID NO 540
<211> LENGTH: 60
<212> TYPE: DNA
<213> ORGANISM: Mycobacterium avium

<400> SEQUENCE: 540
gcccgaggag cgtcagcgcg gtatcaccat caacatctcc cacgtggagt accagaccga 60

<210> SEQ ID NO 541
<211> LENGTH: 60
<212> TYPE: DNA
<213> ORGANISM: Mycobacterium avium

<400> SEQUENCE: 541
gcccgaggag cgtcagcgcg gtatcaccat caacatctcc cacgtggagt accagaccga 60

<210> SEQ ID NO 542
<211> LENGTH: 60
<212> TYPE: DNA
<213> ORGANISM: Mycobacterium intracellulare

<400> SEQUENCE: 542
tcccgaggag cgtcagcgcg gtatcacgat caacatctcc cacgtggagt accagaccga 60

<210> SEQ ID NO 543
<211> LENGTH: 60
<212> TYPE: DNA
<213> ORGANISM: Mycobacterium kansasii

<400> SEQUENCE: 543
tcctgaggag cgccagcgcg gtatcacgat caacatcgcg cacgtggagt accagaccga 60

<210> SEQ ID NO 544
<211> LENGTH: 60
<212> TYPE: DNA
<213> ORGANISM: Mycobacterium tuberculosis

<400> SEQUENCE: 544
ccccgaggag cgtcagcgcg gtatcaccat caacatcgcg cacgtggagt accagaccga 60

<210> SEQ ID NO 545
<211> LENGTH: 60
<212> TYPE: DNA
<213> ORGANISM: Mycobacterium tuberculosis

<400> SEQUENCE: 545
ccccgaggag cgtcagcgcg gtatcaccat caacatcgcg cacgtggagt accagaccga 60

<210> SEQ ID NO 546
<211> LENGTH: 60
<212> TYPE: DNA
<213> ORGANISM: Mycobacterium avium

<400> SEQUENCE: 546
gcctgaagag cgtcagcgcg gtatcaccat caacatctcg catgttgagt accagaccga 60

<210> SEQ ID NO 547
<211> LENGTH: 60
<212> TYPE: DNA
<213> ORGANISM: Corynebacterium diphtheriae

<400> SEQUENCE: 547
accggaagag aaagagcgtg gtattaccat caacatctcc cacgtggagt accagaccga 60

<210> SEQ ID NO 548
<211> LENGTH: 60
<212> TYPE: DNA
<213> ORGANISM: Neisseria meningitidis

<400> SEQUENCE: 548
acccgaagaa aaagcacgcg gtattaccat taacacctcg cacgtggaat acgaaaccga 60

<210> SEQ ID NO 549
<211> LENGTH: 60
<212> TYPE: DNA
<213> ORGANISM: Neisseria meningitidis

<400> SEQUENCE: 549
acccgaagaa aaagcacgcg gtattaccat taacacctcg cacgtggaat acgaaaccga 60

<210> SEQ ID NO 550
<211> LENGTH: 59
<212> TYPE: DNA
<213> ORGANISM: Neisseria meningitidis

<400> SEQUENCE: 550
cccgaagaaa aagcacgcgg tattaccatt aacacctcgc acgtggaata cgaaaccga 59

<210> SEQ ID NO 551
<211> LENGTH: 60
<212> TYPE: DNA
<213> ORGANISM: Mycoplasma pneumoniae

<400> SEQUENCE: 551
aaacagacac tatgctcacg tagactgtcc aggtcacgct gactacgtta agaacatgat 60

<210> SEQ ID NO 552
<211> LENGTH: 60
<212> TYPE: DNA
<213> ORGANISM: Mycoplasma pneumoniae

<400> SEQUENCE: 552
caagcgtcac tatgctcacg ttgactgtcc aggacacgct gactacatta agaacatgat 60

<210> SEQ ID NO 553
<211> LENGTH: 60
<212> TYPE: DNA
<213> ORGANISM: Legionella pneumophila

<400> SEQUENCE: 553
gagcagacat tatgcgcacg tagactgccc ggggcatgct gactatgtta agaacatgat 60

<210> SEQ ID NO 554
<211> LENGTH: 60
<212> TYPE: DNA
<213> ORGANISM: Legionella pneumophila

<400> SEQUENCE: 554
gagcagacat tatgcgcacg tagactgccc ggggcatgct gactatgtta agaacatgat 60

<210> SEQ ID NO 555
<211> LENGTH: 60
<212> TYPE: DNA
<213> ORGANISM: Legionella pneumophila

<400> SEQUENCE: 555
gagcagacat tatgcacacg tagactgccc gggacatgct gactatgtta agaacatgat 60

<210> SEQ ID NO 556
<211> LENGTH: 60
<212> TYPE: DNA
<213> ORGANISM: Legionella pneumophila

<400> SEQUENCE: 556
gagcagacat tatgcacacg tagactgccc gggacatgct gactatgtta agaacatgat 60

<210> SEQ ID NO 557
<211> LENGTH: 60
<212> TYPE: DNA
<213> ORGANISM: Legionella longbeachiae

<400> SEQUENCE: 557
gaacagacac tatgcgcatg ttgattgccc aggacatgct gactatgtga agaacatgat 60

<210> SEQ ID NO 558
<211> LENGTH: 60
<212> TYPE: DNA
<213> ORGANISM: Fusobacterium nucleatum

<400> SEQUENCE: 558
aaatagacac tatgctcacg ttgactgtcc agggcatgct gactatgtta aaaatatgat 60

<210> SEQ ID NO 559
<211> LENGTH: 60
<212> TYPE: DNA
<213> ORGANISM: Chlamydophila pneumoniae

<400> SEQUENCE: 559
aaatcgtcac tacgctcacg tagactgccc tggtcacgct gactatgtta aaaatatgat 60

<210> SEQ ID NO 560
<211> LENGTH: 60
<212> TYPE: DNA
<213> ORGANISM: Enterococcus faecalis

<400> SEQUENCE: 560
aactcgtcac tatgcacacg ttgactgccc aggacacgcg gactacgtta aaaacatgat 60

<210> SEQ ID NO 561
<211> LENGTH: 60
<212> TYPE: DNA
<213> ORGANISM: Enterococcus faecalis

<400> SEQUENCE: 561
aactcgtcac tatgcacacg ttgactgccc aggacatgcg gactacgtta aaaacatgat 60

<210> SEQ ID NO 562
<211> LENGTH: 60
<212> TYPE: DNA
<213> ORGANISM: Staphylococcus aureus

<400> SEQUENCE: 562
caaacgtcac tacgctcacg ttgactgccc aggacacgct gactacgtta aaaacatgat 60

<210> SEQ ID NO 563
<211> LENGTH: 60
<212> TYPE: DNA
<213> ORGANISM: Staphylococcus aureus

<400> SEQUENCE: 563
caaacgtcac tacgctcacg ttgactgccc aggacacgct gactacgtta aaaacatgat 60

<210> SEQ ID NO 564
<211> LENGTH: 60
<212> TYPE: DNA
<213> ORGANISM: Staphylococcus aureus

<400> SEQUENCE: 564
caaacgtcac tacgctcacg ttgactgccc aggacacgct gactacgtta aaaacatgat 60

<210> SEQ ID NO 565
<211> LENGTH: 60
<212> TYPE: DNA
<213> ORGANISM: Staphylococcus aureus

<400> SEQUENCE: 565
caaacgtcac tacgctcacg ttgactgccc aggacacgct gactacgtta aaaacatgat 60

<210> SEQ ID NO 566
<211> LENGTH: 60
<212> TYPE: DNA
<213> ORGANISM: Staphylococcus aureus

<400> SEQUENCE: 566
caaacgtcac tacgctcacg ttgactgccc aggacacgct gactatgtta aaaacatgat 60

<210> SEQ ID NO 567
<211> LENGTH: 60
<212> TYPE: DNA
<213> ORGANISM: Staphylococcus epidermidis

<400> SEQUENCE: 567
caaacgtcac tatgctcacg ttgactgccc aggacacgct gactatgtta aaaacatgat 60

<210> SEQ ID NO 568
<211> LENGTH: 60
<212> TYPE: DNA
<213> ORGANISM: Staphylococcus epidermidis

<400> SEQUENCE: 568
caaacgtcac tatgctcacg ttgactgccc aggacacgct gactatgtta aaaacatgat 60

<210> SEQ ID NO 569
<211> LENGTH: 60
<212> TYPE: DNA
<213> ORGANISM: Streptococcus mitis

<400> SEQUENCE: 569
aaaacgtcac tacgctcaca tcgacgctcc aggacacgcg gactacgtta aaaacatgat 60

<210> SEQ ID NO 570
<211> LENGTH: 60
<212> TYPE: DNA
<213> ORGANISM: Streptococcus sanguis

<400> SEQUENCE: 570
taagcgtcac tacgctcaca tcgacgctcc aggacacgcg gactacgtta aaaacatgat 60

<210> SEQ ID NO 571
<211> LENGTH: 60
<212> TYPE: DNA
<213> ORGANISM: Streptococcus mitis

<400> SEQUENCE: 571
aaaacgtcac tacgctcaca tcgacgctcc aggacacgcg gactatgtta aaaacatgat 60

<210> SEQ ID NO 572
<211> LENGTH: 60
<212> TYPE: DNA
<213> ORGANISM: Streptococcus pneumoniae

<400> SEQUENCE: 572
aaaacgtcac tacgctcaca tcgacgctcc aggacacgcg gactacgtta aaaacatgat 60

<210> SEQ ID NO 573
<211> LENGTH: 60
<212> TYPE: DNA
<213> ORGANISM: Streptococcus pyogenes

<400> SEQUENCE: 573
aactcgtcac tatgcgcaca tcgacgctcc aggacacgcg gactacgtta aaaacatgat 60

<210> SEQ ID NO 574
<211> LENGTH: 60
<212> TYPE: DNA
<213> ORGANISM: Streptococcus mutans

<400> SEQUENCE: 574
aaaacgtcac tatgctcaca ttgacgctcc aggacacgcg gactatgtta aaaacatgat 60

<210> SEQ ID NO 575
<211> LENGTH: 60
<212> TYPE: DNA
<213> ORGANISM: Streptococcus mutans

<400> SEQUENCE: 575
aaaacgtcac tatgctcaca ttgatgctcc aggacacgcg gactatgtta aaaacatgat 60

<210> SEQ ID NO 576
<211> LENGTH: 60
<212> TYPE: DNA
<213> ORGANISM: Haemophilus influenzae

<400> SEQUENCE: 576
gactcgccac tacgcacacg tagactgtcc gggacacgcc gactatgtta aaaatatgat 60

<210> SEQ ID NO 577
<211> LENGTH: 60
<212> TYPE: DNA
<213> ORGANISM: Moraxella catarrhalis

<400> SEQUENCE: 577
agctcgtcac tacgcacatg tagactgccc aggccacgct gactatgtta aaaacatgat 60

<210> SEQ ID NO 578
<211> LENGTH: 60
<212> TYPE: DNA
<213> ORGANISM: Bordetella pertussis

<400> SEQUENCE: 578
gacgcgtcac tacgcgcacg ttgattgccc gggtcacgct gactacgtga agaacatgat 60

<210> SEQ ID NO 579
<211> LENGTH: 60
<212> TYPE: DNA
<213> ORGANISM: Bordetella parapertussis

<400> SEQUENCE: 579
gacgcgtcac tacgcgcacg ttgattgccc gggtcacgct gactacgtga agaacatgat 60

<210> SEQ ID NO 580
<211> LENGTH: 60
<212> TYPE: DNA
<213> ORGANISM: Burkholderia cepacia

<400> SEQUENCE: 580
gaaccgccac tacgcgcacg tcgactgccc gggccacgcc gactacgtga agaacatgat 60

<210> SEQ ID NO 581
<211> LENGTH: 60
<212> TYPE: DNA
<213> ORGANISM: Burkholderia pseudomallei

<400> SEQUENCE: 581
gaaccgccac tacgcacacg tggactgccc gggccacgcc gactacgtga agaacatgat 60

<210> SEQ ID NO 582
<211> LENGTH: 60
<212> TYPE: DNA
<213> ORGANISM: Stenotrophomonas maltophilia

<400> SEQUENCE: 582
gatccgtcac tacgcccacg ttgactgccc gggccacgct gactacgtca agaacatgat 60

<210> SEQ ID NO 583
<211> LENGTH: 60
<212> TYPE: DNA
<213> ORGANISM: Pseudomonas aeruginosa

<400> SEQUENCE: 583
tgttcgtcac tacgcccacg ttgactgccc cggtcacgcc gactacgtga agaacatgat 60

<210> SEQ ID NO 584
<211> LENGTH: 60
<212> TYPE: DNA
<213> ORGANISM: Klebsiella pneumoniae

<400> SEQUENCE: 584
gactcgccac tacgcgcacg tagactgccc gggccacgcc gactatgtta aaaacatgat 60

<210> SEQ ID NO 585
<211> LENGTH: 60
<212> TYPE: DNA
<213> ORGANISM: Mycobacterium avium

<400> SEQUENCE: 585
caagcggcac tacgctcacg tcgacgcccc gggtcacgcc gactacatca agaacatgat 60

<210> SEQ ID NO 586
<211> LENGTH: 60
<212> TYPE: DNA
<213> ORGANISM: Mycobacterium avium

<400> SEQUENCE: 586
caagcggcac tacgctcacg tcgacgcccc gggtcacgcc gactacatca agaacatgat 60

<210> SEQ ID NO 587
<211> LENGTH: 60
<212> TYPE: DNA
<213> ORGANISM: Mycobacterium intracellulare

<400> SEQUENCE: 587
caagcggcac tatgcccacg tcgacgcccc gggtcacgcc gactacatca agaacatgat 60

<210> SEQ ID NO 588
<211> LENGTH: 60
<212> TYPE: DNA
<213> ORGANISM: Mycobacterium kansasii

<400> SEQUENCE: 588
gaagcggcac tatgcacacg tcgacgcgcc gggccacgcc gactacatca agaacatgat 60

<210> SEQ ID NO 589
<211> LENGTH: 60
<212> TYPE: DNA
<213> ORGANISM: Mycobacterium tuberculosis

<400> SEQUENCE: 589
caagcggcac tacgcacacg tcgacgcccc tggccacgcc gactacatca agaacatgat 60

<210> SEQ ID NO 590
<211> LENGTH: 60
<212> TYPE: DNA
<213> ORGANISM: Mycobacterium tuberculosis

<400> SEQUENCE: 590
caagcggcac tacgcacacg tcgacgcccc tggccacgcc gactacatca agaacatgat 60

<210> SEQ ID NO 591
<211> LENGTH: 60
<212> TYPE: DNA
<213> ORGANISM: Mycobacterium avium

<400> SEQUENCE: 591
gaagcgccac tacgcacacg tggacgcccc cggccacgcg gactacatca agaacatgat 60

<210> SEQ ID NO 592
<211> LENGTH: 60
<212> TYPE: DNA
<213> ORGANISM: Corynebacterium diphtheriae

<400> SEQUENCE: 592
gaagcgccac tacgcacacg ttgacgctcc aggtcacgct gactacatca agaacatgat 60

<210> SEQ ID NO 593
<211> LENGTH: 60
<212> TYPE: DNA
<213> ORGANISM: Neisseria meningitidis

<400> SEQUENCE: 593
aacccgccac tacgcacacg tagactgccc ggggcacgcc gactacgtta aaaacatgat 60

<210> SEQ ID NO 594
<211> LENGTH: 60
<212> TYPE: DNA
<213> ORGANISM: Neisseria meningitidis

<400> SEQUENCE: 594
aacccgccac tacgcacacg tagactgtcc ggggcacgcc gactacgtta aaaacatgat 60

<210> SEQ ID NO 595
<211> LENGTH: 60
<212> TYPE: DNA
<213> ORGANISM: Neisseria meningitidis

<400> SEQUENCE: 595
aacccgccac tacgcacacg tagactgccc ggggcacgcc gactacgtta aaaacatgat 60

<210> SEQ ID NO 596
<211> LENGTH: 60
<212> TYPE: DNA
<213> ORGANISM: Mycoplasma pneumoniae

<400> SEQUENCE: 596
tactggtgct gctcaaatgg atggtgcaat cttagtagtt gctgcatctg atggaccaat 60

<210> SEQ ID NO 597
<211> LENGTH: 60
<212> TYPE: DNA
<213> ORGANISM: Mycoplasma pneumoniae

<400> SEQUENCE: 597
tactggtgct gcacaaatgg atggtgccat tctagtagtt tcagcaactg acagtgttat 60

<210> SEQ ID NO 598
<211> LENGTH: 60
<212> TYPE: DNA
<213> ORGANISM: Legionella pneumophila

<400> SEQUENCE: 598
tactggtgct gcgcaaatgg acggagcgat actggttgta tcagcagctg atggtcctat 60

<210> SEQ ID NO 599
<211> LENGTH: 60
<212> TYPE: DNA
<213> ORGANISM: Legionella pneumophila

<400> SEQUENCE: 599
tactggtgct gcgcaaatgg acggagcgat actggttgta tcagcagctg atggtcctat 60

<210> SEQ ID NO 600
<211> LENGTH: 60
<212> TYPE: DNA
<213> ORGANISM: Legionella pneumophila

<400> SEQUENCE: 600
tactggtgct gcgcaaatgg acggagcgat actggttgta tcagcagctg atggtcctat 60

<210> SEQ ID NO 601
<211> LENGTH: 60
<212> TYPE: DNA
<213> ORGANISM: Legionella pneumophila

<400> SEQUENCE: 601
tactggtgct gcgcaaatgg acggagcgat actggttgta tcagcagctg atggtcctat 60

<210> SEQ ID NO 602
<211> LENGTH: 60
<212> TYPE: DNA
<213> ORGANISM: Legionella longbeachiae

<400> SEQUENCE: 602
tacaggtgct gcacaaatgg acggagcgat acttgtagta tctgcagcag atggtcctat 60

<210> SEQ ID NO 603
<211> LENGTH: 60
<212> TYPE: DNA
<213> ORGANISM: Fusobacterium nucleatum

<400> SEQUENCE: 603
aactggtgct gcacaaatgg atggagctat acttgttgta tcagctgctg atggtcctat 60

<210> SEQ ID NO 604
<211> LENGTH: 60
<212> TYPE: DNA
<213> ORGANISM: Chlamydophila pneumoniae

<400> SEQUENCE: 604
tacaggcgcc gctcaaatgg acggagctat cctagtcgtt tcagctacag acggagctat 60

<210> SEQ ID NO 605
<211> LENGTH: 60
<212> TYPE: DNA
<213> ORGANISM: Enterococcus faecalis

<400> SEQUENCE: 605
cactggtgct gctcaaatgg acggagctat cttagtagtt tctgctgctg atggtcctat 60

<210> SEQ ID NO 606
<211> LENGTH: 60
<212> TYPE: DNA
<213> ORGANISM: Enterococcus faecalis

<400> SEQUENCE: 606
cactggtgct gctcaaatgg acggagctat cttagtagtt tctgctgctg atggtcctat 60

<210> SEQ ID NO 607
<211> LENGTH: 60
<212> TYPE: DNA
<213> ORGANISM: Staphylococcus aureus

<400> SEQUENCE: 607
cactggtgct gctcaaatgg acggcggtat cttagtagta tctgctgctg acggtccaat 60

<210> SEQ ID NO 608
<211> LENGTH: 60
<212> TYPE: DNA
<213> ORGANISM: Staphylococcus aureus

<400> SEQUENCE: 608
cactggtgct gctcaaatgg acggcggtat cttagtagta tctgctgctg acggtccaat 60

<210> SEQ ID NO 609
<211> LENGTH: 60
<212> TYPE: DNA
<213> ORGANISM: Staphylococcus aureus

<400> SEQUENCE: 609
cactggtgct gctcaaatgg acggcggtat cttagtagta tctgctgctg acggtccaat 60

<210> SEQ ID NO 610
<211> LENGTH: 60
<212> TYPE: DNA
<213> ORGANISM: Staphylococcus aureus

<400> SEQUENCE: 610
cactggtgct gctcaaatgg acggcggtat cttagtagta tctgctgctg acggtccaat 60

<210> SEQ ID NO 611
<211> LENGTH: 60
<212> TYPE: DNA
<213> ORGANISM: Staphylococcus aureus

<400> SEQUENCE: 611
cactggtgct gctcaaatgg acggtggtat cttagtagta tctgctgctg acggtccaat 60

<210> SEQ ID NO 612
<211> LENGTH: 60
<212> TYPE: DNA
<213> ORGANISM: Staphylococcus epidermidis

<400> SEQUENCE: 612
cactggtgca gctcaaatgg acggcggtat cttagttgta tctgctgctg acggtccaat 60

<210> SEQ ID NO 613
<211> LENGTH: 60
<212> TYPE: DNA
<213> ORGANISM: Staphylococcus epidermidis

<400> SEQUENCE: 613
cactggtgca gctcaaatgg acggcggtat cttagttgta tctgctgctg acggtccaat 60

<210> SEQ ID NO 614
<211> LENGTH: 60
<212> TYPE: DNA
<213> ORGANISM: Streptococcus mitis

<400> SEQUENCE: 614
cactggtgcc gctcaaatgg acggagctat ccttgtagta gcttcaactg acggaccaat 60

<210> SEQ ID NO 615
<211> LENGTH: 60
<212> TYPE: DNA
<213> ORGANISM: Streptococcus sanguis

<400> SEQUENCE: 615
cactggtgcc gctcaaatgg acggagctat ccttgtagta gcttcaactg acggaccaat 60

<210> SEQ ID NO 616
<211> LENGTH: 60
<212> TYPE: DNA
<213> ORGANISM: Streptococcus mitis

<400> SEQUENCE: 616
cactggtgcc gctcaaatgg acggagctat ccttgtagta gcttcaactg acggaccaat 60

<210> SEQ ID NO 617
<211> LENGTH: 60
<212> TYPE: DNA
<213> ORGANISM: Streptococcus pneumoniae

<400> SEQUENCE: 617
cactggtgct gctcaaatgg acggagctat ccttgtagta gcttcaactg acggaccaat 60

<210> SEQ ID NO 618
<211> LENGTH: 60
<212> TYPE: DNA
<213> ORGANISM: Streptococcus pyogenes

<400> SEQUENCE: 618
cactggtgcc gctcaaatgg acggagctat ccttgtagtt gcttcaactg atggaccaat 60

<210> SEQ ID NO 619
<211> LENGTH: 60
<212> TYPE: DNA
<213> ORGANISM: Streptococcus mutans

<400> SEQUENCE: 619
tactggtgct gcccaaatgg atggtgctat ccttgtagta gcttcaactg atggtccaat 60

<210> SEQ ID NO 620
<211> LENGTH: 60
<212> TYPE: DNA
<213> ORGANISM: Streptococcus mutans

<400> SEQUENCE: 620
cactggtgct gcccaaatgg atggtgctat ccttgtagta gcttcaactg atggaccaat 60

<210> SEQ ID NO 621
<211> LENGTH: 60
<212> TYPE: DNA
<213> ORGANISM: Haemophilus influenza

<400> SEQUENCE: 621
tactggtgcg gcacaaatgg atggtgctat tttagtagta gcagcaacag atggtcctat 60

<210> SEQ ID NO 622
<211> LENGTH: 60
<212> TYPE: DNA
<213> ORGANISM: Moraxella catarrhalis

<400> SEQUENCE: 622
cacaggtgct gcacagatgg acggcgcaat cttggttgtt tctgcaactg acggcccaat 60

<210> SEQ ID NO 623
<211> LENGTH: 60
<212> TYPE: DNA
<213> ORGANISM: Bordetella pertussis

<400> SEQUENCE: 623
cacgggtgct gcgcagatgg acggcgcgat cctggtggtg tcggccgcag acggcccgat 60

<210> SEQ ID NO 624
<211> LENGTH: 60
<212> TYPE: DNA
<213> ORGANISM: Bordetella parapertussis

<400> SEQUENCE: 624
cacgggtgct gcgcagatgg acggcgcgat cctggtggtg tcggccgcag acggcccgat 60

<210> SEQ ID NO 625
<211> LENGTH: 60
<212> TYPE: DNA
<213> ORGANISM: Burkholderia cepacia

<400> SEQUENCE: 625
cacgggtgca gcgcagatgg acggcgcaat cctggtgtgc tcggccgcag acggcccgat 60

<210> SEQ ID NO 626
<211> LENGTH: 60
<212> TYPE: DNA
<213> ORGANISM: Burkholderia pseudomallei

<400> SEQUENCE: 626
cacgggcgcg gcgcagatgg acggcgcgat cctggtgtgc tcggccgctg acggcccgat 60

<210> SEQ ID NO 627
<211> LENGTH: 60
<212> TYPE: DNA
<213> ORGANISM: Stenotrophomonas maltophilia

<400> SEQUENCE: 627
caccggtgcc gcccagatgg acggcgcgat cctggtgtgc tcggccgctg acggcccgat 60

<210> SEQ ID NO 628
<211> LENGTH: 60
<212> TYPE: DNA
<213> ORGANISM: Pseudomonas aeruginosa

<400> SEQUENCE: 628
caccggtgct gcccagatgg acggcgcgat cctggtttgc tcggctgccg acggccccat 60

<210> SEQ ID NO 629
<211> LENGTH: 60
<212> TYPE: DNA
<213> ORGANISM: Klebsiella pneumoniae

<400> SEQUENCE: 629
caccggtgct gcgcagatgg acggcgcgat cctggttgtt gctgcgactg acggcccgat 60

<210> SEQ ID NO 630
<211> LENGTH: 60
<212> TYPE: DNA
<213> ORGANISM: Mycobacterium avium

<400> SEQUENCE: 630
caccggcgcc gcccagatgg acggcgcgat cctggtggtc gccgccaccg acggcccgat 60

<210> SEQ ID NO 631
<211> LENGTH: 60
<212> TYPE: DNA
<213> ORGANISM: Mycobacterium avium

<400> SEQUENCE: 631
caccggcgcc gcccagatgg acggcgcgat cctggtggtc gccgccaccg acggcccgat 60

<210> SEQ ID NO 632
<211> LENGTH: 60
<212> TYPE: DNA
<213> ORGANISM: Mycobacterium intracellulare

<400> SEQUENCE: 632
caccggtgcg gcccagatgg acggcgcgat cctggtggtt gccgccaccg acggcccgat 60

<210> SEQ ID NO 633
<211> LENGTH: 60
<212> TYPE: DNA
<213> ORGANISM: Mycobacterium kansasii

<400> SEQUENCE: 633
caccggcgcc gcccagatgg acggcgcgat cctggtggtc gccgccacgg acggcccgat 60

<210> SEQ ID NO 634
<211> LENGTH: 60
<212> TYPE: DNA
<213> ORGANISM: Mycobacterium tuberculosis

<400> SEQUENCE: 634
caccggcgcc gcgcagatgg acggtgcgat cctggtggtc gccgccaccg acggcccgat 60

<210> SEQ ID NO 635
<211> LENGTH: 60
<212> TYPE: DNA
<213> ORGANISM: Mycobacterium tuberculosis

<400> SEQUENCE: 635
caccggcgcc gcgcagatgg acggtgcgat cctggtggtc gccgccaccg acggcccgat 60

<210> SEQ ID NO 636
<211> LENGTH: 60
<212> TYPE: DNA
<213> ORGANISM: Mycobacterium avium

<400> SEQUENCE: 636
caccggtgcc gcccagatgg acggcgcgat cctggtggtc gccgcgaccg acggcccgat 60

<210> SEQ ID NO 637
<211> LENGTH: 60
<212> TYPE: DNA
<213> ORGANISM: Corynebacterium diphtheriae

<400> SEQUENCE: 637
caccggtgct gctcagatgg acggcgcaat cctcgttgtt gctgccaccg acggcccaat 60

<210> SEQ ID NO 638
<211> LENGTH: 60
<212> TYPE: DNA
<213> ORGANISM: Neisseria meningitidis

<400> SEQUENCE: 638
taccggcgcc gcacaaatgg acggtgcaat cctggtatgt tccgcagccg acggccctat 60

<210> SEQ ID NO 639
<211> LENGTH: 60
<212> TYPE: DNA
<213> ORGANISM: Neisseria meningitidis

<400> SEQUENCE: 639
taccggcgca gcacaaatgg acggtgcaat cctggtatgt tccgcagccg acggccctat 60

<210> SEQ ID NO 640
<211> LENGTH: 60
<212> TYPE: DNA
<213> ORGANISM: Neisseria meningitidis

<400> SEQUENCE: 640
taccggtgcc gcacaaatgg acggtgcaat cctggtatgt tccgcagccg acggccctat 60

<210> SEQ ID NO 641
<211> LENGTH: 60
<212> TYPE: DNA
<213> ORGANISM: Mycoplasma pneumoniae

<400> SEQUENCE: 641
gccacaaaca agagaacaca tcttattagc tagacaagtt ggtgttccta aaatggtagt 60

<210> SEQ ID NO 642
<211> LENGTH: 60
<212> TYPE: DNA
<213> ORGANISM: Mycoplasma pneumoniae

<400> SEQUENCE: 642
gccccaaacc cgtgaacaca ttttgttggc ccgccaagtg ggtgtgccac gcatggtagt 60

<210> SEQ ID NO 643
<211> LENGTH: 60
<212> TYPE: DNA
<213> ORGANISM: Legionella pneumophila

<400> SEQUENCE: 643
gccacaaacg agggaacaca ttctattgtc tcgccaggta ggtgttccat atattgttgt 60

<210> SEQ ID NO 644
<211> LENGTH: 60
<212> TYPE: DNA
<213> ORGANISM: Legionella pneumophila

<400> SEQUENCE: 644
gccacaaacg agggaacaca ttctattgtc tcgccaggta ggtgttccat atattgttgt 60

<210> SEQ ID NO 645
<211> LENGTH: 60
<212> TYPE: DNA
<213> ORGANISM: Legionella pneumophila

<400> SEQUENCE: 645
gccacaaacg agggaacaca ttctattgtc tcgccaggta ggtgttccat atattgttgt 60

<210> SEQ ID NO 646
<211> LENGTH: 60
<212> TYPE: DNA
<213> ORGANISM: Legionella pneumophila

<400> SEQUENCE: 646
gccacaaacg agggaacaca ttctattgtc tcgccaggta ggtgttccat atattgttgt 60

<210> SEQ ID NO 647
<211> LENGTH: 60
<212> TYPE: DNA
<213> ORGANISM: Legionella longbeachiae

<400> SEQUENCE: 647
gcctcaaact agagaacata ttctattgtc acgacaagta ggggtgccct acatagtagt 60

<210> SEQ ID NO 648
<211> LENGTH: 60
<212> TYPE: DNA
<213> ORGANISM: Fusobacterium nucleatum

<400> SEQUENCE: 648
gcctcaaaca agagaacata tcttactttc tagacaagtt ggagtaccat atattattgt 60

<210> SEQ ID NO 649
<211> LENGTH: 60
<212> TYPE: DNA
<213> ORGANISM: Chlamydophila pneumoniae

<400> SEQUENCE: 649
gccacaaact aaagaacata tcttgctagc tcgccaggtt ggagttcctt atatcgttgt 60

<210> SEQ ID NO 650
<211> LENGTH: 60
<212> TYPE: DNA
<213> ORGANISM: Enterococcus faecalis

<400> SEQUENCE: 650
gcctcaaaca cgtgaacata tcttattatc acgtaacgtt ggtgtaccat acatcgttgt 60

<210> SEQ ID NO 651
<211> LENGTH: 60
<212> TYPE: DNA
<213> ORGANISM: Enterococcus faecalis

<400> SEQUENCE: 651
gcctcaaaca cgtgaacata tcttattatc acgtaacgtt ggtgtaccat acatcgttgt 60

<210> SEQ ID NO 652
<211> LENGTH: 60
<212> TYPE: DNA
<213> ORGANISM: Staphylococcus aureus

<400> SEQUENCE: 652
gccacaaact cgtgaacaca ttcttttatc acgtaacgtt ggtgtaccag cattagtagt    60

<210> SEQ ID NO 653
<211> LENGTH: 60
<212> TYPE: DNA
<213> ORGANISM: Staphylococcus aureus

<400> SEQUENCE: 653
gccacaaact cgtgaacaca ttcttttatc acgtaacgtt ggtgtaccag cattagtagt    60

<210> SEQ ID NO 654
<211> LENGTH: 60
<212> TYPE: DNA
<213> ORGANISM: Staphylococcus aureus

<400> SEQUENCE: 654
gccacaaact cgtgaacaca ttcttttatc acgtaacgtt ggtgtaccag cattagtagt    60

<210> SEQ ID NO 655
<211> LENGTH: 60
<212> TYPE: DNA
<213> ORGANISM: Staphylococcus aureus

<400> SEQUENCE: 655
gccacaaact cgtgaacaca ttcttttatc acgtaacgtt ggtgtaccag cattagtagt    60

<210> SEQ ID NO 656
<211> LENGTH: 60
<212> TYPE: DNA
<213> ORGANISM: Staphylococcus aureus

<400> SEQUENCE: 656
gccacaaact cgtgaacaca ttcttttatc acgtaacgtt ggtgtaccag cattagtagt    60

<210> SEQ ID NO 657
<211> LENGTH: 60
<212> TYPE: DNA
<213> ORGANISM: Staphylococcus epidermidis

<400> SEQUENCE: 657
gccacaaact cgtgaacaca tcttattatc acgtaacgtt ggtgtaccag cattagttgt    60

<210> SEQ ID NO 658
<211> LENGTH: 60
<212> TYPE: DNA
<213> ORGANISM: Staphylococcus epidermidis

<400> SEQUENCE: 658
gccacaaact cgtgaacaca tcttattatc acgtaacgtt ggtgtaccag cattagttgt    60

<210> SEQ ID NO 659
<211> LENGTH: 60
<212> TYPE: DNA
<213> ORGANISM: Streptococcus mitis

<400> SEQUENCE: 659
gccacaaact cgtgagcaca tccttctttc acgtcaggtt ggtgttaaac acttgatcgt    60

<210> SEQ ID NO 660
<211> LENGTH: 60
<212> TYPE: DNA
<213> ORGANISM: Streptococcus sanguis

<400> SEQUENCE: 660
gccacaaact cgtgagcaca tcttgctttc acgtcaggtt ggtgttaaac acttgatcgt 60

<210> SEQ ID NO 661
<211> LENGTH: 60
<212> TYPE: DNA
<213> ORGANISM: Streptococcus mitis

<400> SEQUENCE: 661
gccacaaact cgtgagcaca tccttctttc acgtcaggtt ggtgttaaac accttatcgt 60

<210> SEQ ID NO 662
<211> LENGTH: 60
<212> TYPE: DNA
<213> ORGANISM: Streptococcus pneumoniae

<400> SEQUENCE: 662
gccacaaact cgtgagcaca tccttctttc acgtcaggtt ggtgttaaac accttatcgt 60

<210> SEQ ID NO 663
<211> LENGTH: 60
<212> TYPE: DNA
<213> ORGANISM: Streptococcus pyogenes

<400> SEQUENCE: 663
gccacaaact cgtgagcaca tccttctttc acgtcaggtt ggtgttaaac accttatcgt 60

<210> SEQ ID NO 664
<211> LENGTH: 60
<212> TYPE: DNA
<213> ORGANISM: Streptococcus mutans

<400> SEQUENCE: 664
gccacaaact cgtgaacaca ttcttctttc acgtcaagtt ggtgttaaat accttattgt 60

<210> SEQ ID NO 665
<211> LENGTH: 60
<212> TYPE: DNA
<213> ORGANISM: Streptococcus mutans

<400> SEQUENCE: 665
gccacaaact cgtgaacaca ttcttctttc acgtcaagtt ggtgttaaat acctcattgt 60

<210> SEQ ID NO 666
<211> LENGTH: 60
<212> TYPE: DNA
<213> ORGANISM: Haemophilus influenzae

<400> SEQUENCE: 666
gccacaaact cgtgaacaca tcttattagg tcgccaagta ggtgttccat acatcatcgt 60

<210> SEQ ID NO 667
<211> LENGTH: 60
<212> TYPE: DNA
<213> ORGANISM: Moraxella catarrhalis

<400> SEQUENCE: 667
gccacaaact cgtgagcaca tcctactgtc tcgtcaggtt ggtgtaccat atatcatggt 60

<210> SEQ ID NO 668
<211> LENGTH: 60
<212> TYPE: DNA
<213> ORGANISM: Bordetella pertussis

<400> SEQUENCE: 668
gccgcagacg cgcgagcaca ttttgctgtc gcgccaggtt ggcgtgccgt acatcatcgt 60

<210> SEQ ID NO 669
<211> LENGTH: 60
<212> TYPE: DNA
<213> ORGANISM: Bordetella parapertussis

<400> SEQUENCE: 669
gccgcagacg cgcgagcaca ttttgctgtc gcgccaggtt ggcgtgccgt acatcatcgt 60

<210> SEQ ID NO 670
<211> LENGTH: 60
<212> TYPE: DNA
<213> ORGANISM: Burkholderia cepacia

<400> SEQUENCE: 670
gccgcaaacg cgtgagcaca tcctgctggc gcgtcaggtt ggcgttccgt acatcatcgt 60

<210> SEQ ID NO 671
<211> LENGTH: 60
<212> TYPE: DNA
<213> ORGANISM: Burkholderia pseudomallei

<400> SEQUENCE: 671
gccgcaaacg cgtgagcaca tcctgctggc gcgtcaggtc ggtgtgccgt acatcatcgt 60

<210> SEQ ID NO 672
<211> LENGTH: 60
<212> TYPE: DNA
<213> ORGANISM: Stenotrophomonas maltophilia

<400> SEQUENCE: 672
gccgcagacc cgtgagcaca tcctgctgtc gcgccaggtc ggcgtgccgt acatcgtcgt 60

<210> SEQ ID NO 673
<211> LENGTH: 60
<212> TYPE: DNA
<213> ORGANISM: Pseudomonas aeruginosa

<400> SEQUENCE: 673
gccgcagacc cgcgagcaca tcctgctgtc ccgccaggta ggcgttccct acatcgtcgt 60

<210> SEQ ID NO 674
<211> LENGTH: 60
<212> TYPE: DNA
<213> ORGANISM: Klebsiella pneumoniae

<400> SEQUENCE: 674
gccgcagact cgtgagcaca tcctgctggg tcgtcaggta ggcgttccgt acatcatcgt 60

<210> SEQ ID NO 675
<211> LENGTH: 60
<212> TYPE: DNA
<213> ORGANISM: Mycobacterium avium

<400> SEQUENCE: 675
gccgcagacc cgcgagcacg tgctgctggc ccgtcaggtc ggtgtgccct acatcctggt 60

<210> SEQ ID NO 676
<211> LENGTH: 60
<212> TYPE: DNA
<213> ORGANISM: Mycobacterium avium

<400> SEQUENCE: 676
gccgcagacc cgcgagcacg tgctgctggc ccgtcaggtc ggtgtgccct acatcctggt 60

<210> SEQ ID NO 677
<211> LENGTH: 60
<212> TYPE: DNA
<213> ORGANISM: Mycobacterium intracellulare

<400> SEQUENCE: 677
gccgcagacc cgtgagcacg tgctgctcgc gcgtcaggtc ggggtgccct acatcctggt 60

<210> SEQ ID NO 678
<211> LENGTH: 60
<212> TYPE: DNA
<213> ORGANISM: Mycobacterium kansasii

<400> SEQUENCE: 678
gccgcagacc cgtgagcacg tgctgctcgc acgtcaggtg ggtgtgccct acatcctggt 60

<210> SEQ ID NO 679
<211> LENGTH: 60
<212> TYPE: DNA
<213> ORGANISM: Mycobacterium tuberculosis

<400> SEQUENCE: 679
gccccagacc cgcgagcacg ttctgctggc gcgtcaagtg ggtgtgccct acatcctggt 60

<210> SEQ ID NO 680
<211> LENGTH: 60
<212> TYPE: DNA
<213> ORGANISM: Mycobacterium tuberculosis

<400> SEQUENCE: 680
gccccagacc cgcgagcacg ttctgctggc gcgtcaagtg ggtgtgccct acatcctggt 60

<210> SEQ ID NO 681
<211> LENGTH: 60
<212> TYPE: DNA
<213> ORGANISM: Mycobacterium avium

<400> SEQUENCE: 681
gccgcagacc cgcgagcacg tgctgctcgg ccgtcaggtg ggtgtgccct acatcctcgt 60

<210> SEQ ID NO 682
<211> LENGTH: 60
<212> TYPE: DNA
<213> ORGANISM: Corynebacterium diphtheriae

<400> SEQUENCE: 682
gcctcagacc cgtgagcacg ttctgctcgc tcgccaggtc ggcgttcctt acatcctcgt 60

<210> SEQ ID NO 683
<211> LENGTH: 60
<212> TYPE: DNA
<213> ORGANISM: Neisseria meningitidis

<400> SEQUENCE: 683
gccgcaaacc cgcgaacaca tcctgctggc ccgccaagta ggcgtacctt acatcatcgt 60

<210> SEQ ID NO 684
<211> LENGTH: 60
<212> TYPE: DNA
<213> ORGANISM: Neisseria meningitidis

<400> SEQUENCE: 684
gccgcaaacc cgcgaacaca tcctgctggc ccgtcaagta ggcgtacctt acatcatcgt 60

<210> SEQ ID NO 685
<211> LENGTH: 60
<212> TYPE: DNA
<213> ORGANISM: Neisseria meningitidis

<400> SEQUENCE: 685
gccgcaaacc cgcgaacaca tcctgctggc ccgtcaagta ggcgtacctt acatcatcgt 60

<210> SEQ ID NO 686
<211> LENGTH: 54
<212> TYPE: DNA
<213> ORGANISM: Mycoplasma pneumoniae

<400> SEQUENCE: 686
tttcttaaac aaatgtgata tggtatctga tgctgaaatg caagacctag taga 54

<210> SEQ ID NO 687
<211> LENGTH: 54
<212> TYPE: DNA
<213> ORGANISM: Mycoplasma pneumoniae

<400> SEQUENCE: 687
gttcctaaac aagtgtgaca ttgcaactga tgaagaagtg caagagttag tagc 54

<210> SEQ ID NO 688
<211> LENGTH: 54
<212> TYPE: DNA
<213> ORGANISM: Legionella pneumophila

<400> SEQUENCE: 688
gttcatgaac aaagcggata tggttgatga ccctgagtta ttagagttag tgga 54

<210> SEQ ID NO 689
<211> LENGTH: 54
<212> TYPE: DNA
<213> ORGANISM: Legionella pneumophila

<400> SEQUENCE: 689
gttcatgaac aaagcggata tggttgatga ccctgagtta ttagagttag tgga 54

<210> SEQ ID NO 690
<211> LENGTH: 54
<212> TYPE: DNA
<213> ORGANISM: Legionella pneumophila

<400> SEQUENCE: 690
gttcatgaac aaagcggata tggttgatga ccctgagtta ttagagttag tgga 54

<210> SEQ ID NO 691
<211> LENGTH: 54
<212> TYPE: DNA
<213> ORGANISM: Legionella pneumophila

<400> SEQUENCE: 691
gttcatgaac aaagcggata tggttgatga ccctgagtta ttagagttag tgga 54

<210> SEQ ID NO 692
<211> LENGTH: 54
<212> TYPE: DNA
<213> ORGANISM: Legionella longbeachiae

<400> SEQUENCE: 692
gtttatgaat aaagcggaca tggttgatga tccagagctc ttagagcttg taga 54

<210> SEQ ID NO 693
<211> LENGTH: 54
<212> TYPE: DNA
<213> ORGANISM: Fusobacterium nucleatum

<400> SEQUENCE: 693
ttatttaaat aaatcagata tggttgatga tgaagaatta ctagaattgg taga 54

<210> SEQ ID NO 694
<211> LENGTH: 60
<212> TYPE: DNA
<213> ORGANISM: Chlamydophila pneumoniae

<400> SEQUENCE: 694
tttcttgaat aaagtagata tgatctctca agaagatgct gaacttattg accttgttga 60

<210> SEQ ID NO 695
<211> LENGTH: 54
<212> TYPE: DNA
<213> ORGANISM: Enterococcus faecalis

<400> SEQUENCE: 695
attcttaaac aaaatggata tggttgatga cgaagaatta ttagaattag taga 54

<210> SEQ ID NO 696
<211> LENGTH: 54
<212> TYPE: DNA
<213> ORGANISM: Enterococcus faecalis

<400> SEQUENCE: 696
attcttaaac aaaatggata tggttgatga cgaagaatta ttagaattag taga 54

<210> SEQ ID NO 697
<211> LENGTH: 54
<212> TYPE: DNA
<213> ORGANISM: Staphylococcus aureus

<400> SEQUENCE: 697
attcttaaac aaagttgaca tggttgacga tgaagaatta ttagaattag taga 54

<210> SEQ ID NO 698
<211> LENGTH: 54
<212> TYPE: DNA
<213> ORGANISM: Staphylococcus aureus

<400> SEQUENCE: 698
attcttaaac aaagttgaca tggttgacga tgaagaatta ttagaattag taga 54

<210> SEQ ID NO 699
<211> LENGTH: 54
<212> TYPE: DNA
<213> ORGANISM: Staphylococcus aureus

<400> SEQUENCE: 699
attcttaaac aaagttgaca tggttgacga tgaagaatta ttagaattag taga 54

<210> SEQ ID NO 700
<211> LENGTH: 54
<212> TYPE: DNA
<213> ORGANISM: Staphylococcus aureus

<400> SEQUENCE: 700
attcttaaac aaagttgaca tggttgacga tgaagaatta ttagaattag taga 54

<210> SEQ ID NO 701
<211> LENGTH: 54
<212> TYPE: DNA
<213> ORGANISM: Staphylococcus aureus

<400> SEQUENCE: 701
attcttaaac aaagttgaca tggttgacga tgaagaatta ttagaattag taga 54

<210> SEQ ID NO 702
<211> LENGTH: 54
<212> TYPE: DNA
<213> ORGANISM: Staphylococcus epidermidis

<400> SEQUENCE: 702
attcttaaac aaagttgaca tggtagacga cgaagaatta ttagaattag ttga 54

<210> SEQ ID NO 703
<211> LENGTH: 54
<212> TYPE: DNA
<213> ORGANISM: Staphylococcus epidermidis

<400> SEQUENCE: 703
attcttaaac aaagttgaca tggtagacga cgaagaatta ttagaattag ttga 54

<210> SEQ ID NO 704
<211> LENGTH: 54
<212> TYPE: DNA
<213> ORGANISM: Streptococcus mitis

<400> SEQUENCE: 704
cttcatgaac aaagttgact tggttgacga tgaagaattg cttgaattgg ttga 54

<210> SEQ ID NO 705
<211> LENGTH: 54
<212> TYPE: DNA
<213> ORGANISM: Streptococcus sanguis

<400> SEQUENCE: 705
cttcatgaac aaagttgact tggttgacga tgaagaattg cttgaattgg ttga 54

<210> SEQ ID NO 706
<211> LENGTH: 54
<212> TYPE: DNA
<213> ORGANISM: Streptococcus mitis

<400> SEQUENCE: 706
cttcatgaac aaagttgact tggttgacga cgaagaattg cttgaattgg ttga 54

<210> SEQ ID NO 707
<211> LENGTH: 54
<212> TYPE: DNA
<213> ORGANISM: Streptococcus pneumoniae

<400> SEQUENCE: 707
cttcatgaac aaagttgact tggttgacga cgaagaattg cttgaattgg ttga 54

<210> SEQ ID NO 708
<211> LENGTH: 54
<212> TYPE: DNA
<213> ORGANISM: Streptococcus pyogenes

<400> SEQUENCE: 708
gttcatgaac aaagttgacc ttgttgatga cgaagagttg cttgaattag ttga 54

<210> SEQ ID NO 709
<211> LENGTH: 54
<212> TYPE: DNA
<213> ORGANISM: Streptococcus mutans

<400> SEQUENCE: 709
cttcatgaat aaggttgatt tggttgatga tgaagaactg cttgaattgg ttga 54

<210> SEQ ID NO 710
<211> LENGTH: 54
<212> TYPE: DNA
<213> ORGANISM: Streptococcus mutans

<400> SEQUENCE: 710
cttcatgaat aaagttgatt tggttgacga tgaagaattg cttgaattgg ttga 54

<210> SEQ ID NO 711
<211> LENGTH: 54
<212> TYPE: DNA
<213> ORGANISM: Haemophilus influenzae

<400> SEQUENCE: 711
attcttaaac aaatgcgaca tggtagatga cgaagagtta ttagaattag tcga 54

<210> SEQ ID NO 712
<211> LENGTH: 54
<212> TYPE: DNA
<213> ORGANISM: Moraxella catarrhalis

<400> SEQUENCE: 712
attcatgaac aagtgcgaca tggtagatga tgaagagcta ctagaattgg ttga 54

<210> SEQ ID NO 713
<211> LENGTH: 54
<212> TYPE: DNA
<213> ORGANISM: Bordetella pertussis

<400> SEQUENCE: 713
gttcctgaac aaggcggaca tggttgatga cgcggagctg ctcgagctgg tgga 54

<210> SEQ ID NO 714
<211> LENGTH: 54
<212> TYPE: DNA
<213> ORGANISM: Bordetella parapertussis

<400> SEQUENCE: 714
gttcctgaac aaggcggaca tggttgatga cgcggagctg ctcgagctgg tgga 54

<210> SEQ ID NO 715
<211> LENGTH: 54
<212> TYPE: DNA
<213> ORGANISM: Burkholderia cepacia

<400> SEQUENCE: 715
gttcctgaac aagtgcgaca tggtggacga cgctgaactg ctcgagctgg tcga 54

<210> SEQ ID NO 716
<211> LENGTH: 54
<212> TYPE: DNA
<213> ORGANISM: Burkholderia pseudomallei

<400> SEQUENCE: 716
gttcctgaac aagtgcgata tggtggacga cgcggagctg ctcgagctgg tcga 54

<210> SEQ ID NO 717
<211> LENGTH: 54
<212> TYPE: DNA
<213> ORGANISM: Stenotrophomonas maltophilia

<400> SEQUENCE: 717
gttcctgaac aaggccgaca tggtcgacga cgccgagctg ctcgagctgg tcga 54

<210> SEQ ID NO 718
<211> LENGTH: 54
<212> TYPE: DNA
<213> ORGANISM: Pseudomonas aeruginosa

<400> SEQUENCE: 718
gttcctgaac aaggccgaca tggtcgacga cgccgagctg ctggaactgg tcga 54

<210> SEQ ID NO 719
<211> LENGTH: 54
<212> TYPE: DNA
<213> ORGANISM: Klebsiella pneumoniae

<400> SEQUENCE: 719
gttcctgaac aaatgcgaca tggttgatga cgaagagctg ctggaactgg ttga 54

<210> SEQ ID NO 720
<211> LENGTH: 54
<212> TYPE: DNA
<213> ORGANISM: Mycobacterium avium

<400> SEQUENCE: 720
cgcgctgaac aaggccgaca tggtcgacga cgaggagctg ctcgagctcg tcga 54

<210> SEQ ID NO 721
<211> LENGTH: 54
<212> TYPE: DNA
<213> ORGANISM: Mycobacterium avium

<400> SEQUENCE: 721
cgcgctgaac aaggccgaca tggtcgacga cgaggagctg ctcgagctcg tcga 54

<210> SEQ ID NO 722
<211> LENGTH: 54
<212> TYPE: DNA
<213> ORGANISM: Mycobacterium intracellulare

<400> SEQUENCE: 722
cgccctcaac aaggccgaca tggtcgacga cgaggagctc ctcgagctcg tcga 54

<210> SEQ ID NO 723
<211> LENGTH: 54
<212> TYPE: DNA
<213> ORGANISM: Mycobacterium kansasii

<400> SEQUENCE: 723
cgcgctgaac aaggccgacg ccgtcgacga cgaggagttg ctcgaactcg tcga 54

<210> SEQ ID NO 724
<211> LENGTH: 54
<212> TYPE: DNA
<213> ORGANISM: Mycobacterium tuberculosis

<400> SEQUENCE: 724
agcgctgaac aaggccgacg cagtggacga cgaggagctg ctcgaactcg tcga 54

<210> SEQ ID NO 725
<211> LENGTH: 54
<212> TYPE: DNA
<213> ORGANISM: Mycobacterium tuberculosis

<400> SEQUENCE: 725
agcgctgaac aaggccgacg cagtggacga cgaggagctg ctcgaactcg tcga 54

<210> SEQ ID NO 726
<211> LENGTH: 54
<212> TYPE: DNA
<213> ORGANISM: Mycobacterium avium

<400> SEQUENCE: 726
ggcgctgaac aagtcggaca tggtcgacga cgaggagctc ctcgagctcg tcga 54

<210> SEQ ID NO 727
<211> LENGTH: 54
<212> TYPE: DNA
<213> ORGANISM: Corynebacterium diphtheriae

<400> SEQUENCE: 727
tgctctgaac aagtgcgaca tggttgatga tgaggaaatc atcgagctcg tcga 54

<210> SEQ ID NO 728
<211> LENGTH: 54
<212> TYPE: DNA
<213> ORGANISM: Neisseria meningitidis

<400> SEQUENCE: 728
gttcatgaac aaatgcgaca tggtcgacga tgccgagctg ttggaactgg ttga 54

<210> SEQ ID NO 729
<211> LENGTH: 54
<212> TYPE: DNA
<213> ORGANISM: Neisseria meningitidis

<400> SEQUENCE: 729
gttcatgaac aaatgcgaca tggtcgacga tgccgagctg ttggaactgg ttga 54

<210> SEQ ID NO 730
<211> LENGTH: 54
<212> TYPE: DNA
<213> ORGANISM: Neisseria meningitidis

<400> SEQUENCE: 730
gttcatgaac aaatgcgaca tggtcgacga tgccgagctg ttggaactgg ttga 54

<210> SEQ ID NO 731
<211> LENGTH: 60
<212> TYPE: DNA
<213> ORGANISM: Mycoplasma pneumoniae

<400> SEQUENCE: 731
aatggaagtt agagaattac tttcttctta tggttttgat ggagataaca ctccagttat 60

<210> SEQ ID NO 732
<211> LENGTH: 60
<212> TYPE: DNA
<213> ORGANISM: Mycoplasma pneumoniae

<400> SEQUENCE: 732
agaagaggta cgtgacttat taacttctta cggctttgat ggcaagaaca cccctattat 60

<210> SEQ ID NO 733
<211> LENGTH: 60
<212> TYPE: DNA
<213> ORGANISM: Legionella pneumophila

<400> SEQUENCE: 733
aatggaagtg cgagatttat taagcagtta cgatttccca ggggatgaca tacctattgt 60

<210> SEQ ID NO 734
<211> LENGTH: 60
<212> TYPE: DNA
<213> ORGANISM: Legionella pneumophila

<400> SEQUENCE: 734
aatggaagtg cgagatttat taagcagtta cgatttccca ggggatgaca tacccattgt 60

<210> SEQ ID NO 735
<211> LENGTH: 60
<212> TYPE: DNA
<213> ORGANISM: Legionella pneumophila

<400> SEQUENCE: 735
aatggaagtg cgagatttat taagcagtta cgatttccca ggggatgaca tacctattgt 60

<210> SEQ ID NO 736
<211> LENGTH: 60
<212> TYPE: DNA
<213> ORGANISM: Legionella pneumophila

<400> SEQUENCE: 736
aatggaagtg cgagatttat taagcagtta cgatttccca ggggatgata tacctattat 60

<210> SEQ ID NO 737
<211> LENGTH: 60
<212> TYPE: DNA
<213> ORGANISM: Legionella longbeachiae

<400> SEQUENCE: 737
aatggaagtc cgtgatttgt tgagcagtta tgattttcct ggtgatgata ttccaattgt 60

<210> SEQ ID NO 738
<211> LENGTH: 60
<212> TYPE: DNA
<213> ORGANISM: Fusobacterium nucleatum

<400> SEQUENCE: 738
aatggaagtt agagaattat taactgaata tggattccca ggagatgaca tccctgtaat 60

<210> SEQ ID NO 739
<211> LENGTH: 54
<212> TYPE: DNA
<213> ORGANISM: Chlamydophila pneumoniae

<400> SEQUENCE: 739
gatggaactt agtgagcttc ttgaagaaaa aggctacaaa ggatgcccta ttat 54

<210> SEQ ID NO 740
<211> LENGTH: 60
<212> TYPE: DNA
<213> ORGANISM: Enterococcus faecalis

<400> SEQUENCE: 740
aatggaagtt cgtgacttat tatcagaata cgatttccca ggcgatgatg ttccagttat 60

<210> SEQ ID NO 741
<211> LENGTH: 60
<212> TYPE: DNA
<213> ORGANISM: Enterococcus faecalis

<400> SEQUENCE: 741
aatggaagtt cgtgacttat tatcagaata cgatttccca ggcgatgatg ttccagttat 60

<210> SEQ ID NO 742
<211> LENGTH: 60
<212> TYPE: DNA
<213> ORGANISM: Staphylococcus aureus

<400> SEQUENCE: 742
aatggaagtt cgtgacttat taagcgaata tgacttccca ggtgacgatg tacctgtaat 60

<210> SEQ ID NO 743
<211> LENGTH: 60
<212> TYPE: DNA
<213> ORGANISM: Staphylococcus aureus

<400> SEQUENCE: 743
aatggaagtt cgtgacttat taagcgaata tgacttccca ggtgacgatg tacctgtaat 60

<210> SEQ ID NO 744
<211> LENGTH: 60
<212> TYPE: DNA
<213> ORGANISM: Staphylococcus aureus

<400> SEQUENCE: 744
aatggaagtt cgtgacttat taagcgaata tgacttccca ggtgacgatg tacctgtaat 60

<210> SEQ ID NO 745
<211> LENGTH: 60
<212> TYPE: DNA
<213> ORGANISM: Staphylococcus aureus

<400> SEQUENCE: 745
aatggaagtt cgtgacttat taagcgaata tgacttccca ggtgacgatg tacctgtaat 60

<210> SEQ ID NO 746
<211> LENGTH: 60
<212> TYPE: DNA
<213> ORGANISM: Staphylococcus aureus

<400> SEQUENCE: 746
aatggaagtt cgtgacttat taagcgaata tgacttccca ggtgacgatg tacctgtaat 60

<210> SEQ ID NO 747
<211> LENGTH: 60
<212> TYPE: DNA
<213> ORGANISM: Staphylococcus epidermidis

<400> SEQUENCE: 747
aatggaagtt cgtgacttat taagcgaata tgacttccca ggtgacgatg tacctgtaat 60

<210> SEQ ID NO 748
<211> LENGTH: 60
<212> TYPE: DNA
<213> ORGANISM: Staphylococcus epidermidis

<400> SEQUENCE: 748
aatggaagtt cgtgacttat taagcgaata tgacttccca ggtgacgatg tacctgtaat 60

<210> SEQ ID NO 749
<211> LENGTH: 60
<212> TYPE: DNA
<213> ORGANISM: Streptococcus mitis

<400> SEQUENCE: 749
aatggaaatc cgtgaccttc tttcagaata cgatttccca ggtgatgacc ttccagttat 60

<210> SEQ ID NO 750
<211> LENGTH: 60
<212> TYPE: DNA
<213> ORGANISM: Streptococcus sanguis

<400> SEQUENCE: 750
aatggaaatc cgtgacctct tgtcagaata cgacttccca ggtgacgatc ttccagttat 60

<210> SEQ ID NO 751
<211> LENGTH: 60
<212> TYPE: DNA
<213> ORGANISM: Streptococcus mitis

<400> SEQUENCE: 751
aatggaaatc cgtgacctat tgtcagaata cgacttccca ggtgacgatc ttccagttat 60

<210> SEQ ID NO 752
<211> LENGTH: 60
<212> TYPE: DNA
<213> ORGANISM: Streptococcus pneumoniae

<400> SEQUENCE: 752
aatggaaatc cgtgacctat tgtcagaata cgacttccca ggtgacgatc ttccagttat 60

<210> SEQ ID NO 753
<211> LENGTH: 60
<212> TYPE: DNA
<213> ORGANISM: Streptococcus pyogenes

<400> SEQUENCE: 753
gatggaaatt cgtgaccttc tttcagaata cgatttccca ggtgatgacc ttccagttat 60

<210> SEQ ID NO 754
<211> LENGTH: 60
<212> TYPE: DNA
<213> ORGANISM: Streptococcus mutans

<400> SEQUENCE: 754
aatggaaatc cgtgatcttc tttcagaata tgatttccca ggtgatgata ttccagttat 60

<210> SEQ ID NO 755
<211> LENGTH: 60
<212> TYPE: DNA
<213> ORGANISM: Streptococcus mutans

<400> SEQUENCE: 755
aatggaaatc cgtgatcttc tttcagaata tgatttccca ggtgatgata ttccagttat 60

<210> SEQ ID NO 756
<211> LENGTH: 60
<212> TYPE: DNA
<213> ORGANISM: Haemophilus influenzae

<400> SEQUENCE: 756
aatggaagtt cgtgaacttc tatctcaata tgacttccca ggtgacgata caccaatcgt 60

<210> SEQ ID NO 757
<211> LENGTH: 60
<212> TYPE: DNA
<213> ORGANISM: Moraxella catarrhalis

<400> SEQUENCE: 757
aatggaagtt cgtgaacttc tatctgacta tgacttccca ggtgatgaca ccccaatcat 60

<210> SEQ ID NO 758
<211> LENGTH: 60
<212> TYPE: DNA
<213> ORGANISM: Bordetella pertussis

<400> SEQUENCE: 758
gatggaagtc cgcgaactgc tgagcaagta cgatttcccg ggcgatgaca cgccgatcgt 60

<210> SEQ ID NO 759
<211> LENGTH: 60
<212> TYPE: DNA
<213> ORGANISM: Bordetella parapertussis

<400> SEQUENCE: 759
gatggaagtc cgcgaactgc tgagcaagta cgatttcccg ggcgatgaca cgccgatcgt 60

<210> SEQ ID NO 760
<211> LENGTH: 60
<212> TYPE: DNA
<213> ORGANISM: Burkholderia cepacia

<400> SEQUENCE: 760
gatggaagtt cgcgaactgc tgtcgaagta cgacttcccg ggcgacgaca cgccgatcat 60

<210> SEQ ID NO 761
<211> LENGTH: 60
<212> TYPE: DNA
<213> ORGANISM: Burkholderia pseudomallei

<400> SEQUENCE: 761
aatggaagtg cgcgaactgc tgtcgaagta cgacttcccg ggcgacgaca cgccgatcat 60

<210> SEQ ID NO 762
<211> LENGTH: 60
<212> TYPE: DNA
<213> ORGANISM: Stenotrophomonas maltophilia

<400> SEQUENCE: 762
gatggaagtg cgcgaactgc tgagcaagta cgagttcccg ggcgacgaca ccccgatcat 60

<210> SEQ ID NO 763
<211> LENGTH: 60
<212> TYPE: DNA
<213> ORGANISM: Pseudomonas aeruginosa

<400> SEQUENCE: 763
gatggaagtt cgcgatctgc tgaacaccta cgacttcccg ggcgacgaca ctccgatcat 60

<210> SEQ ID NO 764
<211> LENGTH: 60
<212> TYPE: DNA
<213> ORGANISM: Klebsiella pneumoniae

<400> SEQUENCE: 764
gatggaagtt cgtgaactgc tgtctcagta cgatttcccg ggcgacgaca ccccgatcgt 60

<210> SEQ ID NO 765
<211> LENGTH: 57
<212> TYPE: DNA
<213> ORGANISM: Mycobacterium avium

<400> SEQUENCE: 765
gatggaggtc cgcgagctgc tggccgccca ggagttcgac gaggacgccc cggtggt 57

<210> SEQ ID NO 766
<211> LENGTH: 57
<212> TYPE: DNA
<213> ORGANISM: Mycobacterium avium

<400> SEQUENCE: 766
gatggaggtc cgcgagctgc tggccgccca ggagttcgac gaggacgccc cggtggt 57

<210> SEQ ID NO 767
<211> LENGTH: 57
<212> TYPE: DNA
<213> ORGANISM: Mycobacterium intracellulare

<400> SEQUENCE: 767
gatggaggtc cgcgaactgc tggccgccca ggagttcgac gaggacgccc cggtggt 57

<210> SEQ ID NO 768
<211> LENGTH: 57
<212> TYPE: DNA
<213> ORGANISM: Mycobacterium kansasii

<400> SEQUENCE: 768
gatggaggtc cgcgagctgc tggccgccca ggagttcgac gaggacgccc cggtggt 57

<210> SEQ ID NO 769
<211> LENGTH: 57
<212> TYPE: DNA
<213> ORGANISM: Mycobacterium tuberculosis

<400> SEQUENCE: 769
gatggaggtc cgcgagctgc tggctgccca ggaattcgac gaggacgccc cggttgt 57

<210> SEQ ID NO 770
<211> LENGTH: 57
<212> TYPE: DNA
<213> ORGANISM: Mycobacterium tuberculosis

<400> SEQUENCE: 770
gatggaggtc cgcgagctgc tggctgccca ggaattcgac gaggacgccc cggttgt 57

<210> SEQ ID NO 771
<211> LENGTH: 57
<212> TYPE: DNA
<213> ORGANISM: Mycobacterium avium

<400> SEQUENCE: 771
gatggaggtc cgcgaactgc tggccgccca ggagttcgac gaggacgccc cggtcat 57

<210> SEQ ID NO 772
<211> LENGTH: 57
<212> TYPE: DNA
<213> ORGANISM: Corynebacterium diphtheriae

<400> SEQUENCE: 772
gatggagatc cgtgagctgc tcgctgagca ggattacgac gaagaggctc caatcat 57

<210> SEQ ID NO 773
<211> LENGTH: 60
<212> TYPE: DNA
<213> ORGANISM: Neisseria meningitidis

<400> SEQUENCE: 773
aatggaaatc cgcgacctgc tgtccagcta cgacttcccc ggcgatgact gcccgattgt 60

<210> SEQ ID NO 774
<211> LENGTH: 60
<212> TYPE: DNA
<213> ORGANISM: Neisseria meningitidis

<400> SEQUENCE: 774
aatggaaatc cgcgacctgc tgtccagcta cgacttcccc ggcgacgact gcccgatcgt 60

<210> SEQ ID NO 775
<211> LENGTH: 60
<212> TYPE: DNA
<213> ORGANISM: Neisseria meningitidis

<400> SEQUENCE: 775
aatggaaatc cgcgacctgc tgtccagcta cgacttcccc ggcgacgact gcccgattgt 60

<210> SEQ ID NO 776
<211> LENGTH: 52
<212> TYPE: DNA
<213> ORGANISM: Mycoplasma pneumoniae

<400> SEQUENCE: 776
tagaggttca gctttaaaag cattagaagg tgatgctact tgagaagcta aa 52

<210> SEQ ID NO 777
<211> LENGTH: 52
<212> TYPE: DNA
<213> ORGANISM: Mycoplasma pneumoniae

<400> SEQUENCE: 777
ttatggttct gcacttaaag cgcttgaagg tgatcctaag tgggaagcta ag 52

<210> SEQ ID NO 778
<211> LENGTH: 57
<212> TYPE: DNA
<213> ORGANISM: Legionella pneumophila

<400> SEQUENCE: 778
tgttggttca gctttgaaag cattggaagg tgaagacagt gatataggcg ttaaggc 57

<210> SEQ ID NO 779
<211> LENGTH: 57
<212> TYPE: DNA
<213> ORGANISM: Legionella pneumophila

<400> SEQUENCE: 779
tgttggttca gctttgaaag cattggaagg tgaagacagt gatataggcg ttaaggc 57

<210> SEQ ID NO 780
<211> LENGTH: 57
<212> TYPE: DNA
<213> ORGANISM: Legionella pneumophila

<400> SEQUENCE: 780
tgttggttca gctttgaaag cattggaagg tgaagacagt gatataggcg ttaaggc 57

<210> SEQ ID NO 781
<211> LENGTH: 57
<212> TYPE: DNA
<213> ORGANISM: Legionella pneumophila

<400> SEQUENCE: 781
tgttggttca gctttgaaag cattggaagg tgaagacagt gatataggtg ttaaggc 57

<210> SEQ ID NO 782
<211> LENGTH: 57
<212> TYPE: DNA
<213> ORGANISM: Legionella longbeachiae

<400> SEQUENCE: 782
tgttggatct gcattgaaag cattagaagg tgataccagt gatattgggg tgccagc 57

<210> SEQ ID NO 783
<211> LENGTH: 52
<212> TYPE: DNA
<213> ORGANISM: Fusobacterium nucleatum

<400> SEQUENCE: 783
tagaggttca tcattaggag ctttaaatgg tgaagaaaaa tggatagaaa ag 52

<210> SEQ ID NO 784
<211> LENGTH: 53
<212> TYPE: DNA
<213> ORGANISM: Chlamydophila pneumoniae

<400> SEQUENCE: 784
ccgtggttct gctttgaaag ctcttgaagg tgatgcaaat tatatcgaaa aag 53

<210> SEQ ID NO 785
<211> LENGTH: 52
<212> TYPE: DNA
<213> ORGANISM: Enterococcus faecalis

<400> SEQUENCE: 785
cgcaggttct gctttgaaag ctttagaagg cgacgagtct tatgaagaaa aa 52

<210> SEQ ID NO 786
<211> LENGTH: 52
<212> TYPE: DNA
<213> ORGANISM: Enterococcus faecalis

<400> SEQUENCE: 786
cgcaggttct gctttgaaag ctttagaagg cgacgagtct tatgaagaaa aa 52

<210> SEQ ID NO 787
<211> LENGTH: 52
<212> TYPE: DNA
<213> ORGANISM: Staphylococcus aureus

<400> SEQUENCE: 787
cgctggttca gcattaaaag ctttagaagg cgatgctcaa tacgaagaaa aa 52

<210> SEQ ID NO 788
<211> LENGTH: 52
<212> TYPE: DNA
<213> ORGANISM: Staphylococcus aureus

<400> SEQUENCE: 788
cgctggttca gcattaaaag ctttagaagg cgatgctcaa tacgaagaaa aa 52

<210> SEQ ID NO 789
<211> LENGTH: 52
<212> TYPE: DNA
<213> ORGANISM: Staphylococcus aureus

<400> SEQUENCE: 789
cgctggttca gcattaaaag ctttagaagg cgatgctcaa tacgaagaaa aa 52

<210> SEQ ID NO 790
<211> LENGTH: 52
<212> TYPE: DNA
<213> ORGANISM: Staphylococcus aureus

<400> SEQUENCE: 790
cgctggttca gcattaaaag ctttagaagg cgatgctcaa tacgaagaaa aa 52

<210> SEQ ID NO 791
<211> LENGTH: 52
<212> TYPE: DNA
<213> ORGANISM: Staphylococcus aureus

<400> SEQUENCE: 791
cgctggttca gcattaaaag ctttagaagg cgatgctcaa tacgaagaaa aa 52

<210> SEQ ID NO 792
<211> LENGTH: 52
<212> TYPE: DNA
<213> ORGANISM: Staphylococcus epidermidis

<400> SEQUENCE: 792
cgctggttct gcattaaaag cattagaagg cgatgctgaa tacgaacaaa aa 52

<210> SEQ ID NO 793
<211> LENGTH: 52
<212> TYPE: DNA
<213> ORGANISM: Staphylococcus epidermidis

<400> SEQUENCE: 793
cgctggttct gcattaaaag cattagaagg cgatgctgaa tacgaacaaa aa 52

<210> SEQ ID NO 794
<211> LENGTH: 52
<212> TYPE: DNA
<213> ORGANISM: Streptococcus mitis

<400> SEQUENCE: 794
ccaaggttca gctcttaaag ctcttgaagg tgatgctaaa tacgaagaca tc 52

<210> SEQ ID NO 795
<211> LENGTH: 52
<212> TYPE: DNA
<213> ORGANISM: Streptococcus sanguis

<400> SEQUENCE: 795
ccaaggttca gctcttaaag ctcttgaagg tgactctaaa tatgaagaca tc 52

<210> SEQ ID NO 796
<211> LENGTH: 52
<212> TYPE: DNA
<213> ORGANISM: Streptococcus mitis

<400> SEQUENCE: 796
ccaaggttca gctcttaaag cccttgaagg tgacactaaa tacgaagaca tc 52

<210> SEQ ID NO 797
<211> LENGTH: 52
<212> TYPE: DNA
<213> ORGANISM: Streptococcus pneumoniae

<400> SEQUENCE: 797
ccaaggttca gcacttaaag ctcttgaagg tgactctaaa tacgaagaca tc 52

<210> SEQ ID NO 798
<211> LENGTH: 52
<212> TYPE: DNA
<213> ORGANISM: Streptococcus pyogenes

<400> SEQUENCE: 798
ccaaggttca gctcttaaag ctcttgaagg cgacactaaa tttgaagaca tc 52

<210> SEQ ID NO 799
<211> LENGTH: 52
<212> TYPE: DNA
<213> ORGANISM: Streptococcus mutans

<400> SEQUENCE: 799
tcaaggttca gctcttaaag ctcttgaagg tgatactgct caagaagata tc 52

<210> SEQ ID NO 800
<211> LENGTH: 52
<212> TYPE: DNA
<213> ORGANISM: Streptococcus mutans

<400> SEQUENCE: 800
tcaaggttca gctcttaaag ctcttgaagg cgatactgct caagaagata tc 52

<210> SEQ ID NO 801
<211> LENGTH: 52
<212> TYPE: DNA
<213> ORGANISM: Haemophilus influenzae

<400> SEQUENCE: 801
acgtggttca gcattacaag cgttaaacgg cgtagcagaa tgggaagaaa aa 52

<210> SEQ ID NO 802
<211> LENGTH: 57
<212> TYPE: DNA
<213> ORGANISM: Moraxella catarrhalis

<400> SEQUENCE: 802
caaaggttca gcactagaag cattgaatgg ttctgacggt aaatatggtg agcctgc 57

<210> SEQ ID NO 803
<211> LENGTH: 57
<212> TYPE: DNA
<213> ORGANISM: Bordetella pertussis

<400> SEQUENCE: 803
gaagggttcg gccaagctgg cgctggaagg cgacaagggc gaactgggcg agcaggc 57

<210> SEQ ID NO 804
<211> LENGTH: 57
<212> TYPE: DNA
<213> ORGANISM: Bordetella parapertussis

<400> SEQUENCE: 804
gaagggttcg gccaagctgg cgctggaagg cgacaagggc gaactgggcg agcaggc 57

<210> SEQ ID NO 805
<211> LENGTH: 57
<212> TYPE: DNA
<213> ORGANISM: Burkholderia cepacia

<400> SEQUENCE: 805
caagggttcg gcaaagctgg cgctggaagg cgacaagggc gagctgggcg aaacggc 57

<210> SEQ ID NO 806
<211> LENGTH: 57
<212> TYPE: DNA
<213> ORGANISM: Burkholderia pseudomallei

<400> SEQUENCE: 806
caagggttcg gcgaagctgg cgctggaagg cgacaagggc gagctgggcg aagtggc 57

<210> SEQ ID NO 807
<211> LENGTH: 57
<212> TYPE: DNA
<213> ORGANISM: Stenotrophomonas maltophilia

<400> SEQUENCE: 807
cgccggttcg gcccgcctgg cgctggaagg cgaccagagc gacatcggcg tgccggc 57

<210> SEQ ID NO 808
<211> LENGTH: 60
<212> TYPE: DNA
<213> ORGANISM: Pseudomonas aeruginosa

<400> SEQUENCE: 808
catcggttcc gcgctgatgg cgctggaagg caaggatgac aacggcatcg gcgtaagcgc 60

<210> SEQ ID NO 809
<211> LENGTH: 51
<212> TYPE: DNA
<213> ORGANISM: Klebsiella pneumoniae

<400> SEQUENCE: 809
tcgtggttct gctctgaaag cgctggaagg cgacgcagag tgggaagcga a 51

<210> SEQ ID NO 810
<211> LENGTH: 51
<212> TYPE: DNA
<213> ORGANISM: Mycobacterium avium

<400> SEQUENCE: 810
gcgggtgtcg gcgctcaagg cgctcgaggg cgacgccaag tgggtggagt c 51

<210> SEQ ID NO 811
<211> LENGTH: 51
<212> TYPE: DNA
<213> ORGANISM: Mycobacterium avium

<400> SEQUENCE: 811
gcgggtgtcg gcgctcaagg cgctcgaggg cgacgccaag tgggtggagt c 51

<210> SEQ ID NO 812
<211> LENGTH: 51
<212> TYPE: DNA
<213> ORGANISM: Mycobacterium intracellulare

<400> SEQUENCE: 812
gcgcgtctcg gcgctgaagg cgctcgaggg cgacgccaag tgggtggagt c 51

<210> SEQ ID NO 813
<211> LENGTH: 51
<212> TYPE: DNA
<213> ORGANISM: Mycobacterium kansasii

<400> SEQUENCE: 813
gcgggtctcg gcactgaagg ccctcgaggg cgaccccaag tgggtggagt c 51

<210> SEQ ID NO 814
<211> LENGTH: 51
<212> TYPE: DNA
<213> ORGANISM: Mycobacterium tuberculosis

<400> SEQUENCE: 814
gcgggtctcg gcgctcaagg cgctcgaggg tgacgcgaag tgggttgcct c 51

<210> SEQ ID NO 815
<211> LENGTH: 51
<212> TYPE: DNA
<213> ORGANISM: Mycobacterium tuberculosis

<400> SEQUENCE: 815
gcgggtctcg gcgctcaagg cgctcgaggg tgacgcgaag tgggttgcct c 51

<210> SEQ ID NO 816
<211> LENGTH: 51
<212> TYPE: DNA
<213> ORGANISM: Mycobacterium avium

<400> SEQUENCE: 816
ccgcgtctcc gcgctgaagg cgctggaggg tgacccgaag tgggtcaagt c 51

<210> SEQ ID NO 817
<211> LENGTH: 51
<212> TYPE: DNA
<213> ORGANISM: Corynebacterium diphtheriae

<400> SEQUENCE: 817
ccacatctcc gcactgaagg ctcttgaggg cgacgagaag tggacccagt c 51

<210> SEQ ID NO 818
<211> LENGTH: 51
<212> TYPE: DNA
<213> ORGANISM: Neisseria meningitidis

<400> SEQUENCE: 818
acaaggttcc gcactgaaag ccttggaagg cgatgccgct tacgaagaaa a 51

<210> SEQ ID NO 819
<211> LENGTH: 51
<212> TYPE: DNA
<213> ORGANISM: Neisseria meningitidis

<400> SEQUENCE: 819
acaaggttcc gcactgaaag ccttggaagg cgatgccgct tacgaagaaa a 51

<210> SEQ ID NO 820
<211> LENGTH: 51
<212> TYPE: DNA
<213> ORGANISM: Neisseria meningitidis

<400> SEQUENCE: 820
acaaggttct gcactgaaag ccttggaagg cgatgccgct tatgaagaga a 51

<210> SEQ ID NO 821
<211> LENGTH: 59
<212> TYPE: DNA
<213> ORGANISM: Mycoplasma pneumoniae

<400> SEQUENCE: 821
attgatgaat taatggcttc agtagatagc tacatcccaa ctccaacaag agatacaga 59

<210> SEQ ID NO 822
<211> LENGTH: 59
<212> TYPE: DNA
<213> ORGANISM: Mycoplasma pneumoniae

<400> SEQUENCE: 822
atccatgatt taatgaatgc agttgatgaa tggattccaa ctcctgaacg tgaagtgga 59

<210> SEQ ID NO 823
<211> LENGTH: 60
<212> TYPE: DNA
<213> ORGANISM: Legionella pneumophila

<400> SEQUENCE: 823
tatagagaaa ttggttgaaa caatggattc atacattcct gagccagtta gaaacataga 60

<210> SEQ ID NO 824
<211> LENGTH: 60
<212> TYPE: DNA
<213> ORGANISM: Legionella pneumophila

<400> SEQUENCE: 824
tattgagaaa ttggttgaaa caatggattc atacattcct gagccagtta gaaatataga 60

<210> SEQ ID NO 825
<211> LENGTH: 60
<212> TYPE: DNA
<213> ORGANISM: Legionella pneumophila

<400> SEQUENCE: 825
tattgagaaa ttggttgaaa caatggattc atacattcct gagccagtta gaaacataga 60

<210> SEQ ID NO 826
<211> LENGTH: 60
<212> TYPE: DNA
<213> ORGANISM: Legionella pneumophila

<400> SEQUENCE: 826
tattgagaaa ttagttgaaa caatggattc atacattcct gagccagtta gaaacataga 60

<210> SEQ ID NO 827
<211> LENGTH: 60
<212> TYPE: DNA
<213> ORGANISM: Legionella longbeachiae

<400> SEQUENCE: 827
aatagagaaa ttggtagaga ctatggattc ttatattcca gagcctgtaa gaaacattga 60

<210> SEQ ID NO 828
<211> LENGTH: 59
<212> TYPE: DNA
<213> ORGANISM: Fusobacterium nucleatum

<400> SEQUENCE: 828
ataatggaac ttatggatgc agtagatagc tatatcccta ctcctgaaag agcagtaga 59

<210> SEQ ID NO 829
<211> LENGTH: 58
<212> TYPE: DNA
<213> ORGANISM: Chlamydophila pneumoniae

<400> SEQUENCE: 829
ttcgagaact tatgcaagct gtggatgaca acatccctac accagaaaga gaaattga 58

<210> SEQ ID NO 830
<211> LENGTH: 59
<212> TYPE: DNA
<213> ORGANISM: Enterococcus faecalis

<400> SEQUENCE: 830
atcttagaat taatggctgc agttgacgaa tatatcccaa ctccagaacg tgatactga 59

<210> SEQ ID NO 831
<211> LENGTH: 59
<212> TYPE: DNA
<213> ORGANISM: Enterococcus faecalis

<400> SEQUENCE: 831
atcttagaat taatggctgc agttgacgaa tatatcccaa ctccagaacg tgatactga 59

<210> SEQ ID NO 832
<211> LENGTH: 59
<212> TYPE: DNA
<213> ORGANISM: Staphylococcus aureus

<400> SEQUENCE: 832
atcttagaat taatggaagc tgtagatact tacattccaa ctccagaacg tgattctga 59

<210> SEQ ID NO 833
<211> LENGTH: 59
<212> TYPE: DNA
<213> ORGANISM: Staphylococcus aureus

<400> SEQUENCE: 833
atcttagaat taatggaagc tgtagatact tacattccaa ctccagaacg tgattctga 59

<210> SEQ ID NO 834
<211> LENGTH: 59
<212> TYPE: DNA
<213> ORGANISM: Staphylococcus aureus

<400> SEQUENCE: 834
atcttagaat taatggaagc tgtagatact tacattccaa ctccagaacg tgattctga 59

<210> SEQ ID NO 835
<211> LENGTH: 59
<212> TYPE: DNA
<213> ORGANISM: Staphylococcus aureus

<400> SEQUENCE: 835
atcttagaat taatggaagc tgtagatact tacattccaa ctccagaacg tgattctga 59

<210> SEQ ID NO 836
<211> LENGTH: 59
<212> TYPE: DNA
<213> ORGANISM: Staphylococcus aureus

<400> SEQUENCE: 836
atcttagaat taatggaagc tgtagatact tacattccaa ctccagaacg tgattctga 59

<210> SEQ ID NO 837
<211> LENGTH: 59
<212> TYPE: DNA
<213> ORGANISM: Staphylococcus epidermidis

<400> SEQUENCE: 837
atcttagact taatgcaagc agttgatgat tacattccaa ctccagaacg tgattctga 59

<210> SEQ ID NO 838
<211> LENGTH: 59
<212> TYPE: DNA
<213> ORGANISM: Staphylococcus epidermidis

<400> SEQUENCE: 838
atcttagact taatgcaagc agttgatgat tacattccaa ctccagaacg tgattctga 59

<210> SEQ ID NO 839
<211> LENGTH: 59
<212> TYPE: DNA
<213> ORGANISM: Streptococcus mitis

<400> SEQUENCE: 839
atcatggact tgatgaacac tgttgatgag tacatcccag aaccagaacg cgatactga 59

<210> SEQ ID NO 840
<211> LENGTH: 59
<212> TYPE: DNA
<213> ORGANISM: Streptococcus sanguis

<400> SEQUENCE: 840
atcatggaat tgatggacac tgttgatgag tacatcccag aaccagaacg cgatactga 59

<210> SEQ ID NO 841
<211> LENGTH: 59
<212> TYPE: DNA
<213> ORGANISM: Streptococcus mitis

<400> SEQUENCE: 841
gttatggaat tgatgaacac agttgatgag tacatcccag aaccagaacg tgacactga 59

<210> SEQ ID NO 842
<211> LENGTH: 59
<212> TYPE: DNA
<213> ORGANISM: Streptococcus pneumoniae

<400> SEQUENCE: 842
gttatggaat tgatgaacac agttgatgag tatatcccag aaccagaacg tgacactga 59

<210> SEQ ID NO 843
<211> LENGTH: 59
<212> TYPE: DNA
<213> ORGANISM: Streptococcus pyogenes

<400> SEQUENCE: 843
atcatggaat tgatggatac tgttgattca tacattccag aaccagaacg cgacactga 59

<210> SEQ ID NO 844
<211> LENGTH: 59
<212> TYPE: DNA
<213> ORGANISM: Streptococcus mutans

<400> SEQUENCE: 844
atcatggaat taatgcatac tgttgatgac tacattccag atccagaacg tgatactga 59

<210> SEQ ID NO 845
<211> LENGTH: 59
<212> TYPE: DNA
<213> ORGANISM: Streptococcus mutans

<400> SEQUENCE: 845
atcatggaat taatgcatac tgttgatgac tacattccag atccagaacg tgatactga 59

<210> SEQ ID NO 846
<211> LENGTH: 59
<212> TYPE: DNA
<213> ORGANISM: Haemophilus influenzae

<400> SEQUENCE: 846
atccttgagt tagcaaacca cttagatact tacatcccag aaccagaacg tgcgattga 59

<210> SEQ ID NO 847
<211> LENGTH: 60
<212> TYPE: DNA
<213> ORGANISM: Moraxella catarrhalis

<400> SEQUENCE: 847
tgttctagaa ctactagaca cgctagattc atacatccca gagcctgagc gtgacatcga 60

<210> SEQ ID NO 848
<211> LENGTH: 60
<212> TYPE: DNA
<213> ORGANISM: Bordetella pertussis

<400> SEQUENCE: 848
gattctgtcg ctggcgcaag cgctggacac gtacattccg acgccggagc gcgcggtcga 60

<210> SEQ ID NO 849
<211> LENGTH: 60
<212> TYPE: DNA
<213> ORGANISM: Bordetella parapertussis

<400> SEQUENCE: 849
gattctgtcg ctggcgcaag cgctggacac gtacattccg acgccggagc gcgcggtcga 60

<210> SEQ ID NO 850
<211> LENGTH: 60
<212> TYPE: DNA
<213> ORGANISM: Burkholderia cepacia

<400> SEQUENCE: 850
gatcatgaac ctggccgacg cgctggacac gtacatcccg acgccggagc gcgcggtgga 60

<210> SEQ ID NO 851
<211> LENGTH: 60
<212> TYPE: DNA
<213> ORGANISM: Burkholderia pseudomallei

<400> SEQUENCE: 851
gatcatgaac ctggccgacg cgctggacac gtacatcccg acgccggagc gtgcggtcga 60

<210> SEQ ID NO 852
<211> LENGTH: 60
<212> TYPE: DNA
<213> ORGANISM: Stenotrophomonas maltophilia

<400> SEQUENCE: 852
catcctgaag ctggtcgacg cgctggacag ctggattccg gagccggagc gtgcgatcga 60

<210> SEQ ID NO 853
<211> LENGTH: 60
<212> TYPE: DNA
<213> ORGANISM: Pseudomonas aeruginosa

<400> SEQUENCE: 853
cgtgcagaag ctggtagaga ccctggactc ctacattccg gagccggttc gtgccatcga 60

<210> SEQ ID NO 854
<211> LENGTH: 60
<212> TYPE: DNA
<213> ORGANISM: Klebsiella pneumoniae

<400> SEQUENCE: 854
aatcatcgaa ctggctggcc acctggatac ctatatcccg gaaccagagc gtgcgattga 60

<210> SEQ ID NO 855
<211> LENGTH: 60
<212> TYPE: DNA
<213> ORGANISM: Mycobacterium avium

<400> SEQUENCE: 855
cgtcgagcag ctgatggagg ccgtcgacga gtcgatcccg gacccggtcc gcgagacgga 60

<210> SEQ ID NO 856
<211> LENGTH: 60
<212> TYPE: DNA
<213> ORGANISM: Mycobacterium avium

<400> SEQUENCE: 856
cgtcgagcag ctgatggagg ccgtcgacga gtcgatcccg gacccggtcc gcgagacgga 60

<210> SEQ ID NO 857
<211> LENGTH: 60
<212> TYPE: DNA
<213> ORGANISM: Mycobacterium intracellulare

<400> SEQUENCE: 857
ggtcgagcag ctgatggagg ccgtcgacga gtcgatcccg gaccccgtcc gtgagaccga 60

<210> SEQ ID NO 858
<211> LENGTH: 60
<212> TYPE: DNA
<213> ORGANISM: Mycobacterium kansasii

<400> SEQUENCE: 858
ggtggagcag ctgatggatg cggtcgacga gtcgatcccc gacccggtcc gtgagaccga 60

<210> SEQ ID NO 859
<211> LENGTH: 60
<212> TYPE: DNA
<213> ORGANISM: Mycobacterium tuberculosis

<400> SEQUENCE: 859
tgtcgaggaa ctgatgaacg cggtcgacga gtcgattccg gacccggtcc gcgagaccga 60

<210> SEQ ID NO 860
<211> LENGTH: 60
<212> TYPE: DNA
<213> ORGANISM: Mycobacterium tuberculosis

<400> SEQUENCE: 860
tgtcgaggaa ctgatgaacg cggtcgacga gtcgattccg gacccggtcc gcgagaccga 60

<210> SEQ ID NO 861
<211> LENGTH: 60
<212> TYPE: DNA
<213> ORGANISM: Mycobacterium avium

<400> SEQUENCE: 861
ggttgaggac ctcatggagg ccgtcgacga gtcgatcccg gatccggttc gcgagaccga 60

<210> SEQ ID NO 862
<211> LENGTH: 60
<212> TYPE: DNA
<213> ORGANISM: Corynebacterium diphtheriae

<400> SEQUENCE: 862
catcatcgac ctcatgcagg cttgcgatga ttccatccca gacccagagc gtgagaccga 60

<210> SEQ ID NO 863
<211> LENGTH: 60
<212> TYPE: DNA
<213> ORGANISM: Neisseria meningitidis

<400> SEQUENCE: 863
aatcttcgaa ctggctgccg cattggacag ctacatcccg actcccgagc gagccgtgga 60

<210> SEQ ID NO 864
<211> LENGTH: 60
<212> TYPE: DNA
<213> ORGANISM: Neisseria meningitidis

<400> SEQUENCE: 864
aatcttcgaa ttggctgctg cattggacag ctacatcccg actcccgagc gtgccgtgga 60

<210> SEQ ID NO 865
<211> LENGTH: 60
<212> TYPE: DNA
<213> ORGANISM: Neisseria meningitidis

<400> SEQUENCE: 865
aatcttcgaa ctggctgccg cattggacag ctacatcccg actcccgagc gtgccgtgga 60

<210> SEQ ID NO 866
<211> LENGTH: 60
<212> TYPE: DNA
<213> ORGANISM: Mycoplasma pneumoniae

<400> SEQUENCE: 866
caaacctttc ttattagcgg tagaagacgt tatgactatt actggtagag gtactgtagt 60

<210> SEQ ID NO 867
<211> LENGTH: 60
<212> TYPE: DNA
<213> ORGANISM: Mycoplasma pneumoniae

<400> SEQUENCE: 867
caaacccttc ttgttggcaa tcgaagacac catgacgatt actggccgtg gtaccgtggt 60

<210> SEQ ID NO 868
<211> LENGTH: 60
<212> TYPE: DNA
<213> ORGANISM: Legionella pneumophila

<400> SEQUENCE: 868
caagccattt ttgttaccga ttgaagacgt attttcaatt tctggacgcg gaacagtggt 60

<210> SEQ ID NO 869
<211> LENGTH: 60
<212> TYPE: DNA
<213> ORGANISM: Legionella pneumophila

<400> SEQUENCE: 869
caagccattt ttgttaccga ttgaagacgt attttcaatt tctggacgcg gaacagtggt 60

<210> SEQ ID NO 870
<211> LENGTH: 60
<212> TYPE: DNA
<213> ORGANISM: Legionella pneumophila

<400> SEQUENCE: 870
caagccattt ttgttgccga ttgaagacgt attttcaatt tctggacgcg gaacagtggt 60

<210> SEQ ID NO 871
<211> LENGTH: 60
<212> TYPE: DNA
<213> ORGANISM: Legionella pneumophila

<400> SEQUENCE: 871
caagccattc ttgttgccga ttgaagacgt gttttcaatt tctggacgcg gaacagtggt 60

<210> SEQ ID NO 872
<211> LENGTH: 60
<212> TYPE: DNA
<213> ORGANISM: Legionella longbeachiae

<400> SEQUENCE: 872
caaatcgttc ttattaccga ttgaagatgt attttcaata tctggccgag gaacagtagt 60

<210> SEQ ID NO 873
<211> LENGTH: 60
<212> TYPE: DNA
<213> ORGANISM: Fusobacterium nucleatum

<400> SEQUENCE: 873
tcaaccattc ttgatgccaa tagaagacgt tttcactatc acaggaagag gaacagttgt 60

<210> SEQ ID NO 874
<211> LENGTH: 60
<212> TYPE: DNA
<213> ORGANISM: Chlamydophila pneumoniae

<400> SEQUENCE: 874
taagcctttc ttaatgccta tcgaagacgt attctcaatc tctggtcgtg gtactgtggt 60

<210> SEQ ID NO 875
<211> LENGTH: 60
<212> TYPE: DNA
<213> ORGANISM: Enterococcus faecalis

<400> SEQUENCE: 875
caaaccattc atgatgccag tcgaagacgt attctcaatc actggacgtg gtactgttgc 60

<210> SEQ ID NO 876
<211> LENGTH: 60
<212> TYPE: DNA
<213> ORGANISM: Enterococcus faecalis

<400> SEQUENCE: 876
caaaccattc atgatgccag tcgaagacgt attctcaatc actggacgtg gtactgttgc 60

<210> SEQ ID NO 877
<211> LENGTH: 60
<212> TYPE: DNA
<213> ORGANISM: Staphylococcus aureus

<400> SEQUENCE: 877
caaaccattc atgatgccag ttgaggacgt attctcaatc actggtcgtg gtactgttgc 60

<210> SEQ ID NO 878
<211> LENGTH: 60
<212> TYPE: DNA
<213> ORGANISM: Staphylococcus aureus

<400> SEQUENCE: 878
caaaccattc atgatgccag ttgaggacgt attctcaatc actggtcgtg gtactgttgc 60

<210> SEQ ID NO 879
<211> LENGTH: 60
<212> TYPE: DNA
<213> ORGANISM: Staphylococcus aureus

<400> SEQUENCE: 879
caaaccattc atgatgccag ttgaggacgt attctcaatc actggtcgtg gtactgttgc 60

<210> SEQ ID NO 880
<211> LENGTH: 60
<212> TYPE: DNA
<213> ORGANISM: Staphylococcus aureus

<400> SEQUENCE: 880
caaaccattc atgatgccag ttgaggacgt attctcaatc actggtcgtg gtactgttgc 60

<210> SEQ ID NO 881
<211> LENGTH: 60
<212> TYPE: DNA
<213> ORGANISM: Staphylococcus aureus

<400> SEQUENCE: 881
caaaccattc atgatgccag ttgaggacgt attctcaatc actggtcgtg gtactgttgc 60

<210> SEQ ID NO 882
<211> LENGTH: 60
<212> TYPE: DNA
<213> ORGANISM: Staphylococcus epidermidis

<400> SEQUENCE: 882
caaaccattc atgatgccag ttgaggacgt attctcaatc actggtcgtg gtactgttgc 60

<210> SEQ ID NO 883
<211> LENGTH: 60
<212> TYPE: DNA
<213> ORGANISM: Staphylococcus epidermidis

<400> SEQUENCE: 883
caaaccattc atgatgccag ttgaggacgt attctcaatc actggtcgtg gtactgttgc 60

<210> SEQ ID NO 884
<211> LENGTH: 60
<212> TYPE: DNA
<213> ORGANISM: Streptococcus mitis

<400> SEQUENCE: 884
caaaccattg cttcttccag tcgaagacgt attctcaatc actggacgtg gtactgtagc 60

<210> SEQ ID NO 885
<211> LENGTH: 60
<212> TYPE: DNA
<213> ORGANISM: Streptococcus sanguis

<400> SEQUENCE: 885
caagccattg cttcttccag tcgaagacgt attctcaatc actggtcgtg gtacagttgc 60

<210> SEQ ID NO 886
<211> LENGTH: 60
<212> TYPE: DNA
<213> ORGANISM: Streptococcus mitis

<400> SEQUENCE: 886
caaaccattg cttcttccag tcgaagacgt attctcaatc actggtcgtg gtacagttgc 60

<210> SEQ ID NO 887
<211> LENGTH: 60
<212> TYPE: DNA
<213> ORGANISM: Streptococcus pneumoniae

<400> SEQUENCE: 887
caaaccattg cttcttccag tcgaggacgt attctcaatc actggacgtg gtacagttgc 60

<210> SEQ ID NO 888
<211> LENGTH: 60
<212> TYPE: DNA
<213> ORGANISM: Streptococcus pyogenes

<400> SEQUENCE: 888
caaaccattg cttcttccag tcgaagacgt attctcaatt acaggtcgtg gtacagttgc 60

<210> SEQ ID NO 889
<211> LENGTH: 60
<212> TYPE: DNA
<213> ORGANISM: Streptococcus mutans

<400> SEQUENCE: 889
taagccactc cttcttccag tcgaagatgt tttctcaatc actggtcgtg gtactgttgc 60

<210> SEQ ID NO 890
<211> LENGTH: 60
<212> TYPE: DNA
<213> ORGANISM: Streptococcus mutans

<400> SEQUENCE: 890
caagccgctc cttcttccag tcgaagatgt tttctcaatc actggtcgtg gtactgttgc 60

<210> SEQ ID NO 891
<211> LENGTH: 60
<212> TYPE: DNA
<213> ORGANISM: Haemophilus influenzae

<400> SEQUENCE: 891
ccaaccgttc cttcttccaa tcgaagatgt gttctcaatc tcaggtcgtg gtactgtagt 60

<210> SEQ ID NO 892
<211> LENGTH: 60
<212> TYPE: DNA
<213> ORGANISM: Moraxella catarrhalis

<400> SEQUENCE: 892
taagtcattc ctaatgccaa tcgaagatgt cttctcaatc tcaggtcgtg gtactgttgt 60

<210> SEQ ID NO 893
<211> LENGTH: 60
<212> TYPE: DNA
<213> ORGANISM: Bordetella pertussis

<400> SEQUENCE: 893
cggtgcgttc ctgatgccgg tggaagacgt gttctcgatc tcgggccgtg gcacggtggt 60

<210> SEQ ID NO 894
<211> LENGTH: 60
<212> TYPE: DNA
<213> ORGANISM: Bordetella parapertussis

<400> SEQUENCE: 894
cggtgcgttc ctgatgccgg tggaagacgt gttctcgatc tcgggccgtg gcacggtggt 60

<210> SEQ ID NO 895
<211> LENGTH: 60
<212> TYPE: DNA
<213> ORGANISM: Burkholderia cepacia

<400> SEQUENCE: 895
cggtacgttc ctgatgccgg tggaagacgt gttctcgatc tcgggccgcg gtacggtggt 60

<210> SEQ ID NO 896
<211> LENGTH: 60
<212> TYPE: DNA
<213> ORGANISM: Burkholderia pseudomallei

<400> SEQUENCE: 896
cggcgcgttc ctgatgccgg tggaagacgt gttctcgatc tcgggccgtg gtacggtggt 60

<210> SEQ ID NO 897
<211> LENGTH: 60
<212> TYPE: DNA
<213> ORGANISM: Stenotrophomonas maltophilia

<400> SEQUENCE: 897
caagccgttc ctgatgccgg tggaagacgt gttctcgatc tcgggccgcg gcaccgtggt 60

<210> SEQ ID NO 898
<211> LENGTH: 60
<212> TYPE: DNA
<213> ORGANISM: Pseudomonas aeruginosa

<400> SEQUENCE: 898
ccagccgttc ctgatgccga tcgaagacgt gttctcgatc tccggccgcg gtaccgtggt 60

<210> SEQ ID NO 899
<211> LENGTH: 60
<212> TYPE: DNA
<213> ORGANISM: Klebsiella pneumoniae

<400> SEQUENCE: 899
caagccgttc ctgctgccga tcgaagacgt attctccatc tccggtcgtg gtaccgttgt 60

<210> SEQ ID NO 900
<211> LENGTH: 60
<212> TYPE: DNA
<213> ORGANISM: Mycobacterium avium

<400> SEQUENCE: 900
caagccgttc ctgatgccgg tggaggacgt cttcaccatc accggtcgtg gcacggtggt 60

<210> SEQ ID NO 901
<211> LENGTH: 60
<212> TYPE: DNA
<213> ORGANISM: Mycobacterium avium

<400> SEQUENCE: 901
caagccgttc ctgatgccgg tggaggacgt cttcaccatc accggtcgtg gcacggtggt 60

<210> SEQ ID NO 902
<211> LENGTH: 60
<212> TYPE: DNA
<213> ORGANISM: Mycobacterium intracellulare

<400> SEQUENCE: 902
gaagccgttc ctgatgccgg tggaggacgt cttcacgatc accggtcgtg gcaccgtggt 60

<210> SEQ ID NO 903
<211> LENGTH: 60
<212> TYPE: DNA
<213> ORGANISM: Mycobacterium kansasii

<400> SEQUENCE: 903
caagccgttc ctgatgcccg tcgaggacgt cttcacgatc accggccgcg gcaccgtggt 60

<210> SEQ ID NO 904
<211> LENGTH: 60
<212> TYPE: DNA
<213> ORGANISM: Mycobacterium tuberculosis

<400> SEQUENCE: 904
caagccgttc ctgatgccgg tcgaggacgt cttcaccatt accggccgcg gaaccgtggt 60

<210> SEQ ID NO 905
<211> LENGTH: 60
<212> TYPE: DNA
<213> ORGANISM: Mycobacterium tuberculosis

<400> SEQUENCE: 905
caagccgttc ctgatgccgg tcgaggacgt cttcaccatt accggccgcg gaaccgtggt 60

<210> SEQ ID NO 906
<211> LENGTH: 60
<212> TYPE: DNA
<213> ORGANISM: Mycobacterium avium

<400> SEQUENCE: 906
caagccgttc ctgatgcccg tcgaggacgt cttcaccatc accggtcgtg gcaccgtggt 60

<210> SEQ ID NO 907
<211> LENGTH: 60
<212> TYPE: DNA
<213> ORGANISM: Corynebacterium diphtheriae

<400> SEQUENCE: 907
caagccattc ctcatgccta tcgaggacat cttcaccatc accggccgcg gtaccgttgt 60

-continued

<210> SEQ ID NO 908
<211> LENGTH: 60
<212> TYPE: DNA
<213> ORGANISM: Neisseria meningitidis

<400> SEQUENCE: 908
caaaccgttc ctgctgccta tcgaagacgt gttctccatt tccggccgcg gtacagtagt 60

<210> SEQ ID NO 909
<211> LENGTH: 60
<212> TYPE: DNA
<213> ORGANISM: Neisseria meningitidis

<400> SEQUENCE: 909
caaacctttc ttgttgccta tcgaagacgt attctctatt tccggtcgtg gtacagtagt 60

<210> SEQ ID NO 910
<211> LENGTH: 60
<212> TYPE: DNA
<213> ORGANISM: Neisseria meningitidis

<400> SEQUENCE: 910
caaacctttc ctgctgccta tcgaagacgt gttctccatt tccggccgag gtacagtagt 60

<210> SEQ ID NO 911
<211> LENGTH: 60
<212> TYPE: DNA
<213> ORGANISM: Mycoplasma pneumoniae

<400> SEQUENCE: 911
aactggtaga gttgaaagag gtactttaaa attaaacgat gaagttgaaa tcgttggtat 60

<210> SEQ ID NO 912
<211> LENGTH: 60
<212> TYPE: DNA
<213> ORGANISM: Mycoplasma pneumoniae

<400> SEQUENCE: 912
taccggtcgg gttgaacgtg gtgaattgaa agtaggtcaa gaaattgaaa tcgttggttt 60

<210> SEQ ID NO 913
<211> LENGTH: 60
<212> TYPE: DNA
<213> ORGANISM: Legionella pneumophila

<400> SEQUENCE: 913
aactggtcgt gttgagagtg gaattgttaa agttggtgag gaagttgaaa ttgttggaat 60

<210> SEQ ID NO 914
<211> LENGTH: 60
<212> TYPE: DNA
<213> ORGANISM: Legionella pneumophila

<400> SEQUENCE: 914
aactggtcgt gttgagagtg gaattgttaa agttggtgag gaagttgaaa ttgttggaat 60

<210> SEQ ID NO 915
<211> LENGTH: 60
<212> TYPE: DNA
<213> ORGANISM: Legionella pneumophila

<400> SEQUENCE: 915
aactggtcgt gtagagagtg gaattgttaa agttggtgag gaagttgaaa ttgttggaat 60

<210> SEQ ID NO 916
<211> LENGTH: 60
<212> TYPE: DNA
<213> ORGANISM: Legionella pneumophila

<400> SEQUENCE: 916
aactggtcgt gttgagagtg gaattgttaa agttggtgag gaagttgaaa ttgttggaat 60

<210> SEQ ID NO 917
<211> LENGTH: 60
<212> TYPE: DNA
<213> ORGANISM: Legionella longbeachiae

<400> SEQUENCE: 917
aacaggacgt atcgaaagcg gaattatcaa agttggcgaa gagatcgaaa ttgtaggaat 60

<210> SEQ ID NO 918
<211> LENGTH: 60
<212> TYPE: DNA
<213> ORGANISM: Fusobacterium nucleatum

<400> SEQUENCE: 918
tacaggaaga gttgaaagag gaatcatcaa agttggagaa gaaattgaaa tagttggaat 60

<210> SEQ ID NO 919
<211> LENGTH: 60
<212> TYPE: DNA
<213> ORGANISM: Chlamydophila pneumoniae

<400> SEQUENCE: 919
tacaggaaga atcgagcgtg gaatcgttaa agtttctgat aaagttcagc tcgtgggatt 60

<210> SEQ ID NO 920
<211> LENGTH: 60
<212> TYPE: DNA
<213> ORGANISM: Enterococcus faecalis

<400> SEQUENCE: 920
tacaggacgt gttgaacgtg gtgaagttcg cgttggtgac gaagttgaaa tcgttggtat 60

<210> SEQ ID NO 921
<211> LENGTH: 60
<212> TYPE: DNA
<213> ORGANISM: Enterococcus faecalis

<400> SEQUENCE: 921
tacaggccgt gttgaacgtg gtgaagttcg cgttggtgac gaagttgaaa tcgttggtat 60

<210> SEQ ID NO 922
<211> LENGTH: 60
<212> TYPE: DNA
<213> ORGANISM: Staphylococcus aureus

<400> SEQUENCE: 922
tacaggccgt gttgaacgtg gtcaaatcaa agttggtgaa gaagttgaaa tcatcggttt 60

<210> SEQ ID NO 923
<211> LENGTH: 60
<212> TYPE: DNA
<213> ORGANISM: Staphylococcus aureus

<400> SEQUENCE: 923
tacaggccgt gttgaacgtg gtcaaatcaa agttggtgaa gaagttgaaa tcatcggttt 60

<210> SEQ ID NO 924
<211> LENGTH: 60
<212> TYPE: DNA
<213> ORGANISM: Staphylococcus aureus

<400> SEQUENCE: 924
tacaggccgt gttgaacgtg gtcaaatcaa agttggtgaa gaagttgaaa tcatcggttt 60

<210> SEQ ID NO 925
<211> LENGTH: 60
<212> TYPE: DNA
<213> ORGANISM: Staphylococcus aureus

<400> SEQUENCE: 925
tacaggccgt gttgaacgtg gtcaaatcaa agttggtgaa gaagttgaaa tcatcggttt 60

<210> SEQ ID NO 926
<211> LENGTH: 60
<212> TYPE: DNA
<213> ORGANISM: Staphylococcus aureus

<400> SEQUENCE: 926
tacaggccgt gttgaacgtg gtcaaatcaa agttggtgaa gaagttgaaa tcatcggttt 60

<210> SEQ ID NO 927
<211> LENGTH: 60
<212> TYPE: DNA
<213> ORGANISM: Staphylococcus epidermidis

<400> SEQUENCE: 927
tacaggccgt gttgaacgtg gtcaaatcaa agttggtgaa gaagttgaaa tcatcggtat 60

<210> SEQ ID NO 928
<211> LENGTH: 60
<212> TYPE: DNA
<213> ORGANISM: Staphylococcus epidermidis

<400> SEQUENCE: 928
tacaggccgt gttgaacgtg gtcaaatcaa agttggtgaa gaagttgaaa tcatcggtat 60

<210> SEQ ID NO 929
<211> LENGTH: 60
<212> TYPE: DNA
<213> ORGANISM: Streptococcus mitis

<400> SEQUENCE: 929
atcaggacgt atcgaccgtg gtatcgttaa agtcaacgac gaaatcgaaa tcgttggtat 60

<210> SEQ ID NO 930
<211> LENGTH: 60
<212> TYPE: DNA
<213> ORGANISM: Streptococcus sanguis

<400> SEQUENCE: 930
ttcaggacgt atcgaccgtg gtatcgttaa agtcaacgac gaaatcgaaa tcgttggtat 60

<210> SEQ ID NO 931
<211> LENGTH: 60
<212> TYPE: DNA
<213> ORGANISM: Streptococcus mitis

<400> SEQUENCE: 931
ttcaggacgt atcgaccgtg gtatcgttaa agtcaacgac gaaatcgaaa tcgttggtat 60

<210> SEQ ID NO 932
<211> LENGTH: 60
<212> TYPE: DNA
<213> ORGANISM: Streptococcus pneumoniae

<400> SEQUENCE: 932
ttcaggacgt atcgaccgtg gtatcgttaa agtcaacgac gaaatcgaaa tcgttggtat 60

<210> SEQ ID NO 933
<211> LENGTH: 60
<212> TYPE: DNA
<213> ORGANISM: Streptococcus pyogenes

<400> SEQUENCE: 933
ttcaggacgt atcgaccgtg gtactgttcg tgtcaacgac gaaatcgaaa tcgttggtat 60

<210> SEQ ID NO 934
<211> LENGTH: 60
<212> TYPE: DNA
<213> ORGANISM: Streptococcus mutans

<400> SEQUENCE: 934
ttcaggacgt attgatcgtg gtactgttaa agttaacgat gaagttgaaa tcgttggtat 60

<210> SEQ ID NO 935
<211> LENGTH: 60
<212> TYPE: DNA
<213> ORGANISM: Streptococcus mutans

<400> SEQUENCE: 935
ttcaggacgt attgatcgtg gtactgttaa agttaacgat gaagttgaaa tcgttggtat 60

<210> SEQ ID NO 936
<211> LENGTH: 60
<212> TYPE: DNA
<213> ORGANISM: Haemophilus influenzae

<400> SEQUENCE: 936
aacaggtcgt gtagaacgag gtattatccg tacaggtgat gaagtagaaa tcgtcggtat 60

<210> SEQ ID NO 937
<211> LENGTH: 60
<212> TYPE: DNA
<213> ORGANISM: Moraxella catarrhalis

<400> SEQUENCE: 937
aactggccgt gttgaatcag gcattattaa agttggtgat gaaattgaaa tcatcggtat 60

<210> SEQ ID NO 938
<211> LENGTH: 60
<212> TYPE: DNA
<213> ORGANISM: Bordetella pertussis

<400> SEQUENCE: 938
gactggccgt atcgagcgcg gcgtggtgaa ggttggcgag gaaatcgaaa tcgtgggcat 60

<210> SEQ ID NO 939
<211> LENGTH: 60
<212> TYPE: DNA
<213> ORGANISM: Bordetella parapertussis

<400> SEQUENCE: 939
gactggccgt atcgagcgcg gcgtggtgaa ggttggcgag gaaatcgaaa tcgtgggtat 60

<210> SEQ ID NO 940
<211> LENGTH: 60
<212> TYPE: DNA
<213> ORGANISM: Burkholderia cepacia

<400> SEQUENCE: 940
gacgggtcgt gtggagcgcg gcgtggtgaa ggtcggtgag gaaatcgaaa tcgtcggtat 60

<210> SEQ ID NO 941
<211> LENGTH: 60
<212> TYPE: DNA
<213> ORGANISM: Burkholderia pseudomallei

<400> SEQUENCE: 941
gacgggtcgt gtcgagcgcg gcgtgatcaa ggttggcgag gaaatcgaaa tcgtcggtat 60

<210> SEQ ID NO 942
<211> LENGTH: 60
<212> TYPE: DNA
<213> ORGANISM: Stenotrophomonas maltophilia

<400> SEQUENCE: 942
gaccggtcgt atcgagcgcg gcgtgatcaa ggttggcgac gaaatcgaaa tcgtcggcat 60

<210> SEQ ID NO 943
<211> LENGTH: 60
<212> TYPE: DNA
<213> ORGANISM: Pseudomonas aeruginosa

<400> SEQUENCE: 943
aaccggtcgt gtagagcgcg gcatcatcaa ggtccaggaa gaagtggaaa tcgtcggcat 60

<210> SEQ ID NO 944
<211> LENGTH: 60
<212> TYPE: DNA
<213> ORGANISM: Klebsiella pneumoniae

<400> SEQUENCE: 944
taccggtcgt gtagagcgcg gtatcatcaa agtaggtgaa gaagttgaaa tcgttggtat 60

<210> SEQ ID NO 945
<211> LENGTH: 60
<212> TYPE: DNA
<213> ORGANISM: Mycobacterium avium

<400> SEQUENCE: 945
caccggccgt gtcgagcgcg gcgtgatcaa cgtgaacgag gaagtcgaga tcgtcggcat 60

<210> SEQ ID NO 946
<211> LENGTH: 60
<212> TYPE: DNA
<213> ORGANISM: Mycobacterium avium

<400> SEQUENCE: 946
caccggccgt gtcgagcgcg gcgtgatcaa cgtgaacgag gaagtcgaga tcgtcggcat 60

<210> SEQ ID NO 947
<211> LENGTH: 60
<212> TYPE: DNA
<213> ORGANISM: Mycobacterium intracellulare

<400> SEQUENCE: 947
caccggtcgt gtcgagcgcg gtgtgatcaa cgtgaacgag gaagtcgaga tcgtcggtat 60

<210> SEQ ID NO 948
<211> LENGTH: 60
<212> TYPE: DNA
<213> ORGANISM: Mycobacterium kansasii

<400> SEQUENCE: 948
caccggtcgt gtggagcgcg gcgtggtcaa cgtcaacgag gaagtcgaga tcgtcggcat 60

<210> SEQ ID NO 949
<211> LENGTH: 60
<212> TYPE: DNA
<213> ORGANISM: Mycobacterium tuberculosis

<400> SEQUENCE: 949
caccggacgt gtggagcgcg gcgtgatcaa cgtgaacgag gaagttgaga tcgtcggcat 60

<210> SEQ ID NO 950
<211> LENGTH: 60
<212> TYPE: DNA
<213> ORGANISM: Mycobacterium tuberculosis

<400> SEQUENCE: 950
caccggacgt gtggagcgcg gcgtgatcaa cgtgaacgag gaagttgaga tcgtcggcat 60

<210> SEQ ID NO 951
<211> LENGTH: 60
<212> TYPE: DNA
<213> ORGANISM: Mycobacterium avium

<400> SEQUENCE: 951
gaccggtcgc gtcgagcgtg gcgtgatcaa cgtcaacgaa gaggtcgaga tcgtcggcat 60

<210> SEQ ID NO 952
<211> LENGTH: 60
<212> TYPE: DNA
<213> ORGANISM: Corynebacterium diphtheriae

<400> SEQUENCE: 952
taccggccgt gttgagcgtg gctccctgaa ggtcaacgag gacgtcgaga tcatcggtat 60

<210> SEQ ID NO 953
<211> LENGTH: 60
<212> TYPE: DNA
<213> ORGANISM: Neisseria meningitidis

<400> SEQUENCE: 953
aaccggccgt gtagagcgcg gtatcatcca cgttggtgac gagattgaaa tcgtcggtct 60

<210> SEQ ID NO 954
<211> LENGTH: 60
<212> TYPE: DNA
<213> ORGANISM: Neisseria meningitidis

<400> SEQUENCE: 954
aaccggtcgt gtagagcgcg gtatcatcca cgtcggtgac gagatcgaaa tcgtcggtct 60

<210> SEQ ID NO 955
<211> LENGTH: 60
<212> TYPE: DNA
<213> ORGANISM: Neisseria meningitidis

<400> SEQUENCE: 955
aaccggccgt gtagagcgcg gtatcatcca cgttggtgac gagattgaaa tcgtcggtct 60

<210> SEQ ID NO 956
<211> LENGTH: 57
<212> TYPE: DNA
<213> ORGANISM: Mycoplasma pneumoniae

<400> SEQUENCE: 956
ccatgatact agaaaagcag ttgttactgg tatggaaatg ttaagaaaaa cattaga 57

<210> SEQ ID NO 957
<211> LENGTH: 57
<212> TYPE: DNA
<213> ORGANISM: Mycoplasma pneumoniae

<400> SEQUENCE: 957
acgtccaatc cgtaaagcag ttgttaccgg aatcgaaatg ttcaaaaagg aacttga 57

<210> SEQ ID NO 958
<211> LENGTH: 57
<212> TYPE: DNA
<213> ORGANISM: Legionella pneumophila

<400> SEQUENCE: 958
aagagacact caaaagacga cttgtacggg tgttgagatg ttccgtaaat tacttga 57

<210> SEQ ID NO 959
<211> LENGTH: 57
<212> TYPE: DNA
<213> ORGANISM: Legionella pneumophila

<400> SEQUENCE: 959
aagagacacc caaaagacga cttgtacggg tgttgagatg ttccgtaaat tacttga 57

<210> SEQ ID NO 960
<211> LENGTH: 57
<212> TYPE: DNA
<213> ORGANISM: Legionella pneumophila

<400> SEQUENCE: 960
aagagacacc caaaagacga cttgtacggg tgttgagatg ttccgtaaat tacttga 57

<210> SEQ ID NO 961
<211> LENGTH: 57
<212> TYPE: DNA
<213> ORGANISM: Legionella pneumophila

<400> SEQUENCE: 961
aagagacacc caaaagacga cttgtactgg tgttgagatg ttccgtaaat tacttga 57

<210> SEQ ID NO 962
<211> LENGTH: 57
<212> TYPE: DNA
<213> ORGANISM: Legionella longbeachiae

<400> SEQUENCE: 962
tcgtgatact gcaaagacta cctgtactgg tgttgagatg ttccgtaagt tattaga 57

<210> SEQ ID NO 963
<211> LENGTH: 57
<212> TYPE: DNA
<213> ORGANISM: Fusobacterium nucleatum

<400> SEQUENCE: 963
taaacctaca actaaaacaa cttgtacagg ggttgaaatg tttagaaaac ttcttga 57

<210> SEQ ID NO 964
<211> LENGTH: 57
<212> TYPE: DNA
<213> ORGANISM: Chlamydophila pneumoniae

<400> SEQUENCE: 964
aggagagact aaagaaacaa tcgttactgg agtcgaaatg ttcaggaaag aacttcc 57

<210> SEQ ID NO 965
<211> LENGTH: 60
<212> TYPE: DNA
<213> ORGANISM: Enterococcus faecalis

<400> SEQUENCE: 965
taaagacgaa acatctaaaa caactgttac aggtgttgaa atgttccgta aattattaga 60

<210> SEQ ID NO 966
<211> LENGTH: 60
<212> TYPE: DNA
<213> ORGANISM: Enterococcus faecalis

<400> SEQUENCE: 966
taaagacgaa acatctaaaa caactgttac aggtgttgaa atgttccgta aattattaga 60

<210> SEQ ID NO 967
<211> LENGTH: 57
<212> TYPE: DNA
<213> ORGANISM: Staphylococcus aureus

<400> SEQUENCE: 967
acatgacaca tctaaaacaa ctgttacagg tgttgaaatg ttccgtaaat tattaga 57

<210> SEQ ID NO 968
<211> LENGTH: 57
<212> TYPE: DNA
<213> ORGANISM: Staphylococcus aureus

<400> SEQUENCE: 968
acatgacaca tctaaaacaa ctgttacagg tgttgaaatg ttccgtaaat tattaga 57

<210> SEQ ID NO 969
<211> LENGTH: 57
<212> TYPE: DNA
<213> ORGANISM: Staphylococcus aureus

<400> SEQUENCE: 969
acatgacaca tctaaaacaa ctgttacagg tgttgaaatg ttccgtaaat tattaga 57

<210> SEQ ID NO 970
<211> LENGTH: 57
<212> TYPE: DNA
<213> ORGANISM: Staphylococcus aureus

<400> SEQUENCE: 970
acatgacaca tctaaaacaa ctgttacagg tgttgaaatg ttccgtaaat tattaga 57

<210> SEQ ID NO 971
<211> LENGTH: 57
<212> TYPE: DNA
<213> ORGANISM: Staphylococcus aureus

<400> SEQUENCE: 971
acatgacaca tctaaaacaa ctgttacagg tgttgaaatg ttccgtaaat tattaga 57

<210> SEQ ID NO 972
<211> LENGTH: 57
<212> TYPE: DNA
<213> ORGANISM: Staphylococcus epidermidis

<400> SEQUENCE: 972
gcacgaaact tctaaaacaa ctgttactgg tgtagaaatg ttccgtaaat tattaga 57

<210> SEQ ID NO 973
<211> LENGTH: 57
<212> TYPE: DNA
<213> ORGANISM: Staphylococcus epidermidis

<400> SEQUENCE: 973
gcacgaaact tctaaaacaa ctgttactgg tgtagaaatg ttccgtaaat tattaga 57

<210> SEQ ID NO 974
<211> LENGTH: 60
<212> TYPE: DNA
<213> ORGANISM: Streptococcus mitis

<400> SEQUENCE: 974
taaagaagaa atccaaaaag cggttgttac tggtgttgaa atgttccgta aacaacttga 60

<210> SEQ ID NO 975
<211> LENGTH: 60
<212> TYPE: DNA
<213> ORGANISM: Streptococcus sanguis

<400> SEQUENCE: 975
caaagaagaa atccaaaaag cagttgttac tggtgttgaa atgttccgta aacagcttga 60

<210> SEQ ID NO 976
<211> LENGTH: 60
<212> TYPE: DNA
<213> ORGANISM: Streptococcus mitis

<400> SEQUENCE: 976
caaagaagaa actcaaaaag cagttgttac tggtgttgaa atgttccgta aacaacttga 60

<210> SEQ ID NO 977
<211> LENGTH: 60
<212> TYPE: DNA
<213> ORGANISM: Streptococcus pneumoniae

<400> SEQUENCE: 977
caaagaagaa actcaaaaag cagttgttac tggtgttgaa atgttccgta aacaacttga 60

<210> SEQ ID NO 978
<211> LENGTH: 60
<212> TYPE: DNA
<213> ORGANISM: Streptococcus pyogenes

<400> SEQUENCE: 978
caaagaagaa actaaaaaag ctgttgttac tggtgttgaa atgttccgta aacaacttga 60

<210> SEQ ID NO 979
<211> LENGTH: 60
<212> TYPE: DNA
<213> ORGANISM: Streptococcus mutans

<400> SEQUENCE: 979
ccgtgatgac attcaaaaag ctgttgttac tggtgttgaa atgttccgta aacaattgga 60

<210> SEQ ID NO 980
<211> LENGTH: 60
<212> TYPE: DNA
<213> ORGANISM: Streptococcus mutans

<400> SEQUENCE: 980
ccgtgatgac attcaaaaag ctgttgttac tggtgttgaa atgttccgta aacaattgga 60

<210> SEQ ID NO 981
<211> LENGTH: 57
<212> TYPE: DNA
<213> ORGANISM: Haemophilus influenzae

<400> SEQUENCE: 981
caaagataca gcgaaaacta ctgtaacggg tgttgaaatg ttccgtaaat tacttga 57

<210> SEQ ID NO 982
<211> LENGTH: 57
<212> TYPE: DNA
<213> ORGANISM: Moraxella catarrhalis

<400> SEQUENCE: 982
caaaccaact actaaaacca cttgtactgg tgttgaaatg ttccgtaagc tgctaga 57

<210> SEQ ID NO 983
<211> LENGTH: 57
<212> TYPE: DNA
<213> ORGANISM: Bordetella pertussis

<400> SEQUENCE: 983
caagccgacg gtgaagacga cctgcacggg cgtggagatg ttccgcaagc tgctgga 57

<210> SEQ ID NO 984
<211> LENGTH: 57
<212> TYPE: DNA
<213> ORGANISM: Bordetella parapertussis

<400> SEQUENCE: 984
caagccgacg gtgaagacga cctgcacggg cgtggagatg ttccgcaagc tgctgga 57

<210> SEQ ID NO 985
<211> LENGTH: 57
<212> TYPE: DNA
<213> ORGANISM: Burkholderia cepacia

<400> SEQUENCE: 985
caagccgacg gtgaagacga cctgcacggg cgttgaaatg ttccgcaagc tgctgga 57

<210> SEQ ID NO 986
<211> LENGTH: 57
<212> TYPE: DNA
<213> ORGANISM: Burkholderia pseudomallei

<400> SEQUENCE: 986
caaggcgacg gcgaagacga cctgcacggg cgtggaaatg ttccgcaagc tgctgga 57

<210> SEQ ID NO 987
<211> LENGTH: 57
<212> TYPE: DNA
<213> ORGANISM: Stenotrophomonas maltophilia

<400> SEQUENCE: 987
ccgtccggtg cagaagacca ccgtgaccgg cgttgaaatg ttccgcaagc tgctgga 57

<210> SEQ ID NO 988
<211> LENGTH: 57
<212> TYPE: DNA
<213> ORGANISM: Pseudomonas aeruginosa

<400> SEQUENCE: 988
caaggcgacc accaagacta cctgcaccgg cgttgaaatg ttccgcaagc tgctcga 57

<210> SEQ ID NO 989
<211> LENGTH: 57
<212> TYPE: DNA
<213> ORGANISM: Klebsiella pneumoniae

<400> SEQUENCE: 989
caaagaaacc gcgaaaacca cctgtactgg cgttgaaatg ttccgcaaac tgctgga 57

<210> SEQ ID NO 990
<211> LENGTH: 60
<212> TYPE: DNA
<213> ORGANISM: Mycobacterium avium

<400> SEQUENCE: 990
ccgcccgtcc agcaccaaga ccacggtcac cggtgtggag atgttccgca agctgctcga 60

<210> SEQ ID NO 991
<211> LENGTH: 60
<212> TYPE: DNA
<213> ORGANISM: Mycobacterium avium

<400> SEQUENCE: 991
ccgcccgtcc agcaccaaga ccacggtcac cggtgtggag atgttccgca agctgctcga 60

<210> SEQ ID NO 992
<211> LENGTH: 60
<212> TYPE: DNA
<213> ORGANISM: Mycobacterium intracellulare

<400> SEQUENCE: 992
caagccgacc agcaccaaga ccaccgtcac cggtgtggag atgttccgca agctgctcga 60

<210> SEQ ID NO 993
<211> LENGTH: 60
<212> TYPE: DNA
<213> ORGANISM: Mycobacterium kansasii

<400> SEQUENCE: 993
ccgtccgacc accaccaaga ccacggtcac cggtgtggag atgttccgca agctgctcga 60

<210> SEQ ID NO 994
<211> LENGTH: 60
<212> TYPE: DNA
<213> ORGANISM: Mycobacterium tuberculosis

<400> SEQUENCE: 994
tcgcccatcg accaccaaga ccaccgtcac cggtgtggag atgttccgca agctgctcga 60

<210> SEQ ID NO 995
<211> LENGTH: 60
<212> TYPE: DNA
<213> ORGANISM: Mycobacterium tuberculosis

<400> SEQUENCE: 995
tcgcccatcg accaccaaga ccaccgtcac cggtgtggag atgttccgca agctgctcga 60

<210> SEQ ID NO 996
<211> LENGTH: 60
<212> TYPE: DNA
<213> ORGANISM: Mycobacterium avium

<400> SEQUENCE: 996
ccgcccgacc acgaccaaga ccaccgtcac cggtgtggaa atgttccgca agctgctcga 60

<210> SEQ ID NO 997
<211> LENGTH: 60
<212> TYPE: DNA
<213> ORGANISM: Corynebacterium diphtheriae

<400> SEQUENCE: 997
ccgcgagaag gctaccacca ccaccgttac cggtatcgag atgttccgta agcttctcga 60

<210> SEQ ID NO 998
<211> LENGTH: 57
<212> TYPE: DNA
<213> ORGANISM: Neisseria meningitidis

<400> SEQUENCE: 998
gaaagaaacc caaaaaacca cttgtaccgg tgttgaaatg ttccgcaaac tgctgga 57

<210> SEQ ID NO 999
<211> LENGTH: 57
<212> TYPE: DNA
<213> ORGANISM: Neisseria meningitidis

<400> SEQUENCE: 999
gaaagaaact caaaaaacca cttgtaccgg tgttgaaatg ttccgcaaac tgctgga 57

<210> SEQ ID NO 1000
<211> LENGTH: 57
<212> TYPE: DNA
<213> ORGANISM: Neisseria meningitidis

<400> SEQUENCE: 1000
gaaagaaacc caaaaaacca cctgtaccgg tgttgaaatg ttccgcaaac tgctgga 57

<210> SEQ ID NO 1001
<211> LENGTH: 60
<212> TYPE: DNA
<213> ORGANISM: Mycoplasma pneumoniae

<400> SEQUENCE: 1001
cgaagtaaaa gctggggata acgctggtat cttattaaga ggtattgata gaaaagatgt 60

<210> SEQ ID NO 1002
<211> LENGTH: 60
<212> TYPE: DNA
<213> ORGANISM: Mycoplasma pneumoniae

<400> SEQUENCE: 1002
ttcagcaatg gctggggaca acgctggggt attactccgt ggtgtggacc gtaaagaagt 60

<210> SEQ ID NO 1003
<211> LENGTH: 60
<212> TYPE: DNA
<213> ORGANISM: Legionella pneumophila

<400> SEQUENCE: 1003
tgaaggtcga gctggtgata acgttggagt gttattacga ggtacgaagc gagatgaagt 60

<210> SEQ ID NO 1004
<211> LENGTH: 60
<212> TYPE: DNA
<213> ORGANISM: Legionella pneumophila

<400> SEQUENCE: 1004
tgaaggtcga gctggtgata acgttggtgt gttattacga ggtacgaagc gagatgaagt 60

<210> SEQ ID NO 1005
<211> LENGTH: 60
<212> TYPE: DNA
<213> ORGANISM: Legionella pneumophila

<400> SEQUENCE: 1005
tgaaggtcga gctggtgata acgttggtgt gttattacga ggtacgaagc gagatgaagt 60

<210> SEQ ID NO 1006
<211> LENGTH: 60
<212> TYPE: DNA
<213> ORGANISM: Legionella pneumophila

<400> SEQUENCE: 1006
tgaaggtcga gctggtgata acgttggtgt gttattacgc ggtacgaagc gagatgaagt 60

<210> SEQ ID NO 1007
<211> LENGTH: 60
<212> TYPE: DNA
<213> ORGANISM: Legionella longbeachiae

<400> SEQUENCE: 1007
cgaaggacgt gcaggtgata acgttggtat attactccgt ggaacaaaac gagacgaagt 60

<210> SEQ ID NO 1008
<211> LENGTH: 60
<212> TYPE: DNA
<213> ORGANISM: Fusobacterium nucleatum

<400> SEQUENCE: 1008
tcaaggtcaa gcaggagata atatcggagt attattaaga ggaactaaga aagaagaagt 60

<210> SEQ ID NO 1009
<211> LENGTH: 60
<212> TYPE: DNA
<213> ORGANISM: Chlamydophila pneumoniae

<400> SEQUENCE: 1009
tgaaggtcgt gcaggagaaa acgttggttt actcctcaga ggtattggaa agaacgatgt 60

<210> SEQ ID NO 1010
<211> LENGTH: 60
<212> TYPE: DNA
<213> ORGANISM: Enterococcus faecalis

<400> SEQUENCE: 1010
ctacgctgaa gcaggcgaca acatcggtgc tttattacgt ggtgtagcac gtgaagatat 60

<210> SEQ ID NO 1011
<211> LENGTH: 60
<212> TYPE: DNA
<213> ORGANISM: Enterococcus faecalis

<400> SEQUENCE: 1011
ctacgctgaa gcaggcgaca acatcggtgc tttattacgt ggtgtagcac gtgaagatat 60

<210> SEQ ID NO 1012
<211> LENGTH: 60
<212> TYPE: DNA
<213> ORGANISM: Staphylococcus aureus

<400> SEQUENCE: 1012
ctacgctgaa gctggtgaca acattggtgc attattacgt ggtgttgctc gtgaagacgt 60

<210> SEQ ID NO 1013
<211> LENGTH: 60
<212> TYPE: DNA
<213> ORGANISM: Staphylococcus aureus

<400> SEQUENCE: 1013
ctacgctgaa gctggtgaca acattggtgc attattacgt ggtgttgctc gtgaagacgt 60

<210> SEQ ID NO 1014
<211> LENGTH: 60
<212> TYPE: DNA
<213> ORGANISM: Staphylococcus aureus

<400> SEQUENCE: 1014
ctacgctgaa gctggtgaca acattggtgc attattacgt ggtgttgctc gtgaagacgt 60

<210> SEQ ID NO 1015
<211> LENGTH: 60
<212> TYPE: DNA
<213> ORGANISM: Staphylococcus aureus

<400> SEQUENCE: 1015
ctacgctgaa gctggtgaca acattggtgc attattacgt ggtgttgctc gtgaagacgt 60

<210> SEQ ID NO 1016
<211> LENGTH: 60
<212> TYPE: DNA
<213> ORGANISM: Staphylococcus aureus

<400> SEQUENCE: 1016
ctacgctgaa gctggtgaca acattggtgc attattacgt ggtgttgctc gtgaagacgt 60

<210> SEQ ID NO 1017
<211> LENGTH: 60
<212> TYPE: DNA
<213> ORGANISM: Staphylococcus epidermidis

<400> SEQUENCE: 1017
ctacgctgaa gctggtgaca acatcggtgc tttattacgt ggtgttgcac gtgaagacgt 60

<210> SEQ ID NO 1018
<211> LENGTH: 60
<212> TYPE: DNA
<213> ORGANISM: Staphylococcus epidermidis

<400> SEQUENCE: 1018
ctacgctgaa gctggtgaca acatcggtgc tttattacgt ggtgttgcac gtgaagacgt 60

<210> SEQ ID NO 1019
<211> LENGTH: 60
<212> TYPE: DNA
<213> ORGANISM: Streptococcus mitis

<400> SEQUENCE: 1019
cgaatgtctt gcaggggaca acgttggtgt gcttcttcgt ggtatccaac gtgatgaaat 60

<210> SEQ ID NO 1020
<211> LENGTH: 60
<212> TYPE: DNA
<213> ORGANISM: Streptococcus sanguis

<400> SEQUENCE: 1020
cgaaggtctt gcaggggaca acgtaggtgt gcttctccgt ggtatccaac gtgatgaaat 60

<210> SEQ ID NO 1021
<211> LENGTH: 60
<212> TYPE: DNA
<213> ORGANISM: Streptococcus mitis

<400> SEQUENCE: 1021
cgaaggtctt gccggagata atgtaggtgt ccttcttcgt ggtgttcaac gtgatgaaat 60

<210> SEQ ID NO 1022
<211> LENGTH: 60
<212> TYPE: DNA
<213> ORGANISM: Streptococcus pneumoniae

<400> SEQUENCE: 1022
cgaaggtctt gctggagata acgtaggtgt ccttcttcgt ggtgttcaac gtgatgaaat 60

<210> SEQ ID NO 1023
<211> LENGTH: 60
<212> TYPE: DNA
<213> ORGANISM: Streptococcus pyogenes

<400> SEQUENCE: 1023
cgaaggtctt gcaggagaca acgtaggtat ccttcttcgt ggtgttcaac gtgacgaaat 60

<210> SEQ ID NO 1024
<211> LENGTH: 60
<212> TYPE: DNA
<213> ORGANISM: Streptococcus mutans

<400> SEQUENCE: 1024
tgaaggtatt gcaggggata atgttggtgt tctccttcgt ggtatccaac gtgatgaaat 60

<210> SEQ ID NO 1025
<211> LENGTH: 60
<212> TYPE: DNA
<213> ORGANISM: Streptococcus mutans

<400> SEQUENCE: 1025
tgaaggtatt gcaggggata atgttggtgt tctccttcgt ggtatccaac gtgatgaaat 60

<210> SEQ ID NO 1026
<211> LENGTH: 60
<212> TYPE: DNA
<213> ORGANISM: Haemophilus influenzae

<400> SEQUENCE: 1026
cgaaggtcgt gcaggtgaaa acatcggtgc attattacgt ggtaccaaac gtgaagaaat 60

<210> SEQ ID NO 1027
<211> LENGTH: 60
<212> TYPE: DNA
<213> ORGANISM: Moraxella catarrhalis

<400> SEQUENCE: 1027
cgaaggtcgt gcaggtgaga actgtggtat cctactacgt ggtactaagc gtgaagaagt 60

<210> SEQ ID NO 1028
<211> LENGTH: 60
<212> TYPE: DNA
<213> ORGANISM: Bordetella pertussis

<400> SEQUENCE: 1028
ccagggccag gcgggcgaca acgtgggtat cttgctgcgc ggcaccaagc gtgaagacgt 60

<210> SEQ ID NO 1029
<211> LENGTH: 60
<212> TYPE: DNA
<213> ORGANISM: Bordetella parapertussis

<400> SEQUENCE: 1029
ccagggccag gcgggcgaca acgtgggtat cttgctgcgc ggcaccaagc gtgaagacgt 60

<210> SEQ ID NO 1030
<211> LENGTH: 60
<212> TYPE: DNA
<213> ORGANISM: Burkholderia cepacia

<400> SEQUENCE: 1030
ccagggtcag gcaggcgaca acgtcggtat cctgctgcgc ggcacgaagc gtgaagacgt 60

<210> SEQ ID NO 1031
<211> LENGTH: 60
<212> TYPE: DNA
<213> ORGANISM: Burkholderia pseudomallei

<400> SEQUENCE: 1031
tcagggtcag gcgggcgaca acgtcggtat cctgctgcgc ggcacgaagc gtgaagacgt 60

<210> SEQ ID NO 1032
<211> LENGTH: 60
<212> TYPE: DNA
<213> ORGANISM: Stenotrophomonas maltophilia

<400> SEQUENCE: 1032
ccagggtcag gcaggcgaca acgctggcct gctgctgcgc ggcaccaagc gtgacgacgt 60

<210> SEQ ID NO 1033
<211> LENGTH: 60
<212> TYPE: DNA
<213> ORGANISM: Pseudomonas aeruginosa

<400> SEQUENCE: 1033
cgaaggtcgt gctggtgaga acgttggtat cctgctgcgt ggcaccaagc gtgaagacgt 60

<210> SEQ ID NO 1034
<211> LENGTH: 60
<212> TYPE: DNA
<213> ORGANISM: Klebsiella pneumoniae

<400> SEQUENCE: 1034
cgaaggccgt gctggtgaga acgtaggtgt tctgctgcgt ggtatcaaac gtgaagaaat 60

<210> SEQ ID NO 1035
<211> LENGTH: 60
<212> TYPE: DNA
<213> ORGANISM: Mycobacterium avium

<400> SEQUENCE: 1035
ccagggccag gccggtgaca acgtcggtct gctgctgcgt ggtatcaagc gtgaggacgt 60

<210> SEQ ID NO 1036
<211> LENGTH: 60
<212> TYPE: DNA
<213> ORGANISM: Mycobacterium avium

<400> SEQUENCE: 1036
ccagggccag gccggtgaca acgtcggtct gctgctgcgt ggtatcaagc gtgaggacgt 60

<210> SEQ ID NO 1037
<211> LENGTH: 60
<212> TYPE: DNA
<213> ORGANISM: Mycobacterium intracellulare

<400> SEQUENCE: 1037
ccagggacag gccggcgaca acgtcggact gttgctgcgt ggcatcaagc gcgaggacgt 60

<210> SEQ ID NO 1038
<211> LENGTH: 60
<212> TYPE: DNA
<213> ORGANISM: Mycobacterium kansasii

<400> SEQUENCE: 1038
ccagggtcag gccggtgaca acgtcgggct gttgctgcgt ggtgtcaagc gtgaggacgt 60

<210> SEQ ID NO 1039
<211> LENGTH: 60
<212> TYPE: DNA
<213> ORGANISM: Mycobacterium tuberculosis

<400> SEQUENCE: 1039
ccagggccag gcgggcgaca acgttggttt gctgctgcgg ggcgtcaagc gcgaggacgt 60

<210> SEQ ID NO 1040
<211> LENGTH: 60
<212> TYPE: DNA
<213> ORGANISM: Mycobacterium tuberculosis

<400> SEQUENCE: 1040
ccagggccag gcgggcgaca acgttggttt gctgctgcgg ggcgtcaagc gcgaggacgt 60

<210> SEQ ID NO 1041
<211> LENGTH: 60
<212> TYPE: DNA
<213> ORGANISM: Mycobacterium avium

<400> SEQUENCE: 1041
ccagggccag gccggcgaca acgtcggtct gctggttcgt ggcatcaagc gcgaggacgt 60

<210> SEQ ID NO 1042
<211> LENGTH: 60
<212> TYPE: DNA
<213> ORGANISM: Corynebacterium diphtheriae

<400> SEQUENCE: 1042
ctacaccgag gctggcgaca actgtggtct gcttctccgt ggcgttaagc gcgaagacgt 60

<210> SEQ ID NO 1043
<211> LENGTH: 60
<212> TYPE: DNA
<213> ORGANISM: Neisseria meningitidis

<400> SEQUENCE: 1043
cgaaggtcag gcgggcgaca acgtaggcgt attgctgcgc ggtaccaaac gtgaagacgt 60

<210> SEQ ID NO 1044
<211> LENGTH: 60
<212> TYPE: DNA
<213> ORGANISM: Neisseria meningitidis

<400> SEQUENCE: 1044
cgaaggtcaa gcaggcgaca acgtaggcgt attgctgcgc ggtaccaaac gtgaagacgt 60

<210> SEQ ID NO 1045
<211> LENGTH: 60
<212> TYPE: DNA
<213> ORGANISM: Neisseria meningitidis

<400> SEQUENCE: 1045
cgaaggtcag gcgggcgaca acgtacgcgt attgctgcgc ggtaccaaac gtgaagacgt 60

<210> SEQ ID NO 1046
<211> LENGTH: 59
<212> TYPE: DNA
<213> ORGANISM: Mycoplasma pneumoniae

<400> SEQUENCE: 1046
tgaacgtgga caagtattag ctaaacctgg ttcaattaaa cctcacaaac aatttgaag 59

<210> SEQ ID NO 1047
<211> LENGTH: 59
<212> TYPE: DNA
<213> ORGANISM: Mycoplasma pneumoniae

<400> SEQUENCE: 1047
ggaacgtggt caagtgttag ctaaaccagg ttcgattaaa ccgcacaaga aatttaaag 59

<210> SEQ ID NO 1048
<211> LENGTH: 59
<212> TYPE: DNA
<213> ORGANISM: Legionella pneumophila

<400> SEQUENCE: 1048
ggagcgtgga caggtattgg caaagccagg taccatcaag ccacacacca agtttgaag 59

<210> SEQ ID NO 1049
<211> LENGTH: 59
<212> TYPE: DNA
<213> ORGANISM: Legionella pneumophila

<400> SEQUENCE: 1049
ggagcgtgga caggtattgg ctaagccagg taccatcaag ccacacacca agtttgaag 59

<210> SEQ ID NO 1050
<211> LENGTH: 59
<212> TYPE: DNA
<213> ORGANISM: Legionella pneumophila

<400> SEQUENCE: 1050
ggagcgtgga caggtattgg cgaagccagg aaccatcaag ccacacacca agtttgaag 59

<210> SEQ ID NO 1051
<211> LENGTH: 59
<212> TYPE: DNA
<213> ORGANISM: Legionella pneumophila

<400> SEQUENCE: 1051
ggagcgcgga caggtattgg ctaagccagg aaccatcaag ccacacacca agtttgaag 59

<210> SEQ ID NO 1052
<211> LENGTH: 59
<212> TYPE: DNA
<213> ORGANISM: Legionella longbeachiae

<400> SEQUENCE: 1052
tgagcgtggt caggtattag ccaaaccagg tacaattaag cctcacacta aatttgaag 59

<210> SEQ ID NO 1053
<211> LENGTH: 59
<212> TYPE: DNA
<213> ORGANISM: Fusobacterium nucleatum

<400> SEQUENCE: 1053
tgaaagagga caagttcttg ctaaaccagg aagtatccac cctcatacaa actttaaag 59

<210> SEQ ID NO 1054
<211> LENGTH: 59
<212> TYPE: DNA
<213> ORGANISM: Chlamydophila pneumoniae

<400> SEQUENCE: 1054
tgaaagaggt atggtggttt gtcagcctaa cagcgtgaag cctcatacga aatttaagt 59

<210> SEQ ID NO 1055
<211> LENGTH: 59
<212> TYPE: DNA
<213> ORGANISM: Enterococcus faecalis

<400> SEQUENCE: 1055
cgaacgtgga caagtattag ctaaaccagc tacaatcact ccacacacaa aattcaaag 59

<210> SEQ ID NO 1056
<211> LENGTH: 59
<212> TYPE: DNA
<213> ORGANISM: Enterococcus faecalis

<400> SEQUENCE: 1056
cgaacgtgga caagtattag ctaaaccagc tacaatcact ccacacacaa aattcaaag 59

<210> SEQ ID NO 1057
<211> LENGTH: 59
<212> TYPE: DNA
<213> ORGANISM: Staphylococcus aureus

<400> SEQUENCE: 1057
acaacgtggt caagtattag ctgctcctgg ttcaattaca ccacatactg aatttaaag 59

<210> SEQ ID NO 1058
<211> LENGTH: 59
<212> TYPE: DNA
<213> ORGANISM: Staphylococcus aureus

<400> SEQUENCE: 1058
acaacgtggt caagtattag ctgctcctgg ttcaattaca ccacatactg aatttaaag 59

<210> SEQ ID NO 1059
<211> LENGTH: 59
<212> TYPE: DNA
<213> ORGANISM: Staphylococcus aureus

<400> SEQUENCE: 1059
acaacgtggt caagtattag ctgctcctgg ttcaattaca ccacatactg aattcaaag 59

<210> SEQ ID NO 1060
<211> LENGTH: 59
<212> TYPE: DNA
<213> ORGANISM: Staphylococcus aureus

<400> SEQUENCE: 1060
acaacgtggt caagtattag ctgctcctgg ttcaattaca ccacatactg aattcaaag 59

<210> SEQ ID NO 1061
<211> LENGTH: 59
<212> TYPE: DNA
<213> ORGANISM: Staphylococcus aureus

<400> SEQUENCE: 1061
acaacgtggt caagtattag ctgctcctgg ttcaattaca ccacatactg aattcaaag 59

<210> SEQ ID NO 1062
<211> LENGTH: 59
<212> TYPE: DNA
<213> ORGANISM: Staphylococcus epidermidis

<400> SEQUENCE: 1062
acaacgtggt caagtattag ctgctcctgg ttctattaca ccacacacaa aattcaaag 59

<210> SEQ ID NO 1063
<211> LENGTH: 59
<212> TYPE: DNA
<213> ORGANISM: Staphylococcus epidermidis

<400> SEQUENCE: 1063
acaacgtggt caagtattag ctgctcctgg ttctattaca ccacacacaa aattcaaag 59

<210> SEQ ID NO 1064
<211> LENGTH: 59
<212> TYPE: DNA
<213> ORGANISM: Streptococcus mitis

<400> SEQUENCE: 1064
cgaacgtgga caagttatcg ctaaaccagg ttcaatcaac ccacacacta aattcaaag 59

<210> SEQ ID NO 1065
<211> LENGTH: 59
<212> TYPE: DNA
<213> ORGANISM: Streptococcus sanguis

<400> SEQUENCE: 1065
cgaacgtgga caagttatcg ctaaaccagg ttcaatcaac ccacacacta aattcaagg 59

<210> SEQ ID NO 1066
<211> LENGTH: 59
<212> TYPE: DNA
<213> ORGANISM: Streptococcus mitis

<400> SEQUENCE: 1066
cgaacgtgga caagttattg ctaaaccagg ttcaatcaac ccacacacta aattcaaag 59

<210> SEQ ID NO 1067
<211> LENGTH: 59
<212> TYPE: DNA
<213> ORGANISM: Streptococcus pneumoniae

<400> SEQUENCE: 1067
cgaacgtgga caagttatcg ctaaaccagg ttcaatcaac ccacacacta aattcaaag 59

<210> SEQ ID NO 1068
<211> LENGTH: 59
<212> TYPE: DNA
<213> ORGANISM: Streptococcus pyogenes

<400> SEQUENCE: 1068
cgaacgtggt caagttattg ctaaaccaag ttcaatcaac ccacacacta aattcaaag 59

<210> SEQ ID NO 1069
<211> LENGTH: 59
<212> TYPE: DNA
<213> ORGANISM: Streptococcus mutans

<400> SEQUENCE: 1069
cgaacgtggt caagttcttg ctaaaccagg ttcaattcac ccacatacta aattcaaag 59

<210> SEQ ID NO 1070
<211> LENGTH: 59
<212> TYPE: DNA
<213> ORGANISM: Streptococcus mutans

<400> SEQUENCE: 1070
cgaacgtggt caagttcttg ctaaaccagg ttcaattcac ccacatacta aattcaaag 59

<210> SEQ ID NO 1071
<211> LENGTH: 59
<212> TYPE: DNA
<213> ORGANISM: Haemophilus influenzae

<400> SEQUENCE: 1071
cgaacgtggt caagtattag cgaaaccagg ttcaatcaca ccacacactg acttcgaat 59

<210> SEQ ID NO 1072
<211> LENGTH: 59
<212> TYPE: DNA
<213> ORGANISM: Moraxella catarrhalis

<400> SEQUENCE: 1072
tcaacgtggt caagtattgg ctaagccagg ttcaatcacc ccacacacca agtttgatg 59

<210> SEQ ID NO 1073
<211> LENGTH: 59
<212> TYPE: DNA
<213> ORGANISM: Bordetella pertussis

<400> SEQUENCE: 1073
cgagcgtggc caggtgctgg ccaagccggg ttcgatcaac ccgcacacgg acttcacgg 59

<210> SEQ ID NO 1074
<211> LENGTH: 59
<212> TYPE: DNA
<213> ORGANISM: Bordetella parapertussis

<400> SEQUENCE: 1074
cgagcgtggc caggtgctgg ccaagccggg ttcgatcaac ccgcacacgg acttcacgg 59

<210> SEQ ID NO 1075
<211> LENGTH: 59
<212> TYPE: DNA
<213> ORGANISM: Burkholderia cepacia

<400> SEQUENCE: 1075
ggagcgcggt caggttctgg cgaagccggg ttcgatcacg ccgcacacgc acttcacgg 59

<210> SEQ ID NO 1076
<211> LENGTH: 59
<212> TYPE: DNA
<213> ORGANISM: Burkholderia pseudomallei

<400> SEQUENCE: 1076
ggagcgcggc caggttctgg cgaagccggg ttcgatcacg ccgcacacgc acttcacgg 59

<210> SEQ ID NO 1077
<211> LENGTH: 59
<212> TYPE: DNA
<213> ORGANISM: Stenotrophomonas maltophilia

<400> SEQUENCE: 1077
cgagcgtggc caggtgctgg ccaagccggg cacgatcaag ccgcacacca agttcgaag 59

<210> SEQ ID NO 1078
<211> LENGTH: 59
<212> TYPE: DNA
<213> ORGANISM: Pseudomonas aeruginosa

<400> SEQUENCE: 1078
agagcgtggc caggtactgg ccaagccggg caccatcaag ccgcacacca agttcgagt 59

<210> SEQ ID NO 1079
<211> LENGTH: 59
<212> TYPE: DNA
<213> ORGANISM: Klebsiella pneumoniae

<400> SEQUENCE: 1079
cgaacgtggt caggtactgg ctaagccggg caccatcaac ccgcacacca agttcgaat 59

<210> SEQ ID NO 1080
<211> LENGTH: 59
<212> TYPE: DNA
<213> ORGANISM: Mycobacterium avium

<400> SEQUENCE: 1080
cgagcgcggt caggtcgtca ccaagcccgg caccaccacg ccgcacaccg agttcgagg 59

<210> SEQ ID NO 1081
<211> LENGTH: 59
<212> TYPE: DNA
<213> ORGANISM: Mycobacterium avium

<400> SEQUENCE: 1081
cgagcgcggt caggtcgtca ccaagcccgg caccaccacg ccgcacaccg agttcgagg 59

<210> SEQ ID NO 1082
<211> LENGTH: 59
<212> TYPE: DNA
<213> ORGANISM: Mycobacterium intracellulare

<400> SEQUENCE: 1082
cgagcgcggt caggtcgtcg tgaagcccgg caccaccacg ccgcacaccg agttcgagg 59

<210> SEQ ID NO 1083
<211> LENGTH: 59
<212> TYPE: DNA
<213> ORGANISM: Mycobacterium kansasii

<400> SEQUENCE: 1083
cgagcgcggc caggtcgtca tcaagcccgg caccacaacc ccgcacaccg agttcgagg 59

<210> SEQ ID NO 1084
<211> LENGTH: 59
<212> TYPE: DNA
<213> ORGANISM: Mycobacterium tuberculosis

<400> SEQUENCE: 1084
cgagcgtggc caggttgtca ccaagcccgg caccaccacg ccgcacaccg agttcgaag 59

<210> SEQ ID NO 1085
<211> LENGTH: 59
<212> TYPE: DNA
<213> ORGANISM: Mycobacterium tuberculosis

<400> SEQUENCE: 1085
cgagcgtggc caggttgtca ccaagcccgg caccaccacg ccgcacaccg agttcgaag 59

<210> SEQ ID NO 1086
<211> LENGTH: 59
<212> TYPE: DNA
<213> ORGANISM: Mycobacterium avium

<400> SEQUENCE: 1086
cgagcgtggc caggttgtgg tcaagcccgg caccaccacc ccgcacaccg agttcgagg 59

<210> SEQ ID NO 1087
<211> LENGTH: 59
<212> TYPE: DNA
<213> ORGANISM: Corynebacterium diphtheriae

<400> SEQUENCE: 1087
tgagcgtggc caggttgttg ttaagccagg cgcttacacc cctcacaccg agttcgagg 59

<210> SEQ ID NO 1088
<211> LENGTH: 59
<212> TYPE: DNA
<213> ORGANISM: Neisseria meningitidis

<400> SEQUENCE: 1088
ggaacgcggt caggtattgg ctaaaccggg tactatcact cctcacacca aattcaaag 59

<210> SEQ ID NO 1089
<211> LENGTH: 59
<212> TYPE: DNA
<213> ORGANISM: Neisseria meningitidis

<400> SEQUENCE: 1089
agagcgtggt caagtattgg ctaaaccggg tacaatcact cctcacacca agttcaaag 59

<210> SEQ ID NO 1090
<211> LENGTH: 60
<212> TYPE: DNA
<213> ORGANISM: Neisseria meningitidis

<400> SEQUENCE: 1090
ggaacgcggt caggtattgg ccaaacccgg gtactatcac tcctcacacc aagttcaaag 60

<210> SEQ ID NO 1091
<211> LENGTH: 60
<212> TYPE: DNA
<213> ORGANISM: Mycoplasma pneumoniae

<400> SEQUENCE: 1091
cagaaatcta tgctcttaaa aaagaagaag gtggaagaca tactccagta ttaaatggat 60

<210> SEQ ID NO 1092
<211> LENGTH: 60
<212> TYPE: DNA
<213> ORGANISM: Mycoplasma pneumoniae

<400> SEQUENCE: 1092
cggaaatcta tgctttaaag aaggaagaag gtggtcgtca caccggtttc ttaaacggtt 60

<210> SEQ ID NO 1093
<211> LENGTH: 60
<212> TYPE: DNA
<213> ORGANISM: Legionella pneumophila

<400> SEQUENCE: 1093
cagaagtgta tgtgttatcc aaggaagaag gcggacgtca cacaccattc tttaatggat 60

<210> SEQ ID NO 1094
<211> LENGTH: 60
<212> TYPE: DNA
<213> ORGANISM: Legionella pneumophila

<400> SEQUENCE: 1094
cagaagtgta tgtattatcc aaggaagaag gcggacgtca cacaccattc tttaatggat 60

<210> SEQ ID NO 1095
<211> LENGTH: 60
<212> TYPE: DNA
<213> ORGANISM: Legionella pneumophila

<400> SEQUENCE: 1095
cagaagtgta tgtattatcc aaggaagaag gcggacgtca cactccattc tttaatggat 60

<210> SEQ ID NO 1096
<211> LENGTH: 60
<212> TYPE: DNA
<213> ORGANISM: Legionella pneumophila

<400> SEQUENCE: 1096
cagaagtgta tgtattatcg aaggaagaag gcggacgtca cactccattc tttaatggat 60

<210> SEQ ID NO 1097
<211> LENGTH: 60
<212> TYPE: DNA
<213> ORGANISM: Legionella longbeachiae

<400> SEQUENCE: 1097
cggaagtata cgtgttatct aaagaagaag gtggacgaca taccccgttt ttcaatggat 60

<210> SEQ ID NO 1098
<211> LENGTH: 60
<212> TYPE: DNA
<213> ORGANISM: Fusobacterium nucleatum

<400> SEQUENCE: 1098
gtgaagtcta tgtattaact aaagatgaag gaggaagaca cactccattt ttcacaggat 60

<210> SEQ ID NO 1099
<211> LENGTH: 60
<212> TYPE: DNA
<213> ORGANISM: Chlamydophila pneumoniae

<400> SEQUENCE: 1099
cagctgttta cgttcttcag aaagaagaag gcggacgtca taagcctttc ttcagcggat 60

<210> SEQ ID NO 1100
<211> LENGTH: 60
<212> TYPE: DNA
<213> ORGANISM: Enterococcus faecalis

<400> SEQUENCE: 1100
ctgaagtata cgtattatca aaagaagaag gcggacgtca cactccattc ttcactaact 60

<210> SEQ ID NO 1101
<211> LENGTH: 60
<212> TYPE: DNA
<213> ORGANISM: Enterococcus faecalis

<400> SEQUENCE: 1101
ctgaagtata cgtattatca aaagaagaag gcggacgtca cactccattc ttcactaact 60

<210> SEQ ID NO 1102
<211> LENGTH: 60
<212> TYPE: DNA
<213> ORGANISM: Staphylococcus aureus

<400> SEQUENCE: 1102
cagaagtata cgtattatca aaagacgaag gtggacgtca cactccattc ttctcaaact 60

<210> SEQ ID NO 1103
<211> LENGTH: 60
<212> TYPE: DNA
<213> ORGANISM: Staphylococcus aureus

<400> SEQUENCE: 1103
cagaagtata cgtattatca aaagacgaag gtggacgtca cactccattc ttctcaaact 60

<210> SEQ ID NO 1104
<211> LENGTH: 60
<212> TYPE: DNA
<213> ORGANISM: Staphylococcus aureus

<400> SEQUENCE: 1104
cagaagtata cgtattatca aaagacgaag gtggacgtca cactccattc ttctcaaact 60

<210> SEQ ID NO 1105
<211> LENGTH: 60
<212> TYPE: DNA
<213> ORGANISM: Staphylococcus aureus

<400> SEQUENCE: 1105
cagaagtata cgtattatca aaagacgaag gtggacgtca cactccattc ttctcaaact 60

<210> SEQ ID NO 1106
<211> LENGTH: 60
<212> TYPE: DNA
<213> ORGANISM: Staphylococcus aureus

<400> SEQUENCE: 1106
cagaagtata cgtattatca aaagacgaag gtggacgtca cactccattc ttctcaaact 60

<210> SEQ ID NO 1107
<211> LENGTH: 60
<212> TYPE: DNA
<213> ORGANISM: Staphylococcus epidermidis

<400> SEQUENCE: 1107
ctgaagtata cgtattatct aaagatgaag gtggacgtca cactccattc ttcactaact 60

<210> SEQ ID NO 1108
<211> LENGTH: 60
<212> TYPE: DNA
<213> ORGANISM: Staphylococcus epidermidis

<400> SEQUENCE: 1108
ctgaagtata cgtattatct aaagatgaag gtggacgtca cactccattc ttcactaact 60

<210> SEQ ID NO 1109
<211> LENGTH: 60
<212> TYPE: DNA
<213> ORGANISM: Streptococcus mitis

<400> SEQUENCE: 1109
gtgaagttta catccttact aaagaagaag gtggacgtca tactccattc ttcaacaact 60

<210> SEQ ID NO 1110
<211> LENGTH: 60
<212> TYPE: DNA
<213> ORGANISM: Streptococcus sanguis

<400> SEQUENCE: 1110
gtgaagttta tatccttact aaagaagaag gcggacgtca cactccattc ttcaacaact 60

<210> SEQ ID NO 1111
<211> LENGTH: 60
<212> TYPE: DNA
<213> ORGANISM: Streptococcus mitis

<400> SEQUENCE: 1111
gtgaagttta catccttact aaagaagaag gtggacgtca cactccattc ttcaacaact 60

<210> SEQ ID NO 1112
<211> LENGTH: 60
<212> TYPE: DNA
<213> ORGANISM: Streptococcus pneumoniae

<400> SEQUENCE: 1112
gtgaagtcta catccttact aaagaagaag gtggacgtca cactccattc ttcaacaact 60

<210> SEQ ID NO 1113
<211> LENGTH: 60
<212> TYPE: DNA
<213> ORGANISM: Streptococcus pyogenes

<400> SEQUENCE: 1113
gtgaagtata tatcctttct aaagacgaag gtggacgtca cactccattc ttcaacaact 60

<210> SEQ ID NO 1114
<211> LENGTH: 60
<212> TYPE: DNA
<213> ORGANISM: Streptococcus mutans

<400> SEQUENCE: 1114
gtgaagttta tatccttact aaagaagaag gtggacgtca tacaccattc ttcaataact 60

<210> SEQ ID NO 1115
<211> LENGTH: 60
<212> TYPE: DNA
<213> ORGANISM: Streptococcus mutans

<400> SEQUENCE: 1115
gtgaagttta tatccttact aaagaggaag gtggacgtca tacaccattc ttcaataact 60

<210> SEQ ID NO 1116
<211> LENGTH: 60
<212> TYPE: DNA
<213> ORGANISM: Haemophilus influenzae

<400> SEQUENCE: 1116
cagaagtgta cgtattatca aaagatgaag gtggtcgtca tactccattc ttcaaaggtt 60

<210> SEQ ID NO 1117
<211> LENGTH: 60
<212> TYPE: DNA
<213> ORGANISM: Moraxella catarrhalis

<400> SEQUENCE: 1117
cagaagtata cgtgctatca aaagaagaag gtggtcgtca taccccattc ctaaatggct 60

<210> SEQ ID NO 1118
<211> LENGTH: 60
<212> TYPE: DNA
<213> ORGANISM: Bordetella pertussis

<400> SEQUENCE: 1118
ccgaggtgta cattctgtcc aaggaagagg gtggccgtca cacgccgttc ttcaacggct 60

<210> SEQ ID NO 1119
<211> LENGTH: 60
<212> TYPE: DNA
<213> ORGANISM: Bordetella parapertussis

<400> SEQUENCE: 1119
ccgaggtgta cattctgtcc aaggaagagg gcggccgtca cacgccgttc ttcaacggct 60

<210> SEQ ID NO 1120
<211> LENGTH: 60
<212> TYPE: DNA
<213> ORGANISM: Burkholderia cepacia

<400> SEQUENCE: 1120
ccgaagtgta cgtgctgagc aaggacgaag gcggccgtca cacgccgttc ttcaacaact 60

<210> SEQ ID NO 1121
<211> LENGTH: 60
<212> TYPE: DNA
<213> ORGANISM: Burkholderia pseudomallei

<400> SEQUENCE: 1121
ctgaagtgta cgtgctgagc aaggacgaag gcggccgcca cacgccgttc ttcaacaact 60

<210> SEQ ID NO 1122
<211> LENGTH: 60
<212> TYPE: DNA
<213> ORGANISM: Stenotrophomonas maltophilia

<400> SEQUENCE: 1122
gcgaagtgta cgtcctgtcg aaggacgaag gcggccgcca caccccgttc ttcaacggct 60

<210> SEQ ID NO 1123
<211> LENGTH: 60
<212> TYPE: DNA
<213> ORGANISM: Pseudomonas aeruginosa

<400> SEQUENCE: 1123
gcgaagtgta cgtgctgtcc aaggaagaag gtggtcgtca caccccgttc ttcaagggct 60

<210> SEQ ID NO 1124
<211> LENGTH: 60
<212> TYPE: DNA
<213> ORGANISM: Klebsiella pneumoniae

<400> SEQUENCE: 1124
ctgaagtgta catcctgtcc aaagacgaag gcggccgtca tactccgttc ttcaaaggct 60

<210> SEQ ID NO 1125
<211> LENGTH: 60
<212> TYPE: DNA
<213> ORGANISM: Mycobacterium avium

<400> SEQUENCE: 1125
gccaggtcta catcctgtcc aaggacgagg gcggccggca cacgccgttc ttcaacaact 60

<210> SEQ ID NO 1126
<211> LENGTH: 60
<212> TYPE: DNA
<213> ORGANISM: Mycobacterium avium

<400> SEQUENCE: 1126
gccaggtcta catcctgtcc aaggacgagg gcggccggca cacgccgttc ttcaacaact 60

<210> SEQ ID NO 1127
<211> LENGTH: 60
<212> TYPE: DNA
<213> ORGANISM: Mycobacterium intracellulare

<400> SEQUENCE: 1127
gcagcgtcta catcctgtcc aaggacgagg gcggccggca cacgccgttc ttcaacaact 60

<210> SEQ ID NO 1128
<211> LENGTH: 60
<212> TYPE: DNA
<213> ORGANISM: Mycobacterium kansasii

<400> SEQUENCE: 1128
gccaggttta catcctgtcc aaggacgagg gtggccggca cacgccgttc ttcaacaact 60

<210> SEQ ID NO 1129
<211> LENGTH: 60
<212> TYPE: DNA
<213> ORGANISM: Mycobacterium tuberculosis

<400> SEQUENCE: 1129
gccaggtcta catcctgtcc aaggacgagg gcggccggca cacgccgttc ttcaacaact 60

<210> SEQ ID NO 1130
<211> LENGTH: 60
<212> TYPE: DNA
<213> ORGANISM: Mycobacterium tuberculosis

<400> SEQUENCE: 1130
gccaggtcta catcctgtcc aaggacgagg gcggccggca cacgccgttc ttcaacaact 60

<210> SEQ ID NO 1131
<211> LENGTH: 60
<212> TYPE: DNA
<213> ORGANISM: Mycobacterium avium

<400> SEQUENCE: 1131
gcagcgtcta catcctgtcc aaggacgagg gcggccgcca cacgccgttc ttcaacaact 60

<210> SEQ ID NO 1132
<211> LENGTH: 60
<212> TYPE: DNA
<213> ORGANISM: Corynebacterium diphtheriae

<400> SEQUENCE: 1132
gctctgtcta cgttctgtcc aaggacgagg gtggccgcca caccccattc ttcgacaact 60

<210> SEQ ID NO 1133
<211> LENGTH: 60
<212> TYPE: DNA
<213> ORGANISM: Neisseria meningitidis

<400> SEQUENCE: 1133
cagaagtata cgtactgagc aaagaagagg gtggtcgtca cactccgttc ttcgccaact 60

<210> SEQ ID NO 1134
<211> LENGTH: 60
<212> TYPE: DNA
<213> ORGANISM: Neisseria meningitidis

<400> SEQUENCE: 1134
cagaagtata cgtactgagc aaagaagagg gcggccgcca taccccgttc ttcgccaact 60

<210> SEQ ID NO 1135
<211> LENGTH: 60
<212> TYPE: DNA
<213> ORGANISM: Neisseria meningitidis

<400> SEQUENCE: 1135
cagacgtgta cgtactgagc aaagaagagg gcggccgcca tactccgttc ttcgccaact 60

<210> SEQ ID NO 1136
<211> LENGTH: 60
<212> TYPE: DNA
<213> ORGANISM: Mycoplasma pneumoniae

<400> SEQUENCE: 1136
atagaccaca attctacttc agaactactg atgttactgg acaaatcaca cttgataaag 60

<210> SEQ ID NO 1137
<211> LENGTH: 60
<212> TYPE: DNA
<213> ORGANISM: Mycoplasma pneumoniae

<400> SEQUENCE: 1137
accgtcccca attctacttc cgtactacag acgttactgg ttcgatttcc ctaccagaaa 60

<210> SEQ ID NO 1138
<211> LENGTH: 60
<212> TYPE: DNA
<213> ORGANISM: Legionella pneumophila

<400> SEQUENCE: 1138
accgtccaca attctatttc agaaccactg acgtgacagg tacttgtgac ttgccatcag 60

<210> SEQ ID NO 1139
<211> LENGTH: 38
<212> TYPE: DNA
<213> ORGANISM: Legionella pneumophila

<400> SEQUENCE: 1139
accgtccaca attctatttc agaaccactg acgtaaca 38

<210> SEQ ID NO 1140
<211> LENGTH: 60
<212> TYPE: DNA
<213> ORGANISM: Legionella pneumophila

<400> SEQUENCE: 1140
accgtccaca attctatttc agaaccactg acgtgacagg tacttgtgac ttgccatcag 60

<210> SEQ ID NO 1141
<211> LENGTH: 60
<212> TYPE: DNA
<213> ORGANISM: Legionella pneumophila

<400> SEQUENCE: 1141
accgtccaca attctatttc agaaccactg acgtgacagg tacttgtgac ttgccatcag 60

<210> SEQ ID NO 1142
<211> LENGTH: 60
<212> TYPE: DNA
<213> ORGANISM: Legionella longbeachiae

<400> SEQUENCE: 1142
atagaccaca gttttatttt agaacaacag acgtaacagg aacttgtgat ttaccatctg 60

<210> SEQ ID NO 1143
<211> LENGTH: 60
<212> TYPE: DNA
<213> ORGANISM: Fusobacterium nucleatum

<400> SEQUENCE: 1143
acagacctca attctatttt agaactactg atatcactgg tgcagtaact ttaccagatg 60

<210> SEQ ID NO 1144
<211> LENGTH: 60
<212> TYPE: DNA
<213> ORGANISM: Chlamydophila pneumoniae

<400> SEQUENCE: 1144
acagacctca gttcttcttc cgtactacag acgtgacagg agtcgtaact cttcctgaag 60

<210> SEQ ID NO 1145
<211> LENGTH: 60
<212> TYPE: DNA
<213> ORGANISM: Enterococcus faecalis

<400> SEQUENCE: 1145
accgtcctca attctacttc cgtacaacag acgttactgg tgttgtagaa ttgccagaag 60

<210> SEQ ID NO 1146
<211> LENGTH: 60
<212> TYPE: DNA
<213> ORGANISM: Enterococcus faecalis

<400> SEQUENCE: 1146
accgtcctca attctacttc cgtacaacag acgttactgg tgttgtagaa ttgccagaag 60

<210> SEQ ID NO 1147
<211> LENGTH: 60
<212> TYPE: DNA
<213> ORGANISM: Staphylococcus aureus

<400> SEQUENCE: 1147
atcgtccaca attctatttc cgtactactg acgtaactgg tgttgttcac ttaccagaag 60

<210> SEQ ID NO 1148
<211> LENGTH: 60
<212> TYPE: DNA
<213> ORGANISM: Staphylococcus aureus

<400> SEQUENCE: 1148
atcgtccaca attctatttc cgtactactg acgtaactgg tgttgttcac ttaccagaag 60

<210> SEQ ID NO 1149
<211> LENGTH: 60
<212> TYPE: DNA
<213> ORGANISM: Staphylococcus aureus

<400> SEQUENCE: 1149
atcgtccaca attctatttc cgtactactg acgtaactgg tgttgttcac ttaccagaag 60

<210> SEQ ID NO 1150
<211> LENGTH: 60
<212> TYPE: DNA
<213> ORGANISM: Staphylococcus aureus

<400> SEQUENCE: 1150
atcgtccaca attctatttc cgtactactg acgtaactgg tgttgttcac ttaccagaag 60

<210> SEQ ID NO 1151
<211> LENGTH: 60
<212> TYPE: DNA
<213> ORGANISM: Staphylococcus aureus

<400> SEQUENCE: 1151
atcgtccaca attctatttc cgtactactg acgtaactgg tgttgttcac ttaccagaag 60

<210> SEQ ID NO 1152
<211> LENGTH: 60
<212> TYPE: DNA
<213> ORGANISM: Staphylococcus epidermidis

<400> SEQUENCE: 1152
atcgcccaca attctatttc cgtactactg acgtaactgg tgttgtaaac ttaccagaag 60

<210> SEQ ID NO 1153
<211> LENGTH: 60
<212> TYPE: DNA
<213> ORGANISM: Staphylococcus epidermidis

<400> SEQUENCE: 1153
atcgcccaca attctatttc cgtactactg acgtaactgg tgttgtaaac ttaccagaag 60

<210> SEQ ID NO 1154
<211> LENGTH: 60
<212> TYPE: DNA
<213> ORGANISM: Streptococcus mitis

<400> SEQUENCE: 1154
accgtccaca gttctacttc cgtacaactg acgtaactgg atctatcgaa cttccagctg 60

<210> SEQ ID NO 1155
<211> LENGTH: 60
<212> TYPE: DNA
<213> ORGANISM: Streptococcus sanguis

<400> SEQUENCE: 1155
accgtccaca gttctacttc cgtacaactg acgttacagg ttcaatcgaa cttccagcag 60

<210> SEQ ID NO 1156
<211> LENGTH: 60
<212> TYPE: DNA
<213> ORGANISM: Streptococcus mitis

<400> SEQUENCE: 1156
accgtccaca attctacttc cgtactactg acgttacagg ttcaatcgaa cttccagcag 60

<210> SEQ ID NO 1157
<211> LENGTH: 60
<212> TYPE: DNA
<213> ORGANISM: Streptococcus pneumoniae

<400> SEQUENCE: 1157
accgtccaca attctacttc cgtactactg acgttacagg ttcaatcgaa cttccagcag 60

<210> SEQ ID NO 1158
<211> LENGTH: 60
<212> TYPE: DNA
<213> ORGANISM: Streptococcus pyogenes

<400> SEQUENCE: 1158
accgtccaca attctacttc cgtacaactg acgtaacagg ttcaatcgaa cttccagcag 60

<210> SEQ ID NO 1159
<211> LENGTH: 60
<212> TYPE: DNA
<213> ORGANISM: Streptococcus mutans

<400> SEQUENCE: 1159
atcgtccaca attctacttc cgtacaactg acgtaactgg ttcaattgag ttgccagcag 60

<210> SEQ ID NO 1160
<211> LENGTH: 60
<212> TYPE: DNA
<213> ORGANISM: Streptococcus mutans

<400> SEQUENCE: 1160
atcgtccaca attctacttc cgtacaactg acgtaactgg ttcaattgag ttgccagcag 60

<210> SEQ ID NO 1161
<211> LENGTH: 60
<212> TYPE: DNA
<213> ORGANISM: Haemophilus influenzae

<400> SEQUENCE: 1161
accgtccaca attctatttc cgtacaacag acgtgactgg tacaatcgaa ttaccagaag 60

<210> SEQ ID NO 1162
<211> LENGTH: 60
<212> TYPE: DNA
<213> ORGANISM: Moraxella catarrhalis

<400> SEQUENCE: 1162
atcgtccaca gttctacttc cgtaccacag acgtaactgg tgccatcacc ctacaagaag 60

<210> SEQ ID NO 1163
<211> LENGTH: 60
<212> TYPE: DNA
<213> ORGANISM: Bordetella pertussis

<400> SEQUENCE: 1163
atcgtccgca gttctacttc cgcacgacgg acgtgaccgg cacgatcgac ctgccggcgg 60

<210> SEQ ID NO 1164
<211> LENGTH: 60
<212> TYPE: DNA
<213> ORGANISM: Bordetella parapertussis

<400> SEQUENCE: 1164
atcgtccgca gttctacttc cgcacgacgg acgtgaccgg cacgatcgac ctgccggcgg 60

<210> SEQ ID NO 1165
<211> LENGTH: 13
<212> TYPE: DNA
<213> ORGANISM: Burkholderia cepacia

<400> SEQUENCE: 1165
accgtccgca gtt 13

<210> SEQ ID NO 1166
<211> LENGTH: 60
<212> TYPE: DNA
<213> ORGANISM: Burkholderia pseudomallei

<400> SEQUENCE: 1166
accgtccgca gttctacttc cgtacgacgg acgtgacggg ctcgatcgag ctgccgaagg 60

<210> SEQ ID NO 1167
<211> LENGTH: 60
<212> TYPE: DNA
<213> ORGANISM: Stenotrophomonas maltophilia

<400> SEQUENCE: 1167
accgtccgca gttctacttc cgcaccaccg acatcaccgg cgcagctgcg ctgccggaag 60

<210> SEQ ID NO 1168
<211> LENGTH: 60
<212> TYPE: DNA
<213> ORGANISM: Pseudomonas aeruginosa

<400> SEQUENCE: 1168
accgtccgca gttctacttc cgtaccaccg atgtgaccgg taactgcgaa ctgccggaag 60

<210> SEQ ID NO 1169
<211> LENGTH: 60
<212> TYPE: DNA
<213> ORGANISM: Klebsiella pneumoniae

<400> SEQUENCE: 1169
accgtccgca gttctacttc cgtactactg acgtgactgg caccatcgaa ctgccggaag 60

<210> SEQ ID NO 1170
<211> LENGTH: 60
<212> TYPE: DNA
<213> ORGANISM: Mycobacterium avium

<400> SEQUENCE: 1170
accgcccgca gttctacttc cgcaccaccg acgtgaccgg tgtggtgacg ctgccggagg 60

<210> SEQ ID NO 1171
<211> LENGTH: 60
<212> TYPE: DNA
<213> ORGANISM: Mycobacterium avium

<400> SEQUENCE: 1171
accgcccgca gttctacttc cgcaccaccg acgtgaccgg tgtggtgacg ctgccggagg 60

```
<210> SEQ ID NO 1172
<211> LENGTH: 60
<212> TYPE: DNA
<213> ORGANISM: Mycobacterium intracellulare

<400> SEQUENCE: 1172

accgtccgca gttctacttc cgcaccaccg acgtgaccgg tgtggtgacg ctgccggagg      60

<210> SEQ ID NO 1173
<211> LENGTH: 60
<212> TYPE: DNA
<213> ORGANISM: Mycobacterium kansasii

<400> SEQUENCE: 1173

accgtccgca gttctacttc cgcaccaccg acgtgaccgg tgtggtgacg ctgccggagg      60

<210> SEQ ID NO 1174
<211> LENGTH: 60
<212> TYPE: DNA
<213> ORGANISM: Mycobacterium tuberculosis

<400> SEQUENCE: 1174

accgtccgca gttctacttc cgcaccaccg acgtgaccgg tgtggtgaca ctgccggagg      60

<210> SEQ ID NO 1175
<211> LENGTH: 60
<212> TYPE: DNA
<213> ORGANISM: Mycobacterium tuberculosis

<400> SEQUENCE: 1175

accgtccgca gttctacttc cgcaccaccg acgtgaccgg tgtggtgaca ctgccggagg      60

<210> SEQ ID NO 1176
<211> LENGTH: 59
<212> TYPE: DNA
<213> ORGANISM: Mycobacterium avium

<400> SEQUENCE: 1176

accgcccgca gttctacttc cgtaccacgg acgtgaccgg cgtggtgacc ctccccgag       59

<210> SEQ ID NO 1177
<211> LENGTH: 60
<212> TYPE: DNA
<213> ORGANISM: Corynebacterium diphtheriae

<400> SEQUENCE: 1177

accgcccaca gttctacttc cgcaccaccg acgttaccgg tgttgtgaag cttcctgagg      60

<210> SEQ ID NO 1178
<211> LENGTH: 60
<212> TYPE: DNA
<213> ORGANISM: Neisseria meningitidis

<400> SEQUENCE: 1178

accgtccgca attctacttc cgtaccaccg acgtaaccgg cgcggttact ttggaagaag      60

<210> SEQ ID NO 1179
<211> LENGTH: 60
<212> TYPE: DNA
<213> ORGANISM: Neisseria meningitidis

<400> SEQUENCE: 1179

accgtcccca attctacttc cgtaccaccg acgtaaccgg cgcggttact ttggaagaag      60
```

<210> SEQ ID NO 1180
<211> LENGTH: 59
<212> TYPE: DNA
<213> ORGANISM: Neisseria meningitidis

<400> SEQUENCE: 1180
accgtccgca ttctacttcc gtaccaccga cgtaaccggc gcggttactt tggaagaag 59

<210> SEQ ID NO 1181
<211> LENGTH: 60
<212> TYPE: DNA
<213> ORGANISM: Mycoplasma pneumoniae

<400> SEQUENCE: 1181
gtgttgaaat gattaaccca ggagataaca ctaagattac tgttgaactt atttctccaa 60

<210> SEQ ID NO 1182
<211> LENGTH: 60
<212> TYPE: DNA
<213> ORGANISM: Mycoplasma pneumoniae

<400> SEQUENCE: 1182
acaccgaaat ggtgctacca ggtgacaata cctcgattac agttgaacta attgcaccaa 60

<210> SEQ ID NO 1183
<211> LENGTH: 60
<212> TYPE: DNA
<213> ORGANISM: Legionella pneumophila

<400> SEQUENCE: 1183
gagttgaaat ggtaatgcct ggagataatg tgcaattagt tgttagcttg catgctccga 60

<210> SEQ ID NO 1184
<211> LENGTH: 60
<212> TYPE: DNA
<213> ORGANISM: Legionella pneumophila

<400> SEQUENCE: 1184
gagttgaaat ggtaatgcct ggagataatg tgcaattagt tgttagcttg catgctccga 60

<210> SEQ ID NO 1185
<211> LENGTH: 60
<212> TYPE: DNA
<213> ORGANISM: Legionella pneumophila

<400> SEQUENCE: 1185
gagttgaaat ggtaatgcct ggagataatg tgcaattagt tgttagcttg catgctccga 60

<210> SEQ ID NO 1186
<211> LENGTH: 38
<212> TYPE: DNA
<213> ORGANISM: Legionella longbeachiae

<400> SEQUENCE: 1186
gagttgaaat ggtaatgcct ggagataacg tacagttg 38

<210> SEQ ID NO 1187
<211> LENGTH: 21
<212> TYPE: DNA
<213> ORGANISM: Fusobacterium nucleatum

<400> SEQUENCE: 1187
gagtagaaat ggttatgcca g 21

<210> SEQ ID NO 1188
<211> LENGTH: 60
<212> TYPE: DNA
<213> ORGANISM: Chlamydophila pneumoniae

<400> SEQUENCE: 1188
gaactgaaat ggtaatgcct ggagataacg ttgagcttga tgttgagctc attggaacag 60

<210> SEQ ID NO 1189
<211> LENGTH: 31
<212> TYPE: DNA
<213> ORGANISM: Enterococcus faecalis

<400> SEQUENCE: 1189
gtactgaaat ggtaatgcct ggtgataacg t 31

<210> SEQ ID NO 1190
<211> LENGTH: 60
<212> TYPE: DNA
<213> ORGANISM: Enterococcus faecalis

<400> SEQUENCE: 1190
gtactgaaat ggtaatgcct ggtgataacg ttgctatgga cgttgaatta attcacccaa 60

<210> SEQ ID NO 1191
<211> LENGTH: 60
<212> TYPE: DNA
<213> ORGANISM: Staphylococcus aureus

<400> SEQUENCE: 1191
gtactgaaat ggtaatgcct ggtgataacg ttgaaatgac agtagaatta atcgctccaa 60

<210> SEQ ID NO 1192
<211> LENGTH: 60
<212> TYPE: DNA
<213> ORGANISM: Staphylococcus aureus

<400> SEQUENCE: 1192
gtactgaaat ggtaatgcct ggtgataacg ttgaaatgac agtagaatta atcgctccaa 60

<210> SEQ ID NO 1193
<211> LENGTH: 60
<212> TYPE: DNA
<213> ORGANISM: Staphylococcus aureus

<400> SEQUENCE: 1193
gtactgaaat ggtaatgcct ggtgataacg ttgaaatgac agtagaatta atcgctccaa 60

<210> SEQ ID NO 1194
<211> LENGTH: 60
<212> TYPE: DNA
<213> ORGANISM: Staphylococcus aureus

<400> SEQUENCE: 1194
gtactgaaat ggtaatgcct ggtgataacg ttgaaatgac agtagaatta atcgctccaa 60

<210> SEQ ID NO 1195
<211> LENGTH: 60
<212> TYPE: DNA
<213> ORGANISM: Staphylococcus aureus

<400> SEQUENCE: 1195
gtactgaaat ggtaatgcct ggtgataacg ttgaaatgac agtagaatta atcgctccaa 60

<210> SEQ ID NO 1196
<211> LENGTH: 60
<212> TYPE: DNA
<213> ORGANISM: Staphylococcus epidermidis

<400> SEQUENCE: 1196
gtacagaaat ggttatgcct ggcgacaacg ttgaaatgac agttgaatta atcgctccaa 60

<210> SEQ ID NO 1197
<211> LENGTH: 60
<212> TYPE: DNA
<213> ORGANISM: Staphylococcus epidermidis

<400> SEQUENCE: 1197
gtacagaaat ggttatgcct ggcgacaacg ttgaaatgac agttgaatta atcgctccaa 60

<210> SEQ ID NO 1198
<211> LENGTH: 44
<212> TYPE: DNA
<213> ORGANISM: Streptococcus mitis

<400> SEQUENCE: 1198
gaactgaaat ggtaatgcct ggtgataacg tgactatcga cgtt 44

<210> SEQ ID NO 1199
<211> LENGTH: 48
<212> TYPE: DNA
<213> ORGANISM: Streptococcus sanguis

<400> SEQUENCE: 1199
gtactgaaat ggtaatgcct ggtgataacg taacaatcga cgttgagt 48

<210> SEQ ID NO 1200
<211> LENGTH: 60
<212> TYPE: DNA
<213> ORGANISM: Streptococcus mitis

<400> SEQUENCE: 1200
gtactgaaat ggtaatgcct ggtgataacg tgacaatcga cgttgagttg atccacccaa 60

<210> SEQ ID NO 1201
<211> LENGTH: 60
<212> TYPE: DNA
<213> ORGANISM: Streptococcus pneumoniae

<400> SEQUENCE: 1201
gtactgaaat ggtaatgcct ggtgataacg tgacaatcga cgttgagttg attcacccaa 60

<210> SEQ ID NO 1202
<211> LENGTH: 60
<212> TYPE: DNA
<213> ORGANISM: Streptococcus pyogenes

<400> SEQUENCE: 1202
gtacagaaat ggttatgcct ggtgataacg tgacaatcaa cgttgagttg atccacccaa 60

<210> SEQ ID NO 1203
<211> LENGTH: 27
<212> TYPE: DNA
<213> ORGANISM: Streptococcus mutans

<400> SEQUENCE: 1203
gtactgaaat ggttatgcct ggtgata 27

<210> SEQ ID NO 1204
<211> LENGTH: 60
<212> TYPE: DNA
<213> ORGANISM: Streptococcus mutans

<400> SEQUENCE: 1204
gtactgaaat ggttatgcct ggtgataacg ttactattga cgttgaattg atccatccaa 60

<210> SEQ ID NO 1205
<211> LENGTH: 60
<212> TYPE: DNA
<213> ORGANISM: Haemophilus influenzae

<400> SEQUENCE: 1205
gcgtggaaat ggtaatgcca ggcgataaca tcaagatgac agtaagctta atccacccaa 60

<210> SEQ ID NO 1206
<211> LENGTH: 59
<212> TYPE: DNA
<213> ORGANISM: Moraxella catarrhalis

<400> SEQUENCE: 1206
gcactgaaat ggttatgcca ggtgataacg ttgagatgag cgttgagcta atcacccaa 59

<210> SEQ ID NO 1207
<211> LENGTH: 60
<212> TYPE: DNA
<213> ORGANISM: Bordetella pertussis

<400> SEQUENCE: 1207
acaaggaaat ggtgctgccg ggcgacaacg tgtcgatgac cgtcaagctg ctggccccga 60

<210> SEQ ID NO 1208
<211> LENGTH: 60
<212> TYPE: DNA
<213> ORGANISM: Bordetella parapertussis

<400> SEQUENCE: 1208
acaaggaaat ggtgctgccg ggcgacaacg tgtcgatgac cgtcaagctg ctggccccga 60

<210> SEQ ID NO 1209
<211> LENGTH: 60
<212> TYPE: DNA
<213> ORGANISM: Burkholderia pseudomallei

<400> SEQUENCE: 1209
acaaggaaat ggtgatgccg ggcgacaacg tgtcgatcac ggtgaagctg atcgcgccga 60

<210> SEQ ID NO 1210
<211> LENGTH: 46
<212> TYPE: DNA
<213> ORGANISM: Stenotrophomonas maltophilia

<400> SEQUENCE: 1210
gcgtcgaaat ggtgatgccg ggtgacaacg tcaagatggt cgtcac 46

<210> SEQ ID NO 1211
<211> LENGTH: 60
<212> TYPE: DNA
<213> ORGANISM: Pseudomonas aeruginosa

<400> SEQUENCE: 1211
gcgtagagat ggtaatgccg ggcgacaaca tcaagatggt tgtcaccctg atcgctccga 60

<210> SEQ ID NO 1212
<211> LENGTH: 39
<212> TYPE: DNA
<213> ORGANISM: Klebsiella pneumoniae

<400> SEQUENCE: 1212
gcgtagagat ggtaatgccg ggcgacaaca tcaaaatgg 39

<210> SEQ ID NO 1213
<211> LENGTH: 60
<212> TYPE: DNA
<213> ORGANISM: Mycobacterium avium

<400> SEQUENCE: 1213
gcaccgagat ggtgatgccc ggtgacaaca ccaacatctc ggtgaagctg atccagcccg 60

<210> SEQ ID NO 1214
<211> LENGTH: 60
<212> TYPE: DNA
<213> ORGANISM: Mycobacterium avium

<400> SEQUENCE: 1214
gcaccgagat ggtgatgccc ggtgacaaca ccaacatctc ggtgaagctg atccagcccg 60

<210> SEQ ID NO 1215
<211> LENGTH: 57
<212> TYPE: DNA
<213> ORGANISM: Mycobacterium intracellulare

<400> SEQUENCE: 1215
gcaccgaaat ggtgatgccc ggtgacaaca ccaacatctc ggtcaagctg atccagc 57

<210> SEQ ID NO 1216
<211> LENGTH: 27
<212> TYPE: DNA
<213> ORGANISM: Mycobacterium kansasii

<400> SEQUENCE: 1216
gcaccgagat ggtgatgccc ggtgaca 27

<210> SEQ ID NO 1217
<211> LENGTH: 60
<212> TYPE: DNA
<213> ORGANISM: Mycobacterium tuberculosis

<400> SEQUENCE: 1217
gcaccgagat ggtgatgccc ggtgacaaca ccaacatctc ggtgaagttg atccagcccg 60

<210> SEQ ID NO 1218
<211> LENGTH: 60
<212> TYPE: DNA
<213> ORGANISM: Mycobacterium tuberculosis

<400> SEQUENCE: 1218
gcaccgagat ggtgatgccc ggtgacaaca ccaacatctc ggtgaagttg atccagcccg 60

<210> SEQ ID NO 1219
<211> LENGTH: 60
<212> TYPE: DNA
<213> ORGANISM: Corynebacterium diphtheriae

<400> SEQUENCE: 1219
gcaccgagat ggtcatgcct ggcgacaacg tcgacatgtc cgtcaccctg atccagcctg 60

<210> SEQ ID NO 1220
<211> LENGTH: 60
<212> TYPE: DNA
<213> ORGANISM: Neisseria meningitidis

<400> SEQUENCE: 1220
gtgtagaaat ggtaatgccg ggtgaaaacg taaccatcac cgtagaactg attgcgccta 60

<210> SEQ ID NO 1221
<211> LENGTH: 60
<212> TYPE: DNA
<213> ORGANISM: Neisseria meningitidis

<400> SEQUENCE: 1221
gtgtggaaat ggtaatgccg ggcgagaacg taaccatcac cgtagaactg attgcgccta 60

<210> SEQ ID NO 1222
<211> LENGTH: 59
<212> TYPE: DNA
<213> ORGANISM: Neisseria meningitidis

<400> SEQUENCE: 1222
gagtggaaat ggtaatgcct ggtgagaacg taaccatcac cgtagactga ttgcgtcta 59

<210> SEQ ID NO 1223
<211> LENGTH: 59
<212> TYPE: DNA
<213> ORGANISM: Mycoplasma pneumoniae

<400> SEQUENCE: 1223
ttgctgttga agaaggaagt aaattctcaa tccgtgaagg tggaagaaca gtaggtgct 59

<210> SEQ ID NO 1224
<211> LENGTH: 59
<212> TYPE: DNA
<213> ORGANISM: Mycoplasma pneumoniae

<400> SEQUENCE: 1224
ttgcttgtga aaaaggtagt aagttctcca tccgtgaagg tggtcgaacg gttggtgct 59

<210> SEQ ID NO 1225
<211> LENGTH: 59
<212> TYPE: DNA
<213> ORGANISM: Legionella pneumophila

<400> SEQUENCE: 1225
ttgcgatgga tgaaggttta agattcgcaa ttagagaggg tggccgaact gttggcgcc 59

<210> SEQ ID NO 1226
<211> LENGTH: 59
<212> TYPE: DNA
<213> ORGANISM: Legionella pneumophila

<400> SEQUENCE: 1226
ttgcgatgga tgaaggttta agattcgcaa ttagagaggg tggccgaact gttggcgcc 59

<210> SEQ ID NO 1227
<211> LENGTH: 59
<212> TYPE: DNA
<213> ORGANISM: Legionella pneumophila

<400> SEQUENCE: 1227
ttgcgatgga tgagggttta agattcgcaa ttagagaggg tggccgaact gttggcgcc 59

<210> SEQ ID NO 1228
<211> LENGTH: 59
<212> TYPE: DNA
<213> ORGANISM: Chlamydophila pneumoniae

<400> SEQUENCE: 1228
ttgctcttga agaaggaatg agatttgcaa ttcgtgaagg tggtcgtact atcggcgct 59

<210> SEQ ID NO 1229
<211> LENGTH: 59
<212> TYPE: DNA
<213> ORGANISM: Enterococcus faecalis

<400> SEQUENCE: 1229
tcgctatcga agacggaact cgtttctcta ttcgtgaagg cggacgtact gtaggttca 59

<210> SEQ ID NO 1230
<211> LENGTH: 59
<212> TYPE: DNA
<213> ORGANISM: Staphylococcus aureus

<400> SEQUENCE: 1230
tcgcgattga agacggtact cgtttctcaa tccgcgaagg tggacgtact gtaggatca 59

<210> SEQ ID NO 1231
<211> LENGTH: 59
<212> TYPE: DNA
<213> ORGANISM: Staphylococcus aureus

<400> SEQUENCE: 1231
tcgcgattga agacggtact cgtttctcaa tccgcgaagg tggacgtact gtaggatca 59

<210> SEQ ID NO 1232
<211> LENGTH: 59
<212> TYPE: DNA
<213> ORGANISM: Staphylococcus aureus

<400> SEQUENCE: 1232
tcgcgattga agacggtact cgtttctcaa tccgtgaagg tggacgtact gtaggatca 59

<210> SEQ ID NO 1233
<211> LENGTH: 59
<212> TYPE: DNA
<213> ORGANISM: Staphylococcus aureus

<400> SEQUENCE: 1233
tcgcgattga agacggtact cgtttctcaa tccgtgaagg tggacgtact gtaggatca 59

<210> SEQ ID NO 1234
<211> LENGTH: 59
<212> TYPE: DNA
<213> ORGANISM: Staphylococcus aureus

<400> SEQUENCE: 1234
tcgcgattga agacggtact cgtttctcaa tccgtgaagg tggacgtact gtaggatca 59

<210> SEQ ID NO 1235
<211> LENGTH: 59
<212> TYPE: DNA
<213> ORGANISM: Staphylococcus epidermidis

<400> SEQUENCE: 1235
tcgctatcga agacggaact cgtttctcaa ttcgtgaagg tggacgtact gttggatca 59

<210> SEQ ID NO 1236
<211> LENGTH: 59
<212> TYPE: DNA
<213> ORGANISM: Staphylococcus epidermidis

<400> SEQUENCE: 1236
tcgctatcga agacggaact cgtttctcaa ttcgtgaagg tggacgtact gttggatca 59

<210> SEQ ID NO 1237
<211> LENGTH: 59
<212> TYPE: DNA
<213> ORGANISM: Streptococcus mitis

<400> SEQUENCE: 1237
tcgccgtaga acaaggtact acattctcta tccgtgaggg tggacgtact gttggttca 59

<210> SEQ ID NO 1238
<211> LENGTH: 59
<212> TYPE: DNA
<213> ORGANISM: Streptococcus pneumoniae

<400> SEQUENCE: 1238
tcgccgtaga acaaggtact acattctcta tccgtgaggg tggacgtact gttggttca 59

<210> SEQ ID NO 1239
<211> LENGTH: 59
<212> TYPE: DNA
<213> ORGANISM: Streptococcus pyogenes

<400> SEQUENCE: 1239
tcgccgtaga acaaggtact actttctcaa tccgtgaagg tggacgtact gttggttca 59

<210> SEQ ID NO 1240
<211> LENGTH: 59
<212> TYPE: DNA
<213> ORGANISM: Streptococcus mutans

<400> SEQUENCE: 1240
tcgctgttga acaaggtact actttctcta ttcgtgaagg tggacgtact gttggttct 59

<210> SEQ ID NO 1241
<211> LENGTH: 59
<212> TYPE: DNA
<213> ORGANISM: Haemophilus influenzae

<400> SEQUENCE: 1241
ttgcgatgga tcaaggttta cgtttcgcaa tccgtgaagg tggccgtaca gtaggtgca 59

<210> SEQ ID NO 1242
<211> LENGTH: 11
<212> TYPE: DNA
<213> ORGANISM: Moraxella catarrhalis

<400> SEQUENCE: 1242
tcgcatggac a 11

<210> SEQ ID NO 1243
<211> LENGTH: 59
<212> TYPE: DNA
<213> ORGANISM: Bordetella pertussis

<400> SEQUENCE: 1243
tcgccatgga agaaggtctg cgtttcgcca tccgtgaagg cggtcgtacc gtcggcgcc 59

<210> SEQ ID NO 1244
<211> LENGTH: 59
<212> TYPE: DNA
<213> ORGANISM: Bordetella parapertussis

<400> SEQUENCE: 1244
tcgccatgga agaaggtctg cgtttcgcca tccgtgaagg cggtcgtacc gtcggcgcc 59

<210> SEQ ID NO 1245
<211> LENGTH: 59
<212> TYPE: DNA
<213> ORGANISM: Burkholderia pseudomallei

<400> SEQUENCE: 1245
tcgcgatgga agaaggtctg cgcttcgcga tccgcgaagg cggtcgcacc gtcggcgcc 59

<210> SEQ ID NO 1246
<211> LENGTH: 59
<212> TYPE: DNA
<213> ORGANISM: Pseudomonas aeruginosa

<400> SEQUENCE: 1246
tcgccatgga agatggcctg cgcttcgcga tccgcgaagg cggccgtacc gttggcgcc 59

<210> SEQ ID NO 1247
<211> LENGTH: 10
<212> TYPE: DNA
<213> ORGANISM: Klebsiella pneumoniae

<400> SEQUENCE: 1247
cccccccccc 10

<210> SEQ ID NO 1248
<211> LENGTH: 59
<212> TYPE: DNA
<213> ORGANISM: Mycobacterium avium

<400> SEQUENCE: 1248
tcgccatgga cgagggtctg cggttcgcca tccgcgaggg tggtcgcacc gtcggcgcc 59

<210> SEQ ID NO 1249
<211> LENGTH: 59
<212> TYPE: DNA
<213> ORGANISM: Mycobacterium avium

<400> SEQUENCE: 1249
tcgccatgga cgagggtctg cggttcgcca tccgcgaggg tggtcgcacc gtcggcgcc 59

<210> SEQ ID NO 1250
<211> LENGTH: 59
<212> TYPE: DNA
<213> ORGANISM: Mycobacterium tuberculosis

<400> SEQUENCE: 1250
tcgccatgga cgaaggtctg cgtttcgcga tccgcgaggg tggccgcacc gtgggcgcc 59

<210> SEQ ID NO 1251
<211> LENGTH: 59
<212> TYPE: DNA
<213> ORGANISM: Mycobacterium tuberculosis

<400> SEQUENCE: 1251
tcgccatgga cgaaggtctg cgtttcgcga tccgcgaggg tggccgcacc gtgggcgcc 59

<210> SEQ ID NO 1252
<211> LENGTH: 59
<212> TYPE: DNA
<213> ORGANISM: Corynebacterium diphtheriae

<400> SEQUENCE: 1252
tcgctatgga tgagggcctg cgcttcgcta tccgcgaggg ctcccgcacc gtcggcgct 59

<210> SEQ ID NO 1253
<211> LENGTH: 59
<212> TYPE: DNA
<213> ORGANISM: Neisseria meningitidis

<400> SEQUENCE: 1253
tcgctatgga agaaggcctg cgctttgcga ttcgcgaagg cggccgtacc gtgggtgcc 59

<210> SEQ ID NO 1254
<211> LENGTH: 59
<212> TYPE: DNA
<213> ORGANISM: Neisseria meningitidis

<400> SEQUENCE: 1254
tcgctatgga agaaggtttg cgctttgcga ttcgcgaagg cggccgtacc gtgggtgcc 59

<210> SEQ ID NO 1255
<211> LENGTH: 44
<212> TYPE: DNA
<213> ORGANISM: Neisseria meningitidis

<400> SEQUENCE: 1255
tcgctatgga agagctgcgc ttgcgtcgtg tcgcgcgtgt ccat 44

<210> SEQ ID NO 1256
<211> LENGTH: 27
<212> TYPE: DNA
<213> ORGANISM: Mycoplasma pneumoniae

<400> SEQUENCE: 1256
ggtacagtaa ctaaagttat taagtaa 27

<210> SEQ ID NO 1257
<211> LENGTH: 27
<212> TYPE: DNA
<213> ORGANISM: Mycoplasma pneumoniae

<400> SEQUENCE: 1257
ggttcagtca cggaagtgct tgaatag 27

<210> SEQ ID NO 1258
<211> LENGTH: 27
<212> TYPE: DNA
<213> ORGANISM: Legionella pneumophila

<400> SEQUENCE: 1258
ggtgtagtcg ctaaaataat cgagtaa 27

<210> SEQ ID NO 1259
<211> LENGTH: 27
<212> TYPE: DNA
<213> ORGANISM: Legionella pneumophila

<400> SEQUENCE: 1259
ggtgtagtcg ctaaaataat cgagtaa 27

<210> SEQ ID NO 1260
<211> LENGTH: 27
<212> TYPE: DNA
<213> ORGANISM: Legionella pneumophila

<400> SEQUENCE: 1260
ggtgtagtcg ctaaaataat cgagtaa 27

<210> SEQ ID NO 1261
<211> LENGTH: 27
<212> TYPE: DNA
<213> ORGANISM: Chlamydophila pneumoniae

<400> SEQUENCE: 1261
ggaacgattt caaagatcaa tgcttaa 27

<210> SEQ ID NO 1262
<211> LENGTH: 27
<212> TYPE: DNA
<213> ORGANISM: Enterococcus faecalis

<400> SEQUENCE: 1262
ggcgttgtta ctgaaatcgt taaataa 27

<210> SEQ ID NO 1263
<211> LENGTH: 27
<212> TYPE: DNA
<213> ORGANISM: Staphylococcus aureus

<400> SEQUENCE: 1263
ggcgttgtta ctgaaatcat taaataa 27

<210> SEQ ID NO 1264
<211> LENGTH: 27
<212> TYPE: DNA
<213> ORGANISM: Staphylococcus aureus

<400> SEQUENCE: 1264
ggcgttgtta ctgaaatcat taaataa 27

<210> SEQ ID NO 1265
<211> LENGTH: 27
<212> TYPE: DNA
<213> ORGANISM: Staphylococcus aureus

<400> SEQUENCE: 1265
ggcgttgtta ctgaaatcat taaataa 27

<210> SEQ ID NO 1266
<211> LENGTH: 27
<212> TYPE: DNA
<213> ORGANISM: Staphylococcus aureus

<400> SEQUENCE: 1266
ggcgttgtta ctgaaatcat taaataa 27

<210> SEQ ID NO 1267
<211> LENGTH: 27
<212> TYPE: DNA
<213> ORGANISM: Staphylococcus aureus

<400> SEQUENCE: 1267
ggcgttgtta ctgaaatcat taaataa 27

<210> SEQ ID NO 1268
<211> LENGTH: 27
<212> TYPE: DNA
<213> ORGANISM: Staphylococcus epidermidis

<400> SEQUENCE: 1268
ggcgttgtaa ctgaaatctt tgaataa 27

<210> SEQ ID NO 1269
<211> LENGTH: 27
<212> TYPE: DNA
<213> ORGANISM: Staphylococcus epidermidis

<400> SEQUENCE: 1269
ggcgttgtaa ctgaaatctt tgaataa 27

<210> SEQ ID NO 1270
<211> LENGTH: 27
<212> TYPE: DNA
<213> ORGANISM: Streptococcus mitis

<400> SEQUENCE: 1270
ggtatggtta cagaaatcga agcttaa 27

<210> SEQ ID NO 1271
<211> LENGTH: 27
<212> TYPE: DNA
<213> ORGANISM: Streptococcus pneumoniae

<400> SEQUENCE: 1271
ggtatggtta cagaaatcga agcttaa 27

<210> SEQ ID NO 1272
<211> LENGTH: 27
<212> TYPE: DNA
<213> ORGANISM: Streptococcus pyogenes

<400> SEQUENCE: 1272
ggtatcgttt cagaaatcga agcttaa 27

<210> SEQ ID NO 1273
<211> LENGTH: 27
<212> TYPE: DNA
<213> ORGANISM: Streptococcus mutans

<400> SEQUENCE: 1273
ggtatcgttt cagaaatcga agcttaa 27

<210> SEQ ID NO 1274
<211> LENGTH: 27
<212> TYPE: DNA
<213> ORGANISM: Haemophilus influenzae

<400> SEQUENCE: 1274
ggcgttgttg cgaaaatcat caaataa 27

<210> SEQ ID NO 1275
<211> LENGTH: 27
<212> TYPE: DNA
<213> ORGANISM: Bordetella pertussis

<400> SEQUENCE: 1275
ggcgtcgtcg ccaagatcat caagtaa 27

<210> SEQ ID NO 1276
<211> LENGTH: 27
<212> TYPE: DNA
<213> ORGANISM: Bordetella parapertussis

<400> SEQUENCE: 1276
ggcgtcgtcg ctaagatcat caagtaa 27

<210> SEQ ID NO 1277
<211> LENGTH: 27
<212> TYPE: DNA
<213> ORGANISM: Burkholderia pseudomallei

<400> SEQUENCE: 1277
ggcgtcgtcg ccaagatcat cgagtaa 27

<210> SEQ ID NO 1278
<211> LENGTH: 27
<212> TYPE: DNA
<213> ORGANISM: Pseudomonas aeruginosa

<400> SEQUENCE: 1278
ggcgtggttg ccaagatcat cgagtaa 27

<210> SEQ ID NO 1279
<211> LENGTH: 10
<212> TYPE: DNA
<213> ORGANISM: Klebsiella pneumoniae

<400> SEQUENCE: 1279
aaaaaaaaaa 10

<210> SEQ ID NO 1280
<211> LENGTH: 27
<212> TYPE: DNA
<213> ORGANISM: Mycobacterium avium

<400> SEQUENCE: 1280
ggccgggtcg tcaagatcat caagtag 27

<210> SEQ ID NO 1281
<211> LENGTH: 27
<212> TYPE: DNA
<213> ORGANISM: Mycobacterium avium

<400> SEQUENCE: 1281
ggccgggtcg tcaagatcat caagtag 27

<210> SEQ ID NO 1282
<211> LENGTH: 27
<212> TYPE: DNA
<213> ORGANISM: Mycobacterium tuberculosis

<400> SEQUENCE: 1282
ggccgggtca ccaagatcat caagtag 27

<210> SEQ ID NO 1283
<211> LENGTH: 27
<212> TYPE: DNA
<213> ORGANISM: Mycobacterium tuberculosis

<400> SEQUENCE: 1283
ggccgggtca ccaagatcat caagtag 27

-continued

```
<210> SEQ ID NO 1284
<211> LENGTH: 27
<212> TYPE: DNA
<213> ORGANISM: Corynebacterium diphtheriae

<400> SEQUENCE: 1284

ggtcgcgtta ccaagatcat caagtaa                                          27


<210> SEQ ID NO 1285
<211> LENGTH: 27
<212> TYPE: DNA
<213> ORGANISM: Neisseria meningitidis

<400> SEQUENCE: 1285

ggcgtggttt cttctgttat cgcttaa                                          27


<210> SEQ ID NO 1286
<211> LENGTH: 27
<212> TYPE: DNA
<213> ORGANISM: Neisseria meningitidis

<400> SEQUENCE: 1286

ggcgtggttt cttctgttat cgcttaa                                          27
```